US006689879B2

(12) United States Patent
Barnett et al.

(10) Patent No.: US 6,689,879 B2
(45) **Date of Patent: *Feb. 10, 2004**

(54) MODIFIED HIV ENV POLYPEPTIDES

(75) Inventors: Susan Barnett, San Francisco, CA (US); Karin Hartog, Piedmont, CA (US); Eric Martin, El Cerrito, CA (US)

(73) Assignee: Chiron Corporation, Emeryville, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/476,242

(22) Filed: Dec. 30, 1999

(65) Prior Publication Data

US 2002/0146683 A1 Oct. 10, 2002

Related U.S. Application Data

(60) Provisional application No. 60/156,670, filed on Sep. 29, 1999, and provisional application No. 60/114,495, filed on Dec. 31, 1998.

(51) Int. Cl.[7] .............................................. C07H 21/04

(52) U.S. Cl. ...................... 536/23.72; 536/23.1; 435/6; 435/320.1

(58) Field of Search ........................... 435/6, 974, 455, 435/320.1; 536/23.1, 23.72

(56) References Cited

U.S. PATENT DOCUMENTS

| | | | | |
|---|---|---|---|---|
| RE33,653 | E | 7/1991 | Mark et al. | |
| 5,032,510 | A | 7/1991 | Kovacevic et al. | |
| 5,128,319 | A | 7/1992 | Arlinghaus | |
| 5,256,767 | A | 10/1993 | Salk et al. | |
| 5,304,472 | A | 4/1994 | Bass et al. | |
| 5,364,773 | A | 11/1994 | Paoletti et al. | |
| 5,419,900 | A | 5/1995 | Lane et al. | |
| 5,503,833 | A | 4/1996 | Redmond et al. | |
| 5,550,280 | A | 8/1996 | Dao-Cong et al. | |
| 5,637,677 | A | 6/1997 | Greene et al. | |
| 5,665,569 | A | 9/1997 | Ohno | |
| 5,665,720 | A | 9/1997 | Young et al. | |
| 5,670,152 | A | 9/1997 | Weiner et al. | |
| 5,683,864 | A | 11/1997 | Houghton et al. | |
| 5,686,078 | A | 11/1997 | Becker et al. | |
| 5,693,755 | A | 12/1997 | Buonagurio et al. | |
| 5,712,088 | A | 1/1998 | Houghton et al. | |
| 5,714,596 | A | 2/1998 | Houghton et al. | |
| 5,728,520 | A | 3/1998 | Weiner et al. | |
| 5,741,492 | A | 4/1998 | Hurwitz et al. | |
| 5,750,373 | A | 5/1998 | Garrard et al. | |
| 5,766,845 | A | 6/1998 | Weiner et al. | |
| 5,817,637 | A | 10/1998 | Weiner et al. | |
| 5,837,242 | A | 11/1998 | Holliger et al. | |
| 5,837,818 | A | 11/1998 | Buonagurio et al. | |
| 5,853,736 | A | 12/1998 | Becker et al. | |
| 5,858,675 | A | 1/1999 | Hillman et al. | |
| 5,866,320 | A | 2/1999 | Rovinski et al. | |
| 5,871,747 | A | 2/1999 | Gengoux-Sedlik et al. | |
| 5,879,907 | A | 3/1999 | Aberg et al. | |
| 5,879,925 | A | 3/1999 | Rovinski et al. | |
| 5,889,176 | A | 3/1999 | Rovinski et al. | |
| 5,932,445 | A | 8/1999 | Lal et al. | |
| 5,951,975 | A | 9/1999 | Falo, Jr. et al. | |
| 5,955,342 | A | 9/1999 | Rovinski et al. | |
| 5,965,726 | A | 10/1999 | Pavlakis et al. | |
| 5,972,596 | A | 10/1999 | Pavlakis et al. | |
| 6,001,977 | A | * 12/1999 | Chang et al. | 530/389.4 |
| 6,004,763 | A | 12/1999 | Gengoux et al. | |
| 6,025,125 | A | 2/2000 | Rovinski et al. | |
| 6,060,273 | A | 5/2000 | Dirks et al. | |
| 6,060,587 | A | 5/2000 | Weiner et al. | |
| 6,063,384 | A | 5/2000 | Morrow et al. | |
| 6,074,636 | A | 6/2000 | Nichols | |
| 6,080,408 | A | 6/2000 | Rovinski et al. | |
| 6,087,486 | A | 7/2000 | Weiner et al. | |
| 6,093,800 | A | 7/2000 | Reiter et al. | |
| 6,096,505 | A | 8/2000 | Selby et al. | |
| 6,099,847 | A | 8/2000 | Tobin et al. | |
| 6,114,148 | A | 9/2000 | Seed et al. | |
| 6,132,973 | A | 10/2000 | Lal et al. | |
| 6,139,833 | A | 10/2000 | Burgess et al. | |
| 6,140,059 | A | 10/2000 | Schawaller | |
| 6,146,635 | A | 11/2000 | Cano et al. | |
| 6,172,201 | B1 | 1/2001 | Weiner et al. | |
| 6,174,666 | B1 | 1/2001 | Pavlakis et al. | |
| 6,214,804 | B1 | 4/2001 | Felgner et al. | |
| 6,291,157 | B1 | 9/2001 | Rovinski et al. | |
| 6,291,664 | B1 | 9/2001 | Pavlakis et al. | |
| 6,316,253 | B1 | 11/2001 | Innis et al. | |
| 6,331,404 | B1 | 12/2001 | Berman et al. | 435/7.1 |

FOREIGN PATENT DOCUMENTS

| | | | |
|---|---|---|---|
| EP | 0187041 | | 7/1986 |
| EP | 0199301 | A1 | 10/1986 |

(List continued on next page.)

OTHER PUBLICATIONS

Cao et al., "Replication and Neutralization of Human Immunodeficiency Virus Type 1 Lacking the V1 and V2 Variable Loops of the gp120 Envelope Glycoprotein," *Journal of Virology 71* (12):9808–9812 (1997).

Jeffs et al., "Antigenicity of Truncated Forms of the Human Immunodeficiency Virus Type 1 Envelope Glycoprotein," *Journal of General Virology 77*(7):1403–1410 (1996).

(List continued on next page.)

*Primary Examiner*—Jeffrey Stucker
(74) *Attorney, Agent, or Firm*—Dahna S. Pasternak; Robert P. Blackburn

(57) ABSTRACT

Polynucleotide encoding modified HIV Env polypeptides are disclosed. The Env polypeptides are modified in the region of amino acids 420–436 so as to expose at least part of the CD4 binding region. Methods of diagnosis, treatment and prevention using the polynucleotides and polypeptides are also provided.

5 Claims, 65 Drawing Sheets

FOREIGN PATENT DOCUMENTS

| | | | |
|---|---|---|---|
| EP | 0 199 301 | A1 | 10/1986 |
| EP | 0242216 | | 10/1987 |
| EP | 0314317 | A1 | 5/1989 |
| EP | 0449116 | B1 | 10/1991 |
| EP | 0617132 | A2 | 9/1994 |
| EP | 0449116 | B1 | 10/1999 |
| WO | WO 86/03224 | | 6/1986 |
| WO | WO 87/02775 | | 5/1987 |
| WO | WO 88/00471 | | 1/1988 |
| WO | WO 88/10300 | | 12/1988 |
| WO | WO 89/01940 | | 3/1989 |
| WO | WO 89/02277 | | 3/1989 |
| WO | WO 89/02922 | | 4/1989 |
| WO | WO 89/03222 | | 4/1989 |
| WO | WO 90/02568 | | 3/1990 |
| WO | WO 90/03984 | | 4/1990 |
| WO | WO 90/10438 | | 9/1990 |
| WO | WO 90/11092 | | 10/1990 |
| WO | WO 90/11359 | | 10/1990 |
| WO | WO 90/12094 | | 10/1990 |
| WO | WO 90/15141 | | 12/1990 |
| WO | WO 91/04273 | | 4/1991 |
| WO | WO 91/06319 | | 5/1991 |
| WO | WO 91/07425 | | 5/1991 |
| WO | WO 91/07510 | | 5/1991 |
| WO | WO 91/13360 | | 9/1991 |
| WO | WO 91/13906 | | 9/1991 |
| WO | WO 91/15238 | | 10/1991 |
| WO | WO 91/15512 | | 10/1991 |
| WO | WO 91/16926 | | 11/1991 |
| WO | WO 91/18928 | | 12/1991 |
| WO | WO 91/19803 | | 12/1991 |
| WO | WO 92/03475 | | 3/1992 |
| WO | WO 92/04046 | | 3/1992 |
| WO | WO 92/05799 | | 4/1992 |
| WO | WO 93/02102 | | 2/1993 |
| WO | WP 93/04090 | | 3/1993 |
| WO | WO 93/08836 | | 5/1993 |
| WO | WO 93/14789 | | 8/1993 |
| WO | WO 93/20212 | | 10/1993 |
| WO | WO 93/21346 | | 10/1993 |
| WO | WO 93/23569 | | 11/1993 |
| WO | WO 94/04574 | | 3/1994 |
| WO | WO 94/07922 | | 4/1994 |
| WO | WO 94/11523 | | 5/1994 |
| WO | WO 94/13804 | | 6/1994 |
| WO | WO 94/15621 | | 7/1994 |
| WO | WO 94/16060 | | 7/1994 |
| WO | WO 94/16737 | | 8/1994 |
| WO | WO 94/18221 | | 8/1994 |
| WO | WO 94/20141 | | 9/1994 |
| WO | WO 94/20640 | | 9/1994 |
| WO | WO 94/22477 | | 10/1994 |
| WO | WO 94/26293 | | 11/1994 |
| WO | WO 94/29339 | | 12/1994 |
| WO | WO 95/03407 | | 2/1995 |
| WO | WO 95/04818 | | 2/1995 |
| WO | WO 95/11317 | | 4/1995 |
| WO | WO 95/11701 | | 5/1995 |
| WO | WO 95/24485 | | 9/1995 |
| WO | WO 95/25124 | | 9/1995 |
| WO | WO 95/27505 | | 10/1995 |
| WO | WO 95/29700 | | 11/1995 |
| WO | WO 95/33206 | | 12/1995 |
| WO | WO 95/33835 | | 12/1995 |
| WO | WO 96/02273 | | 2/1996 |
| WO | WO 96/02557 | | 2/1996 |
| WO | WO 96/04382 | | 2/1996 |
| WO | WO 96/09066 | | 3/1996 |
| WO | WO 96/09378 | | 3/1996 |
| WO | WO 96/16178 | | 5/1996 |
| WO | WO 96/20732 | | 7/1996 |
| WO | WO 96/23509 | | 8/1996 |
| WO | WO 96/25177 | | 8/1996 |
| WO | WO 96/40290 | | 12/1996 |
| WO | WO 97/03198 | | 1/1997 |
| WO | WO 97/11605 | | 4/1997 |
| WO | WO 97/26009 | | 7/1997 |
| WO | WO 97/31115 | | 8/1997 |
| WO | WO 97/48370 | | 12/1997 |
| WO | WO 98/08539 | | 5/1998 |
| WO | WO 98/34640 | | 8/1998 |
| WO | WO 98/41536 | | 9/1998 |
| WO | WO 98/41645 | | 9/1998 |
| WO | WO 98/43182 | | 10/1998 |
| WO | WO 98/48843 | | 11/1998 |
| WO | WO 98/59074 | | 12/1998 |
| WO | WO 99/02694 | | 1/1999 |
| WO | WO 99/06599 | | 2/1999 |
| WO | WO 99/09412 | | 2/1999 |
| WO | WO 99/12416 | | 3/1999 |
| WO | WO 99/13864 | | 3/1999 |
| WO | WO 99/16883 | | 4/1999 |
| WO | WO 99/33346 | | 7/1999 |
| WO | WO 99/41398 | | 8/1999 |
| WO | WO 99/52463 | | 10/1999 |
| WO | WO 99/53960 | | 10/1999 |
| WO | WO 99/37695 | | 12/1999 |
| WO | WO 00/08043 | | 2/2000 |
| WO | WO 00/18929 | | 4/2000 |
| WO | WO 00/21556 | | 4/2000 |
| WO | WO 00/39302 | | 7/2000 |
| WO | WO 00/39303 | | 7/2000 |
| WO | WO 00/39304 | | 7/2000 |
| WO | WO 00/44926 | | 8/2000 |
| WO | WO 00/65076 | | 11/2000 |
| WO | WO 00/66179 | | 11/2000 |
| WO | WO 00/67761 | | 11/2000 |
| WO | WO 00/67787 | | 11/2000 |
| WO | WO 00/71561 | | 11/2000 |
| WO | WO 01/02607 | | 1/2001 |
| WO | WO 01/12223 | | 2/2001 |
| WO | WO 01/16342 | | 3/2001 |
| WO | WO 01/19958 | | 3/2001 |
| WO | WO 01/21270 | | 3/2001 |
| WO | WO 01/26681 | | 4/2001 |
| WO | WO 01/29225 | | 4/2001 |
| WO | WO 01/36614 | | 5/2001 |
| WO | WO 01/42308 | | 6/2001 |
| WO | WO 01/43693 | | 6/2001 |
| WO | WO 01/45748 | | 6/2001 |
| WO | WO 01/46408 | | 6/2001 |
| WO | WO 01/47955 | | 7/2001 |
| WO | WO 01/54701 | | 8/2001 |
| WO | WO 01/54719 | | 8/2001 |
| WO | WO 01/60393 | | 8/2001 |
| WO | WO 01/60838 | | 8/2001 |

OTHER PUBLICATIONS

Stamatatos et al., "An Envelope Modification That Renders a Primary, Neutralization–Resistant Clade B Human Immunodeficiency Virus Type 1 Isolate Highly Susceptible to Neutralization by Sera From Other Clades," *Journal of Virology 72*(10):7840–7845. (1998).

Burton and Montefiori, "The Antibody Response in HIV–Infection," *AIDS 11*(suppl. A):S87–S98 (1997.

Barre–Sinoussi et al., "Isolation of a T–Lymphotropic Retrovirus From a Patient at Risk for Acquired Immune Deficiency Syndrome (AIDS) ," *Science 220:*868–871 (1983).

Bolognesi et al., "HIV Vaccine Development: A Progress Report," *Ann. Int. Med. 8*(7):603–611 (1994).

D'Souza et al., "Evaluation of Monoclonal Antibodies to Human Immunodeficiency Virus Type I Primary Isolates by Neutralization Assays: Performance Criteria for Selecting Candidate Antibodies for Clinical Trials," *J. Infect. Dis. 175:*1056–1062 (1997).

Fiore et al., "The Biological Phenotype of HIV–1 Usually Retained During and After Sexual Transmission," *Virology 204:*297–303 (1994).

Haynes et al., "Toward an Understanding of the Correlates of Protective Immunity to HIV Infection," *Science 271:*324–328 (1996).

Hu et al., "Protection of Macaques Against SIV Infection by Subunit Vaccines of SIV Envelope Glycoprotein gp 160," *Science 255:*456–459 (1992).

Javaherian, et al., "Principal Neutralizing Domain of the Human Immunodeficiency Virus Type 1 Envelope Protein," *Proc. Natl. Acad. Sci. 86:*6768–6772 (1989).

Kang et al., "Evidence for Non–V3–Specific Neutralizing Antibodies that Interfere With gp 120/CD4 Binding in Human Immunodeficiency Virus I–Infected Humans," *Proc. Natl. Acad. Sci. USA 88:*6171–6175 (1991).

Lu et al., "Immunogenicity of DNA Vaccines Expressing Human Immunodeficiency Virus Type I Envelope Glycoprotein With and Without Deletions in the V1/2 and V3 Regions," *AIDS Res. And Human Retroviruses 14*(2):151–155 (1998).

Matthews et al., "Restricted Neutralization of Divergent Human T–Lymphotropic Virus Type III Isolates by Antibodies to the Major Envelope Glycoprotein," *Proc. Natl. Acad. Sci. USA 83:*9709–9713 (1986).

Matsushita, et al., "Characterization of a Human Immunodeficiency Virus Neutralizing Monoclonal Antibody and Mapping of the Neutralizing Epitope," *J. Viol. 62*(6):2107–2144 (1988).

McDougal et al., "Binding of The Human Retrovirus HTLV–III/LAV/ARV/HIV to the CD4 (T4) Molecule: Conformation Dependence, Epitope Mapping, Antibody Inhibition, and Potential for Idiotypic Mimicry," *J. Immunol. 137:*(9):2937–2944 (1986).

Montefiori and Evans, "Toward and HIV Type I Vaccine that Generates Potent, Broadly Cross–Reactive Neutralizing Antibodies," *AIDS Res. Human Retroviruses 15*(8):689–698 (1999).

Nara, et al., "Purified Envelope Glycoproteins From Human Immunodeficiency Virus Type 1 Variants Induce Individual, Type–Specific Neutralizing Antibodies," *J. Virol. 62:*2622–2628 (1988).

Palker et al., "Type–Specific Neutralization of the Human Immunodeficiency Virus With Antibodies to Env–Encoded Synthetic Peptides," Proc. Natl. Acad. Sci. USA 85:1932–1936 (1988).

Putney et al., "HTLV–III/LAV–Neutralizing Antibodies to *E. Coli*–Produced Fragment of the Virus Envelope," Science 234:1392–1395 (1986).

Robert–Guroff et al., "HTLV–III–Neutralizing Antibodies in Patients With AIDS and AIDS–Related Complex," *Nature* (London) 316:72–74 (1985).

Rusche et al., "Antibodies That Inhibit Fusion of Human Immunodeficiency Virus–Infected Cells Bind a 24–Amino Acid Sequence of the Viral Envelope, gp 120," *Proc. Nat. Acad. Sci. USA 85:*3198–3202 (1988).

Stamatatos et al., "Effect of Major Deletions in the V1 and V2 Loops of a Macrophage–Tropic HIV Type 1 Isolate on Viral Envelope Structure, Cell Entry, and Replication," *AIDS Res. Human Retroviruses 14*(13):1129–1139 (1998).

Thali et al., "Characterization of Conserved Human Immunodeficiency Virus Type 1 gp 120 Neutralization Epitopes Exposed Upon gp 120–CD4 Binding," *J. Virol. 67*(7):3978–3988 (1993).

Trkola et al., "Cross–Clade Neutralization of Primary Isolates of Human Immunodeficiency Virus Type 1 by Human Monoclonal Antibodies and Tetrameric CD4–IgG," *J. Virol. 69:*6609–6617 (1995).

Weis et al., "Neutralization of Human T–Lymphotropic Virus Type III by Sera of AIDS and AIDS–Risk Patients," *Nature* (London) 316:69–72 (1985).

Weis et al., "Variable and Conserved Neutralization Antigens of Human Immunodeficiency Virus," *Nature* (London) 324:572–575 (1986).

Wyatt et al., "Involvement of the V1/V2 Variable Loop Structure in the Exposure of Human Immunodeficiency Virus Type 1 gp 120 Epitopes Induced by Receptor Binding," *J. Virol. 69:*(9):5723–5733 (1995).

Zhu et al., "Genotypic and Phenotypic Characterization of HIV–1 in Patients with Primary Infection," *Science 261:*1179–1181 (1993).

Myers et al. "Human Retroviruses and AIDS, 1991" published by the Los Alamos National Laboratory, Los Alamos, NM, 1991, pp. I–A–48 to I–A–56 and II–77 to II–80.*

GenBank accession No.:AF110965.

GenBank accession No.:AF110967.

GenBank accession No.:AF110968.

GenBank accession No.:AF110975.

GenBank accession No.:M65024.

Adams et al., "The Expression of Hybrid Hiv:ty Virus–like Particles in Yeast," *Nature 329:*68–70 (1987).

Anderson, et al., "Human Gene Therapy," *Nature 392*(6679 Suppl):25–30 (1998).

Arthur, et al., "Serological Responses in Chimpanzees Inoculated with Human Immunodeficiency Virus Glycoprotein (Gp 120) Subunit Vaccine," *Proc Natl Acad Sci USA* 84(23):8583–8587 (1987).

Azevedo et al., "Main Features of DNA–Based Immunization Vectors," *Braz J Med Biol. Res. 32*(2):147–153 (1999).

Baker et al., "Structures of Bovine and Human Papillomaviruses. Analysis by Cryoelectron Microscopy and Three–dimensional Image Reconstruction," *Biophys. J. 60:*1445–1456 (1991).

Barr, et al., "Antigenicity and Immunogenicity of Domains of the Human Immunodeficiency Virus (HIV) Envelope Polypeptide Expressed in the Yeast *Saccharomyces cerevisiae," Vaccine 5*(2):90–101 (1987).

Barrett, et al., "Large–scale production and purification of a vaccinia recombinant–derived HIV–1 gp 160 and analysis of its immunogenicity," *AIDS Res Hum Retroviruses* 5(2):159–71 (1989).

Beard, W. A., et al., "Role of the "Helix Clamp" in HIV–1 Reverse Transcriptase Catalytic Cycling as Revealed by Alanine–Scanning Mutagenesis," *Journal Of Biological Chemistry* 271(21):12213–12220 (1996).

Berger, P.B., "New Directions in Research: Report from the 10th International Conference on AIDS," *Canadian Medical Association Journal* 152(12):1991–1995 (1995).

Berman, et al., "Human Immunodeficiency Virus Type 1 Challenge of Chimpanzees Immunized with Recombinant Envelope Glycoprotein gp120," *Proc Natl Acad Sci USA 85*(14):5200–5204 (1988).

Berman, et al., "Expression and Immunogenicity of the Extracellular Domain of the Human Immunodeficiency Virus Type 1 Envelope Glycoprotein, gp160," *J Virol. 63*(8):3489–3498 (1989).

Birx and Redfield, "HIV Vaccine Therapy," *Int J Immunopharmacol. 13*(1):129–132 (1991).

Bolognesi, D.P., "Progress in Vaccines Against AIDS," *Science 246:*1233–1234 (1989).

Borrow, et al., "Virus–Specific CD8+ Cytotoxic T–Lymphocyte Activity Associated with Control of Viremia in Primary Human Immunodeficiency Virus Type 1 Infection," *J Virol. 68*(9):6103–6110 (1994).

Bourgault, et al., "Cytotoxic T–Cell Response and AIDS–Free Survival in Simian Immunodeficiency Virus–Infected Macaques," *AIDS. 7* (Suppl. 2):S73–S79 (1993).

Brown et al., "Chimeric Parvovirus B19 Capsids for the Presentation of Foreign Epitopes," *Virology 198:*477–488 (1994).

Bujacz, G., et al., "The Catalytic Domain of Human Immunodeficiency Virus Integrase: Ordered Active Site in the F185H Mutant," *Febs Letters 398*(2–3):175–178 (1996).

Burton et al., "Why Do We Not Have an HIV Vaccine and How Can We Make One?" *Nat Med. 4*(5 Suppl):495–498 (1998).

Carmichael et al., "Quantitative Analysis of the Human Immunodeficiency Virus Type 1 (Hiv–1)–specific Cytotoxic T Lymphocyte (Ctl) Response at Different Stages of Hiv–1 Infection: Differential Ctl Responses to Hiv–1 and Epstein––barr Virus in Late Disease," *J Exp Med. 177*(2):249–256 (1993).

Chazal N. et al., "Phenotypic Characterization of Insertion Mutants of the Human Immunodeficiency Virus Type 1 Gag Precursor Expressed in Recombinant Baculovirus–infected Cells," *Virology 68*(1):111–122 (1994).

Ciernik et al., "Induction of Cytotoxic T Lymphocytes and Antitumor Immunity with Dna Vaccines Expressing Single T Cell Epitopes," *J. Immunol. 156*(7):2369–2375 (1996).

Clavel et al., "Isolation of a New Human Retrovirus from West African Patients with AIDS," *Science 233:*343–346 (1986).

Clavel et al., "Molecular Cloning and Polymorphism of the Human Immune Deficiency Virus Type 2," *Nature 324:*691–695 (1986).

Daar et al., "Transient High Levels of Viremia in Patients with Primary Human Immunodeficiency Virus Type 1 Infection," *N Engl J Med. 324*(14):961–964 (1991).

Davey et al., "Subcutaneous administration of interleukin–2 in human immunodeficiency virus type 1–infected persons," *J Infect Dis.* 175(4):781–789 (1997).

Davies J. G., et al., "Crystal structure of the ribonuclease H domain of HIV–1 reverse transcriptase," *Science* 252(5002):88–95 (1991).

Deminie et al., "Evaluation of Reverse Transcriptase and Protease Inhibitors in Two–drug Combinations Against Human Immunodeficiency Virus Replication," *Antimicrob Agents Chemother 40*(6):1346–1351 (1996).

Desai et al., "Molecular Cloning and Primary Nucleotide Sequence Analysis of a Distinct Human Immunodeficiency Virus Isolate Reveal Significant Divergence in its Genomic Sequence," *Proc. Natl. Acad. Sci. USA 83:*8380–8384 (1986).

Doe et al., "Induction of HIV–1 Envelope (gp120)–Specific Cytotoxic T Lymphocyte Responses in Mice by Recombinant CHO Cell–Derived gp120 is Enhanced by Enzymatic Removal of N–Linked Glycans," *Eur. J. Immunol. 24:*2369–2376 (1994).

Doe, B. and Walker, C.M. "HIV–1 p24 Gag–Specific Cytotoxic T–Lymphocyte Responses in Mice," *AIDS 10*(7):793–794 (1996).

Dyda F., et al., "Crystal Structure of the Catalytic Domain of HIV–1 Integrase: Similarity to Other Polynucleotidyl Transferases," *Science 266*(5193):1981–1986 (1994).

Earl et al., "Isolate–and Group–specific Immune Responses to the Envelope Protein of Human Immunodeficiency Virus Induced by a Live Recombinant Vaccinia Virus in Macaques," *AIDS Res Hum Retroviruses* 5(1):23–32 (1989).

Edelman, R., "Vaccine Adjuvants," *Rev Infect Dis. 2*(3):370–383 (1980).

Engelman, A. et al., "Structure–based Mutagenesis of the Catalytic Domain of Human Immunodeficiency Virus Type 1 Integrase," *Journal Of Virology 71*(5):3507–3514 (1997).

Esnouf et al., "Mechanism of Inhibition of HIV–1 Reverse Transcriptase by Nonnucleoside Inhibitors," *Structural Biology 2*(4)"303–308 (1995).

Evans et al., "An Engineered Poliovirus Chimaera Elicits Broadly Reactive Hiv–1 Neutralizing Antibodies," *Nature 339*(6223):385–388 (1989).

Faust et al., "Outpatient Biopsies of the Palatine Tonsil: Access to Lymphoid Tissue for Assessment of Human Immunodeficiency Virus RNA Titers," *Otolaryngol Head Neck Surg. 114*(4):593–598 (1996).

Fennie et al., "Model for Intracellular Folding of the Human Immunodeficiency Virus Type 1 gp120," *J Virol 63*(2):639–646 (1989).

Ferre et al., "Combination Therapies Against HIV–1 Infection:Exploring the Concept of Combining Antiretroviral Drug Treatments with HIV–1 Immune–Based Therapies in Asymptomatic Individuals," *AIDS Patient Care STDS 10*(6):357–361 (1996).

Fisher, et al., "Biologically diverse molecular variants within a single HIV–1 isolate," *Nature* 334:444–447 (1988).

Fox et al., "No Winners Against AIDS," *Bio/Technology 12*(2): 128 (1994).

Gamier, L. et al., "Particle Size Determinants in the Human Immunodeficiency Virus Type 1 Gag Protein," *J Virol 72*(6):4667–4677 (1998).

Goldgur, Y. et al., "Three New Structures of the Core Domain of HIV–1 Integrase: an Active Site That Binds Magnesium," *Proceedings Of the National Academy Of Sciences Of the United States Of America 95*(16):9150–9154 (1998).

Goudsmit et al., "Human Immunodeficiency Virus Type 1 Neutralization Epitope with Conserved Architecture Elicits Early Type–specific Antibodies in Experimentally Infected Chimpanzees," *Proc. Natl. Acad. Sci. USA 85:*4478–4482 (1988).

Greene, "AIDS and the Immune System," *Scientific American* Sep.:99–105 (1993).

Griffiths J.C. et al., "Hybrid Human Immunodeficiency Virus Gag Particles as an Antigen Carrier System: Induction of Cytotoxic T–cell and Humoral Responses by a Gag:V3 Fusion," *J. Virol. 67*(6):3191–3198 (1993).
Grimison B. and Laurence, J., "Immunodominant Epitope Regions of HIV–1 Reverse Transcriptase: Correlations with HIV–1+ Serum IgG Inhibitor to Polymerase Activity and With Disease Progression," *Journal Of Acquired Immune Deficiency Syndromes and Human Retrovirology 9*(1):58–68 (1995).
Gurgo et al., "Envelope Sequences of Two New United States HIV–1 Isolates," *Virology 164:*531–536 (1988).
Gurunathan et al., "CD40 Ligand/Trimer DNA Enhances Both Humoral and Cellular Immune Responses and Induces Protective Immunity to Infectious and Tumor Challenge," *J Immunol. 161*(9):4563–4571 (1998).
Guyader et al., "Genome Organization and Transactivation of the Human Immunodeficiency Virus Type 2," *Nature 326:*662–669 (1987).
Hagensee et al., "Three–dimensional Structure of Vaccinia Virus–produced Human Papillomavirus Type 1 Capsids," *J. Virol. 68:*4503–4505 (1994).
Hahn et al., "Genetic Variation in HTLV–III/LAV Over Time in Patients with AIDS or at Risk for AIDS," *Science 232:*1548–1553 (1986).
Hammer et al., "Issues in Combination Antiretroviral Therapy: A Review," *J Acquir Immune Defic Syndr 7*(Suppl 2):S24–S37 (1994).
Haynes et al., "Update on the Issues of Hiv Vaccine Development," *Ann Med. 28*(1):39–41 (1996).
Haynes et al., "Toward an Understanding of the Correlates of Protective Immunity to Hiv Infection" *Science 271:*324–328 (1996).
Heeney et al., "Beta–chemokines and Neutralizing Antibody Titers Correlate with Sterilizing Immunity Generated in HIV–1 Vaccinated Macaques," *Proc Natl Acad Sci USA 95*(18):10803–10808 (1998).
Hickman, A. B., et al., "Biophysical and enzymatic properties of the catalytic domain of HIV–1 integrase," *Journal Of Biological Chemistry* 269(46):29279–29287 (1994).
Ho et al., "Human Immunodeficiency Virus Neutralizing Antibodies Recognize Several Conserved Domains on the Envelope Glycoproteins," *J Virol. 61*(6):2024–2028 (1987).
Jacobo–Molina, A. et al., "Crystal Structure of Human Immunodeficiency Virus Type 1 Reverse Transcriptase Complexed with Double–stranded DNA at 3.0 A Resolution Shows Bent DNA," *Proceedings Of the National Academy Of Sciences Of the United States Of America 90*(13):6320–6324 (1993).
Katz, R. A. and Skalka, A. M., "The Retroviral Enzymes," *Annual Review Of Biochemistry 63:*133–73 (1994).
Keefer, et al., "Safety and Immunogenicity of Env 2–3, a Human Immunodeficiency Virus Type 1 Candidate Vaccine, in Combination with a Novel Adjuvant, MTP–PE/MF59, NIAID AIDS Vaccine Evaluation Group," *AIDS Res Hum Retroviruses. 12*(8):683–693 (1996).
Kirnbauer et al., "Efficient Self–assembly of Human Papillomavirus Type 16 L1 and L1–L2 into Virus–Like Particles," *J. Virol. 67:*6929–6936 (1993).
Klenerman, et al., "Original Antigenic Sin Impairs Cytotoxic T Lymphocyte Responses to Viruses Bearing Variant Epitopes," *Nature 394*(6692):482–485 (1998).
Koff et al., "Development and Testing of AIDS Vaccines," *Science 241:*426–432 (1988).
Koff and Schultz, "Progress and Challenges Toward and AIDS Vaccine: Brother, Can You Spara a Paradigm?" *J. Clinical Immunology 16*(3):127–133 (1996).
Kohl et al., "Active Human Immunodeficiency Virus Protease Is Required for Viral Infectivity," *PNAS USA 85:*4886–4690 (1988).
Kohlstaedt, L. A. et al., "Crystal Structure at 3.5 A Resolution of HIV–1 Reverse Transcriptase Complexed with an Inhibitor," *Science 256*(5065):1783–1790 (1992).
Koup et al., "Temporal Association of Cellular Immune Responses with the Initial Control of Viremia in Primary Human Immunodeficiency Virus Type 1 Syndrome," *J Virol. 68*(7):4650–4655 (1994).
Kovacs et al., "Increases in CD4 T Lymphocytes with Intermittent Courses of Interleukin–2 in Patients with Human Immunodeficiency Virus Infection," *New England J. Med. 332*(9):567–575 (1995).
Kovacs et al., "Controlled Trial of Interleukin–2 Infusions in Patients Infected with the Human Immunodeficiency Virus," *N Engl J Med. 335*(18):1350–1356 (1996).
Krausslich et al., "Processing of in Vitro–synthesized Gag Precursor Proteins of Human Immunodeficiency Virus (HIV) Type 1 by HIV Proteinase Generated in *Escherichia coli,*" *J. Virol. 62:*4393–4397 (1988).
Kreuter J., et al., "Mode of Action of Immunological Adjuvants: Some Physicochemical Factors Influencing the Effectivity of Polyacrylic Adjuvants," *Infect Immun. 19*(2):667–675 (1978).
Krug, M. S. and Berger, S. L., "Reverse Transcriptase from Human Immunodeficiency Virus: a Single Templete–primer Binding Site Serves Two Physically Separable Catalytic Funcitons," *Biochemistry 30*(44):10614–10623 (1991).
Lalvani A. et al., "Rapid effector Function in CD8+ Memory T Cells," *J. Exp. Med. 186:*859–865 (1997).
Lasky et al., "Delineation of a Region of the Human Immunodeficiency Virus Type 1 gp120 Glycoprotein Critical for Interaction with the CD4 Receptor," *Cell 50*(6):975–985 (1987).
Levy et al., "Isolation of Lymphocytopathic Retroviruses from San Francisco Patients with AIDS," *Science 225:*840–842 (1984).
Littman et al., "Unusual Intron in the Immunoglobulin Domain of the Newly Isolated Murine CD4 (L3T4) Gene," *Nature 325*(6103):453–455 (1987).
Looney et al., "Type–restricted Neutralization of Molecular Clones of Human Immunodeficiency Virus," *Science* 241:357–359 (1988).
Maddon et al., "The Isolation and Nucleotide Sequence of a Cdna Encoding the T Cell Surface Protein T4: a New Member of the Immunoglobulin Gene Family," *Cell 42*(1):93–104 (1985).
Maignan, S., et al. "Crystal Structures of the Catalytic Domain of HIV–1 Integrase Free and Complexed with its Metal Cofactor: High Level of Similarity of the Active Site with Other Viral Integrases," *Journal Of Molecular Biology 282*(2):359–368 (1998).
Manca et al., "Antigenicity of Hiv–derived T Helper Determinants in the Context of Carrier Recombinant Proteins: Effect on T Helper Cell Repertoire Selection," *Eur. J Immunol. 26*(10):2461–2469 (1996).
Mazumder, A., et al., "Effects of nucleotide analogues on human immunodeficiency virus type 1 integrase," *Molecular Pharmacology* 49(4):621–628 (1996).

Mazza et al., "Recombinant Interleukin–2 (Ril–2) in Acquired Immune Deficiency Syndrome (Aids): Preliminary Report in Patients with Lymphoma Associated with Hiv Infection," *Eur J Haematol. 49*(1):1–6 (1992).
Mcheyzer–Williams, M.G. et al, "Enumeration and Characterization of Memory Cells in the Th Compartment," *Immunol. Rev. 150:*5–21 (1996).
McCluskie, et al., "Route and method of delivery of DNA vaccine influence immune responses in mice and non–human primates," *Mol Med.* 5(5):287–300 (1999).
McCornack et al., "HIV Protease Substrate Conformation: Modulation by Cyclophilin A," *FEBS Letts 414:*84–88 (1997).
McMichael, A.J. and O'Callaghan, C.A., "A New Look at T Cells," *J. Exp. Med. 187*(9)1367–1371 (1998).
Modrow et al., "Computer–assisted Analysis of Envelope Protein Sequences of Seven Human Immunodeficiency Virus Isolates: Prediction of Antigenic Epitopes in Conserved and Variable Regions," *J. Virol. 61*(2):570–578 (1987).
Montagnier et al., "Human T–Cell Leukemia Viruses: The Family of Human T–Lymphotropic Retroviruses: Their Role in Malignancies and Association with AIDS," *Gallo, Essex & Gross, eds.,* pp. 363–379 (1984).
Myers et al., "Human Retroviruses and AIDS," published by the Los Alamos National Laboratory, Los Alamos, NM, 1991, pp. I–A–48 to I–A–56 and II–77 to II–88.
Nathanson et al., "Biological Considerations in the Development of a Human Immunodeficiency Virus Vaccine," *J Infect Dis. 182*(2):579–589 (2000).
Novitsky et al., "Molecular Cloning and Phylogenetic Analysis of Human Immunodeficiency Virus Type 1 Subtype C: a Set of 23 Full–Length Clones from Botswana," *J. Virol. 73*(5):4427–4432 (1999).
Nowak and Bangham, "Population Dynamics of Immune Responses to Persistent Viruses," *Science 272*(5258):74–79 (1996).
Odile et al., "Anti–HIV Active Immunization, Evidence for Persistent Cell Mediated Immunity after a 2 Year Follow Up," Eighth International Conference on AIDS/III STD World Congress Amsterdam, The Netherlands Jul. 19–24, 1992, Abstract No. MOB 0024.
Okuda et al., "Induction of Potent Humoral and Cell–mediated Immune Responses Following Direct Injection of DNA Encoding the HIV Type 1 Env and Rev gene Products," *AIDS Res Hum Retroviruses.* 11(8):933–943 (1995).
Palaniappan, C. et al., "Mutations Within the Primer Grip Region of HIV–1 Reverse Transcriptase Result in Loss of RNase H Fucntion," *Journal of Biological Chemistry 272*(17):11157–11164 (1997).
Park et al., "Overexpression of The Gag–pol Precursor From Human Immunodeficiency Virus Type 1 Proviral Genomes Results in Efficient Proteolytic Processing in the Absence of Virion Production," *J. Virol. 65*5111 (1991).
Patel et al., "Insights into DNA Polymerization Mechanisms from Structure and Function Analysis of HIV–1 Reverse Transcriptase," *Biochemistry 34:*34:5351–5363 (1995).
Perelson, et al., "Decay Characteristics of Hiv–1–infected Compartments During Combination Therapy," *Nature 387*(6629):188–191 (1997).
Popovic et al., "Detection, Isolation, and Continuous Production of Cytopathic Retroviruses (HTLV–III) from Patients with AIDS and Pre–AIDS," *Science 224:*497–500 (1984).
Pyle et al., "Immune Response to Immunostimulatory Complexes (ISCOMs) Prepared from Human Immunodeficiency Virus Type 1 (HIV–1) or the HIV–1 External Envelope Glycoprotein (gp120)," *Vaccine 7*(5):465–473 (1989).
Redfield and Birx, "Hiv–specific Vaccine Therapy: Concepts, Status, and Future Directions," *AIDS Res Human Retroviruses 8*(6):1051–1058 (1992).
Reicin, A.S. et al., "Linker Insertion Mutations in the Human Immunodeficiency Virus Type 1 Gag Gene: Effects on Virion Particle Assembly, Release, and Infectivity," *J. Virol. 69*(2):642–650 (1995).
Robey, et al., "Prospect for Prevention of Human Immunodeficiency Virus Infection: Purified 120–kDa Envelope Glycoprotein Induces Neutralizing Antibody," *Proc Natl Acad Sci USA 83*(18):7023–7027 (1986).
Rodgers, D. W. et al., "The Structure of Unliganded Reverse Transcriptase from the Human Immunodeficiency Virus Type 1," *Proceedings Of the National Academy Of Sciences Of the United States Of America 92*(4):1222–1226 (1995).
Saag, et al., "Extensive Variation of Human Immunodeficiency Virus Type–1 in vivo," *Nature 334:*440–444 (1988).
Saag and Kuritzkes, "Strategies for Continuing Antiretroviral Therapy," *Int AIDS Society USA 4*(2):16–19 (1996).
Salk et al., "Prospects for the Control of Aids by Immunizing Seropositive Individuals," *Nature 327*(6122):473–476 (1987).
Schernthaner, et al., "Endosperm–specific Activity of a Zein Gene Promoter in Transgenic Tobacco Plants," *The EMBO J.* 71249–1259 (1988).
Schulhafer et al., "Acquired Immunodeficiency Syndrome: Molecular Biology and its Therapeutic Intervention (review)," *In Vivo 3*(2):61–78 (1989).
Sheng N. and Dennis, D., "Active Site Labeling of HIV–1 Reverse Transcriptase," *Biochemistry 32*(18):4938–4942 (1993).
Smith et al., "Blocking of HIV–1 infectivity by a soluble, secreted form of the CD4 antigen," *Science* 238(4834):1704–1707 (1987).
Spence R. A., et al., "Mechanisms of Inhibition of HIV–1 Reverse Transcriptase by Nonnucleoside Inhibitors," *Science 267*(5200):988–993 (1995).
Srinivasan et al., "Molecular Characterization of Human Immunodeficiency Virus from Zaire: Nucleotide Sequence Analysis Identifies Conserved and Variable Domains in the Envelope Gene," *Gene 52:*71–82 (1987).
Starcich et al., "Identification and Characterization of Conserved and Variable Regions in the Envelope Gene of HTLV–III/LAV, the Retrovirus of AIDS," *Cell 45:*637–648 (1986).
Steimer et al., "Genetically Engineered Human Immunodeficiency Envelope Glycoprotein Gp120 Produced in Yeast Is the Target of Neutralizing Antibodies," *Vaccines 87:*236–241 (1987).
Sternberg et al., "Prediction of Antigenic Determinants and Secondary Structures of the Major Aids Virus Proteins," *FEBS Letters 218*(2):231–237 (1987).
Tindle et al., "Chimeric Hepatitis B Core Antigen Particles Containing B– and Th–epitopes of Human Papillomavirus Type 16 E7 Protein Induce Specific Antibody and T–helper Responses in Immunised Mice," *Virology 200:*547–557 (1994).
Vacca et al., "L–735,524: an Orally Bioavailable Human Immunodeficiency Virus Type 1 Protease Inhibitor," *Proc Natl Acad Sci USA 91*(9):4096–4100 (1994).

Verma et al., "Gene therapy—Promises, Problems and Prospects," *Nature 389*(6648):239–242 (1997).
Vilmer et al., "Isolation of New Lymphotropic Retrovirus from Two Siblings with *Haemophilia B,* One with AIDS," *The Lancet 1:*753 (1984).
Wagner R., et al., "Studies on Processing, Particle Formation, and Immunogenicity of the HIV–1 gag Gene Product: a Possible Component of a HIV Vaccine," *Arch Virol. 127:*117–137 (1992).
Wagner et al., "Assembly and Extracellular Release of Chimeric HIV–1 PR55gag Retrovirus–like Particles," *Virology 200:*162–175 (1994).
Wagner et al., "Construction, Expression, and Immunogenicity of Chimeric HIV–1 Virus–like Particles," *Virology 220:*128–140 (1996).
Wakefield, J. K.et al., "In Vitro Enzymatic Activity of Human Immunodeficiency Virus Type 1 Reverse Transcriptase Mutants in the Highly Conserved YMDD Amino Acid Motif Correlates with the Infectious Potential of the Proviral Genome," *Journal Of Virology 66*(11):6806–6812 (1992).
Wan et al., "Autoprocessing: an Essential Step for the Activation of HIV–1 Protease," *Biochem. J. 316:*569–573 (1996).
Wang et al., "Induction of Humoral and Cellular Immune Responses to the Human Immuno–deficiency Type 1 Virus in Nonhuman Primates by in Vivo DNA Inoculation," *Virology 211*(1):102–112 (1995).
Wang C. et al., "Analysis of Minimal Human Immunodeficiency Virus Type 1 Gag Coding Sequences Capable of Virus–like Particle Assembly and Release," *J Virol 72*(10):7950–7959 (1998).
Wu X., et al., "Targeting foreign proteins to human immunodeficiency virus particles via fusion with Vpr and Vpx," *J. Virol.* 69(6):3389–3398 (1995).
Yeni et al., "Antiretroviral and Immune–based Therapies: Update," *AIDS 7*(Suppl 1):S173–S184 (1993).
Yenofsky et al., "A Mutant Neomycin Phosphotransferase II Gene Reduces the Resistance of Transformants to Antibiotic Selection Pressure," *Proc. Natl. Acad. Sci. USA 87:*3435–3439 (1990).
Yourno et al., "Nucleotide Sequence Analysis of the Env Gene of a New Zairian Isolate of HIV–1," *AIDS Res Hum Retroviruses* 4(3):165–73 (1988).
Zagury et al., "Progress Report IV on Aids Vaccine in Human: Phase I Clinical Trial in Hiv Infected Patients," *VII International Conference on AIDS,* Florence Jun. 16–21, 1991, Abstract No. M.A. 67.
Zagury et al., "One–year Follow–up of Vaccine Therapy in Hiv–infected Immune–deficient Indivuduals: a New Strategy," *J. Acquired Immune Deficiency Syndromes 5:*676–681 (1992).
Zhang Y., et al., "Analysis of the Assembly Function of the Human Immunodeficiency Virus Type 1 Gag Protein Nucleocapsid Domain," *J Virol 72*(3):1782–1789 (1998).
zur Megede et al., "Increased Expression and Immunogenicity of Sequence–modified Human Immunodeficiency Virus Type 1 Gag Gene," *J Virol. 74*(6):2628–2635 (2000).

* cited by examiner gp120 core structure

```
                 1                               •                  50
HXB2       (1)   MRVK---EKYQHLWRWGWRWGTMLLGMLMIC-SATEKLWVTVYYGVPVWK
162        (1)   ----------MDAMKRGLCCVLLLCGAVFVSPSAVEKLWVTVYYGVPVWK
SF2        (1)   MKVKGTRRNYQHLWRWG----TLLLGMLMIC-SATEKLWVTVYYGVPVWK
CM236      (1)   MRVKETQMNWPNLWKWG----TLILGLVIIC-SASNNLWVTVYYGVPVWR
US4        (1)   --MR---KHCQHLWRGG----ILLLGILMIC-RATTVLWVTVYYGVPVWK
Consensus  (1)   MRVK     YQHLWRWG    TLLLGMLMIC SATEKLWVTVYYGVPVWK

                 51    •                   •                       100
HXB2       (47)  EATTTLFCASDAKAYDTEVHNVWATHACVPTDPNPQEVVLVNVTENFNMW
162        (41)  EATTTLFCASDAKAYDTEVHNVWATHACVPTDPNPQEIVLENVTENFNMW
SF2        (46)  EATTTLFCASDAKAYDTEVHNVWATHACVPTDPNPQEVVLGNVTENFNMW
CM236      (46)  DADTTLFCASDAKAHETEVHNVWATHACVPTDPNPQEIHLENVTENFNMW
US4        (41)  EATTTLFCASDAKAYKAEAHNVWATHACVPTDPNPQEVNLTNVTENFNMW
Consensus  (51)  EATTTLFCASDAKAYDTEVHNVWATHACVPTDPNPQEVVL NVTENFNMW

                 101                    •↓     •    •              150
HXB2       (97)  KNDMVEQMHEDIISLWDQSLKPCVKLTPLCVSLKCTDL------------
162        (91)  KNNMVEQMHEDIISLWDQSLKPCVKLTPLCVTLHCTNL------------
SF2        (96)  KNNMVEQMQEDIISLWDQSLKPCVKLTPLCVTLNCTDL------------
CM236      (96)  KNNMVEQMQEDVISLWDQSLKPCVKLTPLCVTLNCTNAK-----------
US4        (91)  KNNMVEQMHEDIISLWDQSLKPCVKLTPLCVTLNCTDKLTGSTNGTNSTS
Consensus  (101) KNNMVEQMHEDIISLWDQSLKPCVKLTPLCVTLNCTDL

                 151                           •                   200
HXB2       (135) -------KNDTNTNSSSGRMIMEKGEIKNCSFNISTSIRGKVQKEYAFFY
162        (129) -------KNATNTKSSNWKEMD-RGEIKNCSFKVTTSIRNKMQKEYALFY
SF2        (134) -------GKATNTNSSNWKEEI-KGEIKNCSFNITTSIRDKIQKENALFR
CM236      (135) ------LTNVNNITSVSNTIGNITDEVRNCSFNMTTELRDKKQKVHALFY
US4        (141) GTNSTSGTNSTSTNSTDSWEKMPEGEIKNCSFNITTSVRDKVQKEYSLFY
Consensus  (151)        NATNTNSS  KE M KGEIKNCSFNITTSIRDKVQKEYALFY

                 201                     •        ↓•          •    250
HXB2       (178) KLDIIPIDNDTTS-----YKLTSCNTSVITQACPKVSFEPIPIHYCAPAG
162        (171) KLDVVPIDNDNTS-----YKLINCNTSVITQACPKVSFEPIPIHYCAPAG
SF2        (176) NLDVVPIDNASTTTNYTNYRLIHCNRSVITQACPKVSFEPIPIHYCTPAG
CM236      (179) KLDIVPIEDNKTS---SEYRLINCNTSVIKQACPKISFDPIPIHYCTPAG
US4        (191) KLDVVPIDNDNAS-----YRLINCNTSVITQACPKVSFEPIPIHYCAPAG
Consensus  (201) KLDVVPIDND TS     YRLINCNTSVITQACPKVSFEPIPIHYCAPAG

                 251 •        •      •                             300
HXB2       (223) FAILKCNNKTFNGTGPCTNVSTVQCTHGIRPVVSTQLLLNGSLAEEEVVI
162        (216) FAILKCNDKKFNGSGPCTNVSTVQCTHGIRPVVSTQLLLNGSLAEEGVVI
SF2        (226) FAILKCNNKTFNGKGPCTNVSTVQCTHGIRPIVSTQLLLNGSLAEEEVVI
CM236      (226) YAILKCNDKNFNGTGPCKNVSSVQCTHGIKPVVSTQLLLNGSLAEEEIII
US4        (236) FAILKCKDKKFNGTGPCKNVSTVQCTHGIRPVVSTQLLLNGSLAEEEIVL
Consensus  (251) FAILKCNDK FNGTGPCTNVSTVQCTHGIRPVVSTQLLLNGSLAEEEVVI

                 301                     •                         350
HXB2       (273) RSVNFTDNAKTIIVQLNTSVEINCTRPNNNTRKRIRIQRGPGRAFVTIGK
162        (266) RSENFTDNAKTIIVQLKESVEINCTRPNNNTRKSITI--GPGRAFYATGD
SF2        (276) RSDNFTNNAKTIIVQLNESVAINCTRPNNNTRKSIYI--GPGRAFHTTGR
CM236      (276) RSENLTNNAKTIIVHLNKSVEINCTRPSNNTRTSITI--GPGQVFYRTGD
US4        (286) RSENFTDNAKTIIVQLNESVEINCIRPNNNTRKSIHI--GPGRAFYATGD
Consensus  (301) RSENFTDNAKTIIVQLNESVEINCTRPNNNTRKSI I  GPGRAFY TGD
```

*FIG. 2A*

| | | 351 • 400 |
|---|---|---|
| HXB2 | (323) | I-GNMRQAHCNISRAKWNNTLKQIASKLREQFGNNKTIIFKQSSGGDPEI |
| 162 | (314) | IIGDIRQAHCNISGEKWNNTLKQIVTKLQAQFG-NKTIVFKQSSGGDPEI |
| SF2 | (324) | IIGDIRKAHCNISRAQWNNTLEQIVKKLREQFGNNKTIVFNQSSGGDPEI |
| CM236 | (324) | IIGDIRKAYCEINGTKWNEVLTQVTEKLKEHFN-NKTIIFQPPSGGDLEI |
| US4 | (334) | IIGDIRQAHCNISKANWTNTLEQIVEKLREQFGNNKTIIFNSSSGGDPEI |
| Consensus | (351) | IIGDIRQAHCNISRAKWNNTL QIV KLREQFGNNKTIIFNQSSGGDPEI |

| | | 401 • • •450 |
|---|---|---|
| HXB2 | (372) | VTHSFNCGGEFFYCNSTQLFNSTWFNSTWSTEGSNNTEGSDTITLPCRIK |
| 162 | (363) | VMHSFNCGGEFFYCNSTQLFNSTW-NN---TIGPNNTNG--TITLPCRIK |
| SF2 | (374) | VMHSFNCRGEFFYCNTTQLFNNTWRLN--HTEG---TKGNDTIILPCRIK |
| CM236 | (373) | TMHHFNCRGEFFYCNTTRLFNNTCIEN--GTMG--GCNG--TIILPCKIK |
| US4 | (384) | VFHSFNCGGEFFYCNTSQLFNSTW--N--ITEEVNKTKENDTIILPCRIR |
| Consensus | (401) | VMHSFNCGGEFFYCNTTQLFNSTW N TEG N T G DTIILPCRIK |

↓

| | | 451 ↓ • 500 |
|---|---|---|
| HXB2 | (422) | QIINMWQKVGKAMYAPPISGQIRCSSNITGLLLTRDGG---NSNNESEIF |
| 162 | (407) | QIINRWQEVGKAMYAPPIRGQIRCSSNITGLLLTRDGGK--EISNTTEIF |
| SF2 | (419) | QIINMWQEVGKAMYAPPIGGQISCSSNITGLLLTRDGGT--NVTNDTEVF |
| CM236 | (417) | QIINMWQGAGQAMYAPPISGRINCVSNITGILLTRDGG---AINTTNETF |
| US4 | (430) | QIINMWQEVGKAMYAPPIRGQIKCSSNITGLLLTRDGGTNNNRTNDTETF |
| Consensus | (451) | QIINMWQEVGKAMYAPPI GQIRCSSNITGLLLTRDGG NITNDTEIF |

| | | 501 * 550 |
|---|---|---|
| HXB2 | (469) | RPGGGDMRDNWRSELYKYKVVKIEPLGVAPTKAKRRVVQREKRAVGI-GA |
| 162 | (455) | RPGGGDMRDNWRSELYKYKVVKIEPLGVAPTKAKRRVVQREKRAVTL-GA |
| SF2 | (467) | RPGGGDMRDNWRSELYKYKVVTKIEPLGIAPTKAKRRVVQREKRAVGIVGA |
| CM236 | (464) | RPGGGNIKDNWRSELYKYKVVQIEPLGIAPTRAKRRVVEREKRAVGI-GA |
| US4 | (480) | RPGGGNMKDNWRSELYKYKVVRIEPLGVAPTQAKRRVVQREKRAVGL-GA |
| Consensus | (501) | RPGGGDMRDNWRSELYKYKVVKIEPLGVAPTKAKRRVVQREKRAVGI GA |

| | | 551 600 |
|---|---|---|
| HXB2 | (518) | LFLGFLGAAGSTMGAASMTLTVQARQLLSGIVQQQNNLLRAIEAQQHLLQ |
| 162 | (504) | MFLGFLGAAGSTMGARSLTLTVQARQLLSGIVQQQNNLLRAIEAQQHLLQ |
| SF2 | (517) | MFLGFLGAAGSTMGAVSLTLTVQARQLLSGIVQQQNNLLRAIEAQQHLLQ |
| CM236 | (513) | MIFGFLGAAGSTMGAASITLTVQARQLLSGIVQQQSNLLRAIEAQQHLLQ |
| US4 | (529) | LFIGFLGAAGSTMGAASVTLTVQARQLLSGIVQQQNNLLRAIEAQQHLLQ |
| Consensus | (551) | MFLGFLGAAGSTMGAASLTLTVQARQLLSGIVQQQNNLLRAIEAQQHLLQ |

| | | 601 • • 650 |
|---|---|---|
| HXB2 | (568) | LTVWGIKQLQARILAVERYLKDQQLLGIWGCSGKLICTTAVPWNASWSNK |
| 162 | (554) | LTVWGIKQLQARVLAVERYLKDQQLLGIWGCSGKLICTTAVPWNASWSNK |
| SF2 | (567) | LTVWGIKQLQARVLAVERYLRDQQLLGIWGCSGKLICTTAVPWNASWSNK |
| CM236 | (563) | LTVWGIKQLQARVLAVERYLKDQKFLGLWGCSGKIICTTAVPWNSTWSNR |
| US4 | (579) | LTVWGIKQLQARILAVERYLKDQQLLGIWGCSGKLICTTTVPWNSSWSNK |
| Consensus | (601) | LTVWGIKQLQARVLAVERYLKDQQLLGIWGCSGKLICTTAVPWNASWSNK |

*FIG. 2B*

```
                 651                                              700
     HXB2  (618) SLEQIWNHTTWMEWDREINNYTSLIHSLIEESQNQQEKNEQELLELDKWA
      162  (604) SLDQIWNNMTWMEWEREIDNYTNLIYTLIEESQNQQEKNEQELLELDKWA
      SF2  (617) SLEDIWDNMTWMQWEREIDNYTNTIYTLLEESQNQQEKNEQELLELDKWA
    CM236  (613) SYEEIWNNMTWIEWEREISNYTNQIYEILTESQNQQDRNEKDLLELDKWA
      US4  (629) SLTEIWDNMTWMEWEREIGNYTGLIYNLIEIAQNQQEKNEQELLELDKWA
Consensus  (651) SLEEIWNNMTWMEWEREI NYTNLIYTLIEESQNQQEKNEQELLELDKWA

                 701                                              750
     HXB2  (668) SLWNWFNITNWLWYIKLFIMIVGGLVGLRIVFAVLSIVNRVRQGYSPLSF
      162  (654) SLWNWFDISKWLWYIKIFIMIVGGLVGLRIVFTVLSIVNRVRQGYSPLSF
      SF2  (667) SLWNWFSITNWLWYIKIFIMIVGGLVGLRIVFAVLSIVNRVRQGYSPLSF
    CM236  (663) SLWNWFDITKWLWYIKIFIMIIGGLIGLRIIFAVLSIVNRVRQGYSPLSF
      US4  (679) SLWNWFDITNWLWYIRIFIMIVGGLIGLRIVFAVLSIVNRVRQGYSPISL
Consensus  (701) SLWNWFDITNWLWYIKIFIMIVGGLVGLRIVFAVLSIVNRVRQGYSPLSF

                 751                                             •800
     HXB2  (718) QTHLPTPRGPDRPEGIEEEGGERDRDRSIRLVNGSLALIWDDLRSLCLFS
      162  (704) QTRFPAPRGPDRPEGIEEEGGERDRDRSSPLVHGLLALIWDDLRSLCLFS
      SF2  (717) QTRLPVPRGPDRPDGIEEEGGERDRDRSVRLVDGFLALIWEDLRSLCLFS
    CM236  (713) QTPFHHQREPDRSERIEEGGGEQGRDRSVRLVSGFLALAWDDLRSLCLFS
      US4  (729) QTRLPAQRGPDRPEGIEEEGGERDRDRSNRLVHGLLALIWDDLRSLCLFS
Consensus  (751) QTRLP PRGPDRPEGIEEEGGERDRDRSVRLV G LALIWDDLRSLCLFS

                 801                                              850
     HXB2  (768) YHRLRDLLLIVTRIVELLGR-------RGWEALKYWWNLLQYWSQELKNS
      162  (754) YHRLRDLLLIAARIVELLGR-------RGWEALKYWGNLLQYWIQELKNS
      SF2  (767) YRRLRDLLLIAARTVEILGH-------RGWEALKYWWSLLQYWIQELKNS
    CM236  (763) YHRLRDFLLIAARTVKLLGRSSLKGLRRGWEGLKYLGNLLLYWGQELKIS
      US4  (779) YHRLRDLLLIVARIVELLGR-------RGWEALKYWWNLLQYWSQELKSS
Consensus  (801) YHRLRDLLLIAARIVELLGR       RGWEALKYWWNLLQYW QELKNS

                 851                                              900
     HXB2  (811) AVSLLNATAIAVAEGTDRVIEVVQGACRAIRHIPRRIRQGLERILL----
      162  (797) AVSLFDAIAIAVAEGTDRIIEVAQRIGRAFLHIPRRIRQGFERALL----
      SF2  (810) AVSWLNATAIAVTEGTDRVIEVAQRAYRAILHIHRRIRQGLERLLL----
    CM236  (813) AISLLDATAIIVAGWTDRVIEVAQGAWRAILHIPRRIRQGLERTLL----
      US4  (822) AVSLFNATAIAVAEGTDRIIEIVQRIFRAVIHIPRRIRQGLERALL----
Consensus  (851) AVSLLNATAIAVAEGTDRVIEVAQRAFRAILHIPRRIRQGLER LL
```

*FIG. 2C*

| | | |
|---|---|---|
| | | 1 40 |
| Leu122-Ser199 | (1) | GAATTCGCCACCATGGATGCAATGAAGAGAGGGCTCTGCT |
| Val127-Asn195 | (1) | GAATTCGCCACCATGGATGCAATGAAGAGAGGGCTCTGCT |
| Val120-Ile201B | (1) | GAATTCGCCACCATGGATGCAATGAAGAGAGGGCTCTGCT |
| Val120-Ala204 | (1) | GAATTCGCCACCATGGATGCAATGAAGAGAGGGCTCTGCT |
| Val120-Ile201 | (1) | GAATTCGCCACCATGGATGCAATGAAGAGAGGGCTCTGCT |
| Val120-Thr202 | (1) | GAATTCGCCACCATGGATGCAATGAAGAGAGGGCTCTGCT |
| Lys121-Val200 | (1) | GAATTCGCCACCATGGATGCAATGAAGAGAGGGCTCTGCT |
| Consensus | (1) | GAATTCGCCACCATGGATGCAATGAAGAGAGGGCTCTGCT |
| | | 41 80 |
| Leu122-Ser199 | (41) | GTGTGCTGCTGCTGTGTGGAGCAGTCTTCGTTTCGCCCAG |
| Val127-Asn195 | (41) | GTGTGCTGCTGCTGTGTGGAGCAGTCTTCGTTTCGCCCAG |
| Val120-Ile201B | (41) | GTGTGCTGCTGCTGTGTGGAGCAGTCTTCGTTTCGCCCAG |
| Val120-Ala204 | (41) | GTGTGCTGCTGCTGTGTGGAGCAGTCTTCGTTTCGCCCAG |
| Val120-Ile201 | (41) | GTGTGCTGCTGCTGTGTGGAGCAGTCTTCGTTTCGCCCAG |
| Val120-Thr202 | (41) | GTGTGCTGCTGCTGTGTGGAGCAGTCTTCGTTTCGCCCAG |
| Lys121-Val200 | (41) | GTGTGCTGCTGCTGTGTGGAGCAGTCTTCGTTTCGCCCAG |
| Consensus | (41) | GTGTGCTGCTGCTGTGTGGAGCAGTCTTCGTTTCGCCCAG |
| | | 81 120 |
| Leu122-Ser199 | (81) | CGCCGTGGAGAAGCTGTGGGTGACCGTGTACTACGGCGTG |
| Val127-Asn195 | (81) | CGCCGTGGAGAAGCTGTGGGTGACCGTGTACTACGGCGTG |
| Val120-Ile201B | (81) | CGCCGTGGAGAAGCTGTGGGTGACCGTGTACTACGGCGTG |
| Val120-Ala204 | (81) | CGCCGTGGAGAAGCTGTGGGTGACCGTGTACTACGGCGTG |
| Val120-Ile201 | (81) | CGCCGTGGAGAAGCTGTGGGTGACCGTGTACTACGGCGTG |
| Val120-Thr202 | (81) | CGCCGTGGAGAAGCTGTGGGTGACCGTGTACTACGGCGTG |
| Lys121-Val200 | (81) | CGCCGTGGAGAAGCTGTGGGTGACCGTGTACTACGGCGTG |
| Consensus | (81) | CGCCGTGGAGAAGCTGTGGGTGACCGTGTACTACGGCGTG |
| | | 121 160 |
| Leu122-Ser199 | (121) | CCCGTGTGGAAGGAGGCCACCACCACCCTGTTCTGCGCCA |
| Val127-Asn195 | (121) | CCCGTGTGGAAGGAGGCCACCACCACCCTGTTCTGCGCCA |
| Val120-Ile201B | (121) | CCCGTGTGGAAGGAGGCCACCACCACCCTGTTCTGCGCCA |
| Val120-Ala204 | (121) | CCCGTGTGGAAGGAGGCCACCACCACCCTGTTCTGCGCCA |
| Val120-Ile201 | (121) | CCCGTGTGGAAGGAGGCCACCACCACCCTGTTCTGCGCCA |
| Val120-Thr202 | (121) | CCCGTGTGGAAGGAGGCCACCACCACCCTGTTCTGCGCCA |
| Lys121-Val200 | (121) | CCCGTGTGGAAGGAGGCCACCACCACCCTGTTCTGCGCCA |
| Consensus | (121) | CCCGTGTGGAAGGAGGCCACCACCACCCTGTTCTGCGCCA |
| | | 161 200 |
| Leu122-Ser199 | (161) | GCGACGCCAAGGCCTACGACACCGAGGTGCACAACGTGTG |
| Val127-Asn195 | (161) | GCGACGCCAAGGCCTACGACACCGAGGTGCACAACGTGTG |
| Val120-Ile201B | (161) | GCGACGCCAAGGCCTACGACACCGAGGTGCACAACGTGTG |
| Val120-Ala204 | (161) | GCGACGCCAAGGCCTACGACACCGAGGTGCACAACGTGTG |
| Val120-Ile201 | (161) | GCGACGCCAAGGCCTACGACACCGAGGTGCACAACGTGTG |
| Val120-Thr202 | (161) | GCGACGCCAAGGCCTACGACACCGAGGTGCACAACGTGTG |
| Lys121-Val200 | (161) | GCGACGCCAAGGCCTACGACACCGAGGTGCACAACGTGTG |
| Consensus | (161) | GCGACGCCAAGGCCTACGACACCGAGGTGCACAACGTGTG |
| | | 201 240 |
| Leu122-Ser199 | (201) | GGCCACCCACGCCTGCGTGCCCACCGACCCCAACCCCCAG |
| Val127-Asn195 | (201) | GGCCACCCACGCCTGCGTGCCCACCGACCCCAACCCCCAG |
| Val120-Ile201B | (201) | GGCCACCCACGCCTGCGTGCCCACCGACCCCAACCCCCAG |
| Val120-Ala204 | (201) | GGCCACCCACGCCTGCGTGCCCACCGACCCCAACCCCCAG |
| Val120-Ile201 | (201) | GGCCACCCACGCCTGCGTGCCCACCGACCCCAACCCCCAG |
| Val120-Thr202 | (201) | GGCCACCCACGCCTGCGTGCCCACCGACCCCAACCCCCAG |
| Lys121-Val200 | (201) | GGCCACCCACGCCTGCGTGCCCACCGACCCCAACCCCCAG |
| Consensus | (201) | GGCCACCCACGCCTGCGTGCCCACCGACCCCAACCCCCAG |
| | | 241 280 |
| Leu122-Ser199 | (241) | GAGATCGTGCTGGAGAACGTGACCGAGAACTTCAACATGT |
| Val127-Asn195 | (241) | GAGATCGTGCTGGAGAACGTGACCGAGAACTTCAACATGT |

*FIG. 3A*

```
Val120-Ile201B   (241) GAGATCGTGCTGGAGAACGTGACCGAGAACTTCAACATGT
Val120-Ala204    (241) GAGATCGTGCTGGAGAACGTGACCGAGAACTTCAACATGT
Val120-Ile201    (241) GAGATCGTGCTGGAGAACGTGACCGAGAACTTCAACATGT
Val120-Thr202    (241) GAGATCGTGCTGGAGAACGTGACCGAGAACTTCAACATGT
Lys121-Val200    (241) GAGATCGTGCTGGAGAACGTGACCGAGAACTTCAACATGT
Consensus        (241) GAGATCGTGCTGGAGAACGTGACCGAGAACTTCAACATGT
                       281                                  320
Leu122-Ser199    (281) GGAAGAACAACATGGTGGAGCAGATGCACGAGGACATCAT
Val127-Asn195    (281) GGAAGAACAACATGGTGGAGCAGATGCACGAGGACATCAT
Val120-Ile201B   (281) GGAAGAACAACATGGTGGAGCAGATGCACGAGGACATCAT
Val120-Ala204    (281) GGAAGAACAACATGGTGGAGCAGATGCACGAGGACATCAT
Val120-Ile201    (281) GGAAGAACAACATGGTGGAGCAGATGCACGAGGACATCAT
Val120-Thr202    (281) GGAAGAACAACATGGTGGAGCAGATGCACGAGGACATCAT
Lys121-Val200    (281) GGAAGAACAACATGGTGGAGCAGATGCACGAGGACATCAT
Consensus        (281) GGAAGAACAACATGGTGGAGCAGATGCACGAGGACATCAT
                       321                                  360
Leu122-Ser199    (321) CAGCCTGTGGGACCAGAGCCTGAAGCCCTGCGTGAAGCTG
Val127-Asn195    (321) CAGCCTGTGGGACCAGAGCCTGAAGCCCTGCGTGAAGCTG
Val120-Ile201B   (321) CAGCCTGTGGGACCAGAGCCTGAAGCCCTGCGTGCC----
Val120-Ala204    (321) CAGCCTGTGGGACCAGAGCCTGAAGCCCTGCGTGGG----
Val120-Ile201    (321) CAGCCTGTGGGACCAGAGCCTGAAGCCCTGCGTGGG----
Val120-Thr202    (321) CAGCCTGTGGGACCAGAGCCTGAAGCCCTGCGTGGG----
Lys121-Val200    (321) CAGCCTGTGGGACCAGAGCCTGAAGCCCTGCGTGAAGG--
Consensus        (321) CAGCCTGTGGGACCAGAGCCTGAAGCCCTGCGTG
                       361                                  400
Leu122-Ser199    (361) -----------------GGCAA-------------CAGCG
Val127-Asn195    (361) ACCCCCCTGTGCGTGGGGGCAGGGAACTGCAACACCAGCG
Val120-Ile201B   (357) --------------------------------------CG
Val120-Ala204    (357) ----------------------------------------
Val120-Ile201    (357) --------------------------------------CG
Val120-Thr202    (357) --------------------------------------CG
Lys121-Val200    (359) ----------------------------C-----CCCCG
Consensus        (361)                                       CG
                       401                                  440
Leu122-Ser199    (371) TGATCACCCAGGCCTGCCCCAAGGTGAGCTTCGAGCCCAT
Val127-Asn195    (401) TGATCACCCAGGCCTGCCCCAAGGTGAGCTTCGAGCCCAT
Val120-Ile201B   (359) GCATCACCCAGGCCTGCCCCAAGGTGAGCTTCGAGCCCAT
Val120-Ala204    (357) ----CGCCGGCGCCTGCCCCAAGGTGAGCTTCGAGCCCAT
Val120-Ile201    (359) GCATCACCCAGGCCTGCCCCAAGGTGAGCTTCGAGCCCAT
Val120-Thr202    (359) GCGCCACCCAGGCCTGCCCCAAGGTGAGCTTCGAGCCCAT
Lys121-Val200    (365) TGATCACCCAGGCCTGCCCCAAGGTGAGCTTCGAGCCCAT
Consensus        (401)   ATCACCCAGGCCTGCCCCAAGGTGAGCTTCGAGCCCAT
                       441                                  480
Leu122-Ser199    (411) CCCCATCCACTACTGCGCCCCCGCCGGCTTCGCCATCCTG
Val127-Asn195    (441) CCCCATCCACTACTGCGCCCCCGCCGGCTTCGCCATCCTG
Val120-Ile201B   (399) CCCCATCCACTACTGCGCCCCCGCCGGCTTCGCCATCCTG
Val120-Ala204    (393) CCCCATCCACTACTGCGCCCCCGCCGGCTTCGCCATCCTG
Val120-Ile201    (399) CCCCATCCACTACTGCGCCCCCGCCGGCTTCGCCATCCTG
Val120-Thr202    (399) CCCCATCCACTACTGCGCCCCCGCCGGCTTCGCCATCCTG
Lys121-Val200    (405) CCCCATCCACTACTGCGCCCCCGCCGGCTTCGCCATCCTG
Consensus        (441) CCCCATCCACTACTGCGCCCCCGCCGGCTTCGCCATCCTG
                       481                                  520
Leu122-Ser199    (451) AAGTGCAACGACAAGAAGTTCAACGGCAGCGGCCCCTGCA
Val127-Asn195    (481) AAGTGCAACGACAAGAAGTTCAACGGCAGCGGCCCCTGCA
Val120-Ile201B   (439) AAGTGCAACGACAAGAAGTTCAACGGCAGCGGCCCCTGCA
Val120-Ala204    (433) AAGTGCAACGACAAGAAGTTCAACGGCAGCGGCCCCTGCA
Val120-Ile201    (439) AAGTGCAACGACAAGAAGTTCAACGGCAGCGGCCCCTGCA
```

*FIG. 3B*

```
 Val120-Thr202  (439) AAGTGCAACGACAAGAAGTTCAACGGCAGCGGCCCCTGCA
 Lys121-Val200  (445) AAGTGCAACGACAAGAAGTTCAACGGCAGCGGCCCCTGCA
     Consensus  (481) AAGTGCAACGACAAGAAGTTCAACGGCAGCGGCCCCTGCA
                      521                                   560
 Leu122-Ser199  (491) CCAACGTGAGCACCGTGCAGTGCACCCACGGCATCCGCCC
 Val127-Asn195  (521) CCAACGTGAGCACCGTGCAGTGCACCCACGGCATCCGCCC
Val120-Ile201B  (479) CCAACGTGAGCACCGTGCAGTGCACCCACGGCATCCGCCC
 Val120-Ala204  (473) CCAACGTGAGCACCGTGCAGTGCACCCACGGCATCCGCCC
 Val120-Ile201  (479) CCAACGTGAGCACCGTGCAGTGCACCCACGGCATCCGCCC
 Val120-Thr202  (479) CCAACGTGAGCACCGTGCAGTGCACCCACGGCATCCGCCC
 Lys121-Val200  (485) CCAACGTGAGCACCGTGCAGTGCACCCACGGCATGCGCCC
     Consensus  (521) CCAACGTGAGCACCGTGCAGTGCACCCACGGCATCCGCCC
                      561                                   600
 Leu122-Ser199  (531) CGTGGTGAGCACCCAGCTGCTGCTGAACGGCAGCCTGGCC
 Val127-Asn195  (561) CGTGGTGAGCACCCAGCTGCTGCTGAACGGCAGCCTGGCC
Val120-Ile201B  (519) CGTGGTGAGCACCCAGCTGCTGCTGAACGGCAGCCTGGCC
 Val120-Ala204  (513) CGTGGTGAGCACCCAGCTGCTGCTGAACGGCAGCCTGGCC
 Val120-Ile201  (519) CGTGGTGAGCACCCAGCTGCTGCTGAACGGCAGCCTGGCC
 Val120-Thr202  (519) CGTGGTGAGCACCCAGCTGCTGCTGAACGGCAGCCTGGCC
 Lys121-Val200  (525) CGTGGTGAGCACCCAGCTGCTGCTGAACGGCAGCCTGGCC
     Consensus  (561) CGTGGTGAGCACCCAGCTGCTGCTGAACGGCAGCCTGGCC
                      601                                   640
 Leu122-Ser199  (571) GAGGAGGGCGTGGTGATCCGCAGCGAGAACTTCACCGACA
 Val127-Asn195  (601) GAGGAGGGCGTGGTGATCCGCAGCGAGAACTTCACCGACA
Val120-Ile201B  (559) GAGGAGGGCGTGGTGATCCGCAGCGAGAACTTCACCGACA
 Val120-Ala204  (553) GAGGAGGGCGTGGTGATCCGCAGCGAGAACTTCACCGACA
 Val120-Ile201  (559) GAGGAGGGCGTGGTGATCCGCAGCGAGAACTTCACCGACA
 Val120-Thr202  (559) GAGGAGGGCGTGGTGATCCGCAGCGAGAACTTCACCGACA
 Lys121-Val200  (565) GAGGAGGGCGTGGTGATCCGCAGCGAGAACTTCACCGACA
     Consensus  (601) GAGGAGGGCGTGGTGATCCGCAGCGAGAACTTCACCGACA
                      641                                   680
 Leu122-Ser199  (611) ACGCCAAGACCATCATCGTGCAGCTGAAGGAGAGCGTGGA
 Val127-Asn195  (641) ACGCCAAGACCATCATCGTGCAGCTGAAGGAGAGCGTGGA
Val120-Ile201B  (599) ACGCCAAGACCATCATCGTGCAGCTGAAGGAGAGCGTGGA
 Val120-Ala204  (593) ACGCCAAGACCATCATCGTGCAGCTGAAGGAGAGCGTGGA
 Val120-Ile201  (599) ACGCCAAGACCATCATCGTGCAGCTGAAGGAGAGCGTGGA
 Val120-Thr202  (599) ACGCCAAGACCATCATCGTGCAGCTGAAGGAGAGCGTGGA
 Lys121-Val200  (605) ACGCCAAGACCATCATCGTGCAGCTGAAGGAGAGCGTGGA
     Consensus  (641) ACGCCAAGACCATCATCGTGCAGCTGAAGGAGAGCGTGGA
                      681                                   720
 Leu122-Ser199  (651) GATCAACTGCACCCGCCCCAACAACAACACCCGCAAGAGC
 Val127-Asn195  (681) GATCAACTGCACCCGCCCCAACAACAACACCCGCAAGAGC
Val120-Ile201B  (639) GATCAACTGCACCCGCCCCAACAACAACACCCGCAAGAGC
 Val120-Ala204  (633) GATCAACTGCACCCGCCCCAACAACAACACCCGCAAGAGC
 Val120-Ile201  (639) GATCAACTGCACCCGCCCCAACAACAACACCCGCAAGAGC
 Val120-Thr202  (639) GATCAACTGCACCCGCCCCAACAACAACACCCGCAAGAGC
 Lys121-Val200  (645) GATCAACTGCACCCGCCCCAACAACAACACCCGCAAGAGC
     Consensus  (681) GATCAACTGCACCCGCCCCAACAACAACACCCGCAAGAGC
                      721                                   760
 Leu122-Ser199  (691) ATCACCATCGGCCCCGGCCGCGCCTTCTACGCCACCGGCG
 Val127-Asn195  (721) ATCACCATCGGCCCCGGCCGCGCCTTCTACGCCACCGGCG
Val120-Ile201B  (679) ATCACCATCGGCCCCGGCCGCGCCTTCTACGCCACCGGCG
 Val120-Ala204  (673) ATCACCATCGGCCCCGGCCGCGCCTTCTACGCCACCGGCG
 Val120-Ile201  (679) ATCACCATCGGCCCCGGCCGCGCCTTCTACGCCACCGGCG
 Val120-Thr202  (679) ATCACCATCGGCCCCGGCCGCGCCTTCTACGCCACCGGCG
 Lys121-Val200  (685) ATCACCATCGGCCCCGGCCGCGCCTTCTACGCCACCGGCG
     Consensus  (721) ATCACCATCGGCCCCGGCCGCGCCTTCTACGCCACCGGCG
```

FIG. 3C

| | | |
|---|---|---|
| | | 761 800 |
| Leu122-Ser199 | (731) | ACATCATCGGCGACATCCGCCAGGCCCACTGCAACATCAG |
| Val127-Asn195 | (761) | ACATCATCGGCGACATCCGCCAGGCCCACTGCAACATCAG |
| Val120-Ile201B | (719) | ACATCATCGGCGACATCCGCCAGGCCCACTGCAACATCAG |
| Val120-Ala204 | (713) | ACATCATCGGCGACATCCGCCAGGCCCACTGCAACATCAG |
| Val120-Ile201 | (719) | ACATCATCGGCGACATCCGCCAGGCCCACTGCAACATCAG |
| Val120-Thr202 | (719) | ACATCATCGGCGACATCCGCCAGGCCCACTGCAACATCAG |
| Lys121-Val200 | (725) | ACATCATCGGCGACATCCGCCAGGCCCACTGCAACATCAG |
| Consensus | (761) | ACATCATCGGCGACATCCGCCAGGCCCACTGCAACATCAG |
| | | 801 840 |
| Leu122-Ser199 | (771) | CGGCGAGAAGTGGAACAACACCCTGAAGCAGATCGTGACC |
| Val127-Asn195 | (801) | CGGCGAGAAGTGGAACAACACCCTGAAGCAGATCGTGACC |
| Val120-Ile201B | (759) | CGGCGAGAAGTGGAACAACACCCTGAAGCAGATCGTGACC |
| Val120-Ala204 | (753) | CGGCGAGAAGTGGAACAACACCCTGAAGCAGATCGTGACC |
| Val120-Ile201 | (759) | CGGCGAGAAGTGGAACAACACCCTGAAGCAGATCGTGACC |
| Val120-Thr202 | (759) | CGGCGAGAAGTGGAACAACACCCTGAAGCAGATCGTGACC |
| Lys121-Val200 | (765) | CGGCGAGAAGTGGAACAACACCCTGAAGCAGATCGTGACC |
| Consensus | (801) | CGGCGAGAAGTGGAACAACACCCTGAAGCAGATCGTGACC |
| | | 841 880 |
| Leu122-Ser199 | (811) | AAGCTGCAGGCCCAGTTCGGCAACAAGACCATCGTGTTCA |
| Val127-Asn195 | (841) | AAGCTGCAGGCCCAGTTCGGCAACAAGACCATCGTGTTCA |
| Val120-Ile201B | (799) | AAGCTGCAGGCCCAGTTCGGCAACAAGACCATCGTGTTCA |
| Val120-Ala204 | (793) | AAGCTGCAGGCCCAGTTCGGCAACAAGACCATCGTGTTCA |
| Val120-Ile201 | (799) | AAGCTGCAGGCCCAGTTCGGCAACAAGACCATCGTGTTCA |
| Val120-Thr202 | (799) | AAGCTGCAGGCCCAGTTCGGCAACAAGACCATCGTGTTCA |
| Lys121-Val200 | (805) | AAGCTGCAGGCCCAGTTCGGCAACAAGACCATCGTGTTCA |
| Consensus | (841) | AAGCTGCAGGCCCAGTTCGGCAACAAGACCATCGTGTTCA |
| | | 881 920 |
| Leu122-Ser199 | (851) | AGCAGAGCAGCGGCGGCGACCCCGAGATCGTGATGCACAG |
| Val127-Asn195 | (881) | AGCAGAGCAGCGGCGGCGACCCCGAGATCGTGATGCACAG |
| Val120-Ile201B | (839) | AGCAGAGCAGCGGCGGCGACCCCGAGATCGTGATGCACAG |
| Val120-Ala204 | (833) | AGCAGAGCAGCGGCGGCGACCCCGAGATCGTGATGCACAG |
| Val120-Ile201 | (839) | AGCAGAGCAGCGGCGGCGACCCCGAGATCGTGATGCACAG |
| Val120-Thr202 | (839) | AGCAGAGCAGCGGCGGCGACCCCGAGATCGTGATGCACAG |
| Lys121-Val200 | (845) | AGCAGAGCAGCGGCGGCGACCCCGAGATCGTGATGCACAG |
| Consensus | (881) | AGCAGAGCAGCGGCGGCGACCCCGAGATCGTGATGCACAG |
| | | 921 960 |
| Leu122-Ser199 | (891) | CTTCAACTGCGGCGGCGAGTTCTTCTACTGCAACAGCACC |
| Val127-Asn195 | (921) | CTTCAACTGCGGCGGCGAGTTCTTCTACTGCAACAGCACC |
| Val120-Ile201B | (879) | CTTCAACTGCGGCGGCGAGTTCTTCTACTGCAACAGCACC |
| Val120-Ala204 | (873) | CTTCAACTGCGGCGGCGAGTTCTTCTACTGCAACAGCACC |
| Val120-Ile201 | (879) | CTTCAACTGCGGCGGCGAGTTCTTCTACTGCAACAGCACC |
| Val120-Thr202 | (879) | CTTCAACTGCGGCGGCGAGTTCTTCTACTGCAACAGCACC |
| Lys121-Val200 | (885) | CTTCAACTGCGGCGGCGAGTTCTTCTACTGCAACAGCACC |
| Consensus | (921) | CTTCAACTGCGGCGGCGAGTTCTTCTACTGCAACAGCACC |
| | | 961 1000 |
| Leu122-Ser199 | (931) | CAGCTGTTCAACAGCACCTGGAACAACACCATCGGCCCCA |
| Val127-Asn195 | (961) | CAGCTGTTCAACAGCACCTGGAACAACACCATCGGCCCCA |
| Val120-Ile201B | (919) | CAGCTGTTCAACAGCACCTGGAACAACACCATCGGCCCCA |
| Val120-Ala204 | (913) | CAGCTGTTCAACAGCACCTGGAACAACACCATCGGCCCCA |
| Val120-Ile201 | (919) | CAGCTGTTCAACAGCACCTGGAACAACACCATCGGCCCCA |
| Val120-Thr202 | (919) | CAGCTGTTCAACAGCACCTGGAACAACACCATCGGCCCCA |
| Lys121-Val200 | (925) | CAGCTGTTCAACAGCACCTGGAACAACACCATCGGCCCCA |
| Consensus | (961) | CAGCTGTTCAACAGCACCTGGAACAACACCATCGGCCCCA |
| | | 1001 1040 |
| Leu122-Ser199 | (971) | ACAACACCAACGGCACCATCACCCTGCCCTGCCGCATCAA |
| Val127-Asn195 | (1001) | ACAACACCAACGGCACCATCACCCTGCCCTGCCGCATCAA |

*FIG. 3D*

```
Val120-Ile201B   (959)  ACAACACCAACGGCACCATCACCCTGCCCTGCCGCATCAA
Val120-Ala204    (953)  ACAACACCAACGGCACCATCACCCTGCCCTGCCGCATCAA
Val120-Ile201    (959)  ACAACACCAACGGCACCATCACCCTGCCCTGCCGCATCAA
Val120-Thr202    (959)  ACAACACCAACGGCACCATCACCCTGCCCTGCCGCATCAA
Lys121-Val200    (965)  ACAACACCAACGGCACCATCACCCTGCCCTGCCGCATCAA
Consensus       (1001)  ACAACACCAACGGCACCATCACCCTGCCCTGCCGCATCAA
                        1041                                    1080
Leu122-Ser199   (1011)  GCAGATCATCAACCGCTGGCAGGAGGTGGGCAAGGCCATG
Val127-Asn195   (1041)  GCAGATCATCAACCGCTGGCAGGAGGTGGGCAAGGCCATG
Val120-Ile201B   (999)  GCAGATCATCAACCGCTGGCAGGAGGTGGGCAAGGCCATG
Val120-Ala204    (993)  GCAGATCATCAACCGCTGGCAGGAGGTGGGCAAGGCCATG
Val120-Ile201    (999)  GCAGATCATCAACCGCTGGCAGGAGGTGGGCAAGGCCATG
Val120-Thr202    (999)  GCAGATCATCAACCGCTGGCAGGAGGTGGGCAAGGCCATG
Lys121-Val200   (1005)  GCAGATCATCAACCGCTGGCAGGAGGTGGGCAAGGCCATG
Consensus       (1041)  GCAGATCATCAACCGCTGGCAGGAGGTGGGCAAGGCCATG
                        1081                                    1120
Leu122-Ser199   (1051)  TACGCCCCCCCCATCCGCGGCCAGATCCGCTGCAGCAGCA
Val127-Asn195   (1081)  TACGCCCCCCCCATCCGCGGCCAGATCCGCTGCAGCAGCA
Val120-Ile201B  (1039)  TACGCCCCCCCCATCCGCGGCCAGATCCGCTGCAGCAGCA
Val120-Ala204   (1033)  TACGCCCCCCCCATCCGCGGCCAGATCCGCTGCAGCAGCA
Val120-Ile201   (1039)  TACGCCCCCCCCATCCGCGGCCAGATCCGCTGCAGCAGCA
Val120-Thr202   (1039)  TACGCCCCCCCCATCCGCGGCCAGATCCGCTGCAGCAGCA
Lys121-Val200   (1045)  TACGCCCCCCCCATCCGCGGCCAGATCCGCTGCAGCAGCA
Consensus       (1081)  TACGCCCCCCCCATCCGCGGCCAGATCCGCTGCAGCAGCA
                        1121                                    1160
Leu122-Ser199   (1091)  ACATCACCGGCCTGCTGCTGACCCGCGACGGCGGCAAGGA
Val127-Asn195   (1121)  ACATCACCGGCCTGCTGCTGACCCGCGACGGCGGCAAGGA
Val120-Ile201B  (1079)  ACATCACCGGCCTGCTGCTGACCCGCGACGGCGGCAAGGA
Val120-Ala204   (1073)  ACATCACCGGCCTGCTGCTGACCCGCGACGGCGGCAAGGA
Val120-Ile201   (1079)  ACATCACCGGCCTGCTGCTGACCCGCGACGGCGGCAAGGA
Val120-Thr202   (1079)  ACATCACCGGCCTGCTGCTGACCCGCGACGGCGGCAAGGA
Lys121-Val200   (1085)  ACATCACCGGCCTGCTGCTGACCCGCGACGGCGGCAAGGA
Consensus       (1121)  ACATCACCGGCCTGCTGCTGACCCGCGACGGCGGCAAGGA
                        1161                                    1200
Leu122-Ser199   (1131)  GATCAGCAACACCACCGAGATCTTCCGCCCCGGCGGCGGC
Val127-Asn195   (1161)  GATCAGCAACACCACCGAGATCTTCCGCCCCGGCGGCGGC
Val120-Ile201B  (1119)  GATCAGCAACACCACCGAGATCTTCCGCCCCGGCGGCGGC
Val120-Ala204   (1113)  GATCAGCAACACCACCGAGATCTTCCGCCCCGGCGGCGGC
Val120-Ile201   (1119)  GATCAGCAACACCACCGAGATCTTCCGCCCCGGCGGCGGC
Val120-Thr202   (1119)  GATCAGCAACACCACCGAGATCTTCCGCCCCGGCGGCGGC
Lys121-Val200   (1125)  GATCAGCAACACCACCGAGATCTTCCGCCCCGGCGGCGGC
Consensus       (1161)  GATCAGCAACACCACCGAGATCTTCCGCCCCGGCGGCGGC
                        1201                                    1240
Leu122-Ser199   (1171)  GACATGCGCGACAACTGGCGCAGCGAGCTGTACAAGTACA
Val127-Asn195   (1201)  GACATGCGCGACAACTGGCGCAGCGAGCTGTACAAGTACA
Val120-Ile201B  (1159)  GACATGCGCGACAACTGGCGCAGCGAGCTGTACAAGTACA
Val120-Ala204   (1153)  GACATGCGCGACAACTGGCGCAGCGAGCTGTACAAGTACA
Val120-Ile201   (1159)  GACATGCGCGACAACTGGCGCAGCGAGCTGTACAAGTACA
Val120-Thr202   (1159)  GACATGCGCGACAACTGGCGCAGCGAGCTGTACAAGTACA
Lys121-Val200   (1165)  GACATGCGCGACAACTGGCGCAGCGAGCTGTACAAGTACA
Consensus       (1201)  GACATGCGCGACAACTGGCGCAGCGAGCTGTACAAGTACA
                        1241                                    1280
Leu122-Ser199   (1211)  AGGTGGTGAAGATCGAGCCCCTGGGCGTGGCCCCCACCAA
Val127-Asn195   (1241)  AGGTGGTGAAGATCGAGCCCCTGGGCGTGGCCCCCACCAA
Val120-Ile201B  (1199)  AGGTGGTGAAGATCGAGCCCCTGGGCGTGGCCCCCACCAA
Val120-Ala204   (1193)  AGGTGGTGAAGATCGAGCCCCTGGGCGTGGCCCCCACCAA
Val120-Ile201   (1199)  AGGTGGTGAAGATCGAGCCCCTGGGCGTGGCCCCCACCAA
```

FIG. 3E

```
Val120-Thr202  (1199) AGGTGGTGAAGATCGAGCCCCTGGGCGTGGCCCCCACCAA
Lys121-Val200  (1205) AGGTGGTGAAGATCGAGCCCCTGGGCGTGGCCCCCACCAA
    Consensus  (1241) AGGTGGTGAAGATCGAGCCCCTGGGCGTGGCCCCCACCAA
                      1281                                 1320
Leu122-Ser199  (1251) GGCCAAGCGCCGCGTGGTGCAGCGCGAGAAGCGCGCCGTG
Val127-Asn195  (1281) GGCCAAGCGCCGCGTGGTGCAGCGCGAGAAGCGCGCCGTG
Val120-Ile201B (1239) GGCCAAGCGCCGCGTGGTGCAGCGCGAGAAGCGCGCCGTG
Val120-Ala204  (1233) GGCCAAGCGCCGCGTGGTGCAGCGCGAGAAGCGCGCCGTG
Val120-Ile201  (1239) GGCCAAGCGCCGCGTGGTGCAGCGCGAGAAGCGCGCCGTG
Val120-Thr202  (1239) GGCCAAGCGCCGCGTGGTGCAGCGCGAGAAGCGCGCCGTG
Lys121-Val200  (1245) GGCCAAGCGCCGCGTGGTGCAGCGCGAGAAGCGCGCCGTG
    Consensus  (1281) GGCCAAGCGCCGCGTGGTGCAGCGCGAGAAGCGCGCCGTG
                      1321                                 1360
Leu122-Ser199  (1291) ACCCTGGGCGCCATGTTCCTGGGCTTCCTGGGCGCCGCCG
Val127-Asn195  (1321) ACCCTGGGCGCCATGTTCCTGGGCTTCCTGGGCGCCGCCG
Val120-Ile201B (1279) ACCCTGGGCGCCATGTTCCTGGGCTTCCTGGGCGCCGCCG
Val120-Ala204  (1273) ACCCTGGGCGCCATGTTCCTGGGCTTCCTGGGCGCCGCCG
Val120-Ile201  (1279) ACCCTGGGCGCCATGTTCCTGGGCTTCCTGGGCGCCGCCG
Val120-Thr202  (1279) ACCCTGGGCGCCATGTTCCTGGGCTTCCTGGGCGCCGCCG
Lys121-Val200  (1285) ACCCTGGGCGCCATGTTCCTGGGCTTCCTGGGCGCCGCCG
    Consensus  (1321) ACCCTGGGCGCCATGTTCCTGGGCTTCCTGGGCGCCGCCG
                      1361                                 1400
Leu122-Ser199  (1331) GCAGCACCATGGGCGCCCGCAGCCTGACCCTGACCGTGCA
Val127-Asn195  (1361) GCAGCACCATGGGCGCCCGCAGCCTGACCCTGACCGTGCA
Val120-Ile201B (1319) GCAGCACCATGGGCGCCCGCAGCCTGACCCTGACCGTGCA
Val120-Ala204  (1313) GCAGCACCATGGGCGCCCGCAGCCTGACCCTGACCGTGCA
Val120-Ile201  (1319) GCAGCACCATGGGCGCCCGCAGCCTGACCCTGACCGTGCA
Val120-Thr202  (1319) GCAGCACCATGGGCGCCCGCAGCCTGACCCTGACCGTGCA
Lys121-Val200  (1325) GCAGCACCATGGGCGCCCGCAGCCTGACCCTGACCGTGCA
    Consensus  (1361) GCAGCACCATGGGCGCCCGCAGCCTGACCCTGACCGTGCA
                      1401                                 1440
Leu122-Ser199  (1371) GGCCCGCCAGCTGCTGAGCGGCATCGTGCAGCAGCAGAAC
Val127-Asn195  (1401) GGCCCGCCAGCTGCTGAGCGGCATCGTGCAGCAGCAGAAC
Val120-Ile201B (1359) GGCCCGCCAGCTGCTGAGCGGCATCGTGCAGCAGCAGAAC
Val120-Ala204  (1353) GGCCCGCCAGCTGCTGAGCGGCATCGTGCAGCAGCAGAAC
Val120-Ile201  (1359) GGCCCGCCAGCTGCTGAGCGGCATCGTGCAGCAGCAGAAC
Val120-Thr202  (1359) GGCCCGCCAGCTGCTGAGCGGCATCGTGCAGCAGCAGAAC
Lys121-Val200  (1365) GGCCCGCCAGCTGCTGAGCGGCATCGTGCAGCAGCAGAAC
    Consensus  (1401) GGCCCGCCAGCTGCTGAGCGGCATCGTGCAGCAGCAGAAC
                      1441                                 1480
Leu122-Ser199  (1411) AACCTGCTGCGCGCCATCGAGGCCCAGCAGCACCTGCTGC
Val127-Asn195  (1441) AACCTGCTGCGCGCCATCGAGGCCCAGCAGCACCTGCTGC
Val120-Ile201B (1399) AACCTGCTGCGCGCCATCGAGGCCCAGCAGCACCTGCTGC
Val120-Ala204  (1393) AACCTGCTGCGCGCCATCGAGGCCCAGCAGCACCTGCTGC
Val120-Ile201  (1399) AACCTGCTGCGCGCCATCGAGGCCCAGCAGCACCTGCTGC
Val120-Thr202  (1399) AACCTGCTGCGCGCCATCGAGGCCCAGCAGCACCTGCTGC
Lys121-Val200  (1405) AACCTGCTGCGCGCCATCGAGGCCCAGCAGCACCTGCTGC
    Consensus  (1441) AACCTGCTGCGCGCCATCGAGGCCCAGCAGCACCTGCTGC
                      1481                                 1520
Leu122-Ser199  (1451) AGCTGACCGTGTGGGGCATCAAGCAGCTGCAGGCCCGCGT
Val127-Asn195  (1481) AGCTGACCGTGTGGGGCATCAAGCAGCTGCAGGCCCGCGT
Val120-Ile201B (1439) AGCTGACCGTGTGGGGCATCAAGCAGCTGCAGGCCCGCGT
Val120-Ala204  (1433) AGCTGACCGTGTGGGGCATCAAGCAGCTGCAGGCCCGCGT
Val120-Ile201  (1439) AGCTGACCGTGTGGGGCATCAAGCAGCTGCAGGCCCGCGT
Val120-Thr202  (1439) AGCTGACCGTGTGGGGCATCAAGCAGCTGCAGGCCCGCGT
Lys121-Val200  (1445) AGCTGACCGTGTGGGGCATCAAGCAGCTGCAGGCCCGCGT
    Consensus  (1481) AGCTGACCGTGTGGGGCATCAAGCAGCTGCAGGCCCGCGT
```

*FIG. 3F*

| | | |
|---|---|---|
| | | 1521 1560 |
| Leu122-Ser199 | (1491) | GCTGGCCGTGGAGCGCTACCTGAAGGACCAGCAGCTGCTG |
| Val127-Asn195 | (1521) | GCTGGCCGTGGAGCGCTACCTGAAGGACCAGCAGCTGCTG |
| Val120-Ile201B | (1479) | GCTGGCCGTGGAGCGCTACCTGAAGGACCAGCAGCTGCTG |
| Val120-Ala204 | (1473) | GCTGGCCGTGGAGCGCTACCTGAAGGACCAGCAGCTGCTG |
| Val120-Ile201 | (1479) | GCTGGCCGTGGAGCGCTACCTGAAGGACCAGCAGCTGCTG |
| Val120-Thr202 | (1479) | GCTGGCCGTGGAGCGCTACCTGAAGGACCAGCAGCTGCTG |
| Lys121-Val200 | (1485) | GCTGGCCGTGGAGCGCTACCTGAAGGACCAGCAGCTGCTG |
| Consensus | (1521) | GCTGGCCGTGGAGCGCTACCTGAAGGACCAGCAGCTGCTG |
| | | 1561 1600 |
| Leu122-Ser199 | (1531) | GGCATCTGGGGCTGCAGCGGCAAGCTGATCTGCACCACCG |
| Val127-Asn195 | (1561) | GGCATCTGGGGCTGCAGCGGCAAGCTGATCTGCACCACCG |
| Val120-Ile201B | (1519) | GGCATCTGGGGCTGCAGCGGCAAGCTGATCTGCACCACCG |
| Val120-Ala204 | (1513) | GGCATCTGGGGCTGCAGCGGCAAGCTGATCTGCACCACCG |
| Val120-Ile201 | (1519) | GGCATCTGGGGCTGCAGCGGCAAGCTGATCTGCACCACCG |
| Val120-Thr202 | (1519) | GGCATCTGGGGCTGCAGCGGCAAGCTGATCTGCACCACCG |
| Lys121-Val200 | (1525) | GGCATCTGGGGCTGCAGCGGCAAGCTGATCTGCACCACCG |
| Consensus | (1561) | GGCATCTGGGGCTGCAGCGGCAAGCTGATCTGCACCACCG |
| | | 1601 1640 |
| Leu122-Ser199 | (1571) | CCGTGCCCTGGAACGCCAGCTGGAGCAACAAGAGCCTGGA |
| Val127-Asn195 | (1601) | CCGTGCCCTGGAACGCCAGCTGGAGCAACAAGAGCCTGGA |
| Val120-Ile201B | (1559) | CCGTGCCCTGGAACGCCAGCTGGAGCAACAAGAGCCTGGA |
| Val120-Ala204 | (1553) | CCGTGCCCTGGAACGCCAGCTGGAGCAACAAGAGCCTGGA |
| Val120-Ile201 | (1559) | CCGTGCCCTGGAACGCCAGCTGGAGCAACAAGAGCCTGGA |
| Val120-Thr202 | (1559) | CCGTGCCCTGGAACGCCAGCTGGAGCAACAAGAGCCTGGA |
| Lys121-Val200 | (1565) | CCGTGCCCTGGAACGCCAGCTGGAGCAACAAGAGCCTGGA |
| Consensus | (1601) | CCGTGCCCTGGAACGCCAGCTGGAGCAACAAGAGCCTGGA |
| | | 1641 1680 |
| Leu122-Ser199 | (1611) | CCAGATCTGGAACAACATGACCTGGATGGAGTGGGAGCGC |
| Val127-Asn195 | (1641) | CCAGATCTGGAACAACATGACCTGGATGGAGTGGGAGCGC |
| Val120-Ile201B | (1599) | CCAGATCTGGAACAACATGACCTGGATGGAGTGGGAGCGC |
| Val120-Ala204 | (1593) | CCAGATCTGGAACAACATGACCTGGATGGAGTGGGAGCGC |
| Val120-Ile201 | (1599) | CCAGATCTGGAACAACATGACCTGGATGGAGTGGGAGCGC |
| Val120-Thr202 | (1599) | CCAGATCTGGAACAACATGACCTGGATGGAGTGGGAGCGC |
| Lys121-Val200 | (1605) | CCAGATCTGGAACAACATGACCTGGATGGAGTGGGAGCGC |
| Consensus | (1641) | CCAGATCTGGAACAACATGACCTGGATGGAGTGGGAGCGC |
| | | 1681 1720 |
| Leu122-Ser199 | (1651) | GAGATCGACAACTACACCAACCTGATCTACACCCTGATCG |
| Val127-Asn195 | (1681) | GAGATCGACAACTACACCAACCTGATCTACACCCTGATCG |
| Val120-Ile201B | (1639) | GAGATCGACAACTACACCAACCTGATCTACACCCTGATCG |
| Val120-Ala204 | (1633) | GAGATCGACAACTACACCAACCTGATCTACACCCTGATCG |
| Val120-Ile201 | (1639) | GAGATCGACAACTACACCAACCTGATCTACACCCTGATCG |
| Val120-Thr202 | (1639) | GAGATCGACAACTACACCAACCTGATCTACACCCTGATCG |
| Lys121-Val200 | (1645) | GAGATCGACAACTACACCAACCTGATCTACACCCTGATCG |
| Consensus | (1681) | GAGATCGACAACTACACCAACCTGATCTACACCCTGATCG |
| | | 1721 1760 |
| Leu122-Ser199 | (1691) | AGGAGAGCCAGAACCAGCAGGAGAAGAACGAGCAGGAGCT |
| Val127-Asn195 | (1721) | AGGAGAGCCAGAACCAGCAGGAGAAGAACGAGCAGGAGCT |
| Val120-Ile201B | (1679) | AGGAGAGCCAGAACCAGCAGGAGAAGAACGAGCAGGAGCT |
| Val120-Ala204 | (1673) | AGGAGAGCCAGAACCAGCAGGAGAAGAACGAGCAGGAGCT |
| Val120-Ile201 | (1679) | AGGAGAGCCAGAACCAGCAGGAGAAGAACGAGCAGGAGCT |
| Val120-Thr202 | (1679) | AGGAGAGCCAGAACCAGCAGGAGAAGAACGAGCAGGAGCT |
| Lys121-Val200 | (1685) | AGGAGAGCCAGAACCAGCAGGAGAAGAACGAGCAGGAGCT |
| Consensus | (1721) | AGGAGAGCCAGAACCAGCAGGAGAAGAACGAGCAGGAGCT |
| | | 1761 1800 |
| Leu122-Ser199 | (1731) | GCTGGAGCTGGACAAGTGGGCCAGCCTGTGGAACTGGTTC |
| Val127-Asn195 | (1761) | GCTGGAGCTGGACAAGTGGGCCAGCCTGTGGAACTGGTTC |

FIG. 3G

```
Val120-Ile201B  (1719) GCTGGAGCTGGACAAGTGGGCCAGCCTGTGGAACTGGTTC
Val120-Ala204   (1713) GCTGGAGCTGGACAAGTGGGCCAGCCTGTGGAACTGGTTC
Val120-Ile201   (1719) GCTGGAGCTGGACAAGTGGGCCAGCCTGTGGAACTGGTTC
Val120-Thr202   (1719) GCTGGAGCTGGACAAGTGGGCCAGCCTGTGGAACTGGTTC
Lys121-Val200   (1725) GCTGGAGCTGGACAAGTGGGCCAGCCTGTGGAACTGGTTC
Consensus       (1761) GCTGGAGCTGGACAAGTGGGCCAGCCTGTGGAACTGGTTC
                       1801                                1840
Leu122-Ser199   (1771) GACATCAGCAAGTGGCTGTGGTACATCAAGATCTTCATCA
Val127-Asn195   (1801) GACATCAGCAAGTGGCTGTGGTACATCAAGATCTTCATCA
Val120-Ile201B  (1759) GACATCAGCAAGTGGCTGTGGTACATCAAGATCTTCATCA
Val120-Ala204   (1753) GACATCAGCAAGTGGCTGTGGTACATCAAGATCTTCATCA
Val120-Ile201   (1759) GACATCAGCAAGTGGCTGTGGTACATCAAGATCTTCATCA
Val120-Thr202   (1759) GACATCAGCAAGTGGCTGTGGTACATCAAGATCTTCATCA
Lys121-Val200   (1765) GACATCAGCAAGTGGCTGTGGTACATCAAGATCTTCATCA
Consensus       (1801) GACATCAGCAAGTGGCTGTGGTACATCAAGATCTTCATCA
                       1841                                1880
Leu122-Ser199   (1811) TGATCGTGGGCGGCCTGGTGGGCCTGCGCATCGTGTTCAC
Val127-Asn195   (1841) TGATCGTGGGCGGCCTGGTGGGCCTGCGCATCGTGTTCAC
Val120-Ile201B  (1799) TGATCGTGGGCGGCCTGGTGGGCCTGCGCATCGTGTTCAC
Val120-Ala204   (1793) TGATCGTGGGCGGCCTGGTGGGCCTGCGCATCGTGTTCAC
Val120-Ile201   (1799) TGATCGTGGGCGGCCTGGTGGGCCTGCGCATCGTGTTCAC
Val120-Thr202   (1799) TGATCGTGGGCGGCCTGGTGGGCCTGCGCATCGTGTTCAC
Lys121-Val200   (1805) TGATCGTGGGCGGCCTGGTGGGCCTGCGCATCGTGTTCAC
Consensus       (1841) TGATCGTGGGCGGCCTGGTGGGCCTGCGCATCGTGTTCAC
                       1881                                1920
Leu122-Ser199   (1851) CGTGCTGAGCATCGTGAACCGCGTGCGCCAGGGCTACAGC
Val127-Asn195   (1881) CGTGCTGAGCATCGTGAACCGCGTGCGCCAGGGCTACAGC
Val120-Ile201B  (1839) CGTGCTGAGCATCGTGAACCGCGTGCGCCAGGGCTACAGC
Val120-Ala204   (1833) CGTGCTGAGCATCGTGAACCGCGTGCGCCAGGGCTACAGC
Val120-Ile201   (1839) CGTGCTGAGCATCGTGAACCGCGTGCGCCAGGGCTACAGC
Val120-Thr202   (1839) CGTGCTGAGCATCGTGAACCGCGTGCGCCAGGGCTACAGC
Lys121-Val200   (1845) CGTGCTGAGCATCGTGAACCGCGTGCGCCAGGGCTACAGC
Consensus       (1881) CGTGCTGAGCATCGTGAACCGCGTGCGCCAGGGCTACAGC
                       1921                                1960
Leu122-Ser199   (1891) CCCCTGAGCTTCCAGACCCGCTTCCCCGCCCCCCGCGGCC
Val127-Asn195   (1921) CCCCTGAGCTTCCAGACCCGCTTCCCCGCCCCCCGCGGCC
Val120-Ile201B  (1879) CCCCTGAGCTTCCAGACCCGCTTCCCCGCCCCCCGCGGCC
Val120-Ala204   (1873) CCCCTGAGCTTCCAGACCCGCTTCCCCGCCCCCCGCGGCC
Val120-Ile201   (1879) CCCCTGAGCTTCCAGACCCGCTTCCCCGCCCCCCGCGGCC
Val120-Thr202   (1879) CCCCTGAGCTTCCAGACCCGCTTCCCCGCCCCCCGCGGCC
Lys121-Val200   (1885) CCCCTGAGCTTCCAGACCCGCTTCCCCGCCCCCCGCGGCC
Consensus       (1921) CCCCTGAGCTTCCAGACCCGCTTCCCCGCCCCCCGCGGCC
                       1961                                2000
Leu122-Ser199   (1931) CCGACCGCCCCGAGGGCATCGAGGAGGAGGGCGGCGAGCG
Val127-Asn195   (1961) CCGACCGCCCCGAGGGCATCGAGGAGGAGGGCGGCGAGCG
Val120-Ile201B  (1919) CCGACCGCCCCGAGGGCATCGAGGAGGAGGGCGGCGAGCG
Val120-Ala204   (1913) CCGACCGCCCCGAGGGCATCGAGGAGGAGGGCGGCGAGCG
Val120-Ile201   (1919) CCGACCGCCCCGAGGGCATCGAGGAGGAGGGCGGCGAGCG
Val120-Thr202   (1919) CCGACCGCCCCGAGGGCATCGAGGAGGAGGGCGGCGAGCG
Lys121-Val200   (1925) CCGACCGCCCCGAGGGCATCGAGGAGGAGGGCGGCGAGCG
Consensus       (1961) CCGACCGCCCCGAGGGCATCGAGGAGGAGGGCGGCGAGCG
                       2001                                2040
Leu122-Ser199   (1971) CGACCGCGACCGCAGCAGCCCCCTGGTGCACGGCCTGCTG
Val127-Asn195   (2001) CGACCGCGACCGCAGCAGCCCCCTGGTGCACGGCCTGCTG
Val120-Ile201B  (1959) CGACCGCGACCGCAGCAGCCCCCTGGTGCACGGCCTGCTG
Val120-Ala204   (1953) CGACCGCGACCGCAGCAGCCCCCTGGTGCACGGCCTGCTG
Val120-Ile201   (1959) CGACCGCGACCGCAGCAGCCCCCTGGTGCACGGCCTGCTG
```

*FIG. 3H*

| | | |
|---|---|---|
| Val120-Thr202 | (1959) | CGACCGCGACCGCAGCAGCCCCCTGGTGCACGGCCTGCTG |
| Lys121-Val200 | (1965) | CGACCGCGACCGCAGCAGCCCCCTGGTGCACGGCCTGCTG |
| Consensus | (2001) | CGACCGCGACCGCAGCAGCCCCCTGGTGCACGGCCTGCTG |
| | | 2041 2080 |
| Leu122-Ser199 | (2011) | GCCCTGATCTGGGACGACCTGCGCAGCCTGTGCCTGTTCA |
| Val127-Asn195 | (2041) | GCCCTGATCTGGGACGACCTGCGCAGCCTGTGCCTGTTCA |
| Val120-Ile201B | (1999) | GCCCTGATCTGGGACGACCTGCGCAGCCTGTGCCTGTTCA |
| Val120-Ala204 | (1993) | GCCCTGATCTGGGACGACCTGCGCAGCCTGTGCCTGTTCA |
| Val120-Ile201 | (1999) | GCCCTGATCTGGGACGACCTGCGCAGCCTGTGCCTGTTCA |
| Val120-Thr202 | (1999) | GCCCTGATCTGGGACGACCTGCGCAGCCTGTGCCTGTTCA |
| Lys121-Val200 | (2005) | GCCCTGATCTGGGACGACCTGCGCAGCCTGTGCCTGTTCA |
| Consensus | (2041) | GCCCTGATCTGGGACGACCTGCGCAGCCTGTGCCTGTTCA |
| | | 2081 2120 |
| Leu122-Ser199 | (2051) | GCTACCACCGCCTGCGCGACCTGATCCTGATCGCCGCCCG |
| Val127-Asn195 | (2081) | GCTACCACCGCCTGCGCGACCTGATCCTGATCGCCGCCCG |
| Val120-Ile201B | (2039) | GCTACCACCGCCTGCGCGACCTGATCCTGATCGCCGCCCG |
| Val120-Ala204 | (2033) | GCTACCACCGCCTGCGCGACCTGATCCTGATCGCCGCCCG |
| Val120-Ile201 | (2039) | GCTACCACCGCCTGCGCGACCTGATCCTGATCGCCGCCCG |
| Val120-Thr202 | (2039) | GCTACCACCGCCTGCGCGACCTGATCCTGATCGCCGCCCG |
| Lys121-Val200 | (2045) | GCTACCACCGCCTGCGCGACCTGATCCTGATCGCCGCCCG |
| Consensus | (2081) | GCTACCACCGCCTGCGCGACCTGATCCTGATCGCCGCCCG |
| | | 2121 2160 |
| Leu122-Ser199 | (2091) | CATCGTGGAGCTGCTGGGCCGCCGCGGCTGGGAGGCCCTG |
| Val127-Asn195 | (2121) | CATCGTGGAGCTGCTGGGCCGCCGCGGCTGGGAGGCCCTG |
| Val120-Ile201B | (2079) | CATCGTGGAGCTGCTGGGCCGCCGCGGCTGGGAGGCCCTG |
| Val120-Ala204 | (2073) | CATCGTGGAGCTGCTGGGCCGCCGCGGCTGGGAGGCCCTG |
| Val120-Ile201 | (2079) | CATCGTGGAGCTGCTGGGCCGCCGCGGCTGGGAGGCCCTG |
| Val120-Thr202 | (2079) | CATCGTGGAGCTGCTGGGCCGCCGCGGCTGGGAGGCCCTG |
| Lys121-Val200 | (2085) | CATCGTGGAGCTGCTGGGCCGCCGCGGCTGGGAGGCCCTG |
| Consensus | (2121) | CATCGTGGAGCTGCTGGGCCGCCGCGGCTGGGAGGCCCTG |
| | | 2161 2200 |
| Leu122-Ser199 | (2131) | AAGTACTGGGGCAACCTGCTGCAGTACTGGATCCAGGAGC |
| Val127-Asn195 | (2161) | AAGTACTGGGGCAACCTGCTGCAGTACTGGATCCAGGAGC |
| Val120-Ile201B | (2119) | AAGTACTGGGGCAACCTGCTGCAGTACTGGATCCAGGAGC |
| Val120-Ala204 | (2113) | AAGTACTGGGGCAACCTGCTGCAGTACTGGATCCAGGAGC |
| Val120-Ile201 | (2119) | AAGTACTGGGGCAACCTGCTGCAGTACTGGATCCAGGAGC |
| Val120-Thr202 | (2119) | AAGTACTGGGGCAACCTGCTGCAGTACTGGATCCAGGAGC |
| Lys121-Val200 | (2125) | AAGTACTGGGGCAACCTGCTGCAGTACTGGATCCAGGAGC |
| Consensus | (2161) | AAGTACTGGGGCAACCTGCTGCAGTACTGGATCCAGGAGC |
| | | 2201 2240 |
| Leu122-Ser199 | (2171) | TGAAGAACAGCGCCGTGAGCCTGTTCGACGCCATCGCCAT |
| Val127-Asn195 | (2201) | TGAAGAACAGCGCCGTGAGCCTGTTCGACGCCATCGCCAT |
| Val120-Ile201B | (2159) | TGAAGAACAGCGCCGTGAGCCTGTTCGACGCCATCGCCAT |
| Val120-Ala204 | (2153) | TGAAGAACAGCGCCGTGAGCCTGTTCGACGCCATCGCCAT |
| Val120-Ile201 | (2159) | TGAAGAACAGCGCCGTGAGCCTGTTCGACGCCATCGCCAT |
| Val120-Thr202 | (2159) | TGAAGAACAGCGCCGTGAGCCTGTTCGACGCCATCGCCAT |
| Lys121-Val200 | (2165) | TGAAGAACAGCGCCGTGAGCCTGTTCGACGCCATCGCCAT |
| Consensus | (2201) | TGAAGAACAGCGCCGTGAGCCTGTTCGACGCCATCGCCAT |
| | | 2241 2280 |
| Leu122-Ser199 | (2211) | CGCCGTGGCCGAGGGCACCGACCGCATCATCGAGGTGGCC |
| Val127-Asn195 | (2241) | CGCCGTGGCCGAGGGCACCGACCGCATCATCGAGGTGGCC |
| Val120-Ile201B | (2199) | CGCCGTGGCCGAGGGCACCGACCGCATCATCGAGGTGGCC |
| Val120-Ala204 | (2193) | CGCCGTGGCCGAGGGCACCGACCGCATCATCGAGGTGGCC |
| Val120-Ile201 | (2199) | CGCCGTGGCCGAGGGCACCGACCGCATCATCGAGGTGGCC |
| Val120-Thr202 | (2199) | CGCCGTGGCCGAGGGCACCGACCGCATCATCGAGGTGGCC |
| Lys121-Val200 | (2205) | CGCCGTGGCCGAGGGCACCGACCGCATCATCGAGGTGGCC |
| Consensus | (2241) | CGCCGTGGCCGAGGGCACCGACCGCATCATCGAGGTGGCC |

FIG. 3I

| | | 2281 2320 |
|---|---|---|
| Leu122-Ser199 | (2251) | CAGCGCATCGGCCGCGCCTTCCTGCACATCCCCCGCCGCA |
| Val127-Asn195 | (2281) | CAGCGCATCGGCCGCGCCTTCCTGCACATCCCCCGCCGCA |
| Val120-Ile201B | (2239) | CAGCGCATCGGCCGCGCCTTCCTGCACATCCCCCGCCGCA |
| Val120-Ala204 | (2233) | CAGCGCATCGGCCGCGCCTTCCTGCACATCCCCCGCCGCA |
| Val120-Ile201 | (2239) | CAGCGCATCGGCCGCGCCTTCCTGCACATCCCCCGCCGCA |
| Val120-Thr202 | (2239) | CAGCGCATCGGCCGCGCCTTCCTGCACATCCCCCGCCGCA |
| Lys121-Val200 | (2245) | CAGCGCATCGGCCGCGCCTTCCTGCACATCCCCCGCCGCA |
| Consensus | (2281) | CAGCGCATCGGCCGCGCCTTCCTGCACATCCCCCGCCGCA |
| | | 2321 2360 |
| Leu122-Ser199 | (2291) | TCCGCCAGGGCTTCGAGCGCGCCCTGCTGTAACTCGAGCG |
| Val127-Asn195 | (2321) | TCCGCCAGGGCTTCGAGCGCGCCCTGCTGTAACTCGAG-- |
| Val120-Ile201B | (2279) | TCCGCCAGGGCTTCGAGCGCGCCCTGCTGTAACTCGAGCG |
| Val120-Ala204 | (2273) | TCCGCCAGGGCTTCGAGCGCGCCCTGCTGTAACTCGAG-- |
| Val120-Ile201 | (2279) | TCCGCCAGGGCTTCGAGCGCGCCCTGCTGTAACTCGAG-- |
| Val120-Thr202 | (2279) | TCCGCCAGGGCTTCGAGCGCGCCCTGCTGTAACTCGAG-- |
| Lys121-Val200 | (2285) | TCCGCCAGGGCTTCGAGCGCGCCCTGCTGTAACTCGAGCG |
| Consensus | (2321) | TCCGCCAGGGCTTCGAGCGCGCCCTGCTGTAACTCGAG |
| | | 2361 |
| Leu122-Ser199 | (2331) | TGCT |
| Val127-Asn195 | (2359) | ---- |
| Val120-Ile201B | (2319) | TGCT |
| Val120-Ala204 | (2311) | ---- |
| Val120-Ile201 | (2317) | ---- |
| Val120-Thr202 | (2317) | ---- |
| Lys121-Val200 | (2325) | TGCT |
| Consensus | (2361) | |

FIG. 3J

| | | |
|---|---|---|
| | | 1 40 |
| Ile424-Ala433 | (1) | GAATTCGCCACCATGGATGCAATGAAGAGAGGGCTCTGCT |
| Trp427-Gly431 | (1) | GAATTCGCCACCATGGATGCAATGAAGAGAGGGCTCTGCT |
| Gln422-Tyr435B | (1) | GAATTCGCCACCATGGATGCAATGAAGAGAGGGCTCTGCT |
| Arg426-Gly431 | (1) | GAATTCGCCACCATGGATGCAATGAAGAGAGGGCTCTGCT |
| Ile423-Met434 | (1) | GAATTCGCCACCATGGATGCAATGAAGAGAGGGCTCTGCT |
| Gln422-Tyr435 | (1) | GAATTCGCCACCATGGATGCAATGAAGAGAGGGCTCTGCT |
| Arg426-Lys432 | (1) | GAATTCGCCACCATGGATGCAATGAAGAGAGGGCTCTGCT |
| Arg426-Gly431B | (1) | GAATTCGCCACCATGGATGCAATGAAGAGAGGGCTCTGCT |
| Asn425-Lys432 | (1) | GAATTCGCCACCATGGATGCAATGAAGAGAGGGCTCTGCT |
| Consensus | (1) | GAATTCGCCACCATGGATGCAATGAAGAGAGGGCTCTGCT |
| | | 41 80 |
| Ile424-Ala433 | (41) | GTGTGCTGCTGCTGTGTGGAGCAGTCTTCGTTTCGCCCAG |
| Trp427-Gly431 | (41) | GTGTGCTGCTGCTGTGTGGAGCAGTCTTCGTTTCGCCCAG |
| Gln422-Tyr435B | (41) | GTGTGCTGCTGCTGTGTGGAGCAGTCTTCGTTTCGCCCAG |
| Arg426-Gly431 | (41) | GTGTGCTGCTGCTGTGTGGAGCAGTCTTCGTTTCGCCCAG |
| Ile423-Met434 | (41) | GTGTGCTGCTGCTGTGTGGAGCAGTCTTCGTTTCGCCCAG |
| Gln422-Tyr435 | (41) | GTGTGCTGCTGCTGTGTGGAGCAGTCTTCGTTTCGCCCAG |
| Arg426-Lys432 | (41) | GTGTGCTGCTGCTGTGTGGAGCAGTCTTCGTTTCGCCCAG |
| Arg426-Gly431B | (41) | GTGTGCTGCTGCTGTGTGGAGCAGTCTTCGTTTCGCCCAG |
| Asn425-Lys432 | (41) | GTGTGCTGCTGCTGTGTGGAGCAGTCTTCGTTTCGCCCAG |
| Consensus | (41) | GTGTGCTGCTGCTGTGTGGAGCAGTCTTCGTTTCGCCCAG |
| | | 81 120 |
| Ile424-Ala433 | (81) | CGCCGTGGAGAAGCTGTGGGTGACCGTGTACTACGGCGTG |
| Trp427-Gly431 | (81) | CGCCGTGGAGAAGCTGTGGGTGACCGTGTACTACGGCGTG |
| Gln422-Tyr435B | (81) | CGCCGTGGAGAAGCTGTGGGTGACCGTGTACTACGGCGTG |
| Arg426-Gly431 | (81) | CGCCGTGGAGAAGCTGTGGGTGACCGTGTACTACGGCGTG |
| Ile423-Met434 | (81) | CGCCGTGGAGAAGCTGTGGGTGACCGTGTACTACGGCGTG |
| Gln422-Tyr435 | (81) | CGCCGTGGAGAAGCTGTGGGTGACCGTGTACTACGGCGTG |
| Arg426-Lys432 | (81) | CGCCGTGGAGAAGCTGTGGGTGACCGTGTACTACGGCGTG |
| Arg426-Gly431B | (81) | CGCCGTGGAGAAGCTGTGGGTGACCGTGTACTACGGCGTG |
| Asn425-Lys432 | (81) | CGCCGTGGAGAAGCTGTGGGTGACCGTGTACTACGGCGTG |
| Consensus | (81) | CGCCGTGGAGAAGCTGTGGGTGACCGTGTACTACGGCGTG |
| | | 121 160 |
| Ile424-Ala433 | (121) | CCCGTGTGGAAGGAGGCCACCACCACCCTGTTCTGCGCCA |
| Trp427-Gly431 | (121) | CCCGTGTGGAAGGAGGCCACCACCACCCTGTTCTGCGCCA |
| Gln422-Tyr435B | (121) | CCCGTGTGGAAGGAGGCCACCACCACCCTGTTCTGCGCCA |
| Arg426-Gly431 | (121) | CCCGTGTGGAAGGAGGCCACCACCACCCTGTTCTGCGCCA |
| Ile423-Met434 | (121) | CCCGTGTGGAAGGAGGCCACCACCACCCTGTTCTGCGCCA |
| Gln422-Tyr435 | (121) | CCCGTGTGGAAGGAGGCCACCACCACCCTGTTCTGCGCCA |
| Arg426-Lys432 | (121) | CCCGTGTGGAAGGAGGCCACCACCACCCTGTTCTGCGCCA |
| Arg426-Gly431B | (121) | CCCGTGTGGAAGGAGGCCACCACCACCCTGTTCTGCGCCA |
| Asn425-Lys432 | (121) | CCCGTGTGGAAGGAGGCCACCACCACCCTGTTCTGCGCCA |
| Consensus | (121) | CCCGTGTGGAAGGAGGCCACCACCACCCTGTTCTGCGCCA |
| | | 161 200 |
| Ile424-Ala433 | (161) | GCGACGCCAAGGCCTACGACACCGAGGTGCACAACGTGTG |
| Trp427-Gly431 | (161) | GCGACGCCAAGGCCTACGACACCGAGGTGCACAACGTGTG |
| Gln422-Tyr435B | (161) | GCGACGCCAAGGCCTACGACACCGAGGTGCACAACGTGTG |
| Arg426-Gly431 | (161) | GCGACGCCAAGGCCTACGACACCGAGGTGCACAACGTGTG |
| Ile423-Met434 | (161) | GCGACGCCAAGGCCTACGACACCGAGGTGCACAACGTGTG |
| Gln422-Tyr435 | (161) | GCGACGCCAAGGCCTACGACACCGAGGTGCACAACGTGTG |
| Arg426-Lys432 | (161) | GCGACGCCAAGGCCTACGACACCGAGGTGCACAACGTGTG |
| Arg426-Gly431B | (161) | GCGACGCCAAGGCCTACGACACCGAGGTGCACAACGTGTG |
| Asn425-Lys432 | (161) | GCGACGCCAAGGCCTACGACACCGAGGTGCACAACGTGTG |
| Consensus | (161) | GCGACGCCAAGGCCTACGACACCGAGGTGCACAACGTGTG |
| | | 201 240 |
| Ile424-Ala433 | (201) | GGCCACCCACGCCTGCGTGCCCACCGACCCCAACCCCCAG |

*FIG. 4A*

```
Trp427-Gly431     (201) GGCCACCCACGCCTGCGTGCCCACCGACCCCAACCCCCAG
Gln422-Tyr435B    (201) GGCCACCCACGCCTGCGTGCCCACCGACCCCAACCCCCAG
Arg426-Gly431     (201) GGCCACCCACGCCTGCGTGCCCACCGACCCCAACCCCCAG
Ile423-Met434     (201) GGCCACCCACGCCTGCGTGCCCACCGACCCCAACCCCCAG
Gln422-Tyr435     (201) GGCCACCCACGCCTGCGTGCCCACCGACCCCAACCCCCAG
Arg426-Lys432     (201) GGCCACCCACGCCTGCGTGCCCACCGACCCCAACCCCCAG
Arg426-Gly431B    (201) GGCCACCCACGCCTGCGTGCCCACCGACCCCAACCCCCAG
Asn425-Lys432     (201) GGCCACCCACGCCTGCGTGCCCACCGACCCCAACCCCCAG
Consensus         (201) GGCCACCCACGCCTGCGTGCCCACCGACCCCAACCCCCAG
                        241                                  280
Ile424-Ala433     (241) GAGATCGTGCTGGAGAACGTGACCGAGAACTTCAACATGT
Trp427-Gly431     (241) GAGATCGTGCTGGAGAACGTGACCGAGAACTTCAACATGT
Gln422-Tyr435B    (241) GAGATCGTGCTGGAGAACGTGACCGAGAACTTCAACATGT
Arg426-Gly431     (241) GAGATCGTGCTGGAGAACGTGACCGAGAACTTCAACATGT
Ile423-Met434     (241) GAGATCGTGCTGGAGAACGTGACCGAGAACTTCAACATGT
Gln422-Tyr435     (241) GAGATCGTGCTGGAGAACGTGACCGAGAACTTCAACATGT
Arg426-Lys432     (241) GAGATCGTGCTGGAGAACGTGACCGAGAACTTCAACATGT
Arg426-Gly431B    (241) GAGATCGTGCTGGAGAACGTGACCGAGAACTTCAACATGT
Asn425-Lys432     (241) GAGATCGTGCTGGAGAACGTGACCGAGAACTTCAACATGT
Consensus         (241) GAGATCGTGCTGGAGAACGTGACCGAGAACTTCAACATGT
                        281                                  320
Ile424-Ala433     (281) GGAAGAACAACATGGTGGAGCAGATGCACGAGGACATCAT
Trp427-Gly431     (281) GGAAGAACAACATGGTGGAGCAGATGCACGAGGACATCAT
Gln422-Tyr435B    (281) GGAAGAACAACATGGTGGAGCAGATGCACGAGGACATCAT
Arg426-Gly431     (281) GGAAGAACAACATGGTGGAGCAGATGCACGAGGACATCAT
Ile423-Met434     (281) GGAAGAACAACATGGTGGAGCAGATGCACGAGGACATCAT
Gln422-Tyr435     (281) GGAAGAACAACATGGTGGAGCAGATGCACGAGGACATCAT
Arg426-Lys432     (281) GGAAGAACAACATGGTGGAGCAGATGCACGAGGACATCAT
Arg426-Gly431B    (281) GGAAGAACAACATGGTGGAGCAGATGCACGAGGACATCAT
Asn425-Lys432     (281) GGAAGAACAACATGGTGGAGCAGATGCACGAGGACATCAT
Consensus         (281) GGAAGAACAACATGGTGGAGCAGATGCACGAGGACATCAT
                        321                                  360
Ile424-Ala433     (321) CAGCCTGTGGGACCAGAGCCTGAAGCCCTGCGTGAAGCTG
Trp427-Gly431     (321) CAGCCTGTGGGACCAGAGCCTGAAGCCCTGCGTGAAGCTG
Gln422-Tyr435B    (321) CAGCCTGTGGGACCAGAGCCTGAAGCCCTGCGTGAAGCTG
Arg426-Gly431     (321) CAGCCTGTGGGACCAGAGCCTGAAGCCCTGCGTGAAGCTG
Ile423-Met434     (321) CAGCCTGTGGGACCAGAGCCTGAAGCCCTGCGTGAAGCTG
Gln422-Tyr435     (321) CAGCCTGTGGGACCAGAGCCTGAAGCCCTGCGTGAAGCTG
Arg426-Lys432     (321) CAGCCTGTGGGACCAGAGCCTGAAGCCCTGCGTGAAGCTG
Arg426-Gly431B    (321) CAGCCTGTGGGACCAGAGCCTGAAGCCCTGCGTGAAGCTG
Asn425-Lys432     (321) CAGCCTGTGGGACCAGAGCCTGAAGCCCTGCGTGAAGCTG
Consensus         (321) CAGCCTGTGGGACCAGAGCCTGAAGCCCTGCGTGAAGCTG
                        361                                  400
Ile424-Ala433     (361) ACCCCCCTGTGCGTGACCCTGCACTGCACCAACCTGAAGA
Trp427-Gly431     (361) ACCCCCCTGTGCGTGACCCTGCACTGCACCAACCTGAAGA
Gln422-Tyr435B    (361) ACCCCCCTGTGCGTGACCCTGCACTGCACCAACCTGAAGA
Arg426-Gly431     (361) ACCCCCCTGTGCGTGACCCTGCACTGCACCAACCTGAAGA
Ile423-Met434     (361) ACCCCCCTGTGCGTGACCCTGCACTGCACCAACCTGAAGA
Gln422-Tyr435     (361) ACCCCCCTGTGCGTGACCCTGCACTGCACCAACCTGAAGA
Arg426-Lys432     (361) ACCCCCCTGTGCGTGACCCTGCACTGCACCAACCTGAAGA
Arg426-Gly431B    (361) ACCCCCCTGTGCGTGACCCTGCACTGCACCAACCTGAAGA
Asn425-Lys432     (361) ACCCCCCTGTGCGTGACCCTGCACTGCACCAACCTGAAGA
Consensus         (361) ACCCCCCTGTGCGTGACCCTGCACTGCACCAACCTGAAGA
                        401                                  440
Ile424-Ala433     (401) ACGCCACCAACACCAAGAGCAGCAACTGGAAGGAGATGGA
Trp427-Gly431     (401) ACGCCACCAACACCAAGAGCAGCAACTGGAAGGAGATGGA
Gln422-Tyr435B    (401) ACGCCACCAACACCAAGAGCAGCAACTGGAAGGAGATGGA
```

FIG. 4B

| | | |
|---|---|---|
| Arg426-Gly431 | (401) | ACGCCACCAACACCAAGAGCAGCAACTGGAAGGAGATGGA |
| Ile423-Met434 | (401) | ACGCCACCAACACCAAGAGCAGCAACTGGAAGGAGATGGA |
| Gln422-Tyr435 | (401) | ACGCCACCAACACCAAGAGCAGCAACTGGAAGGAGATGGA |
| Arg426-Lys432 | (401) | ACGCCACCAACACCAAGAGCAGCAACTGGAAGGAGATGGA |
| Arg426-Gly431B | (401) | ACGCCACCAACACCAAGAGCAGCAACTGGAAGGAGATGGA |
| Asn425-Lys432 | (401) | ACGCCACCAACACCAAGAGCAGCAACTGGAAGGAGATGGA |
| Consensus | (401) | ACGCCACCAACACCAAGAGCAGCAACTGGAAGGAGATGGA |
| | | 441 480 |
| Ile424-Ala433 | (441) | CCGCGGCGAGATCAAGAACTGCAGCTTCAAGGTGACCACC |
| Trp427-Gly431 | (441) | CCGCGGCGAGATCAAGAACTGCAGCTTCAAGGTGACCACC |
| Gln422-Tyr435B | (441) | CCGCGGCGAGATCAAGAACTGCAGCTTCAAGGTGACCACC |
| Arg426-Gly431 | (441) | CCGCGGCGAGATCAAGAACTGCAGCTTCAAGGTGACCACC |
| Ile423-Met434 | (441) | CCGCGGCGAGATCAAGAACTGCAGCTTCAAGGTGACCACC |
| Gln422-Tyr435 | (441) | CCGCGGCGAGATCAAGAACTGCAGCTTCAAGGTGACCACC |
| Arg426-Lys432 | (441) | CCGCGGCGAGATCAAGAACTGCAGCTTCAAGGTGACCACC |
| Arg426-Gly431B | (441) | CCGCGGCGAGATCAAGAACTGCAGCTTCAAGGTGACCACC |
| Asn425-Lys432 | (441) | CCGCGGCGAGATCAAGAACTGCAGCTTCAAGGTGACCACC |
| Consensus | (441) | CCGCGGCGAGATCAAGAACTGCAGCTTCAAGGTGACCACC |
| | | 481 520 |
| Ile424-Ala433 | (481) | AGCATCCGCAACAAGATGCAGAAGGAGTACGCCCTGTTCT |
| Trp427-Gly431 | (481) | AGCATCCGCAACAAGATGCAGAAGGAGTACGCCCTGTTCT |
| Gln422-Tyr435B | (481) | AGCATCCGCAACAAGATGCAGAAGGAGTACGCCCTGTTCT |
| Arg426-Gly431 | (481) | AGCATCCGCAACAAGATGCAGAAGGAGTACGCCCTGTTCT |
| Ile423-Met434 | (481) | AGCATCCGCAACAAGATGCAGAAGGAGTACGCCCTGTTCT |
| Gln422-Tyr435 | (481) | AGCATCCGCAACAAGATGCAGAAGGAGTACGCCCTGTTCT |
| Arg426-Lys432 | (481) | AGCATCCGCAACAAGATGCAGAAGGAGTACGCCCTGTTCT |
| Arg426-Gly431B | (481) | AGCATCCGCAACAAGATGCAGAAGGAGTACGCCCTGTTCT |
| Asn425-Lys432 | (481) | AGCATCCGCAACAAGATGCAGAAGGAGTACGCCCTGTTCT |
| Consensus | (481) | AGCATCCGCAACAAGATGCAGAAGGAGTACGCCCTGTTCT |
| | | 521 560 |
| Ile424-Ala433 | (521) | ACAAGCTGGACGTGGTGCCCATCGACAACGACAACACCAG |
| Trp427-Gly431 | (521) | ACAAGCTGGACGTGGTGCCCATCGACAACGACAACACCAG |
| Gln422-Tyr435B | (521) | ACAAGCTGGACGTGGTGCCCATCGACAACGACAACACCAG |
| Arg426-Gly431 | (521) | ACAAGCTGGACGTGGTGCCCATCGACAACGACAACACCAG |
| Ile423-Met434 | (521) | ACAAGCTGGACGTGGTGCCCATCGACAACGACAACACCAG |
| Gln422-Tyr435 | (521) | ACAAGCTGGACGTGGTGCCCATCGACAACGACAACACCAG |
| Arg426-Lys432 | (521) | ACAAGCTGGACGTGGTGCCCATCGACAACGACAACACCAG |
| Arg426-Gly431B | (521) | ACAAGCTGGACGTGGTGCCCATCGACAACGACAACACCAG |
| Asn425-Lys432 | (521) | ACAAGCTGGACGTGGTGCCCATCGACAACGACAACACCAG |
| Consensus | (521) | ACAAGCTGGACGTGGTGCCCATCGACAACGACAACACCAG |
| | | 561 600 |
| Ile424-Ala433 | (561) | CTACAAGCTGATCAACTGCAACACCAGCGTGATCACCCAG |
| Trp427-Gly431 | (561) | CTACAAGCTGATCAACTGCAACACCAGCGTGATCACCCAG |
| Gln422-Tyr435B | (561) | CTACAAGCTGATCAACTGCAACACCAGCGTGATCACCCAG |
| Arg426-Gly431 | (561) | CTACAAGCTGATCAACTGCAACACCAGCGTGATCACCCAG |
| Ile423-Met434 | (561) | CTACAAGCTGATCAACTGCAACACCAGCGTGATCACCCAG |
| Gln422-Tyr435 | (561) | CTACAAGCTGATCAACTGCAACACCAGCGTGATCACCCAG |
| Arg426-Lys432 | (561) | CTACAAGCTGATCAACTGCAACACCAGCGTGATCACCCAG |
| Arg426-Gly431B | (561) | CTACAAGCTGATCAACTGCAACACCAGCGTGATCACCCAG |
| Asn425-Lys432 | (561) | CTACAAGCTGATCAACTGCAACACCAGCGTGATCACCCAG |
| Consensus | (561) | CTACAAGCTGATCAACTGCAACACCAGCGTGATCACCCAG |
| | | 601 640 |
| Ile424-Ala433 | (601) | GCCTGCCCCAAGGTGAGCTTCGAGCCCATCCCCATCCACT |
| Trp427-Gly431 | (601) | GCCTGCCCCAAGGTGAGCTTCGAGCCCATCCCCATCCACT |
| Gln422-Tyr435B | (601) | GCCTGCCCCAAGGTGAGCTTCGAGCCCATCCCCATCCACT |
| Arg426-Gly431 | (601) | GCCTGCCCCAAGGTGAGCTTCGAGCCCATCCCCATCCACT |
| Ile423-Met434 | (601) | GCCTGCCCCAAGGTGAGCTTCGAGCCCATCCCCATCCACT |

*FIG. 4C*

```
 Gln422-Tyr435   (601) GCCTGCCCCAAGGTGAGCTTCGAGCCCATCCCCATCCACT
 Arg426-Lys432   (601) GCCTGCCCCAAGGTGAGCTTCGAGCCCATCCCCATCCACT
Arg426-Gly431B   (601) GCCTGCCCCAAGGTGAGCTTCGAGCCCATCCCCATCCACT
 Asn425-Lys432   (601) GCCTGCCCCAAGGTGAGCTTCGAGCCCATCCCCATCCACT
     Consensus   (601) GCCTGCCCCAAGGTGAGCTTCGAGCCCATCCCCATCCACT
                       641                                   680
 Ile424-Ala433   (641) ACTGCGCCCCCGCCGGCTTCGCCATCCTGAAGTGCAACGA
 Trp427-Gly431   (641) ACTGCGCCCCCGCCGGCTTCGCCATCCTGAAGTGCAACGA
Gln422-Tyr435B   (641) ACTGCGCCCCCGCCGGCTTCGCCATCCTGAAGTGCAACGA
 Arg426-Gly431   (641) ACTGCGCCCCCGCCGGCTTCGCCATCCTGAAGTGCAACGA
 Ile423-Met434   (641) ACTGCGCCCCCGCCGGCTTCGCCATCCTGAAGTGCAACGA
 Gln422-Tyr435   (641) ACTGCGCCCCCGCCGGCTTCGCCATCCTGAAGTGCAACGA
 Arg426-Lys432   (641) ACTGCGCCCCCGCCGGCTTCGCCATCCTGAAGTGCAACGA
Arg426-Gly431B   (641) ACTGCGCCCCCGCCGGCTTCGCCATCCTGAAGTGCAACGA
 Asn425-Lys432   (641) ACTGCGCCCCCGCCGGCTTCGCCATCCTGAAGTGCAACGA
     Consensus   (641) ACTGCGCCCCCGCCGGCTTCGCCATCCTGAAGTGCAACGA
                       681                                   720
 Ile424-Ala433   (681) CAAGAAGTTCAACGGCAGCGGCCCCTGCACCAACGTGAGC
 Trp427-Gly431   (681) CAAGAAGTTCAACGGCAGCGGCCCCTGCACCAACGTGAGC
Gln422-Tyr435B   (681) CAAGAAGTTCAACGGCAGCGGCCCCTGCACCAACGTGAGC
 Arg426-Gly431   (681) CAAGAAGTTCAACGGCAGCGGCCCCTGCACCAACGTGAGC
 Ile423-Met434   (681) CAAGAAGTTCAACGGCAGCGGCCCCTGCACCAACGTGAGC
 Gln422-Tyr435   (681) CAAGAAGTTCAACGGCAGCGGCCCCTGCACCAACGTGAGC
 Arg426-Lys432   (681) CAAGAAGTTCAACGGCAGCGGCCCCTGCACCAACGTGAGC
Arg426-Gly431B   (681) CAAGAAGTTCAACGGCAGCGGCCCCTGCACCAACGTGAGC
 Asn425-Lys432   (681) CAAGAAGTTCAACGGCAGCGGCCCCTGCACCAACGTGAGC
     Consensus   (681) CAAGAAGTTCAACGGCAGCGGCCCCTGCACCAACGTGAGC
                       721                                   760
 Ile424-Ala433   (721) ACCGTGCAGTGCACCCACGGCATCCGCCCCGTGGTGAGCA
 Trp427-Gly431   (721) ACCGTGCAGTGCACCCACGGCATCCGCCCCGTGGTGAGCA
Gln422-Tyr435B   (721) ACCGTGCAGTGCACCCACGGCATCCGCCCCGTGGTGAGCA
 Arg426-Gly431   (721) ACCGTGCAGTGCACCCACGGCATCCGCCCCGTGGTGAGCA
 Ile423-Met434   (721) ACCGTGCAGTGCACCCACGGCATCCGCCCCGTGGTGAGCA
 Gln422-Tyr435   (721) ACCGTGCAGTGCACCCACGGCATCCGCCCCGTGGTGAGCA
 Arg426-Lys432   (721) ACCGTGCAGTGCACCCACGGCATCCGCCCCGTGGTGAGCA
Arg426-Gly431B   (721) ACCGTGCAGTGCACCCACGGCATCCGCCCCGTGGTGAGCA
 Asn425-Lys432   (721) ACCGTGCAGTGCACCCACGGCATCCGCCCCGTGGTGAGCA
     Consensus   (721) ACCGTGCAGTGCACCCACGGCATCCGCCCCGTGGTGAGCA
                       761                                   800
 Ile424-Ala433   (761) CCCAGCTGCTGCTGAACGGCAGCCTGGCCGAGGAGGGCGT
 Trp427-Gly431   (761) CCCAGCTGCTGCTGAACGGCAGCCTGGCCGAGGAGGGCGT
Gln422-Tyr435B   (761) CCCAGCTGCTGCTGAACGGCAGCCTGGCCGAGGAGGGCGT
 Arg426-Gly431   (761) CCCAGCTGCTGCTGAACGGCAGCCTGGCCGAGGAGGGCGT
 Ile423-Met434   (761) CCCAGCTGCTGCTGAACGGCAGCCTGGCCGAGGAGGGCGT
 Gln422-Tyr435   (761) CCCAGCTGCTGCTGAACGGCAGCCTGGCCGAGGAGGGCGT
 Arg426-Lys432   (761) CCCAGCTGCTGCTGAACGGCAGCCTGGCCGAGGAGGGCGT
Arg426-Gly431B   (761) CCCAGCTGCTGCTGAACGGCAGCCTGGCCGAGGAGGGCGT
 Asn425-Lys432   (761) CCCAGCTGCTGCTGAACGGCAGCCTGGCCGAGGAGGGCGT
     Consensus   (761) CCCAGCTGCTGCTGAACGGCAGCCTGGCCGAGGAGGGCGT
                       801                                   840
 Ile424-Ala433   (801) GGTGATCCGCAGCGAGAACTTCACCGACAACGCCAAGACC
 Trp427-Gly431   (801) GGTGATCCGCAGCGAGAACTTCACCGACAACGCCAAGACC
Gln422-Tyr435B   (801) GGTGATCCGCAGCGAGAACTTCACCGACAACGCCAAGACC
 Arg426-Gly431   (801) GGTGATCCGCAGCGAGAACTTCACCGACAACGCCAAGACC
 Ile423-Met434   (801) GGTGATCCGCAGCGAGAACTTCACCGACAACGCCAAGACC
 Gln422-Tyr435   (801) GGTGATCCGCAGCGAGAACTTCACCGACAACGCCAAGACC
 Arg426-Lys432   (801) GGTGATCCGCAGCGAGAACTTCACCGACAACGCCAAGACC
```

*FIG. 4D*

| | | |
|---|---|---|
| Arg426-Gly431B | (801) | GGTGATCCGCAGCGAGAACTTCACCGACAACGCCAAGACC |
| Asn425-Lys432 | (801) | GGTGATCCGCAGCGAGAACTTCACCGACAACGCCAAGACC |
| Consensus | (801) | GGTGATCCGCAGCGAGAACTTCACCGACAACGCCAAGACC |
| | | 841 880 |
| Ile424-Ala433 | (841) | ATCATCGTGCAGCTGAAGGAGAGCGTGGAGATCAACTGCA |
| Trp427-Gly431 | (841) | ATCATCGTGCAGCTGAAGGAGAGCGTGGAGATCAACTGCA |
| Gln422-Tyr435B | (841) | ATCATCGTGCAGCTGAAGGAGAGCGTGGAGATCAACTGCA |
| Arg426-Gly431 | (841) | ATCATCGTGCAGCTGAAGGAGAGCGTGGAGATCAACTGCA |
| Ile423-Met434 | (841) | ATCATCGTGCAGCTGAAGGAGAGCGTGGAGATCAACTGCA |
| Gln422-Tyr435 | (841) | ATCATCGTGCAGCTGAAGGAGAGCGTGGAGATCAACTGCA |
| Arg426-Lys432 | (841) | ATCATCGTGCAGCTGAAGGAGAGCGTGGAGATCAACTGCA |
| Arg426-Gly431B | (841) | ATCATCGTGCAGCTGAAGGAGAGCGTGGAGATCAACTGCA |
| Asn425-Lys432 | (841) | ATCATCGTGCAGCTGAAGGAGAGCGTGGAGATCAACTGCA |
| Consensus | (841) | ATCATCGTGCAGCTGAAGGAGAGCGTGGAGATCAACTGCA |
| | | 881 920 |
| Ile424-Ala433 | (881) | CCCGCCCCAACAACAACACCCGCAAGAGCATCACCATCGG |
| Trp427-Gly431 | (881) | CCCGCCCCAACAACAACACCCGCAAGAGCATCACCATCGG |
| Gln422-Tyr435B | (881) | CCCGCCCCAACAACAACACCCGCAAGAGCATCACCATCGG |
| Arg426-Gly431 | (881) | CCCGCCCCAACAACAACACCCGCAAGAGCATCACCATCGG |
| Ile423-Met434 | (881) | CCCGCCCCAACAACAACACCCGCAAGAGCATCACCATCGG |
| Gln422-Tyr435 | (881) | CCCGCCCCAACAACAACACCCGCAAGAGCATCACCATCGG |
| Arg426-Lys432 | (881) | CCCGCCCCAACAACAACACCCGCAAGAGCATCACCATCGG |
| Arg426-Gly431B | (881) | CCCGCCCCAACAACAACACCCGCAAGAGCATCACCATCGG |
| Asn425-Lys432 | (881) | CCCGCCCCAACAACAACACCCGCAAGAGCATCACCATCGG |
| Consensus | (881) | CCCGCCCCAACAACAACACCCGCAAGAGCATCACCATCGG |
| | | 921 960 |
| Ile424-Ala433 | (921) | CCCCGGCCGCGCCTTCTACGCCACCGGCGACATCATCGGC |
| Trp427-Gly431 | (921) | CCCCGGCCGCGCCTTCTACGCCACCGGCGACATCATCGGC |
| Gln422-Tyr435B | (921) | CCCCGGCCGCGCCTTCTACGCCACCGGCGACATCATCGGC |
| Arg426-Gly431 | (921) | CCCCGGCCGCGCCTTCTACGCCACCGGCGACATCATCGGC |
| Ile423-Met434 | (921) | CCCCGGCCGCGCCTTCTACGCCACCGGCGACATCATCGGC |
| Gln422-Tyr435 | (921) | CCCCGGCCGCGCCTTCTACGCCACCGGCGACATCATCGGC |
| Arg426-Lys432 | (921) | CCCCGGCCGCGCCTTCTACGCCACCGGCGACATCATCGGC |
| Arg426-Gly431B | (921) | CCCCGGCCGCGCCTTCTACGCCACCGGCGACATCATCGGC |
| Asn425-Lys432 | (921) | CCCCGGCCGCGCCTTCTACGCCACCGGCGACATCATCGGC |
| Consensus | (921) | CCCCGGCCGCGCCTTCTACGCCACCGGCGACATCATCGGC |
| | | 961 1000 |
| Ile424-Ala433 | (961) | GACATCCGCCAGGCCCACTGCAACATCAGCGGCGAGAAGT |
| Trp427-Gly431 | (961) | GACATCCGCCAGGCCCACTGCAACATCAGCGGCGAGAAGT |
| Gln422-Tyr435B | (961) | GACATCCGCCAGGCCCACTGCAACATCAGCGGCGAGAAGT |
| Arg426-Gly431 | (961) | GACATCCGCCAGGCCCACTGCAACATCAGCGGCGAGAAGT |
| Ile423-Met434 | (961) | GACATCCGCCAGGCCCACTGCAACATCAGCGGCGAGAAGT |
| Gln422-Tyr435 | (961) | GACATCCGCCAGGCCCACTGCAACATCAGCGGCGAGAAGT |
| Arg426-Lys432 | (961) | GACATCCGCCAGGCCCACTGCAACATCAGCGGCGAGAAGT |
| Arg426-Gly431B | (961) | GACATCCGCCAGGCCCACTGCAACATCAGCGGCGAGAAGT |
| Asn425-Lys432 | (961) | GACATCCGCCAGGCCCACTGCAACATCAGCGGCGAGAAGT |
| Consensus | (961) | GACATCCGCCAGGCCCACTGCAACATCAGCGGCGAGAAGT |
| | | 1001 1040 |
| Ile424-Ala433 | (1001) | GGAACAACACCCTGAAGCAGATCGTGACCAAGCTGCAGGC |
| Trp427-Gly431 | (1001) | GGAACAACACCCTGAAGCAGATCGTGACCAAGCTGCAGGC |
| Gln422-Tyr435B | (1001) | GGAACAACACCCTGAAGCAGATCGTGACCAAGCTGCAGGC |
| Arg426-Gly431 | (1001) | GGAACAACACCCTGAAGCAGATCGTGACCAAGCTGCAGGC |
| Ile423-Met434 | (1001) | GGAACAACACCCTGAAGCAGATCGTGACCAAGCTGCAGGC |
| Gln422-Tyr435 | (1001) | GGAACAACACCCTGAAGCAGATCGTGACCAAGCTGCAGGC |
| Arg426-Lys432 | (1001) | GGAACAACACCCTGAAGCAGATCGTGACCAAGCTGCAGGC |
| Arg426-Gly431B | (1001) | GGAACAACACCCTGAAGCAGATCGTGACCAAGCTGCAGGC |
| Asn425-Lys432 | (1001) | GGAACAACACCCTGAAGCAGATCGTGACCAAGCTGCAGGC |

FIG. 4E

```
       Consensus  (1001) GGAACAACACCCTGAAGCAGATCGTGACCAAGCTGCAGGC
                         1041                                 1080
     Ile424-Ala433  (1041) CCAGTTCGGCAACAAGACCATCGTGTTCAAGCAGAGCAGC
     Trp427-Gly431  (1041) CCAGTTCGGCAACAAGACCATCGTGTTCAAGCAGAGCAGC
    Gln422-Tyr435B  (1041) CCAGTTCGGCAACAAGACCATCGTGTTCAAGCAGAGCAGC
     Arg426-Gly431  (1041) CCAGTTCGGCAACAAGACCATCGTGTTCAAGCAGAGCAGC
     Ile423-Met434  (1041) CCAGTTCGGCAACAAGACCATCGTGTTCAAGCAGAGCAGC
     Gln422-Tyr435  (1041) CCAGTTCGGCAACAAGACCATCGTGTTCAAGCAGAGCAGC
     Arg426-Lys432  (1041) CCAGTTCGGCAACAAGACCATCGTGTTCAAGCAGAGCAGC
    Arg426-Gly431B  (1041) CCAGTTCGGCAACAAGACCATCGTGTTCAAGCAGAGCAGC
     Asn425-Lys432  (1041) CCAGTTCGGCAACAAGACCATCGTGTTCAAGCAGAGCAGC
         Consensus  (1041) CCAGTTCGGCAACAAGACCATCGTGTTCAAGCAGAGCAGC
                           1081                                 1120
     Ile424-Ala433  (1081) GGCGGCGACCCCGAGATCGTGATGCACAGCTTCAACTGCG
     Trp427-Gly431  (1081) GGCGGCGACCCCGAGATCGTGATGCACAGCTTCAACTGCG
    Gln422-Tyr435B  (1081) GGCGGCGACCCCGAGATCGTGATGCACAGCTTCAACTGCG
     Arg426-Gly431  (1081) GGCGGCGACCCCGAGATCGTGATGCACAGCTTCAACTGCG
     Ile423-Met434  (1081) GGCGGCGACCCCGAGATCGTGATGCACAGCTTCAACTGCG
     Gln422-Tyr435  (1081) GGCGGCGACCCCGAGATCGTGATGCACAGCTTCAACTGCG
     Arg426-Lys432  (1081) GGCGGCGACCCCGAGATCGTGATGCACAGCTTCAACTGCG
    Arg426-Gly431B  (1081) GGCGGCGACCCCGAGATCGTGATGCACAGCTTCAACTGCG
     Asn425-Lys432  (1081) GGCGGCGACCCCGAGATCGTGATGCACAGCTTCAACTGCG
         Consensus  (1081) GGCGGCGACCCCGAGATCGTGATGCACAGCTTCAACTGCG
                           1121                                 1160
     Ile424-Ala433  (1121) GCGGCGAGTTCTTCTACTGCAACAGCACCCAGCTGTTCAA
     Trp427-Gly431  (1121) GCGGCGAGTTCTTCTACTGCAACAGCACCCAGCTGTTCAA
    Gln422-Tyr435B  (1121) GCGGCGAGTTCTTCTACTGCAACAGCACCCAGCTGTTCAA
     Arg426-Gly431  (1121) GCGGCGAGTTCTTCTACTGCAACAGCACCCAGCTGTTCAA
     Ile423-Met434  (1121) GCGGCGAGTTCTTCTACTGCAACAGCACCCAGCTGTTCAA
     Gln422-Tyr435  (1121) GCGGCGAGTTCTTCTACTGCAACAGCACCCAGCTGTTCAA
     Arg426-Lys432  (1121) GCGGCGAGTTCTTCTACTGCAACAGCACCCAGCTGTTCAA
    Arg426-Gly431B  (1121) GCGGCGAGTTCTTCTACTGCAACAGCACCCAGCTGTTCAA
     Asn425-Lys432  (1121) GCGGCGAGTTCTTCTACTGCAACAGCACCCAGCTGTTCAA
         Consensus  (1121) GCGGCGAGTTCTTCTACTGCAACAGCACCCAGCTGTTCAA
                           1161                                 1200
     Ile424-Ala433  (1161) CAGCACCTGGAACAACACCATCGGCCCCAACAACACCAAC
     Trp427-Gly431  (1161) CAGCACCTGGAACAACACCATCGGCCCCAACAACACCAAC
    Gln422-Tyr435B  (1161) CAGCACCTGGAACAACACCATCGGCCCCAACAACACCAAC
     Arg426-Gly431  (1161) CAGCACCTGGAACAACACCATCGGCCCCAACAACACCAAC
     Ile423-Met434  (1161) CAGCACCTGGAACAACACCATCGGCCCCAACAACACCAAC
     Gln422-Tyr435  (1161) CAGCACCTGGAACAACACCATCGGCCCCAACAACACCAAC
     Arg426-Lys432  (1161) CAGCACCTGGAACAACACCATCGGCCCCAACAACACCAAC
    Arg426-Gly431B  (1161) CAGCACCTGGAACAACACCATCGGCCCCAACAACACCAAC
     Asn425-Lys432  (1161) CAGCACCTGGAACAACACCATCGGCCCCAACAACACCAAC
         Consensus  (1161) CAGCACCTGGAACAACACCATCGGCCCCAACAACACCAAC
                           1201                                 1240
     Ile424-Ala433  (1201) GGCACCATCACCCTGCCCTGCCGCATCAAGCAGATCATC-
     Trp427-Gly431  (1201) GGCACCATCACCCTGCCCTGCCGCATCAAGCAGATCATCA
    Gln422-Tyr435B  (1201) GGCACCATCACCCTGCCCTGCCGCATCAAGCAG-------
     Arg426-Gly431  (1201) GGCACCATCACCCTGCCCTGCCGCATCAAGCAGATCATCA
     Ile423-Met434  (1201) GGCACCATCACCCTGCCCTGCCGCATCAAGCAGATC----
     Gln422-Tyr435  (1201) GGCACCATCACCCTGCCCTGCCGCATCAAGCAG-------
     Arg426-Lys432  (1201) GGCACCATCACCCTGCCCTGCCGCATCAAGCAGATCATCA
    Arg426-Gly431B  (1201) GGCACCATCACCCTGCCCTGCCGCATCAAGCAGATCATCA
     Asn425-Lys432  (1201) GGCACCATCACCCTGCCCTGCCGCATCAAGCAGATCATCA
         Consensus  (1201) GGCACCATCACCCTGCCCTGCCGCATCAAGCAGATCATCA
                           1241                                 1280
```

*FIG. 4F*

```
Ile424-Ala433   (1240) ---------GGCGGC--G-CCATGTACGCCCCCCCCATCCG
Trp427-Gly431   (1241) ACCGCTGGGGCGGCAAGGCCATGTACGCCCCCCCCATCCG
Gln422-Tyr435B  (1234) ---------GCCCCC---------TACGCCCCGCCCATCCG
Arg426-Gly431   (1241) ACCGCGGCGGCGGCAAGGCCATGTACGCCCCCCCCATCCG
Ile423-Met434   (1237) ---------GGCGGC------ATGTACGCCCCCCCCATCCG
Gln422-Tyr435   (1234) ---------GGCGGC---------TACGCCCCCCCCATCCG
Arg426-Lys432   (1241) ACCGCGGCGGCAACAAGGCCATGTACGCCCCCCCCATCCG
Arg426-Gly431B  (1241) ACCGCGGCAGCGGCAAGGCCATGTACGCCCCCCCCATCCG
Asn425-Lys432   (1241) AC------GCCCCCAAGGCCATGTACGCCCCCCCCATCCG
    Consensus   (1241) AC      GGCGGCAAGGCCATGTACGCCCCCCCCATCCG
                       1281                                1320
Ile424-Ala433   (1269) CGGCCAGATCCGCTGCAGCAGCAACATCACCGGCCTGCTG
Trp427-Gly431   (1281) CGGCCAGATCCGCTGCAGCAGCAACATCACCGGCCTGCTG
Gln422-Tyr435B  (1257) CGGCCAGATCCGCTGCAGCAGCAACATCACCGGCCTGCTG
Arg426-Gly431   (1281) CGGCCAGATCCGCTGCAGCAGCAACATCACCGGCCTGCTG
Ile423-Met434   (1263) CGGCCAGATCCGCTGCAGCAGCAACATCACCGGCCTGCTG
Gln422-Tyr435   (1257) CGGCCAGATCCGCTGCAGCAGCAACATCACCGGCCTGCTG
Arg426-Lys432   (1281) CGGCCAGATCCGCTGCAGCAGCAACATCACCGGCCTGCTG
Arg426-Gly431B  (1281) CGGCCAGATCCGCTGCAGCAGCAACATCACCGGCCTGCTG
Asn425-Lys432   (1275) CGGCCAGATCCGCTGCAGCAGCAACATCACCGGCCTGCTG
    Consensus   (1281) CGGCCAGATCCGCTGCAGCAGCAACATCACCGGCCTGCTG
                       1321                                1360
Ile424-Ala433   (1309) CTGACCCGCGACGGCGGCAAGGAGATCAGCAACACCACCG
Trp427-Gly431   (1321) CTGACCCGCGACGGCGGCAAGGAGATCAGCAACACCACCG
Gln422-Tyr435B  (1297) CTGACCCGCGACGGCGGCAAGGAGATCAGCAACACCACCG
Arg426-Gly431   (1321) CTGACCCGCGACGGCGGCAAGGAGATCAGCAACACCACCG
Ile423-Met434   (1303) CTGACCCGCGACGGCGGCAAGGAGATCAGCAACACCACCG
Gln422-Tyr435   (1297) CTGACCCGCGACGGCGGCAAGGAGATCAGCAACACCACCG
Arg426-Lys432   (1321) CTGACCCGCGACGGCGGCAAGGAGATCAGCAACACCACCG
Arg426-Gly431B  (1321) CTGACCCGCGACGGCGGCAAGGAGATCAGCAACACCACCG
Asn425-Lys432   (1315) CTGACCCGCGACGGCGGCAAGGAGATCAGCAACACCACCG
    Consensus   (1321) CTGACCCGCGACGGCGGCAAGGAGATCAGCAACACCACCG
                       1361                                1400
Ile424-Ala433   (1349) AGATCTTCCGCCCCGGCGGCGGCGACATGCGCGACAACTG
Trp427-Gly431   (1361) AGATCTTCCGCCCCGGCGGCGGCGACATGCGCGACAACTG
Gln422-Tyr435B  (1337) AGATCTTCCGCCCCGGCGGCGGCGACATGCGCGACAACTG
Arg426-Gly431   (1361) AGATCTTCCGCCCCGGCGGCGGCGACATGCGCGACAACTG
Ile423-Met434   (1343) AGATCTTCCGCCCCGGCGGCGGCGACATGCGCGACAACTG
Gln422-Tyr435   (1337) AGATCTTCCGCCCCGGCGGCGGCGACATGCGCGACAACTG
Arg426-Lys432   (1361) AGATCTTCCGCCCCGGCGGCGGCGACATGCGCGACAACTG
Arg426-Gly431B  (1361) AGATCTTCCGCCCCGGCGGCGGCGACATGCGCGACAACTG
Asn425-Lys432   (1355) AGATCTTCCGCCCCGGCGGCGGCGACATGCGCGACAACTG
    Consensus   (1361) AGATCTTCCGCCCCGGCGGCGGCGACATGCGCGACAACTG
                       1401                                1440
Ile424-Ala433   (1389) GCGCAGCGAGCTGTACAAGTACAAGGTGGTGAAGATCGAG
Trp427-Gly431   (1401) GCGCAGCGAGCTGTACAAGTACAAGGTGGTGAAGATCGAG
Gln422-Tyr435B  (1377) GCGCAGCGAGCTGTACAAGTACAAGGTGGTGAAGATCGAG
Arg426-Gly431   (1401) GCGCAGCGAGCTGTACAAGTACAAGGTGGTGAAGATCGAG
Ile423-Met434   (1383) GCGCAGCGAGCTGTACAAGTACAAGGTGGTGAAGATCGAG
Gln422-Tyr435   (1377) GCGCAGCGAGCTGTACAAGTACAAGGTGGTGAAGATCGAG
Arg426-Lys432   (1401) GCGCAGCGAGCTGTACAAGTACAAGGTGGTGAAGATCGAG
Arg426-Gly431B  (1401) GCGCAGCGAGCTGTACAAGTACAAGGTGGTGAAGATCGAG
Asn425-Lys432   (1395) GCGCAGCGAGCTGTACAAGTACAAGGTGGTGAAGATCGAG
    Consensus   (1401) GCGCAGCGAGCTGTACAAGTACAAGGTGGTGAAGATCGAG
                       1441                                1480
Ile424-Ala433   (1429) CCCCTGGGCGTGGCCCCCACCAAGGCCAAGCGCCGCGTGG
Trp427-Gly431   (1441) CCCCTGGGCGTGGCCCCCACCAAGGCCAAGCGCCGCGTGG
```

*FIG. 4G*

```
Gln422-Tyr435B  (1417)  CCCCTGGGCGTGGCCCCCACCAAGGCCAAGCGCCGCGTGG
Arg426-Gly431   (1441)  CCCCTGGGCGTGGCCCCCACCAAGGCCAAGCGCCGCGTGG
Ile423-Met434   (1423)  CCCCTGGGCGTGGCCCCCACCAAGGCCAAGCGCCGCGTGG
Gln422-Tyr435   (1417)  CCCCTGGGCGTGGCCCCCACCAAGGCCAAGCGCCGCGTGG
Arg426-Lys432   (1441)  CCCCTGGGCGTGGCCCCCACCAAGGCCAAGCGCCGCGTGG
Arg426-Gly431B  (1441)  CCCCTGGGCGTGGCCCCCACCAAGGCCAAGCGCCGCGTGG
Asn425-Lys432   (1435)  CCCCTGGGCGTGGCCCCCACCAAGGCCAAGCGCCGCGTGG
    Consensus   (1441)  CCCCTGGGCGTGGCCCCCACCAAGGCCAAGCGCCGCGTGG
                        1481                                    1520
Ile424-Ala433   (1469)  TGCAGCGCGAGAAGCGCGCCGTGACCCTGGGCGCCATGTT
Trp427-Gly431   (1481)  TGCAGCGCGAGAAGCGCGCCGTGACCCTGGGCGCCATGTT
Gln422-Tyr435B  (1457)  TGCAGCGCGAGAAGCGCGCCGTGACCCTGGGCGCCATGTT
Arg426-Gly431   (1481)  TGCAGCGCGAGAAGCGCGCCGTGACCCTGGGCGCCATGTT
Ile423-Met434   (1463)  TGCAGCGCGAGAAGCGCGCCGTGACCCTGGGCGCCATGTT
Gln422-Tyr435   (1457)  TGCAGCGCGAGAAGCGCGCCGTGACCCTGGGCGCCATGTT
Arg426-Lys432   (1481)  TGCAGCGCGAGAAGCGCGCCGTGACCCTGGGCGCCATGTT
Arg426-Gly431B  (1481)  TGCAGCGCGAGAAGCGCGCCGTGACCCTGGGCGCCATGTT
Asn425-Lys432   (1475)  TGCAGCGCGAGAAGCGCGCCGTGACCCTGGGCGCCATGTT
    Consensus   (1481)  TGCAGCGCGAGAAGCGCGCCGTGACCCTGGGCGCCATGTT
                        1521                                    1560
Ile424-Ala433   (1509)  CCTGGGCTTCCTGGGCGCCGCCGGCAGCACCATGGGCGCC
Trp427-Gly431   (1521)  CCTGGGCTTCCTGGGCGCCGCCGGCAGCACCATGGGCGCC
Gln422-Tyr435B  (1497)  CCTGGGCTTCCTGGGCGCCGCCGGCAGCACCATGGGCGCC
Arg426-Gly431   (1521)  CCTGGGCTTCCTGGGCGCCGCCGGCAGCACCATGGGCGCC
Ile423-Met434   (1503)  CCTGGGCTTCCTGGGCGCCGCCGGCAGCACCATGGGCGCC
Gln422-Tyr435   (1497)  CCTGGGCTTCCTGGGCGCCGCCGGCAGCACCATGGGCGCC
Arg426-Lys432   (1521)  CCTGGGCTTCCTGGGCGCCGCCGGCAGCACCATGGGCGCC
Arg426-Gly431B  (1521)  CCTGGGCTTCCTGGGCGCCGCCGGCAGCACCATGGGCGCC
Asn425-Lys432   (1515)  CCTGGGCTTCCTGGGCGCCGCCGGCAGCACCATGGGCGCC
    Consensus   (1521)  CCTGGGCTTCCTGGGCGCCGCCGGCAGCACCATGGGCGCC
                        1561                                    1600
Ile424-Ala433   (1549)  CGCAGCCTGACCCTGACCGTGCAGGCCCGCCAGCTGCTGA
Trp427-Gly431   (1561)  CGCAGCCTGACCCTGACCGTGCAGGCCCGCCAGCTGCTGA
Gln422-Tyr435B  (1537)  CGCAGCCTGACCCTGACCGTGCAGGCCCGCCAGCTGCTGA
Arg426-Gly431   (1561)  CGCAGCCTGACCCTGACCGTGCAGGCCCGCCAGCTGCTGA
Ile423-Met434   (1543)  CGCAGCCTGACCCTGACCGTGCAGGCCCGCCAGCTGCTGA
Gln422-Tyr435   (1537)  CGCAGCCTGACCCTGACCGTGCAGGCCCGCCAGCTGCTGA
Arg426-Lys432   (1561)  CGCAGCCTGACCCTGACCGTGCAGGCCCGCCAGCTGCTGA
Arg426-Gly431B  (1561)  CGCAGCCTGACCCTGACCGTGCAGGCCCGCCAGCTGCTGA
Asn425-Lys432   (1555)  CGCAGCCTGACCCTGACCGTGCAGGCCCGCCAGCTGCTGA
    Consensus   (1561)  CGCAGCCTGACCCTGACCGTGCAGGCCCGCCAGCTGCTGA
                        1601                                    1640
Ile424-Ala433   (1589)  GCGGCATCGTGCAGCAGCAGAACAACCTGCTGCGCGCCAT
Trp427-Gly431   (1601)  GCGGCATCGTGCAGCAGCAGAACAACCTGCTGCGCGCCAT
Gln422-Tyr435B  (1577)  GCGGCATCGTGCAGCAGCAGAACAACCTGCTGCGCGCCAT
Arg426-Gly431   (1601)  GCGGCATCGTGCAGCAGCAGAACAACCTGCTGCGCGCCAT
Ile423-Met434   (1583)  GCGGCATCGTGCAGCAGCAGAACAACCTGCTGCGCGCCAT
Gln422-Tyr435   (1577)  GCGGCATCGTGCAGCAGCAGAACAACCTGCTGCGCGCCAT
Arg426-Lys432   (1601)  GCGGCATCGTGCAGCAGCAGAACAACCTGCTGCGCGCCAT
Arg426-Gly431B  (1601)  GCGGCATCGTGCAGCAGCAGAACAACCTGCTGCGCGCCAT
Asn425-Lys432   (1595)  GCGGCATCGTGCAGCAGCAGAACAACCTGCTGCGCGCCAT
    Consensus   (1601)  GCGGCATCGTGCAGCAGCAGAACAACCTGCTGCGCGCCAT
                        1641                                    1680
Ile424-Ala433   (1629)  CGAGGCCCAGCAGCACCTGCTGCAGCTGACCGTGTGGGGC
Trp427-Gly431   (1641)  CGAGGCCCAGCAGCACCTGCTGCAGCTGACCGTGTGGGGC
Gln422-Tyr435B  (1617)  CGAGGCCCAGCAGCACCTGCTGCAGCTGACCGTGTGGGGC
Arg426-Gly431   (1641)  CGAGGCCCAGCAGCACCTGCTGCAGCTGACCGTGTGGGGC
```

*FIG. 4H*

Ile423-Met434 (1623) CGAGGCCCAGCAGCACCTGCTGCAGCTGACCGTGTGGGGC
Gln422-Tyr435 (1617) CGAGGCCCAGCAGCACCTGCTGCAGCTGACCGTGTGGGGC
Arg426-Lys432 (1641) CGAGGCCCAGCAGCACCTGCTGCAGCTGACCGTGTGGGGC
Arg426-Gly431B (1641) CGAGGCCCAGCAGCACCTGCTGCAGCTGACCGTGTGGGGC
Asn425-Lys432 (1635) CGAGGCCCAGCAGCACCTGCTGCAGCTGACCGTGTGGGGC
Consensus (1641) CGAGGCCCAGCAGCACCTGCTGCAGCTGACCGTGTGGGGC 1681 1720
Ile424-Ala433 (1669) ATCAAGCAGCTGCAGGCCCGCGTGCTGGCCGTGGAGCGCT
Trp427-Gly431 (1681) ATCAAGCAGCTGCAGGCCCGCGTGCTGGCCGTGGAGCGCT
Gln422-Tyr435B (1657) ATCAAGCAGCTGCAGGCCCGCGTGCTGGCCGTGGAGCGCT
Arg426-Gly431 (1681) ATCAAGCAGCTGCAGGCCCGCGTGCTGGCCGTGGAGCGCT
Ile423-Met434 (1663) ATCAAGCAGCTGCAGGCCCGCGTGCTGGCCGTGGAGCGCT
Gln422-Tyr435 (1657) ATCAAGCAGCTGCAGGCCCGCGTGCTGGCCGTGGAGCGCT
Arg426-Lys432 (1681) ATCAAGCAGCTGCAGGCCCGCGTGCTGGCCGTGGAGCGCT
Arg426-Gly431B (1681) ATCAAGCAGCTGCAGGCCCGCGTGCTGGCCGTGGAGCGCT
Asn425-Lys432 (1675) ATCAAGCAGCTGCAGGCCCGCGTGCTGGCCGTGGAGCGCT
Consensus (1681) ATCAAGCAGCTGCAGGCCCGCGTGCTGGCCGTGGAGCGCT 1721 1760
Ile424-Ala433 (1709) ACCTGAAGGACCAGCAGCTGCTGGGCATCTGGGGCTGCAG
Trp427-Gly431 (1721) ACCTGAAGGACCAGCAGCTGCTGGGCATCTGGGGCTGCAG
Gln422-Tyr435B (1697) ACCTGAAGGACCAGCAGCTGCTGGGCATCTGGGGCTGCAG
Arg426-Gly431 (1721) ACCTGAAGGACCAGCAGCTGCTGGGCATCTGGGGCTGCAG
Ile423-Met434 (1703) ACCTGAAGGACCAGCAGCTGCTGGGCATCTGGGGCTGCAG
Gln422-Tyr435 (1697) ACCTGAAGGACCAGCAGCTGCTGGGCATCTGGGGCTGCAG
Arg426-Lys432 (1721) ACCTGAAGGACCAGCAGCTGCTGGGCATCTGGGGCTGCAG
Arg426-Gly431B (1721) ACCTGAAGGACCAGCAGCTGCTGGGCATCTGGGGCTGCAG
Asn425-Lys432 (1715) ACCTGAAGGACCAGCAGCTGCTGGGCATCTGGGGCTGCAG
Consensus (1721) ACCTGAAGGACCAGCAGCTGCTGGGCATCTGGGGCTGCAG 1761 1800
Ile424-Ala433 (1749) CGGCAAGCTGATCTGCACCACCGCCGTGCCCTGGAACGCC
Trp427-Gly431 (1761) CGGCAAGCTGATCTGCACCACCGCCGTGCCCTGGAACGCC
Gln422-Tyr435B (1737) CGGCAAGCTGATCTGCACCACCGCCGTGCCCTGGAACGCC
Arg426-Gly431 (1761) CGGCAAGCTGATCTGCACCACCGCCGTGCCCTGGAACGCC
Ile423-Met434 (1743) CGGCAAGCTGATCTGCACCACCGCCGTGCCCTGGAACGCC
Gln422-Tyr435 (1737) CGGCAAGCTGATCTGCACCACCGCCGTGCCCTGGAACGCC
Arg426-Lys432 (1761) CGGCAAGCTGATCTGCACCACCGCCGTGCCCTGGAACGCC
Arg426-Gly431B (1761) CGGCAAGCTGATCTGCACCACCGCCGTGCCCTGGAACGCC
Asn425-Lys432 (1755) CGGCAAGCTGATCTGCACCACCGCCGTGCCCTGGAACGCC
Consensus (1761) CGGCAAGCTGATCTGCACCACCGCCGTGCCCTGGAACGCC 1801 1840
Ile424-Ala433 (1789) AGCTGGAGCAACAAGAGCCTGGACCAGATCTGGAACAACA
Trp427-Gly431 (1801) AGCTGGAGCAACAAGAGCCTGGACCAGATCTGGAACAACA
Gln422-Tyr435B (1777) AGCTGGAGCAACAAGAGCCTGGACCAGATCTGGAACAACA
Arg426-Gly431 (1801) AGCTGGAGCAACAAGAGCCTGGACCAGATCTGGAACAACA
Ile423-Met434 (1783) AGCTGGAGCAACAAGAGCCTGGACCAGATCTGGAACAACA
Gln422-Tyr435 (1777) AGCTGGAGCAACAAGAGCCTGGACCAGATCTGGAACAACA
Arg426-Lys432 (1801) AGCTGGAGCAACAAGAGCCTGGACCAGATCTGGAACAACA
Arg426-Gly431B (1801) AGCTGGAGCAACAAGAGCCTGGACCAGATCTGGAACAACA
Asn425-Lys432 (1795) AGCTGGAGCAACAAGAGCCTGGACCAGATCTGGAACAACA
Consensus (1801) AGCTGGAGCAACAAGAGCCTGGACCAGATCTGGAACAACA 1841 1880
Ile424-Ala433 (1829) TGACCTGGATGGAGTGGGAGCGCGAGATCGACAACTACAC
Trp427-Gly431 (1841) TGACCTGGATGGAGTGGGAGCGCGAGATCGACAACTACAC
Gln422-Tyr435B (1817) TGACCTGGATGGAGTGGGAGCGCGAGATCGACAACTACAC
Arg426-Gly431 (1841) TGACCTGGATGGAGTGGGAGCGCGAGATCGACAACTACAC
Ile423-Met434 (1823) TGACCTGGATGGAGTGGGAGCGCGAGATCGACAACTACAC
Gln422-Tyr435 (1817) TGACCTGGATGGAGTGGGAGCGCGAGATCGACAACTACAC

FIG. 4I

```
     Arg426-Lys432  (1841) TGACCTGGATGGAGTGGGAGCGCGAGATCGACAACTACAC
    Arg426-Gly431B  (1841) TGACCTGGATGGAGTGGGAGCGCGAGATCGACAACTACAC
     Asn425-Lys432  (1835) TGACCTGGATGGAGTGGGAGCGCGAGATCGACAACTACAC
         Consensus  (1841) TGACCTGGATGGAGTGGGAGCGCGAGATCGACAACTACAC
                           1881                                 1920
     Ile424-Ala433  (1869) CAACCTGATCTACACCCTGATCGAGGAGAGCCAGAACCAG
     Trp427-Gly431  (1881) CAACCTGATCTACACCCTGATCGAGGAGAGCCAGAACCAG
    Gln422-Tyr435B  (1857) CAACCTGATCTACACCCTGATCGAGGAGAGCCAGAACCAG
     Arg426-Gly431  (1881) CAACCTGATCTACACCCTGATCGAGGAGAGCCAGAACCAG
     Ile423-Met434  (1863) CAACCTGATCTACACCCTGATCGAGGAGAGCCAGAACCAG
     Gln422-Tyr435  (1857) CAACCTGATCTACACCCTGATCGAGGAGAGCCAGAACCAG
     Arg426-Lys432  (1881) CAACCTGATCTACACCCTGATCGAGGAGAGCCAGAACCAG
    Arg426-Gly431B  (1881) CAACCTGATCTACACCCTGATCGAGGAGAGCCAGAACCAG
     Asn425-Lys432  (1875) CAACCTGATCTACACCCTGATCGAGGAGAGCCAGAACCAG
         Consensus  (1881) CAACCTGATCTACACCCTGATCGAGGAGAGCCAGAACCAG
                           1921                                 1960
     Ile424-Ala433  (1909) CAGGAGAAGAACGAGCAGGAGCTGCTGGAGCTGGACAAGT
     Trp427-Gly431  (1921) CAGGAGAAGAACGAGCAGGAGCTGCTGGAGCTGGACAAGT
    Gln422-Tyr435B  (1897) CAGGAGAAGAACGAGCAGGAGCTGCTGGAGCTGGACAAGT
     Arg426-Gly431  (1921) CAGGAGAAGAACGAGCAGGAGCTGCTGGAGCTGGACAAGT
     Ile423-Met434  (1903) CAGGAGAAGAACGAGCAGGAGCTGCTGGAGCTGGACAAGT
     Gln422-Tyr435  (1897) CAGGAGAAGAACGAGCAGGAGCTGCTGGAGCTGGACAAGT
     Arg426-Lys432  (1921) CAGGAGAAGAACGAGCAGGAGCTGCTGGAGCTGGACAAGT
    Arg426-Gly431B  (1921) CAGGAGAAGAACGAGCAGGAGCTGCTGGAGCTGGACAAGT
     Asn425-Lys432  (1915) CAGGAGAAGAACGAGCAGGAGCTGCTGGAGCTGGACAAGT
         Consensus  (1921) CAGGAGAAGAACGAGCAGGAGCTGCTGGAGCTGGACAAGT
                           1961                                 2000
     Ile424-Ala433  (1949) GGGCCAGCCTGTGGAACTGGTTCGACATCAGCAAGTGGCT
     Trp427-Gly431  (1961) GGGCCAGCCTGTGGAACTGGTTCGACATCAGCAAGTGGCT
    Gln422-Tyr435B  (1937) GGGCCAGCCTGTGGAACTGGTTCGACATCAGCAAGTGGCT
     Arg426-Gly431  (1961) GGGCCAGCCTGTGGAACTGGTTCGACATCAGCAAGTGGCT
     Ile423-Met434  (1943) GGGCCAGCCTGTGGAACTGGTTCGACATCAGCAAGTGGCT
     Gln422-Tyr435  (1937) GGGCCAGCCTGTGGAACTGGTTCGACATCAGCAAGTGGCT
     Arg426-Lys432  (1961) GGGCCAGCCTGTGGAACTGGTTCGACATCAGCAAGTGGCT
    Arg426-Gly431B  (1961) GGGCCAGCCTGTGGAACTGGTTCGACATCAGCAAGTGGCT
     Asn425-Lys432  (1955) GGGCCAGCCTGTGGAACTGGTTCGACATCAGCAAGTGGCT
         Consensus  (1961) GGGCCAGCCTGTGGAACTGGTTCGACATCAGCAAGTGGCT
                           2001                                 2040
     Ile424-Ala433  (1989) GTGGTACATCAAGATCTTCATCATGATCGTGGGCGGCCTG
     Trp427-Gly431  (2001) GTGGTACATCAAGATCTTCATCATGATCGTGGGCGGCCTG
    Gln422-Tyr435B  (1977) GTGGTACATCAAGATCTTCATCATGATCGTGGGCGGCCTG
     Arg426-Gly431  (2001) GTGGTACATCAAGATCTTCATCATGATCGTGGGCGGCCTG
     Ile423-Met434  (1983) GTGGTACATCAAGATCTTCATCATGATCGTGGGCGGCCTG
     Gln422-Tyr435  (1977) GTGGTACATCAAGATCTTCATCATGATCGTGGGCGGCCTG
     Arg426-Lys432  (2001) GTGGTACATCAAGATCTTCATCATGATCGTGGGCGGCCTG
    Arg426-Gly431B  (2001) GTGGTACATCAAGATCTTCATCATGATCGTGGGCGGCCTG
     Asn425-Lys432  (1995) GTGGTACATCAAGATCTTCATCATGATCGTGGGCGGCCTG
         Consensus  (2001) GTGGTACATCAAGATCTTCATCATGATCGTGGGCGGCCTG
                           2041                                 2080
     Ile424-Ala433  (2029) GTGGGCCTGCGCATCGTGTTCACCGTGCTGAGCATCGTGA
     Trp427-Gly431  (2041) GTGGGCCTGCGCATCGTGTTCACCGTGCTGAGCATCGTGA
    Gln422-Tyr435B  (2017) GTGGGCCTGCGCATCGTGTTCACCGTGCTGAGCATCGTGA
     Arg426-Gly431  (2041) GTGGGCCTGCGCATCGTGTTCACCGTGCTGAGCATCGTGA
     Ile423-Met434  (2023) GTGGGCCTGCGCATCGTGTTCACCGTGCTGAGCATCGTGA
     Gln422-Tyr435  (2017) GTGGGCCTGCGCATCGTGTTCACCGTGCTGAGCATCGTGA
     Arg426-Lys432  (2041) GTGGGCCTGCGCATCGTGTTCACCGTGCTGAGCATCGTGA
    Arg426-Gly431B  (2041) GTGGGCCTGCGCATCGTGTTCACCGTGCTGAGCATCGTGA
```

FIG. 4J

```
  Asn425-Lys432   (2035) GTGGGCCTGCGCATCGTGTTCACCGTGCTGAGCATCGTGA
      Consensus   (2041) GTGGGCCTGCGCATCGTGTTCACCGTGCTGAGCATCGTGA
                         2081                                   2120
  Ile424-Ala433   (2069) ACCGCGTGCGCCAGGGCTACAGCCCCCTGAGCTTCCAGAC
  Trp427-Gly431   (2081) ACCGCGTGCGCCAGGGCTACAGCCCCCTGAGCTTCCAGAC
 Gln422-Tyr435B   (2057) ACCGCGTGCGCCAGGGCTACAGCCCCCTGAGCTTCCAGAC
  Arg426-Gly431   (2081) ACCGCGTGCGCCAGGGCTACAGCCCCCTGAGCTTCCAGAC
  Ile423-Met434   (2063) ACCGCGTGCGCCAGGGCTACAGCCCCCTGAGCTTCCAGAC
  Gln422-Tyr435   (2057) ACCGCGTGCGCCAGGGCTACAGCCCCCTGAGCTTCCAGAC
  Arg426-Lys432   (2081) ACCGCGTGCGCCAGGGCTACAGCCCCCTGAGCTTCCAGAC
 Arg426-Gly431B   (2081) ACCGCGTGCGCCAGGGCTACAGCCCCCTGAGCTTCCAGAC
  Asn425-Lys432   (2075) ACCGCGTGCGCCAGGGCTACAGCCCCCTGAGCTTCCAGAC
      Consensus   (2081) ACCGCGTGCGCCAGGGCTACAGCCCCCTGAGCTTCCAGAC
                         2121                                   2160
  Ile424-Ala433   (2109) CCGCTTCCCCGCCCCCCGCGGCCCCGACCGCCCCGAGGGC
  Trp427-Gly431   (2121) CCGCTTCCCCGCCCCCCGCGGCCCCGACCGCCCCGAGGGC
 Gln422-Tyr435B   (2097) CCGCTTCCCCGCCCCCCGCGGCCCCGACCGCCCCGAGGGC
  Arg426-Gly431   (2121) CCGCTTCCCCGCCCCCCGCGGCCCCGACCGCCCCGAGGGC
  Ile423-Met434   (2103) CCGCTTCCCCGCCCCCCGCGGCCCCGACCGCCCCGAGGGC
  Gln422-Tyr435   (2097) CCGCTTCCCCGCCCCCCGCGGCCCCGACCGCCCCGAGGGC
  Arg426-Lys432   (2121) CCGCTTCCCCGCCCCCCGCGGCCCCGACCGCCCCGAGGGC
 Arg426-Gly431B   (2121) CCGCTTCCCCGCCCCCCGCGGCCCCGACCGCCCCGAGGGC
  Asn425-Lys432   (2115) CCGCTTCCCCGCCCCCCGCGGCCCCGACCGCCCCGAGGGC
      Consensus   (2121) CCGCTTCCCCGCCCCCCGCGGCCCCGACCGCCCCGAGGGC
                         2161                                   2200
  Ile424-Ala433   (2149) ATCGAGGAGGAGGGCGGCGAGCGCGACCGCGACCGCAGCA
  Trp427-Gly431   (2161) ATCGAGGAGGAGGGCGGCGAGCGCGACCGCGACCGCAGCA
 Gln422-Tyr435B   (2137) ATCGAGGAGGAGGGCGGCGAGCGCGACCGCGACCGCAGCA
  Arg426-Gly431   (2161) ATCGAGGAGGAGGGCGGCGAGCGCGACCGCGACCGCAGCA
  Ile423-Met434   (2143) ATCGAGGAGGAGGGCGGCGAGCGCGACCGCGACCGCAGCA
  Gln422-Tyr435   (2137) ATCGAGGAGGAGGGCGGCGAGCGCGACCGCGACCGCAGCA
  Arg426-Lys432   (2161) ATCGAGGAGGAGGGCGGCGAGCGCGACCGCGACCGCAGCA
 Arg426-Gly431B   (2161) ATCGAGGAGGAGGGCGGCGAGCGCGACCGCGACCGCAGCA
  Asn425-Lys432   (2155) ATCGAGGAGGAGGGCGGCGAGCGCGACCGCGACCGCAGCA
      Consensus   (2161) ATCGAGGAGGAGGGCGGCGAGCGCGACCGCGACCGCAGCA
                         2201                                   2240
  Ile424-Ala433   (2189) GCCCCCTGGTGCACGGCCTGCTGGCCCTGATCTGGGACGA
  Trp427-Gly431   (2201) GCCCCCTGGTGCACGGCCTGCTGGCCCTGATCTGGGACGA
 Gln422-Tyr435B   (2177) GCCCCCTGGTGCACGGCCTGCTGGCCCTGATCTGGGACGA
  Arg426-Gly431   (2201) GCCCCCTGGTGCACGGCCTGCTGGCCCTGATCTGGGACGA
  Ile423-Met434   (2183) GCCCCCTGGTGCACGGCCTGCTGGCCCTGATCTGGGACGA
  Gln422-Tyr435   (2177) GCCCCCTGGTGCACGGCCTGCTGGCCCTGATCTGGGACGA
  Arg426-Lys432   (2201) GCCCCCTGGTGCACGGCCTGCTGGCCCTGATCTGGGACGA
 Arg426-Gly431B   (2201) GCCCCCTGGTGCACGGCCTGCTGGCCCTGATCTGGGACGA
  Asn425-Lys432   (2195) GCCCCCTGGTGCACGGCCTGCTGGCCCTGATCTGGGACGA
      Consensus   (2201) GCCCCCTGGTGCACGGCCTGCTGGCCCTGATCTGGGACGA
                         2241                                   2280
  Ile424-Ala433   (2229) CCTGCGCAGCCTGTGCCTGTTCAGCTACCACCGCCTGCGC
  Trp427-Gly431   (2241) CCTGCGCAGCCTGTGCCTGTTCAGCTACCACCGCCTGCGC
 Gln422-Tyr435B   (2217) CCTGCGCAGCCTGTGCCTGTTCAGCTACCACCGCCTGCGC
  Arg426-Gly431   (2241) CCTGCGCAGCCTGTGCCTGTTCAGCTACCACCGCCTGCGC
  Ile423-Met434   (2223) CCTGCGCAGCCTGTGCCTGTTCAGCTACCACCGCCTGCGC
  Gln422-Tyr435   (2217) CCTGCGCAGCCTGTGCCTGTTCAGCTACCACCGCCTGCGC
  Arg426-Lys432   (2241) CCTGCGCAGCCTGTGCCTGTTCAGCTACCACCGCCTGCGC
 Arg426-Gly431B   (2241) CCTGCGCAGCCTGTGCCTGTTCAGCTACCACCGCCTGCGC
  Asn425-Lys432   (2235) CCTGCGCAGCCTGTGCCTGTTCAGCTACCACCGCCTGCGC
      Consensus   (2241) CCTGCGCAGCCTGTGCCTGTTCAGCTACCACCGCCTGCGC
```

*FIG. 4K*

| | | |
|---|---|---|
| | | 2281 2320 |
| Ile424-Ala433 | (2269) | GACCTGATCCTGATCGCCGCCCGCATCGTGGAGCTGCTGG |
| Trp427-Gly431 | (2281) | GACCTGATCCTGATCGCCGCCCGCATCGTGGAGCTGCTGG |
| Gln422-Tyr435B | (2257) | GACCTGATCCTGATCGCCGCCCGCATCGTGGAGCTGCTGG |
| Arg426-Gly431 | (2281) | GACCTGATCCTGATCGCCGCCCGCATCGTGGAGCTGCTGG |
| Ile423-Met434 | (2263) | GACCTGATCCTGATCGCCGCCCGCATCGTGGAGCTGCTGG |
| Gln422-Tyr435 | (2257) | GACCTGATCCTGATCGCCGCCCGCATCGTGGAGCTGCTGG |
| Arg426-Lys432 | (2281) | GACCTGATCCTGATCGCCGCCCGCATCGTGGAGCTGCTGG |
| Arg426-Gly431B | (2281) | GACCTGATCCTGATCGCCGCCCGCATCGTGGAGCTGCTGG |
| Asn425-Lys432 | (2275) | GACCTGATCCTGATCGCCGCCCGCATCGTGGAGCTGCTGG |
| Consensus | (2281) | GACCTGATCCTGATCGCCGCCCGCATCGTGGAGCTGCTGG |
| | | 2321 2360 |
| Ile424-Ala433 | (2309) | GCCGCCGCGGCTGGGAGGCCCTGAAGTACTGGGGCAACCT |
| Trp427-Gly431 | (2321) | GCCGCCGCGGCTGGGAGGCCCTGAAGTACTGGGGCAACCT |
| Gln422-Tyr435B | (2297) | GCCGCCGCGGCTGGGAGGCCCTGAAGTACTGGGGCAACCT |
| Arg426-Gly431 | (2321) | GCCGCCGCGGCTGGGAGGCCCTGAAGTACTGGGGCAACCT |
| Ile423-Met434 | (2303) | GCCGCCGCGGCTGGGAGGCCCTGAAGTACTGGGGCAACCT |
| Gln422-Tyr435 | (2297) | GCCGCCGCGGCTGGGAGGCCCTGAAGTACTGGGGCAACCT |
| Arg426-Lys432 | (2321) | GCCGCCGCGGCTGGGAGGCCCTGAAGTACTGGGGCAACCT |
| Arg426-Gly431B | (2321) | GCCGCCGCGGCTGGGAGGCCCTGAAGTACTGGGGCAACCT |
| Asn425-Lys432 | (2315) | GCCGCCGCGGCTGGGAGGCCCTGAAGTACTGGGGCAACCT |
| Consensus | (2321) | GCCGCCGCGGCTGGGAGGCCCTGAAGTACTGGGGCAACCT |
| | | 2361 2400 |
| Ile424-Ala433 | (2349) | GCTGCAGTACTGGATCCAGGAGCTGAAGAACAGCGCCGTG |
| Trp427-Gly431 | (2361) | GCTGCAGTACTGGATCCAGGAGCTGAAGAACAGCGCCGTG |
| Gln422-Tyr435B | (2337) | GCTGCAGTACTGGATCCAGGAGCTGAAGAACAGCGCCGTG |
| Arg426-Gly431 | (2361) | GCTGCAGTACTGGATCCAGGAGCTGAAGAACAGCGCCGTG |
| Ile423-Met434 | (2343) | GCTGCAGTACTGGATCCAGGAGCTGAAGAACAGCGCCGTG |
| Gln422-Tyr435 | (2337) | GCTGCAGTACTGGATCCAGGAGCTGAAGAACAGCGCCGTG |
| Arg426-Lys432 | (2361) | GCTGCAGTACTGGATCCAGGAGCTGAAGAACAGCGCCGTG |
| Arg426-Gly431B | (2361) | GCTGCAGTACTGGATCCAGGAGCTGAAGAACAGCGCCGTG |
| Asn425-Lys432 | (2355) | GCTGCAGTACTGGATCCAGGAGCTGAAGAACAGCGCCGTG |
| Consensus | (2361) | GCTGCAGTACTGGATCCAGGAGCTGAAGAACAGCGCCGTG |
| | | 2401 2440 |
| Ile424-Ala433 | (2389) | AGCCTGTTCGACGCCATCGCCATCGCCGTGGCCGAGGGCA |
| Trp427-Gly431 | (2401) | AGCCTGTTCGACGCCATCGCCATCGCCGTGGCCGAGGGCA |
| Gln422-Tyr435B | (2377) | AGCCTGTTCGACGCCATCGCCATCGCCGTGGCCGAGGGCA |
| Arg426-Gly431 | (2401) | AGCCTGTTCGACGCCATCGCCATCGCCGTGGCCGAGGGCA |
| Ile423-Met434 | (2383) | AGCCTGTTCGACGCCATCGCCATCGCCGTGGCCGAGGGCA |
| Gln422-Tyr435 | (2377) | AGCCTGTTCGACGCCATCGCCATCGCCGTGGCCGAGGGCA |
| Arg426-Lys432 | (2401) | AGCCTGTTCGACGCCATCGCCATCGCCGTGGCCGAGGGCA |
| Arg426-Gly431B | (2401) | AGCCTGTTCGACGCCATCGCCATCGCCGTGGCCGAGGGCA |
| Asn425-Lys432 | (2395) | AGCCTGTTCGACGCCATCGCCATCGCCGTGGCCGAGGGCA |
| Consensus | (2401) | AGCCTGTTCGACGCCATCGCCATCGCCGTGGCCGAGGGCA |
| | | 2441 2480 |
| Ile424-Ala433 | (2429) | CCGACCGCATCATCGAGGTGGCCCAGCGCATCGGCCGCGC |
| Trp427-Gly431 | (2441) | CCGACCGCATCATCGAGGTGGCCCAGCGCATCGGCCGCGC |
| Gln422-Tyr435B | (2417) | CCGACCGCATCATCGAGGTGGCCCAGCGCATCGGCCGCGC |
| Arg426-Gly431 | (2441) | CCGACCGCATCATCGAGGTGGCCCAGCGCATCGGCCGCGC |
| Ile423-Met434 | (2423) | CCGACCGCATCATCGAGGTGGCCCAGCGCATCGGCCGCGC |
| Gln422-Tyr435 | (2417) | CCGACCGCATCATCGAGGTGGCCCAGCGCATCGGCCGCGC |
| Arg426-Lys432 | (2441) | CCGACCGCATCATCGAGGTGGCCCAGCGCATCGGCCGCGC |
| Arg426-Gly431B | (2441) | CCGACCGCATCATCGAGGTGGCCCAGCGCATCGGCCGCGC |
| Asn425-Lys432 | (2435) | CCGACCGCATCATCGAGGTGGCCCAGCGCATCGGCCGCGC |
| Consensus | (2441) | CCGACCGCATCATCGAGGTGGCCCAGCGCATCGGCCGCGC |
| | | 2481 2520 |
| Ile424-Ala433 | (2469) | CTTCCTGGAGATCCGCGGCGGCATCCGCCAGGGCTTCGAG |

*FIG. 4L*

| | | |
|---|---|---|
| Trp427-Gly431 | (2481) | CTTCCTGCACATCCCCCGCCGCATCCGCCAGGGCTTCGAG |
| Gln422-Tyr435B | (2457) | CTTCCTGCACATCCCCCGCCGCATCCGCCAGGGCTTCGAG |
| Arg426-Gly431 | (2481) | CTTCCTGCACATCCCCCGCCGCATCCGCCAGGGCTTCGAG |
| Ile423-Met434 | (2463) | CTTCCTGCACATCCCCCGCCGCATCCGCCAGGGCTTCGAG |
| Gln422-Tyr435 | (2457) | CTTCCTGCACATCCCCCGCCGCATCCGCCAGGGCTTCGAG |
| Arg426-Lys432 | (2481) | CTTCCTGCACATCCCCCGCCGCATCCGCCAGGGCTTCGAG |
| Arg426-Gly431B | (2481) | CTTCCTGCACATCCCCCGCCGCATCCGCCAGGGCTTCGAG |
| Asn425-Lys432 | (2475) | CTTCCTGCACATCCCCCGCCGCATCCGCCAGGGCTTCGAG |
| Consensus | (2481) | CTTCCTGCACATCCCCCGCCGCATCCGCCAGGGCTTCGAG |
| | | 2521 2541 |
| Ile424-Ala433 | (2509) | CGCGCCCTGCTGTAACTCGAG |
| Trp427-Gly431 | (2521) | CGCGCCCTGCTGTAACTCGAG |
| Gln422-Tyr435B | (2497) | CGCGCCCTGCTGTAACTCGAG |
| Arg426-Gly431 | (2521) | CGCGCCCTGCTGTAACTCGAG |
| Ile423-Met434 | (2503) | CGCGCCCTGCTGTAACTCGAG |
| Gln422-Tyr435 | (2497) | CGCGCCCTGCTGTAACTCGAG |
| Arg426-Lys432 | (2521) | CGCGCCCTGCTGTAACTCGAG |
| Arg426-Gly431B | (2521) | CGCGCCCTGCTGTAACTCGAG |
| Asn425-Lys432 | (2515) | CGCGCCCTGCTGTAACTCGAG |
| Consensus | (2521) | CGCGCCCTGCTGTAACTCGAG |

FIG. 4M

| | | |
|---|---|---|
| | | 1 30 |
| Leu122-Ser199-Tryp427-Gly431 | (1) | GAATTCGCCACCATGGATGCAATGAAGAGA |
| Val127-Asn195-Arg426-Gly431 | (1) | GAATTCGCCACCATGGATGCAATGAAGAGA |
| Val120-Thr202-Ile424-Ala433 | (1) | GAATTCGCCACCATGGATGCAATGAAGAGA |
| Leu122-Ser199-Arg426-Lys432 | (1) | GAATTCGCCACCATGGATGCAATGAAGAGA |
| Leu122-Ser199-Arg426-Gly431 | (1) | GAATTCGCCACCATGGATGCAATGAAGAGA |
| Lys121-Val200-Asn425-Lys432 | (1) | GAATTCGCCACCATGGATGCAATGAAGAGA |
| Val120-Ile201-Ile424-Ala433 | (1) | GAATTCGCCACCATGGATGCAATGAAGAGA |
| Val120-Ile201B-Ile424-Ala433 | (1) | GAATTCGCCACCATGGATGCAATGAAGAGA |
| Consensus | (1) | GAATTCGCCACCATGGATGCAATGAAGAGA |
| | | 31 60 |
| Leu122-Ser199-Tryp427-Gly431 | (31) | GGGCTCTGCTGTGTGCTGCTGCTGTGTGGA |
| Val127-Asn195-Arg426-Gly431 | (31) | GGGCTCTGCTGTGTGCTGCTGCTGTGTGGA |
| Val120-Thr202-Ile424-Ala433 | (31) | GGGCTCTGCTGTGTGCTGCTGCTGTGTGGA |
| Leu122-Ser199-Arg426-Lys432 | (31) | GGGCTCTGCTGTGTGCTGCTGCTGTGTGGA |
| Leu122-Ser199-Arg426-Gly431 | (31) | GGGCTCTGCTGTGTGCTGCTGCTGTGTGGA |
| Lys121-Val200-Asn425-Lys432 | (31) | GGGCTCTGCTGTGTGCTGCTGCTGTGTGGA |
| Val120-Ile201-Ile424-Ala433 | (31) | GGGCTCTGCTGTGTGCTGCTGCTGTGTGGA |
| Val120-Ile201B-Ile424-Ala433 | (31) | GGGCTCTGCTGTGTGCTGCTGCTGTGTGGA |
| Consensus | (31) | GGGCTCTGCTGTGTGCTGCTGCTGTGTGGA |
| | | 61 90 |
| Leu122-Ser199-Tryp427-Gly431 | (61) | GCAGTCTTCGTTTCGCCCAGCGCCGTGGAG |
| Val127-Asn195-Arg426-Gly431 | (61) | GCAGTCTTCGTTTCGCCCAGCGCCGTGGAG |
| Val120-Thr202-Ile424-Ala433 | (61) | GCAGTCTTCGTTTCGCCCAGCGCCGTGGAG |
| Leu122-Ser199-Arg426-Lys432 | (61) | GCAGTCTTCGTTTCGCCCAGCGCCGTGGAG |
| Leu122-Ser199-Arg426-Gly431 | (61) | GCAGTCTTCGTTTCGCCCAGCGCCGTGGAG |
| Lys121-Val200-Asn425-Lys432 | (61) | GCAGTCTTCGTTTCGCCCAGCGCCGTGGAG |
| Val120-Ile201-Ile424-Ala433 | (61) | GCAGTCTTCGTTTCGCCCAGCGCCGTGGAG |
| Val120-Ile201B-Ile424-Ala433 | (61) | GCAGTCTTCGTTTCGCCCAGCGCCGTGGAG |
| Consensus | (61) | GCAGTCTTCGTTTCGCCCAGCGCCGTGGAG |
| | | 91 120 |
| Leu122-Ser199-Tryp427-Gly431 | (91) | AAGCTGTGGGTGACCGTGTACTACGGCGTG |
| Val127-Asn195-Arg426-Gly431 | (91) | AAGCTGTGGGTGACCGTGTACTACGGCGTG |
| Val120-Thr202-Ile424-Ala433 | (91) | AAGCTGTGGGTGACCGTGTACTACGGCGTG |
| Leu122-Ser199-Arg426-Lys432 | (91) | AAGCTGTGGGTGACCGTGTACTACGGCGTG |
| Leu122-Ser199-Arg426-Gly431 | (91) | AAGCTGTGGGTGACCGTGTACTACGGCGTG |
| Lys121-Val200-Asn425-Lys432 | (91) | AAGCTGTGGGTGACCGTGTACTACGGCGTG |
| Val120-Ile201-Ile424-Ala433 | (91) | AAGCTGTGGGTGACCGTGTACTACGGCGTG |
| Val120-Ile201B-Ile424-Ala433 | (91) | AAGCTGTGGGTGACCGTGTACTACGGCGTG |
| Consensus | (91) | AAGCTGTGGGTGACCGTGTACTACGGCGTG |
| | | 121 150 |
| Leu122-Ser199-Tryp427-Gly431 | (121) | CCCGTGTGGAAGGAGGCCACCACCACCCTG |
| Val127-Asn195-Arg426-Gly431 | (121) | CCCGTGTGGAAGGAGGCCACCACCACCCTG |
| Val120-Thr202-Ile424-Ala433 | (121) | CCCGTGTGGAAGGAGGCCACCACCACCCTG |
| Leu122-Ser199-Arg426-Lys432 | (121) | CCCGTGTGGAAGGAGGCCACCACCACCCTG |
| Leu122-Ser199-Arg426-Gly431 | (121) | CCCGTGTGGAAGGAGGCCACCACCACCCTG |
| Lys121-Val200-Asn425-Lys432 | (121) | CCCGTGTGGAAGGAGGCCACCACCACCCTG |
| Val120-Ile201-Ile424-Ala433 | (121) | CCCGTGTGGAAGGAGGCCACCACCACCCTG |
| Val120-Ile201B-Ile424-Ala433 | (121) | CCCGTGTGGAAGGAGGCCACCACCACCCTG |
| Consensus | (121) | CCCGTGTGGAAGGAGGCCACCACCACCCTG |
| | | 151 180 |
| Leu122-Ser199-Tryp427-Gly431 | (151) | TTCTGCGCCAGCGACGCCAAGGCCTACGAC |
| Val127-Asn195-Arg426-Gly431 | (151) | TTCTGCGCCAGCGACGCCAAGGCCTACGAC |
| Val120-Thr202-Ile424-Ala433 | (151) | TTCTGCGCCAGCGACGCCAAGGCCTACGAC |
| Leu122-Ser199-Arg426-Lys432 | (151) | TTCTGCGCCAGCGACGCCAAGGCCTACGAC |
| Leu122-Ser199-Arg426-Gly431 | (151) | TTCTGCGCCAGCGACGCCAAGGCCTACGAC |
| Lys121-Val200-Asn425-Lys432 | (151) | TTCTGCGCCAGCGACGCCAAGGCCTACGAC |

*FIG. 5A*

| | | |
|---|---|---|
| Val120-Ile201-Ile424-Ala433 | (151) | TTCTGCGCCAGCGACGCCAAGGCCTACGAC |
| Val120-Ile201B-Ile424-Ala433 | (151) | TTCTGCGCCAGCGACGCCAAGGCCTACGAC |
| Consensus | (151) | TTCTGCGCCAGCGACGCCAAGGCCTACGAC |
| | | 181 210 |
| Leu122-Ser199-Tryp427-Gly431 | (181) | ACCGAGGTGCACAACGTGTGGGCCACCCAC |
| Val127-Asn195-Arg426-Gly431 | (181) | ACCGAGGTGCACAACGTGTGGGCCACCCAC |
| Val120-Thr202-Ile424-Ala433 | (181) | ACCGAGGTGCACAACGTGTGGGCCACCCAC |
| Leu122-Ser199-Arg426-Lys432 | (181) | ACCGAGGTGCACAACGTGTGGGCCACCCAC |
| Leu122-Ser199-Arg426-Gly431 | (181) | ACCGAGGTGCACAACGTGTGGGCCACCCAC |
| Lys121-Val200-Asn425-Lys432 | (181) | ACCGAGGTGCACAACGTGTGGGCCACCCAC |
| Val120-Ile201-Ile424-Ala433 | (181) | ACCGAGGTGCACAACGTGTGGGCCACCCAC |
| Val120-Ile201B-Ile424-Ala433 | (181) | ACCGAGGTGCACAACGTGTGGGCCACCCAC |
| Consensus | (181) | ACCGAGGTGCACAACGTGTGGGCCACCCAC |
| | | 211 240 |
| Leu122-Ser199-Tryp427-Gly431 | (211) | GCCTGCGTGCCCACCGACCCCAACCCCCAG |
| Val127-Asn195-Arg426-Gly431 | (211) | GCCTGCGTGCCCACCGACCCCAACCCCCAG |
| Val120-Thr202-Ile424-Ala433 | (211) | GCCTGCGTGCCCACCGACCCCAACCCCCAG |
| Leu122-Ser199-Arg426-Lys432 | (211) | GCCTGCGTGCCCACCGACCCCAACCCCCAG |
| Leu122-Ser199-Arg426-Gly431 | (211) | GCCTGCGTGCCCACCGACCCCAACCCCCAG |
| Lys121-Val200-Asn425-Lys432 | (211) | GCCTGCGTGCCCACCGACCCCAACCCCCAG |
| Val120-Ile201-Ile424-Ala433 | (211) | GCCTGCGTGCCCACCGACCCCAACCCCCAG |
| Val120-Ile201B-Ile424-Ala433 | (211) | GCCTGCGTGCCCACCGACCCCAACCCCCAG |
| Consensus | (211) | GCCTGCGTGCCCACCGACCCCAACCCCCAG |
| | | 241 270 |
| Leu122-Ser199-Tryp427-Gly431 | (241) | GAGATCGTGCTGGAGAACGTGACCGAGAAC |
| Val127-Asn195-Arg426-Gly431 | (241) | GAGATCGTGCTGGAGAACGTGACCGAGAAC |
| Val120-Thr202-Ile424-Ala433 | (241) | GAGATCGTGCTGGAGAACGTGACCGAGAAC |
| Leu122-Ser199-Arg426-Lys432 | (241) | GAGATCGTGCTGGAGAACGTGACCGAGAAC |
| Leu122-Ser199-Arg426-Gly431 | (241) | GAGATCGTGCTGGAGAACGTGACCGAGAAC |
| Lys121-Val200-Asn425-Lys432 | (241) | GAGATCGTGCTGGAGAACGTGACCGAGAAC |
| Val120-Ile201-Ile424-Ala433 | (241) | GAGATCGTGCTGGAGAACGTGACCGAGAAC |
| Val120-Ile201B-Ile424-Ala433 | (241) | GAGATCGTGCTGGAGAACGTGACCGAGAAC |
| Consensus | (241) | GAGATCGTGCTGGAGAACGTGACCGAGAAC |
| | | 271 300 |
| Leu122-Ser199-Tryp427-Gly431 | (271) | TTCAACATGTGGAAGAACAACATGGTGGAG |
| Val127-Asn195-Arg426-Gly431 | (271) | TTCAACATGTGGAAGAACAACATGGTGGAG |
| Val120-Thr202-Ile424-Ala433 | (271) | TTCAACATGTGGAAGAACAACATGGTGGAG |
| Leu122-Ser199-Arg426-Lys432 | (271) | TTCAACATGTGGAAGAACAACATGGTGGAG |
| Leu122-Ser199-Arg426-Gly431 | (271) | TTCAACATGTGGAAGAACAACATGGTGGAG |
| Lys121-Val200-Asn425-Lys432 | (271) | TTCAACATGTGGAAGAACAACATGGTGGAG |
| Val120-Ile201-Ile424-Ala433 | (271) | TTCAACATGTGGAAGAACAACATGGTGGAG |
| Val120-Ile201B-Ile424-Ala433 | (271) | TTCAACATGTGGAAGAACAACATGGTGGAG |
| Consensus | (271) | TTCAACATGTGGAAGAACAACATGGTGGAG |
| | | 301 330 |
| Leu122-Ser199-Tryp427-Gly431 | (301) | CAGATGCACGAGGACATCATCAGCCTGTGG |
| Val127-Asn195-Arg426-Gly431 | (301) | CAGATGCACGAGGACATCATCAGCCTGTGG |
| Val120-Thr202-Ile424-Ala433 | (301) | CAGATGCACGAGGACATCATCAGCCTGTGG |
| Leu122-Ser199-Arg426-Lys432 | (301) | CAGATGCACGAGGACATCATCAGCCTGTGG |
| Leu122-Ser199-Arg426-Gly431 | (301) | CAGATGCACGAGGACATCATCAGCCTGTGG |
| Lys121-Val200-Asn425-Lys432 | (301) | CAGATGCACGAGGACATCATCAGCCTGTGG |
| Val120-Ile201-Ile424-Ala433 | (301) | CAGATGCACGAGGACATCATCAGCCTGTGG |
| Val120-Ile201B-Ile424-Ala433 | (301) | CAGATGCACGAGGACATCATCAGCCTGTGG |
| Consensus | (301) | CAGATGCACGAGGACATCATCAGCCTGTGG |
| | | 331 360 |
| Leu122-Ser199-Tryp427-Gly431 | (331) | GACCAGAGCCTGAAGCCCTGCGTGAAGCTG |
| Val127-Asn195-Arg426-Gly431 | (331) | GACCAGAGCCTGAAGCCCTGCGTGAAGCTG |
| Val120-Thr202-Ile424-Ala433 | (331) | GACCAGAGCCTGAAGCCCTGCGTG------ |

FIG. 5B

| | | |
|---|---|---|
| Leu122-Ser199-Arg426-Lys432 | (331) | GACCAGAGCCTGAAGCCCTGCGTGAAGCTG |
| Leu122-Ser199-Arg426-Gly431 | (331) | GACCAGAGCCTGAAGCCCTGCGTGAAGCTG |
| Lys121-Val200-Asn425-Lys432 | (331) | GACCAGAGCCTGAAGCCCTGCGTGAA---- |
| Val120-Ile201-Ile424-Ala433 | (331) | GACCAGAGCCTGAAGCCCTGCGTG------ |
| Val120-Ile201B-Ile424-Ala433 | (331) | GACCAGAGCCTGAAGCCCTGCGTG------ |
| Consensus | (331) | GACCAGAGCCTGAAGCCCTGCGTGAAGCTG |
| | | 361 390 |
| Leu122-Ser199-Tryp427-Gly431 | (361) | --------------GG-------------- |
| Val127-Asn195-Arg426-Gly431 | (361) | ACCCCCCTGTGCGTGGGGGCAGGGAACTGC |
| Val120-Thr202-Ile424-Ala433 | (355) | --------------GG-------------- |
| Leu122-Ser199-Arg426-Lys432 | (361) | --------------GG-------------- |
| Leu122-Ser199-Arg426-Gly431 | (361) | --------------GG-------------- |
| Lys121-Val200-Asn425-Lys432 | (357) | --------------GG-------------- |
| Val120-Ile201-Ile424-Ala433 | (355) | ------------------------------ |
| Val120-Ile201B-Ile424-Ala433 | (355) | ------------------------------ |
| Consensus | (361) | GG |
| | | 391 420 |
| Leu122-Ser199-Tryp427-Gly431 | (363) | --CAACAGCGTGATCACCCAGGCCTGCCCC |
| Val127-Asn195-Arg426-Gly431 | (391) | AACACCAGCGTGATCACCCAGGCCTGCCCC |
| Val120-Thr202-Ile424-Ala433 | (357) | -----CGGCGC---CACCCAGGCCTGCCCC |
| Leu122-Ser199-Arg426-Lys432 | (363) | --CAACAGCGTGATCACCCAGGCCTGCCCC |
| Leu122-Ser199-Arg426-Gly431 | (363) | --CAACAGCGTGATCACCCAGGCCTGCCCC |
| Lys121-Val200-Asn425-Lys432 | (359) | ----CCCCCGTGATCACCCAGGCCTGCCCC |
| Val120-Ile201-Ile424-Ala433 | (355) | ------GGCGGCATCACCCAGGCCTGCCCC |
| Val120-Ile201B-Ile424-Ala433 | (355) | ------CCCGGCATCACCCAGGCCTGCCCC |
| Consensus | (391) | CA CAGCGTGATCACCCAGGCCTGCCCC |
| | | 421 450 |
| Leu122-Ser199-Tryp427-Gly431 | (391) | AAGGTGAGCTTCGAGCCCATCCCCATCCAC |
| Val127-Asn195-Arg426-Gly431 | (421) | AAGGTGAGCTTCGAGCCCATCCCCATCCAC |
| Val120-Thr202-Ile424-Ala433 | (379) | AAGGTGAGCTTCGAGCCCATCCCCATCCAC |
| Leu122-Ser199-Arg426-Lys432 | (391) | AAGGTGAGCTTCGAGCCCATCCCCATCCAC |
| Leu122-Ser199-Arg426-Gly431 | (391) | AAGGTGAGCTTCGAGCCCATCCCCATCCAC |
| Lys121-Val200-Asn425-Lys432 | (385) | AAGGTGAGCTTCGAGCCCATCCCCATCCAC |
| Val120-Ile201-Ile424-Ala433 | (379) | AAGGTGAGCTTCGAGCCCATCCCCATCCAC |
| Val120-Ile201B-Ile424-Ala433 | (379) | AAGGTGAGCTTCGAGCCCATCCCCATCCAC |
| Consensus | (421) | AAGGTGAGCTTCGAGCCCATCCCCATCCAC |
| | | 451 480 |
| Leu122-Ser199-Tryp427-Gly431 | (421) | TACTGCGCCCCCGCCGGCTTCGCCATCCTG |
| Val127-Asn195-Arg426-Gly431 | (451) | TACTGCGCCCCCGCCGGCTTCGCCATCCTG |
| Val120-Thr202-Ile424-Ala433 | (409) | TACTGCGCCCCCGCCGGCTTCGCCATCCTG |
| Leu122-Ser199-Arg426-Lys432 | (421) | TACTGCGCCCCCGCCGGCTTCGCCATCCTG |
| Leu122-Ser199-Arg426-Gly431 | (421) | TACTGCGCCCCCGCCGGCTTCGCCATCCTG |
| Lys121-Val200-Asn425-Lys432 | (415) | TACTGCGCCCCCGCCGGCTTCGCCATCCTG |
| Val120-Ile201-Ile424-Ala433 | (409) | TACTGCGCCCCCGCCGGCTTCGCCATCCTG |
| Val120-Ile201B-Ile424-Ala433 | (409) | TACTGCGCCCCCGCCGGCTTCGCCATCCTG |
| Consensus | (451) | TACTGCGCCCCCGCCGGCTTCGCCATCCTG |
| | | 481 510 |
| Leu122-Ser199-Tryp427-Gly431 | (451) | AAGTGCAACGACAAGAAGTTCAACGGCAGC |
| Val127-Asn195-Arg426-Gly431 | (481) | AAGTGCAACGACAAGAAGTTCAACGGCAGC |
| Val120-Thr202-Ile424-Ala433 | (439) | AAGTGCAACGACAAGAAGTTCAACGGCAGC |
| Leu122-Ser199-Arg426-Lys432 | (451) | AAGTGCAACGACAAGAAGTTCAACGGCAGC |
| Leu122-Ser199-Arg426-Gly431 | (451) | AAGTGCAACGACAAGAAGTTCAACGGCAGC |
| Lys121-Val200-Asn425-Lys432 | (445) | AAGTGCAACGACAAGAAGTTCAACGGCAGC |
| Val120-Ile201-Ile424-Ala433 | (439) | AAGTGCAACGACAAGAAGTTCAACGGCAGC |
| Val120-Ile201B-Ile424-Ala433 | (439) | AAGTGCAACGACAAGAAGTTCAACGGCAGC |
| Consensus | (481) | AAGTGCAACGACAAGAAGTTCAACGGCAGC |
| | | 511 540 |

*FIG. 5C*

```
Leu122-Ser199-Tryp427-Gly431   (481) GGCCCCTGCACCAACGTGAGCACCGTGCAG
 Val127-Asn195-Arg426-Gly431   (511) GGCCCCTGCACCAACGTGAGCACCGTGCAG
 Val120-Thr202-Ile424-Ala433   (469) GGCCCCTGCACCAACGTGAGCACCGTGCAG
 Leu122-Ser199-Arg426-Lys432   (481) GGCCCCTGCACCAACGTGAGCACCGTGCAG
 Leu122-Ser199-Arg426-Gly431   (481) GGCCCCTGCACCAACGTGAGCACCGTGCAG
 Lys121-Val200-Asn425-Lys432   (475) GGCCCCTGCACCAACGTGAGCACCGTGCAG
 Val120-Ile201-Ile424-Ala433   (469) GGCCCCTGCACCAACGTGAGCACCGTGCAG
Val120-Ile201B-Ile424-Ala433   (469) GGCCCCTGCACCAACGTGAGCACCGTGCAG
                   Consensus   (511) GGCCCCTGCACCAACGTGAGCACCGTGCAG
                                     541                        570
Leu122-Ser199-Tryp427-Gly431   (511) TGCACCCACGGCATCCGCCCCGTGGTGAGC
 Val127-Asn195-Arg426-Gly431   (541) TGCACCCACGGCATCCGCCCCGTGGTGAGC
 Val120-Thr202-Ile424-Ala433   (499) TGCACCCACGGCATCCGCCCCGTGGTGAGC
 Leu122-Ser199-Arg426-Lys432   (511) TGCACCCACGGCATCCGCCCCGTGGTGAGC
 Leu122-Ser199-Arg426-Gly431   (511) TGCACCCACGGCATCCGCCCCGTGGTGAGC
 Lys121-Val200-Asn425-Lys432   (505) TGCACCCACGGCATCCGCCCCGTGGTGAGC
 Val120-Ile201-Ile424-Ala433   (499) TGCACCCACGGCATCCGCCCCGTGGTGAGC
Val120-Ile201B-Ile424-Ala433   (499) TGCACCCACGGCATCCGCCCCGTGGTGAGC
                   Consensus   (541) TGCACCCACGGCATCCGCCCCGTGGTGAGC
                                     571                        600
Leu122-Ser199-Tryp427-Gly431   (541) ACCCAGCTGCTGCTGAACGGCAGCCTGGCC
 Val127-Asn195-Arg426-Gly431   (571) ACCCAGCTGCTGCTGAACGGCAGCCTGGCC
 Val120-Thr202-Ile424-Ala433   (529) ACCCAGCTGCTGCTGAACGGCAGCCTGGCC
 Leu122-Ser199-Arg426-Lys432   (541) ACCCAGCTGCTGCTGAACGGCAGCCTGGCC
 Leu122-Ser199-Arg426-Gly431   (541) ACCCAGCTGCTGCTGAACGGCAGCCTGGCC
 Lys121-Val200-Asn425-Lys432   (535) ACCCAGCTGCTGCTGAACGGCAGCCTGGCC
 Val120-Ile201-Ile424-Ala433   (529) ACCCAGCTGCTGCTGAACGGCAGCCTGGCC
Val120-Ile201B-Ile424-Ala433   (529) ACCCAGCTGCTGCTGAACGGCAGCCTGGCC
                   Consensus   (571) ACCCAGCTGCTGCTGAACGGCAGCCTGGCC
                                     601                        630
Leu122-Ser199-Tryp427-Gly431   (571) GAGGAGGGCGTGGTGATCCGCAGCGAGAAC
 Val127-Asn195-Arg426-Gly431   (601) GAGGAGGGCGTGGTGATCCGCAGCGAGAAC
 Val120-Thr202-Ile424-Ala433   (559) GAGGAGGGCGTGGTGATCCGCAGCGAGAAC
 Leu122-Ser199-Arg426-Lys432   (571) GAGGAGGGCGTGGTGATCCGCAGCGAGAAC
 Leu122-Ser199-Arg426-Gly431   (571) GAGGAGGGCGTGGTGATCCGCAGCGAGAAC
 Lys121-Val200-Asn425-Lys432   (565) GAGGAGGGCGTGGTGATCCGCAGCGAGAAC
 Val120-Ile201-Ile424-Ala433   (559) GAGGAGGGCGTGGTGATCCGCAGCGAGAAC
Val120-Ile201B-Ile424-Ala433   (559) GAGGAGGGCGTGGTGATCCGCAGCGAGAAC
                   Consensus   (601) GAGGAGGGCGTGGTGATCCGCAGCGAGAAC
                                     631                        660
Leu122-Ser199-Tryp427-Gly431   (601) TTCACCGACAACGCCAAGACCATCATCGTG
 Val127-Asn195-Arg426-Gly431   (631) TTCACCGACAACGCCAAGACCATCATCGTG
 Val120-Thr202-Ile424-Ala433   (589) TTCACCGACAACGCCAAGACCATCATCGTG
 Leu122-Ser199-Arg426-Lys432   (601) TTCACCGACAACGCCAAGACCATCATCGTG
 Leu122-Ser199-Arg426-Gly431   (601) TTCACCGACAACGCCAAGACCATCATCGTG
 Lys121-Val200-Asn425-Lys432   (595) TTCACCGACAACGCCAAGACCATCATCGTG
 Val120-Ile201-Ile424-Ala433   (589) TTCACCGACAACGCCAAGACCATCATCGTG
Val120-Ile201B-Ile424-Ala433   (589) TTCACCGACAACGCCAAGACCATCATCGTG
                   Consensus   (631) TTCACCGACAACGCCAAGACCATCATCGTG
                                     661                        690
Leu122-Ser199-Tryp427-Gly431   (631) CAGCTGAAGGAGAGCGTGGAGATCAACTGC
 Val127-Asn195-Arg426-Gly431   (661) CAGCTGAAGGAGAGCGTGGAGATCAACTGC
 Val120-Thr202-Ile424-Ala433   (619) CAGCTGAAGGAGAGCGTGGAGATCAACTGC
 Leu122-Ser199-Arg426-Lys432   (631) CAGCTGAAGGAGAGCGTGGAGATCAACTGC
 Leu122-Ser199-Arg426-Gly431   (631) CAGCTGAAGGAGAGCGTGGAGATCAACTGC
 Lys121-Val200-Asn425-Lys432   (625) CAGCTGAAGGAGAGCGTGGAGATCAACTGC
 Val120-Ile201-Ile424-Ala433   (619) CAGCTGAAGGAGAGCGTGGAGATCAACTGC
```

*FIG. 5D*

| | | |
|---|---|---|
| Val120-Ile201B-Ile424-Ala433 | (619) | CAGCTGAAGGAGAGCGTGGAGATCAACTGC |
| Consensus | (661) | CAGCTGAAGGAGAGCGTGGAGATCAACTGC |
| | | 691 720 |
| Leu122-Ser199-Tryp427-Gly431 | (661) | ACCCGCCCCAACAACAACACCCGCAAGAGC |
| Val127-Asn195-Arg426-Gly431 | (691) | ACCCGCCCCAACAACAACACCCGCAAGAGC |
| Val120-Thr202-Ile424-Ala433 | (649) | ACCCGCCCCAACAACAACACCCGCAAGAGC |
| Leu122-Ser199-Arg426-Lys432 | (661) | ACCCGCCCCAACAACAACACCCGCAAGAGC |
| Leu122-Ser199-Arg426-Gly431 | (661) | ACCCGCCCCAACAACAACACCCGCAAGAGC |
| Lys121-Val200-Asn425-Lys432 | (655) | ACCCGCCCCAACAACAACACCCGCAAGAGC |
| Val120-Ile201-Ile424-Ala433 | (649) | ACCCGCCCCAACAACAACACCCGCAAGAGC |
| Val120-Ile201B-Ile424-Ala433 | (649) | ACCCGCCCCAACAACAACACCCGCAAGAGC |
| Consensus | (691) | ACCCGCCCCAACAACAACACCCGCAAGAGC |
| | | 721 750 |
| Leu122-Ser199-Tryp427-Gly431 | (691) | ATCACCATCGGCCCCGGCCGCGCCTTCTAC |
| Val127-Asn195-Arg426-Gly431 | (721) | ATCACCATCGGCCCCGGCCGCGCCTTCTAC |
| Val120-Thr202-Ile424-Ala433 | (679) | ATCACCATCGGCCCCGGCCGCGCCTTCTAC |
| Leu122-Ser199-Arg426-Lys432 | (691) | ATCACCATCGGCCCCGGCCGCGCCTTCTAC |
| Leu122-Ser199-Arg426-Gly431 | (691) | ATCACCATCGGCCCCGGCCGCGCCTTCTAC |
| Lys121-Val200-Asn425-Lys432 | (685) | ATCACCATCGGCCCCGGCCGCGCCTTCTAC |
| Val120-Ile201-Ile424-Ala433 | (679) | ATCACCATCGGCCCCGGCCGCGCCTTCTAC |
| Val120-Ile201B-Ile424-Ala433 | (679) | ATCACCATCGGCCCCGGCCGCGCCTTCTAC |
| Consensus | (721) | ATCACCATCGGCCCCGGCCGCGCCTTCTAC |
| | | 751 780 |
| Leu122-Ser199-Tryp427-Gly431 | (721) | GCCACCGGCGACATCATCGGCGACATCCGC |
| Val127-Asn195-Arg426-Gly431 | (751) | GCCACCGGCGACATCATCGGCGACATCCGC |
| Val120-Thr202-Ile424-Ala433 | (709) | GCCACCGGCGACATCATCGGCGACATCCGC |
| Leu122-Ser199-Arg426-Lys432 | (721) | GCCACCGGCGACATCATCGGCGACATCCGC |
| Leu122-Ser199-Arg426-Gly431 | (721) | GCCACCGGCGACATCATCGGCGACATCCGC |
| Lys121-Val200-Asn425-Lys432 | (715) | GCCACCGGCGACATCATCGGCGACATCCGC |
| Val120-Ile201-Ile424-Ala433 | (709) | GCCACCGGCGACATCATCGGCGACATCCGC |
| Val120-Ile201B-Ile424-Ala433 | (709) | GCCACCGGCGACATCATCGGCGACATCCGC |
| Consensus | (751) | GCCACCGGCGACATCATCGGCGACATCCGC |
| | | 781 810 |
| Leu122-Ser199-Tryp427-Gly431 | (751) | CAGGCCCACTGCAACATCAGCGGCGAGAAG |
| Val127-Asn195-Arg426-Gly431 | (781) | CAGGCCCACTGCAACATCAGCGGCGAGAAG |
| Val120-Thr202-Ile424-Ala433 | (739) | CAGGCCCACTGCAACATCAGCGGCGAGAAG |
| Leu122-Ser199-Arg426-Lys432 | (751) | CAGGCCCACTGCAACATCAGCGGCGAGAAG |
| Leu122-Ser199-Arg426-Gly431 | (751) | CAGGCCCACTGCAACATCAGCGGCGAGAAG |
| Lys121-Val200-Asn425-Lys432 | (745) | CAGGCCCACTGCAACATCAGCGGCGAGAAG |
| Val120-Ile201-Ile424-Ala433 | (739) | CAGGCCCACTGCAACATCAGCGGCGAGAAG |
| Val120-Ile201B-Ile424-Ala433 | (739) | CAGGCCCACTGCAACATCAGCGGCGAGAAG |
| Consensus | (781) | CAGGCCCACTGCAACATCAGCGGCGAGAAG |
| | | 811 840 |
| Leu122-Ser199-Tryp427-Gly431 | (781) | TGGAACAACACCCTGAAGCAGATCGTGACC |
| Val127-Asn195-Arg426-Gly431 | (811) | TGGAACAACACCCTGAAGCAGATCGTGACC |
| Val120-Thr202-Ile424-Ala433 | (769) | TGGAACAACACCCTGAAGCAGATCGTGACC |
| Leu122-Ser199-Arg426-Lys432 | (781) | TGGAACAACACCCTGAAGCAGATCGTGACC |
| Leu122-Ser199-Arg426-Gly431 | (781) | TGGAACAACACCCTGAAGCAGATCGTGACC |
| Lys121-Val200-Asn425-Lys432 | (775) | TGGAACAACACCCTGAAGCAGATCGTGACC |
| Val120-Ile201-Ile424-Ala433 | (769) | TGGAACAACACCCTGAAGCAGATCGTGACC |
| Val120-Ile201B-Ile424-Ala433 | (769) | TGGAACAACACCCTGAAGCAGATCGTGACC |
| Consensus | (811) | TGGAACAACACCCTGAAGCAGATCGTGACC |
| | | 841 870 |
| Leu122-Ser199-Tryp427-Gly431 | (811) | AAGCTGCAGGCCCAGTTCGGCAACAAGACC |
| Val127-Asn195-Arg426-Gly431 | (841) | AAGCTGCAGGCCCAGTTCGGCAACAAGACC |
| Val120-Thr202-Ile424-Ala433 | (799) | AAGCTGCAGGCCCAGTTCGGCAACAAGACC |
| Leu122-Ser199-Arg426-Lys432 | (811) | AAGCTGCAGGCCCAGTTCGGCAACAAGACC |

FIG. 5E

| | | |
|---|---|---|
| Leu122-Ser199-Arg426-Gly431 | (811) | AAGCTGCAGGCCCAGTTCGGCAACAAGACC |
| Lys121-Val200-Asn425-Lys432 | (805) | AAGCTGCAGGCCCAGTTCGGCAACAAGACC |
| Val120-Ile201-Ile424-Ala433 | (799) | AAGCTGCAGGCCCAGTTCGGCAACAAGACC |
| Val120-Ile201B-Ile424-Ala433 | (799) | AAGCTGCAGGCCCAGTTCGGCAACAAGACC |
| Consensus | (841) | AAGCTGCAGGCCCAGTTCGGCAACAAGACC |
| | | 871 900 |
| Leu122-Ser199-Tryp427-Gly431 | (841) | ATCGTGTTCAAGCAGAGCAGCGGCGGCGAC |
| Val127-Asn195-Arg426-Gly431 | (871) | ATCGTGTTCAAGCAGAGCAGCGGCGGCGAC |
| Val120-Thr202-Ile424-Ala433 | (829) | ATCGTGTTCAAGCAGAGCAGCGGCGGCGAC |
| Leu122-Ser199-Arg426-Lys432 | (841) | ATCGTGTTCAAGCAGAGCAGCGGCGGCGAC |
| Leu122-Ser199-Arg426-Gly431 | (841) | ATCGTGTTCAAGCAGAGCAGCGGCGGCGAC |
| Lys121-Val200-Asn425-Lys432 | (835) | ATCGTGTTCAAGCAGAGCAGCGGCGGCGAC |
| Val120-Ile201-Ile424-Ala433 | (829) | ATCGTGTTCAAGCAGAGCAGCGGCGGCGAC |
| Val120-Ile201B-Ile424-Ala433 | (829) | ATCGTGTTCAAGCAGAGCAGCGGCGGCGAC |
| Consensus | (871) | ATCGTGTTCAAGCAGAGCAGCGGCGGCGAC |
| | | 901 930 |
| Leu122-Ser199-Tryp427-Gly431 | (871) | CCCGAGATCGTGATGCACAGCTTCAACTGC |
| Val127-Asn195-Arg426-Gly431 | (901) | CCCGAGATCGTGATGCACAGCTTCAACTGC |
| Val120-Thr202-Ile424-Ala433 | (859) | CCCGAGATCGTGATGCACAGCTTCAACTGC |
| Leu122-Ser199-Arg426-Lys432 | (871) | CCCGAGATCGTGATGCACAGCTTCAACTGC |
| Leu122-Ser199-Arg426-Gly431 | (871) | CCCGAGATCGTGATGCACAGCTTCAACTGC |
| Lys121-Val200-Asn425-Lys432 | (865) | CCCGAGATCGTGATGCACAGCTTCAACTGC |
| Val120-Ile201-Ile424-Ala433 | (859) | CCCGAGATCGTGATGCACAGCTTCAACTGC |
| Val120-Ile201B-Ile424-Ala433 | (859) | CCCGAGATCGTGATGCACAGCTTCAACTGC |
| Consensus | (901) | CCCGAGATCGTGATGCACAGCTTCAACTGC |
| | | 931 960 |
| Leu122-Ser199-Tryp427-Gly431 | (901) | GGCGGCGAGTTCTTCTACTGCAACAGCACC |
| Val127-Asn195-Arg426-Gly431 | (931) | GGCGGCGAGTTCTTCTACTGCAACAGCACC |
| Val120-Thr202-Ile424-Ala433 | (889) | GGCGGCGAGTTCTTCTACTGCAACAGCACC |
| Leu122-Ser199-Arg426-Lys432 | (901) | GGCGGCGAGTTCTTCTACTGCAACAGCACC |
| Leu122-Ser199-Arg426-Gly431 | (901) | GGCGGCGAGTTCTTCTACTGCAACAGCACC |
| Lys121-Val200-Asn425-Lys432 | (895) | GGCGGCGAGTTCTTCTACTGCAACAGCACC |
| Val120-Ile201-Ile424-Ala433 | (889) | GGCGGCGAGTTCTTCTACTGCAACAGCACC |
| Val120-Ile201B-Ile424-Ala433 | (889) | GGCGGCGAGTTCTTCTACTGCAACAGCACC |
| Consensus | (931) | GGCGGCGAGTTCTTCTACTGCAACAGCACC |
| | | 961 990 |
| Leu122-Ser199-Tryp427-Gly431 | (931) | CAGCTGTTCAACAGCACCTGGAACAACACC |
| Val127-Asn195-Arg426-Gly431 | (961) | CAGCTGTTCAACAGCACCTGGAACAACACC |
| Val120-Thr202-Ile424-Ala433 | (919) | CAGCTGTTCAACAGCACCTGGAACAACACC |
| Leu122-Ser199-Arg426-Lys432 | (931) | CAGCTGTTCAACAGCACCTGGAACAACACC |
| Leu122-Ser199-Arg426-Gly431 | (931) | CAGCTGTTCAACAGCACCTGGAACAACACC |
| Lys121-Val200-Asn425-Lys432 | (925) | CAGCTGTTCAACAGCACCTGGAACAACACC |
| Val120-Ile201-Ile424-Ala433 | (919) | CAGCTGTTCAACAGCACCTGGAACAACACC |
| Val120-Ile201B-Ile424-Ala433 | (919) | CAGCTGTTCAACAGCACCTGGAACAACACC |
| Consensus | (961) | CAGCTGTTCAACAGCACCTGGAACAACACC |
| | | 991 1020 |
| Leu122-Ser199-Tryp427-Gly431 | (961) | ATCGGCCCCAACAACACCAACGGCACCATC |
| Val127-Asn195-Arg426-Gly431 | (991) | ATCGGCCCCAACAACACCAACGGCACCATC |
| Val120-Thr202-Ile424-Ala433 | (949) | ATCGGCCCCAACAACACCAACGGCACCATC |
| Leu122-Ser199-Arg426-Lys432 | (961) | ATCGGCCCCAACAACACCAACGGCACCATC |
| Leu122-Ser199-Arg426-Gly431 | (961) | ATCGGCCCCAACAACACCAACGGCACCATC |
| Lys121-Val200-Asn425-Lys432 | (955) | ATCGGCCCCAACAACACCAACGGCACCATC |
| Val120-Ile201-Ile424-Ala433 | (949) | ATCGGCCCCAACAACACCAACGGCACCATC |
| Val120-Ile201B-Ile424-Ala433 | (949) | ATCGGCCCCAACAACACCAACGGCACCATC |
| Consensus | (991) | ATCGGCCCCAACAACACCAACGGCACCATC |
| | | 1021 1050 |
| Leu122-Ser199-Tryp427-Gly431 | (991) | ACCCTGCCCTGCCGCATCAAGCAGATCATC |

FIG. 5F

| | | |
|---|---|---|
| Val127-Asn195-Arg426-Gly431 | (1021) | ACCCTGCCCTGCCGCATCAAGCAGATCATC |
| Val120-Thr202-Ile424-Ala433 | (979) | ACCCTGCCCTGCCGCATCAAGCAGATCATC |
| Leu122-Ser199-Arg426-Lys432 | (991) | ACCCTGCCCTGCCGCATCAAGCAGATCATC |
| Leu122-Ser199-Arg426-Gly431 | (991) | ACCCTGCCCTGCCGCATCAAGCAGATCATC |
| Lys121-Val200-Asn425-Lys432 | (985) | ACCCTGCCCTGCCGCATCAAGCAGATCATC |
| Val120-Ile201-Ile424-Ala433 | (979) | ACCCTGCCCTGCCGCATCAAGCAGATCATC |
| Val120-Ile201B-Ile424-Ala433 | (979) | ACCCTGCCCTGCCGCATCAAGCAGATCATC |
| Consensus | (1021) | ACCCTGCCCTGCCGCATCAAGCAGATCATC |
| | | 1051 1080 |
| Leu122-Ser199 Tryp427-Gly431 | (1021) | AACCGCTGGGGCGGCAAGGCCATGTACGCC |
| Val127-Asn195-Arg426-Gly431 | (1051) | AACCGCGGCGGCGGCAAGGCCATGTACGCC |
| Val120-Thr202-Ile424-Ala433 | (1009) | ---------GGCGGC---GCCATGTACGCC |
| Leu122-Ser199-Arg426-Lys432 | (1021) | AACCGCGGCGGCAACAAGGCCATGTACGCC |
| Leu122-Ser199-Arg426-Gly431 | (1021) | AACCGCGGCAGCGGCAAGGCCATGTACGCC |
| Lys121-Val200-Asn425-Lys432 | (1015) | AAC------GCCCCCAAGGCCATGTACGCC |
| Val120-Ile201-Ile424-Ala433 | (1009) | ---------GGCGGC---GCCATGTACGCC |
| Val120-Ile201B-Ile424-Ala433 | (1009) | ---------GGCGGC---GCCATGTACGCC |
| Consensus | (1051) | AACCGC G GGCGGCAAGGCCATGTACGCC |
| | | 1081 1110 |
| Leu122-Ser199 Tryp427-Gly431 | (1051) | CCCCCCATCCGCGGCCAGATCCGCTGCAGC |
| Val127-Asn195-Arg426-Gly431 | (1081) | CCCCCCATCCGCGGCCAGATCCGCTGCAGC |
| Val120-Thr202-Ile424-Ala433 | (1027) | CCCCCCATCCGCGGCCAGATCCGCTGCAGC |
| Leu122-Ser199-Arg426-Lys432 | (1051) | CCCCCCATCCGCGGCCAGATCCGCTGCAGC |
| Leu122-Ser199-Arg426-Gly431 | (1051) | CCCCCCATCCGCGGCCAGATCCGCTGCAGC |
| Lys121-Val200-Asn425-Lys432 | (1039) | CCCCCCATCCGCGGCCAGATCCGCTGCAGC |
| Val120-Ile201-Ile424-Ala433 | (1027) | CCCCCCATCCGCGGCCAGATCCGCTGCAGC |
| Val120-Ile201B-Ile424-Ala433 | (1027) | CCCCCCATCCGCGGCCAGATCCGCTGCAGC |
| Consensus | (1081) | CCCCCCATCCGCGGCCAGATCCGCTGCAGC |
| | | 1111 1140 |
| Leu122-Ser199 Tryp427-Gly431 | (1081) | AGCAACATCACCGGCCTGCTGCTGACCCGC |
| Val127-Asn195-Arg426-Gly431 | (1111) | AGCAACATCACCGGCCTGCTGCTGACCCGC |
| Val120-Thr202-Ile424-Ala433 | (1057) | AGCAACATCACCGGCCTGCTGCTGACCCGC |
| Leu122-Ser199-Arg426-Lys432 | (1081) | AGCAACATCACCGGCCTGCTGCTGACCCGC |
| Leu122-Ser199-Arg426-Gly431 | (1081) | AGCAACATCACCGGCCTGCTGCTGACCCGC |
| Lys121-Val200-Asn425-Lys432 | (1069) | AGCAACATCACCGGCCTGCTGCTGACCCGC |
| Val120-Ile201-Ile424-Ala433 | (1057) | AGCAACATCACCGGCCTGCTGCTGACCCGC |
| Val120-Ile201B-Ile424-Ala433 | (1057) | AGCAACATCACCGGCCTGCTGCTGACCCGC |
| Consensus | (1111) | AGCAACATCACCGGCCTGCTGCTGACCCGC |
| | | 1141 1170 |
| Leu122-Ser199 Tryp427-Gly431 | (1111) | GACGGCGGCAAGGAGATCAGCAACACCACC |
| Val127-Asn195-Arg426-Gly431 | (1141) | GACGGCGGCAAGGAGATCAGCAACACCACC |
| Val120-Thr202-Ile424-Ala433 | (1087) | GACGGCGGCAAGGAGATCAGCAACACCACC |
| Leu122-Ser199-Arg426-Lys432 | (1111) | GACGGCGGCAAGGAGATCAGCAACACCACC |
| Leu122-Ser199-Arg426-Gly431 | (1111) | GACGGCGGCAAGGAGATCAGCAACACCACC |
| Lys121-Val200-Asn425-Lys432 | (1099) | GACGGCGGCAAGGAGATCAGCAACACCACC |
| Val120-Ile201-Ile424-Ala433 | (1087) | GACGGCGGCAAGGAGATCAGCAACACCACC |
| Val120-Ile201B-Ile424-Ala433 | (1087) | GACGGCGGCAAGGAGATCAGCAACACCACC |
| Consensus | (1141) | GACGGCGGCAAGGAGATCAGCAACACCACC |
| | | 1171 1200 |
| Leu122-Ser199 Tryp427-Gly431 | (1141) | GAGATCTTCCGCCCCGGCGGCGGCGACATG |
| Val127-Asn195-Arg426-Gly431 | (1171) | GAGATCTTCCGCCCCGGCGGCGGCGACATG |
| Val120-Thr202-Ile424-Ala433 | (1117) | GAGATCTTCCGCCCCGGCGGCGGCGACATG |
| Leu122-Ser199-Arg426-Lys432 | (1141) | GAGATCTTCCGCCCCGGCGGCGGCGACATG |
| Leu122-Ser199-Arg426-Gly431 | (1141) | GAGATCTTCCGCCCCGGCGGCGGCGACATG |
| Lys121-Val200-Asn425-Lys432 | (1129) | GAGATCTTCCGCCCCGGCGGCGGCGACATG |
| Val120-Ile201-Ile424-Ala433 | (1117) | GAGATCTTCCGCCCCGGCGGCGGCGACATG |
| Val120-Ile201B-Ile424-Ala433 | (1117) | GAGATCTTCCGCCCCGGCGGCGGCGACATG |

FIG. 5G

|                               |        |                                |
|-------------------------------|--------|--------------------------------|
| Consensus                     | (1171) | GAGATCTTCCGCCCCGGCGGCGGCGACATG |
|                               |        | 1201                      1230 |
| Leu122-Ser199 Tryp427-Gly431  | (1171) | CGCGACAACTGGCGCAGCGAGCTGTACAAG |
| Val127-Asn195-Arg426-Gly431   | (1201) | CGCGACAACTGGCGCAGCGAGCTGTACAAG |
| Val120-Thr202-Ile424-Ala433   | (1147) | CGCGACAACTGGCGCAGCGAGCTGTACAAG |
| Leu122-Ser199-Arg426-Lys432   | (1171) | CGCGACAACTGGCGCAGCGAGCTGTACAAG |
| Leu122-Ser199-Arg426-Gly431   | (1171) | CGCGACAACTGGCGCAGCGAGCTGTACAAG |
| Lys121-Val200-Asn425-Lys432   | (1159) | CGCGACAACTGGCGCAGCGAGCTGTACAAG |
| Val120-Ile201-Ile424-Ala433   | (1147) | CGCGACAACTGGCGCAGCGAGCTGTACAAG |
| Val120-Ile201B-Ile424-Ala433  | (1147) | CGCGACAACTGGCGCAGCGAGCTGTACAAG |
| Consensus                     | (1201) | CGCGACAACTGGCGCAGCGAGCTGTACAAG |
|                               |        | 1231                      1260 |
| Leu122-Ser199 Tryp427-Gly431  | (1201) | TACAAGGTGGTGAAGATCGAGCCCCTGGGC |
| Val127-Asn195-Arg426-Gly431   | (1231) | TACAAGGTGGTGAAGATCGAGCCCCTGGGC |
| Val120-Thr202-Ile424-Ala433   | (1177) | TACAAGGTGGTGAAGATCGAGCCCCTGGGC |
| Leu122-Ser199-Arg426-Lys432   | (1201) | TACAAGGTGGTGAAGATCGAGCCCCTGGGC |
| Leu122-Ser199-Arg426-Gly431   | (1201) | TACAAGGTGGTGAAGATCGAGCCCCTGGGC |
| Lys121-Val200-Asn425-Lys432   | (1189) | TACAAGGTGGTGAAGATCGAGCCCCTGGGC |
| Val120-Ile201-Ile424-Ala433   | (1177) | TACAAGGTGGTGAAGATCGAGCCCCTGGGC |
| Val120-Ile201B-Ile424-Ala433  | (1177) | TACAAGGTGGTGAAGATCGAGCCCCTGGGC |
| Consensus                     | (1231) | TACAAGGTGGTGAAGATCGAGCCCCTGGGC |
|                               |        | 1261                      1290 |
| Leu122-Ser199 Tryp427-Gly431  | (1231) | GTGGCCCCCACCAAGGCCAAGCGCCGCGTG |
| Val127-Asn195-Arg426-Gly431   | (1261) | GTGGCCCCCACCAAGGCCAAGCGCCGCGTG |
| Val120-Thr202-Ile424-Ala433   | (1207) | GTGGCCCCCACCAAGGCCAAGCGCCGCGTG |
| Leu122-Ser199-Arg426-Lys432   | (1231) | GTGGCCCCCACCAAGGCCAAGCGCCGCGTG |
| Leu122-Ser199-Arg426-Gly431   | (1231) | GTGGCCCCCACCAAGGCCAAGCGCCGCGTG |
| Lys121-Val200-Asn425-Lys432   | (1219) | GTGGCCCCCACCAAGGCCAAGCGCCGCGTG |
| Val120-Ile201-Ile424-Ala433   | (1207) | GTGGCCCCCACCAAGGCCAAGCGCCGCGTG |
| Val120-Ile201B-Ile424-Ala433  | (1207) | GTGGCCCCCACCAAGGCCAAGCGCCGCGTG |
| Consensus                     | (1261) | GTGGCCCCCACCAAGGCCAAGCGCCGCGTG |
|                               |        | 1291                      1320 |
| Leu122-Ser199 Tryp427-Gly431  | (1261) | GTGCAGCGCGAGAAGCGCGCCGTGACCCTG |
| Val127-Asn195-Arg426-Gly431   | (1291) | GTGCAGCGCGAGAAGCGCGCCGTGACCCTG |
| Val120-Thr202-Ile424-Ala433   | (1237) | GTGCAGCGCGAGAAGCGCGCCGTGACCCTG |
| Leu122-Ser199-Arg426-Lys432   | (1261) | GTGCAGCGCGAGAAGCGCGCCGTGACCCTG |
| Leu122-Ser199-Arg426-Gly431   | (1261) | GTGCAGCGCGAGAAGCGCGCCGTGACCCTG |
| Lys121-Val200-Asn425-Lys432   | (1249) | GTGCAGCGCGAGAAGCGCGCCGTGACCCTG |
| Val120-Ile201-Ile424-Ala433   | (1237) | GTGCAGCGCGAGAAGGGCGCCGTGACCCTG |
| Val120-Ile201B-Ile424-Ala433  | (1237) | GTGCAGCGCGAGAAGCGCGCCGTGACCCTG |
| Consensus                     | (1291) | GTGCAGCGCGAGAAGCGCGCCGTGACCCTG |
|                               |        | 1321                      1350 |
| Leu122-Ser199 Tryp427-Gly431  | (1291) | GGCGCCATGTTCCTGGGCTTCCTGGGCGCC |
| Val127-Asn195-Arg426-Gly431   | (1321) | GGCGCCATGTTCCTGGGCTTCCTGGGCGCC |
| Val120-Thr202-Ile424-Ala433   | (1267) | GGCGCCATGTTCCTGGGCTTCCTGGGCGCC |
| Leu122-Ser199-Arg426-Lys432   | (1291) | GGCGCCATGTTCCTGGGCTTCCTGGGCGCC |
| Leu122-Ser199-Arg426-Gly431   | (1291) | GGCGCCATGTTCCTGGGCTTCCTGGGCGCC |
| Lys121-Val200-Asn425-Lys432   | (1279) | GGCGCCATGTTCCTGGGCTTCCTGGGCGCC |
| Val120-Ile201-Ile424-Ala433   | (1267) | GGCGCCATGTTCCTGGGCTTCCTGGGCGCC |
| Val120-Ile201B-Ile424-Ala433  | (1267) | GGCGCCATGTTCCTGGGCTTCCTGGGCGCC |
| Consensus                     | (1321) | GGCGCCATGTTCCTGGGCTTCCTGGGCGCC |
|                               |        | 1351                      1380 |
| Leu122-Ser199 Tryp427-Gly431  | (1321) | GCCGGCAGCACCATGGGCGCCCGCAGCCTG |
| Val127-Asn195-Arg426-Gly431   | (1351) | GCCGGCAGCACCATGGGCGCCCGCAGCCTG |
| Val120-Thr202-Ile424-Ala433   | (1297) | GCCGGCAGCACCATGGGCGCCCGCAGCCTG |
| Leu122-Ser199-Arg426-Lys432   | (1321) | GCCGGCAGCACCATGGGCGCCCGCAGCCTG |
| Leu122-Ser199-Arg426-Gly431   | (1321) | GCCGGCAGCACCATGGGCGCCCGCAGCCTG |

*FIG. 5H*

```
 Lys121-Val200-Asn425-Lys432  (1309) GCCGGCAGCACCATGGGCGCCCGCAGCCTG
 Val120-Ile201-Ile424-Ala433  (1297) GCCGGCAGCACCATGGGCGCCCGCAGCCTG
Val120-Ile201B-Ile424-Ala433  (1297) GCCGGCAGCACCATGGGCGCCCGCAGCCTG
                   Consensus  (1351) GCCGGCAGCACCATGGGCGCCCGCAGCCTG
                                     1381                      1410
Leu122-Ser199 Tryp427-Gly431  (1351) ACCCTGACCGTGCAGGCCCGCCAGCTGCTG
 Val127-Asn195-Arg426-Gly431  (1381) ACCCTGACCGTGCAGGCCCGCCAGCTGCTG
 Val120-Thr202-Ile424-Ala433  (1327) ACCCTGACCGTGCAGGCCCGCCAGCTGCTG
 Leu122-Ser199-Arg426-Lys432  (1351) ACCCTGACCGTGCAGGCCCGCCAGCTGCTG
 Leu122-Ser199-Arg426-Gly431  (1351) ACCCTGACCGTGCAGGCCCGCCAGCTGCTG
 Lys121-Val200-Asn425-Lys432  (1339) ACCCTGACCGTGCAGGCCCGCCAGCTGCTG
 Val120-Ile201-Ile424-Ala433  (1327) ACCCTGACCGTGCAGGCCCGCCAGCTGCTG
Val120-Ile201B-Ile424-Ala433  (1327) ACCCTGACCGTGCAGGCCCGCCAGCTGCTG
                   Consensus  (1381) ACCCTGACCGTGCAGGCCCGCCAGCTGCTG
                                     1411                      1440
Leu122-Ser199 Tryp427-Gly431  (1381) AGCGGCATCGTGCAGCAGCAGAACAACCTG
 Val127-Asn195-Arg426-Gly431  (1411) AGCGGCATCGTGCAGCAGCAGAACAACCTG
 Val120-Thr202-Ile424-Ala433  (1357) AGCGGCATCGTGCAGCAGCAGAACAACCTG
 Leu122-Ser199-Arg426-Lys432  (1381) AGCGGCATCGTGCAGCAGCAGAACAACCTG
 Leu122-Ser199-Arg426-Gly431  (1381) AGCGGCATCGTGCAGCAGCAGAACAACCTG
 Lys121-Val200-Asn425-Lys432  (1369) AGCGGCATCGTGCAGCAGCAGAACAACCTG
 Val120-Ile201-Ile424-Ala433  (1357) AGCGGCATCGTGCAGCAGCAGAACAACCTG
Val120-Ile201B-Ile424-Ala433  (1357) AGCGGCATCGTGCAGCAGCAGAACAACCTG
                   Consensus  (1411) AGCGGCATCGTGCAGCAGCAGAACAACCTG
                                     1441                      1470
Leu122-Ser199 Tryp427-Gly431  (1411) CTGCGCGCCATCGAGGCCCAGCAGCACCTG
 Val127-Asn195-Arg426-Gly431  (1441) CTGCGCGCCATCGAGGCCCAGCAGCACCTG
 Val120-Thr202-Ile424-Ala433  (1387) CTGCGCGCCATCGAGGCCCAGCAGCACCTG
 Leu122-Ser199-Arg426-Lys432  (1411) CTGCGCGCCATCGAGGCCCAGCAGCACCTG
 Leu122-Ser199-Arg426-Gly431  (1411) CTGCGCGCCATCGAGGCCCAGCAGCACCTG
 Lys121-Val200-Asn425-Lys432  (1399) CTGCGCGCCATCGAGGCCCAGCAGCACCTG
 Val120-Ile201-Ile424-Ala433  (1387) CTGCGCGCCATCGAGGCCCAGCAGCACCTG
Val120-Ile201B-Ile424-Ala433  (1387) CTGCGCGCCATCGAGGCCCAGCAGCACCTG
                   Consensus  (1441) CTGCGCGCCATCGAGGCCCAGCAGCACCTG
                                     1471                      1500
Leu122-Ser199 Tryp427-Gly431  (1441) CTGCAGCTGACCGTGTGGGGCATCAAGCAG
 Val127-Asn195-Arg426-Gly431  (1471) CTGCAGCTGACCGTGTGGGGCATCAAGCAG
 Val120-Thr202-Ile424-Ala433  (1417) CTGCAGCTGACCGTGTGGGGCATCAAGCAG
 Leu122-Ser199-Arg426-Lys432  (1441) CTGCAGCTGACCGTGTGGGGCATCAAGCAG
 Leu122-Ser199-Arg426-Gly431  (1441) CTGCAGCTGACCGTGTGGGGCATCAAGCAG
 Lys121-Val200-Asn425-Lys432  (1429) CTGCAGCTGACCGTGTGGGGCATCAAGCAG
 Val120-Ile201-Ile424-Ala433  (1417) CTGCAGCTGACCGTGTGGGGCATCAAGCAG
Val120-Ile201B-Ile424-Ala433  (1417) CTGCAGCTGACCGTGTGGGGCATCAAGCAG
                   Consensus  (1471) CTGCAGCTGACCGTGTGGGGCATCAAGCAG
                                     1501                      1530
Leu122-Ser199 Tryp427-Gly431  (1471) CTGCAGGCCCGCGTGCTGGCCGTGGAGCGC
 Val127-Asn195-Arg426-Gly431  (1501) CTGCAGGCCCGCGTGCTGGCCGTGGAGCGC
 Val120-Thr202-Ile424-Ala433  (1447) CTGCAGGCCCGCGTGCTGGCCGTGGAGCGC
 Leu122-Ser199-Arg426-Lys432  (1471) CTGCAGGCCCGCGTGCTGGCCGTGGAGCGC
 Leu122-Ser199-Arg426-Gly431  (1471) CTGCAGGCCCGCGTGCTGGCCGTGGAGCGC
 Lys121-Val200-Asn425-Lys432  (1459) CTGCAGGCCCGCGTGCTGGCCGTGGAGCGC
 Val120-Ile201-Ile424-Ala433  (1447) CTGCAGGCCCGCGTGCTGGCCGTGGAGCGC
Val120-Ile201B-Ile424-Ala433  (1447) CTGCAGGCCCGCGTGCTGGCCGTGGAGCGC
                   Consensus  (1501) CTGCAGGCCCGCGTGCTGGCCGTGGAGCGC
                                     1531                      1560
Leu122-Ser199 Tryp427-Gly431  (1501) TACCTGAAGGACCAGCAGCTGCTGGGCATC
 Val127-Asn195-Arg426-Gly431  (1531) TACCTGAAGGACCAGCAGCTGCTGGGCATC
```

FIG. 5L

| | | |
|---|---|---|
| Val120-Thr202-Ile424-Ala433 | (1477) | TACCTGAAGGACCAGCAGCTGCTGGGCATC |
| Leu122-Ser199-Arg426-Lys432 | (1501) | TACCTGAAGGACCAGCAGCTGCTGGGCATC |
| Leu122-Ser199-Arg426-Gly431 | (1501) | TACCTGAAGGACCAGCAGCTGCTGGGCATC |
| Lys121-Val200-Asn425-Lys432 | (1489) | TACCTGAAGGACCAGCAGCTGCTGGGCATC |
| Val120-Ile201-Ile424-Ala433 | (1477) | TACCTGAAGGACCAGCAGCTGCTGGGCATC |
| Val120-Ile201B-Ile424-Ala433 | (1477) | TACCTGAAGGACCAGCAGCTGCTGGGCATC |
| Consensus | (1531) | TACCTGAAGGACCAGCAGCTGCTGGGCATC |
| | | 1561 1590 |
| Leu122-Ser199 Tryp427-Gly431 | (1531) | TGGGGCTGCAGCGGCAAGCTGATCTGCACC |
| Val127-Asn195-Arg426-Gly431 | (1561) | TGGGGCTGCAGCGGCAAGCTGATCTGCACC |
| Val120-Thr202-Ile424-Ala433 | (1507) | TGGGGCTGCAGCGGCAAGCTGATCTGCACC |
| Leu122-Ser199-Arg426-Lys432 | (1531) | TGGGGCTGCAGCGGCAAGCTGATCTGCACC |
| Leu122-Ser199-Arg426-Gly431 | (1531) | TGGGGCTGCAGCGGCAAGCTGATCTGCACC |
| Lys121-Val200-Asn425-Lys432 | (1519) | TGGGGCTGCAGCGGCAAGCTGATCTGCACC |
| Val120-Ile201-Ile424-Ala433 | (1507) | TGGGGCTGCAGCGGCAAGCTGATCTGCACC |
| Val120-Ile201B-Ile424-Ala433 | (1507) | TGGGGCTGCAGCGGCAAGCTGATCTGCACC |
| Consensus | (1561) | TGGGGCTGCAGCGGCAAGCTGATCTGCACC |
| | | 1591 1620 |
| Leu122-Ser199 Tryp427-Gly431 | (1561) | ACCGCCGTGCCCTGGAACGCCAGCTGGAGC |
| Val127-Asn195-Arg426-Gly431 | (1591) | ACCGCCGTGCCCTGGAACGCCAGCTGGAGC |
| Val120-Thr202-Ile424-Ala433 | (1537) | ACCGCCGTGCCCTGGAACGCCAGCTGGAGC |
| Leu122-Ser199-Arg426-Lys432 | (1561) | ACCGCCGTGCCCTGGAACGCCAGCTGGAGC |
| Leu122-Ser199-Arg426-Gly431 | (1561) | ACCGCCGTGCCCTGGAACGCCAGCTGGAGC |
| Lys121-Val200-Asn425-Lys432 | (1549) | ACCGCCGTGCCCTGGAACGCCAGCTGGAGC |
| Val120-Ile201-Ile424-Ala433 | (1537) | ACCGCCGTGCCCTGGAACGCCAGCTGGAGC |
| Val120-Ile201B-Ile424-Ala433 | (1537) | ACCGCCGTGCCCTGGAACGCCAGCTGGAGC |
| Consensus | (1591) | ACCGCCGTGCCCTGGAACGCCAGCTGGAGC |
| | | 1621 1650 |
| Leu122-Ser199 Tryp427-Gly431 | (1591) | AACAAGAGCCTGGACCAGATCTGGAACAAC |
| Val127-Asn195-Arg426-Gly431 | (1621) | AACAAGAGCCTGGACCAGATCTGGAACAAC |
| Val120-Thr202-Ile424-Ala433 | (1567) | AACAAGAGCCTGGACCAGATCTGGAACAAC |
| Leu122-Ser199-Arg426-Lys432 | (1591) | AACAAGAGCCTGGACCAGATCTGGAACAAC |
| Leu122-Ser199-Arg426-Gly431 | (1591) | AACAAGAGCCTGGACCAGATCTGGAACAAC |
| Lys121-Val200-Asn425-Lys432 | (1579) | AACAAGAGCCTGGACCAGATCTGGAACAAC |
| Val120-Ile201-Ile424-Ala433 | (1567) | AACAAGAGCCTGGACCAGATCTGGAACAAC |
| Val120-Ile201B-Ile424-Ala433 | (1567) | AACAAGAGCCTGGACCAGATCTGGAACAAC |
| Consensus | (1621) | AACAAGAGCCTGGACCAGATCTGGAACAAC |
| | | 1651 1680 |
| Leu122-Ser199 Tryp427-Gly431 | (1621) | ATGACCTGGATGGAGTGGGAGCGCGAGATC |
| Val127-Asn195-Arg426-Gly431 | (1651) | ATGACCTGGATGGAGTGGGAGCGCGAGATC |
| Val120-Thr202-Ile424-Ala433 | (1597) | ATGACCTGGATGGAGTGGGAGCGCGAGATC |
| Leu122-Ser199-Arg426-Lys432 | (1621) | ATGACCTGGATGGAGTGGGAGCGCGAGATC |
| Leu122-Ser199-Arg426-Gly431 | (1621) | ATGACCTGGATGGAGTGGGAGCGCGAGATC |
| Lys121-Val200-Asn425-Lys432 | (1609) | ATGACCTGGATGGAGTGGGAGCGCGAGATC |
| Val120-Ile201-Ile424-Ala433 | (1597) | ATGACCTGGATGGAGTGGGAGCGCGAGATC |
| Val120-Ile201B-Ile424-Ala433 | (1597) | ATGACCTGGATGGAGTGGGAGCGCGAGATC |
| Consensus | (1651) | ATGACCTGGATGGAGTGGGAGCGCGAGATC |
| | | 1681 1710 |
| Leu122-Ser199 Tryp427-Gly431 | (1651) | GACAACTACACCAACCTGATCTACACCCTG |
| Val127-Asn195-Arg426-Gly431 | (1681) | GACAACTACACCAACCTGATCTACACCCTG |
| Val120-Thr202-Ile424-Ala433 | (1627) | GACAACTACACCAACCTGATCTACACCCTG |
| Leu122-Ser199-Arg426-Lys432 | (1651) | GACAACTACACCAACCTGATCTACACCCTG |
| Leu122-Ser199-Arg426-Gly431 | (1651) | GACAACTACACCAACCTGATCTACACCCTG |
| Lys121-Val200-Asn425-Lys432 | (1639) | GACAACTACACCAACCTGATCTACACCCTG |
| Val120-Ile201-Ile424-Ala433 | (1627) | GACAACTACACCAACCTGATCTACACCCTG |
| Val120-Ile201B-Ile424-Ala433 | (1627) | GACAACTACACCAACCTGATCTACACCCTG |
| Consensus | (1681) | GACAACTACACCAACCTGATCTACACCCTG |

*FIG. 5J*

| | | |
|---|---|---|
| | | 1711 1740 |
| Leu122-Ser199 Tryp427-Gly431 | (1681) | ATCGAGGAGAGCCAGAACCAGCAGGAGAAG |
| Val127-Asn195-Arg426-Gly431 | (1711) | ATCGAGGAGAGCCAGAACCAGCAGGAGAAG |
| Val120-Thr202-Ile424-Ala433 | (1657) | ATCGAGGAGAGCCAGAACCAGCAGGAGAAG |
| Leu122-Ser199-Arg426-Lys432 | (1681) | ATCGAGGAGAGCCAGAACCAGCAGGAGAAG |
| Leu122-Ser199-Arg426-Gly431 | (1681) | ATCGAGGAGAGCCAGAACCAGCAGGAGAAG |
| Lys121-Val200-Asn425-Lys432 | (1669) | ATCGAGGAGAGCCAGAACCAGCAGGAGAAG |
| Val120-Ile201-Ile424-Ala433 | (1657) | ATCGAGGAGAGCCAGAACCAGCAGGAGAAG |
| Val120-Ile201B-Ile424-Ala433 | (1657) | ATCGAGGAGAGCCAGAACCAGCAGGAGAAG |
| Consensus | (1711) | ATCGAGGAGAGCCAGAACCAGCAGGAGAAG |
| | | 1741 1770 |
| Leu122-Ser199 Tryp427-Gly431 | (1711) | AACGAGCAGGAGCTGCTGGAGCTGGACAAG |
| Val127-Asn195-Arg426-Gly431 | (1741) | AACGAGCAGGAGCTGCTGGAGCTGGACAAG |
| Val120-Thr202-Ile424-Ala433 | (1687) | AACGAGCAGGAGCTGCTGGAGCTGGACAAG |
| Leu122-Ser199-Arg426-Lys432 | (1711) | AACGAGCAGGAGCTGCTGGAGCTGGACAAG |
| Leu122-Ser199-Arg426-Gly431 | (1711) | AACGAGCAGGAGCTGCTGGAGCTGGACAAG |
| Lys121-Val200-Asn425-Lys432 | (1699) | AACGAGCAGGAGCTGCTGGAGCTGGACAAG |
| Val120-Ile201-Ile424-Ala433 | (1687) | AACGAGCAGGAGCTGCTGGAGCTGGACAAG |
| Val120-Ile201B-Ile424-Ala433 | (1687) | AACGAGCAGGAGCTGCTGGAGCTGGACAAG |
| Consensus | (1741) | AACGAGCAGGAGCTGCTGGAGCTGGACAAG |
| | | 1771 1800 |
| Leu122-Ser199 Tryp427-Gly431 | (1741) | TGGGCCAGCCTGTGGAACTGGTTCGACATC |
| Val127-Asn195-Arg426-Gly431 | (1771) | TGGGCCAGCCTGTGGAACTGGTTCGACATC |
| Val120-Thr202-Ile424-Ala433 | (1717) | TGGGCCAGCCTGTGGAACTGGTTCGACATC |
| Leu122-Ser199-Arg426-Lys432 | (1741) | TGGGCCAGCCTGTGGAACTGGTTCGACATC |
| Leu122-Ser199-Arg426-Gly431 | (1741) | TGGGCCAGCCTGTGGAACTGGTTCGACATC |
| Lys121-Val200-Asn425-Lys432 | (1729) | TGGGCCAGCCTGTGGAACTGGTTCGACATC |
| Val120-Ile201-Ile424-Ala433 | (1717) | TGGGCCAGCCTGTGGAACTGGTTCGACATC |
| Val120-Ile201B-Ile424-Ala433 | (1717) | TGGGCCAGCCTGTGGAACTGGTTCGACATC |
| Consensus | (1771) | TGGGCCAGCCTGTGGAACTGGTTCGACATC |
| | | 1801 1830 |
| Leu122-Ser199 Tryp427-Gly431 | (1771) | AGCAAGTGGCTGTGGTACATCAAGATCTTC |
| Val127-Asn195-Arg426-Gly431 | (1801) | AGCAAGTGGCTGTGGTACATCAAGATCTTC |
| Val120-Thr202-Ile424-Ala433 | (1747) | AGCAAGTGGCTGTGGTACATCAAGATCTTC |
| Leu122-Ser199-Arg426-Lys432 | (1771) | AGCAAGTGGCTGTGGTACATCAAGATCTTC |
| Leu122-Ser199-Arg426-Gly431 | (1771) | AGCAAGTGGCTGTGGTACATCAAGATCTTC |
| Lys121-Val200-Asn425-Lys432 | (1759) | AGCAAGTGGCTGTGGTACATCAAGATCTTC |
| Val120-Ile201-Ile424-Ala433 | (1747) | AGCAAGTGGCTGTGGTACATCAAGATCTTC |
| Val120-Ile201B-Ile424-Ala433 | (1747) | AGCAAGTGGCTGTGGTACATCAAGATCTTC |
| Consensus | (1801) | AGCAAGTGGCTGTGGTACATCAAGATCTTC |
| | | 1831 1860 |
| Leu122-Ser199 Tryp427-Gly431 | (1801) | ATCATGATCGTGGGCGGCCTGGTGGGCCTG |
| Val127-Asn195-Arg426-Gly431 | (1831) | ATCATGATCGTGGGCGGCCTGGTGGGCCTG |
| Val120-Thr202-Ile424-Ala433 | (1777) | ATCATGATCGTGGGCGGCCTGGTGGGCCTG |
| Leu122-Ser199-Arg426-Lys432 | (1801) | ATCATGATCGTGGGCGGCCTGGTGGGCCTG |
| Leu122-Ser199-Arg426-Gly431 | (1801) | ATCATGATCGTGGGCGGCCTGGTGGGCCTG |
| Lys121-Val200-Asn425-Lys432 | (1789) | ATCATGATCGTGGGCGGCCTGGTGGGCCTG |
| Val120-Ile201-Ile424-Ala433 | (1777) | ATCATGATCGTGGGCGGCCTGGTGGGCCTG |
| Val120-Ile201B-Ile424-Ala433 | (1777) | ATCATGATCGTGGGCGGCCTGGTGGGCCTG |
| Consensus | (1831) | ATCATGATCGTGGGCGGCCTGGTGGGCCTG |
| | | 1861 1890 |
| Leu122-Ser199 Tryp427-Gly431 | (1831) | CGCATCGTGTTCACCGTGCTGAGCATCGTG |
| Val127-Asn195-Arg426-Gly431 | (1861) | CGCATCGTGTTCACCGTGCTGAGCATCGTG |
| Val120-Thr202-Ile424-Ala433 | (1807) | CGCATCGTGTTCACCGTGCTGAGCATCGTG |
| Leu122-Ser199-Arg426-Lys432 | (1831) | CGCATCGTGTTCACCGTGCTGAGCATCGTG |
| Leu122-Ser199-Arg426-Gly431 | (1831) | CGCATCGTGTTCACCGTGCTGAGCATCGTG |
| Lys121-Val200-Asn425-Lys432 | (1819) | CGCATCGTGTTCACCGTGCTGAGCATCGTG |

FIG. 5K

| | | |
|---|---|---|
| Val120-Ile201-Ile424-Ala433 | (1807) | CGCATCGTGTTCACCGTGCTGAGCATCGTG |
| Val120-Ile201B-Ile424-Ala433 | (1807) | CGCATCGTGTTCACCGTGCTGAGCATCGTG |
| Consensus | (1861) | CGCATCGTGTTCACCGTGCTGAGCATCGTG |
| | | 1891 1920 |
| Leu122-Ser199 Tryp427-Gly431 | (1861) | AACCGCGTGCGCCAGGGCTACAGCCCCCTG |
| Val127-Asn195-Arg426-Gly431 | (1891) | AACCGCGTGCGCCAGGGCTACAGCCCCCTG |
| Val120-Thr202-Ile424-Ala433 | (1837) | AACCGCGTGCGCCAGGGCTACAGCCCCCTG |
| Leu122-Ser199-Arg426-Lys432 | (1861) | AACCGCGTGCGCCAGGGCTACAGCCCCCTG |
| Leu122-Ser199-Arg426-Gly431 | (1861) | AACCGCGTGCGCCAGGGCTACAGCCCCCTG |
| Lys121-Val200-Asn425-Lys432 | (1849) | AACCGCGTGCGCCAGGGCTACAGCCCCCTG |
| Val120-Ile201-Ile424-Ala433 | (1837) | AACCGCGTGCGCCAGGGCTACAGCCCCCTG |
| Val120-Ile201B-Ile424-Ala433 | (1837) | AACCGCGTGCGCCAGGGCTACAGCCCCCTG |
| Consensus | (1891) | AACCGCGTGCGCCAGGGCTACAGCCCCCTG |
| | | 1921 1950 |
| Leu122-Ser199 Tryp427-Gly431 | (1891) | AGCTTCCAGACCCGCTTCCCCGCCCCCCGC |
| Val127-Asn195-Arg426-Gly431 | (1921) | AGCTTCCAGACCCGCTTCCCCGCCCCCCGC |
| Val120-Thr202-Ile424-Ala433 | (1867) | AGCTTCCAGACCCGCTTCCCCGCCCCCCGC |
| Leu122-Ser199-Arg426-Lys432 | (1891) | AGCTTCCAGACCCGCTTCCCCGCCCCCCGC |
| Leu122-Ser199-Arg426-Gly431 | (1891) | AGCTTCCAGACCCGCTTCCCCGCCCCCCGC |
| Lys121-Val200-Asn425-Lys432 | (1879) | AGCTTCCAGACCCGCTTCCCCGCCCCCCGC |
| Val120-Ile201-Ile424-Ala433 | (1867) | AGCTTCCAGACCCGCTTCCCCGCCCCCCGC |
| Val120-Ile201B-Ile424-Ala433 | (1867) | AGCTTCCAGACCCGCTTCCCCGCCCCCCGC |
| Consensus | (1921) | AGCTTCCAGACCCGCTTCCCCGCCCCCCGC |
| | | 1951 1980 |
| Leu122-Ser199 Tryp427-Gly431 | (1921) | GGCCCCGACCGCCCCGAGGGCATCGAGGAG |
| Val127-Asn195-Arg426-Gly431 | (1951) | GGCCCCGACCGCCCCGAGGGCATCGAGGAG |
| Val120-Thr202-Ile424-Ala433 | (1897) | GGCCCCGACCGCCCCGAGGGCATCGAGGAG |
| Leu122-Ser199-Arg426-Lys432 | (1921) | GGCCCCGACCGCCCCGAGGGCATCGAGGAG |
| Leu122-Ser199-Arg426-Gly431 | (1921) | GGCCCCGACCGCCCCGAGGGCATCGAGGAG |
| Lys121-Val200-Asn425-Lys432 | (1909) | GGCCCCGACCGCCCCGAGGGCATCGAGGAG |
| Val120-Ile201-Ile424-Ala433 | (1897) | GGCCCCGACCGCCCCGAGGGCATCGAGGAG |
| Val120-Ile201B-Ile424-Ala433 | (1897) | GGCCCCGACCGCCCCGAGGGCATCGAGGAG |
| Consensus | (1951) | GGCCCCGACCGCCCCGAGGGCATCGAGGAG |
| | | 1981 2010 |
| Leu122-Ser199 Tryp427-Gly431 | (1951) | GAGGGCGGCGAGCGCGACCGCGACCGCAGC |
| Val127-Asn195-Arg426-Gly431 | (1981) | GAGGGCGGCGAGCGCGACCGCGACCGCAGC |
| Val120-Thr202-Ile424-Ala433 | (1927) | GAGGGCGGCGAGCGCGACCGCGACCGCAGC |
| Leu122-Ser199-Arg426-Lys432 | (1951) | GAGGGCGGCGAGCGCGACCGCGACCGCAGC |
| Leu122-Ser199-Arg426-Gly431 | (1951) | GAGGGCGGCGAGCGCGACCGCGACCGCAGC |
| Lys121-Val200-Asn425-Lys432 | (1939) | GAGGGCGGCGAGCGCGACCGCGACCGCAGC |
| Val120-Ile201-Ile424-Ala433 | (1927) | GAGGGCGGCGAGCGCGACCGCGACCGCAGC |
| Val120-Ile201B-Ile424-Ala433 | (1927) | GAGGGCGGCGAGCGCGACCGCGACCGCAGC |
| Consensus | (1981) | GAGGGCGGCGAGCGCGACCGCGACCGCAGC |
| | | 2011 2040 |
| Leu122-Ser199 Tryp427-Gly431 | (1981) | AGCCCCCTGGTGCACGGCCTGCTGGCCCTG |
| Val127-Asn195-Arg426-Gly431 | (2011) | AGCCCCCTGGTGCACGGCCTGCTGGCCCTG |
| Val120-Thr202-Ile424-Ala433 | (1957) | AGCCCCCTGGTGCACGGCCTGCTGGCCCTG |
| Leu122-Ser199-Arg426-Lys432 | (1981) | AGCCCCCTGGTGCACGGCCTGCTGGCCCTG |
| Leu122-Ser199-Arg426-Gly431 | (1981) | AGCCCCCTGGTGCACGGCCTGCTGGCCCTG |
| Lys121-Val200-Asn425-Lys432 | (1969) | AGCCCCCTGGTGCACGGCCTGCTGGCCCTG |
| Val120-Ile201-Ile424-Ala433 | (1957) | AGCCCCCTGGTGCACGGCCTGCTGGCCCTG |
| Val120-Ile201B-Ile424-Ala433 | (1957) | AGCCCCCTGGTGCACGGCCTGCTGGCCCTG |
| Consensus | (2011) | AGCCCCCTGGTGCACGGCCTGCTGGCCCTG |
| | | 2041 2070 |
| Leu122-Ser199 Tryp427-Gly431 | (2011) | ATCTGGGACGACCTGCGCAGCCTGTGCCTG |
| Val127-Asn195-Arg426-Gly431 | (2041) | ATCTGGGACGACCTGCGCAGCCTGTGCCTG |
| Val120-Thr202-Ile424-Ala433 | (1987) | ATCTGGGACGACCTGCGCAGCCTGTGCCTG |

*FIG. 5L*

```
       Leu122-Ser199-Arg426-Lys432  (2011) ATCTGGGACGACCTGCGCAGCCTGTGCCTG
       Leu122-Ser199-Arg426-Gly431  (2011) ATCTGGGACGACCTGCGCAGCCTGTGCCTG
       Lys121-Val200-Asn425-Lys432  (1999) ATCTGGGACGACCTGCGCAGCCTGTGCCTG
       Val120-Ile201-Ile424-Ala433  (1987) ATCTGGGACGACCTGCGCAGCCTGTGCCTG
      Val120-Ile201B-Ile424-Ala433  (1987) ATCTGGGACGACCTGCGCAGCCTGTGCCTG
                         Consensus  (2041) ATCTGGGACGACCTGCGCAGCCTGTGCCTG
                                           2071                      2100
      Leu122-Ser199 Tryp427-Gly431  (2041) TTCAGCTACCACCGCCTGCGCGACCTGATC
       Val127-Asn195-Arg426-Gly431  (2071) TTCAGCTACCACCGCCTGCGCGACCTGATC
       Val120-Thr202-Ile424-Ala433  (2017) TTCAGCTACCACCGCCTGCGCGACCTGATC
       Leu122-Ser199-Arg426-Lys432  (2041) TTCAGCTACCACCGCCTGCGCGACCTGATC
       Leu122-Ser199-Arg426-Gly431  (2041) TTCAGCTACCACCGCCTGCGCGACCTGATC
       Lys121-Val200-Asn425-Lys432  (2029) TTCAGCTACCACCGCCTGCGCGACCTGATC
       Val120-Ile201-Ile424-Ala433  (2017) TTCAGCTACCACCGCCTGCGCGACCTGATC
      Val120-Ile201B-Ile424-Ala433  (2017) TTCAGCTACCACCGCCTGCGCGACCTGATC
                         Consensus  (2071) TTCAGCTACCACCGCCTGCGCGACCTGATC
                                           2101                      2130
      Leu122-Ser199 Tryp427-Gly431  (2071) CTGATCGCCGCCCGCATCGTGGAGCTGCTG
       Val127-Asn195-Arg426-Gly431  (2101) CTGATCGCCGCCCGCATCGTGGAGCTGCTG
       Val120-Thr202-Ile424-Ala433  (2047) CTGATCGCCGCCCGCATCGTGGAGCTGCTG
       Leu122-Ser199-Arg426-Lys432  (2071) CTGATCGCCGCCCGCATCGTGGAGCTGCTG
       Leu122-Ser199-Arg426-Gly431  (2071) CTGATCGCCGCCCGCATCGTGGAGCTGCTG
       Lys121-Val200-Asn425-Lys432  (2059) CTGATCGCCGCCCGCATCGTGGAGCTGCTG
       Val120-Ile201-Ile424-Ala433  (2047) CTGATCGCCGCCCGCATCGTGGAGCTGCTG
      Val120-Ile201B-Ile424-Ala433  (2047) CTGATCGCCGCCCGCATCGTGGAGCTGCTG
                         Consensus  (2101) CTGATCGCCGCCCGCATCGTGGAGCTGCTG
                                           2131                      2160
      Leu122-Ser199 Tryp427-Gly431  (2101) GGCCGCCGCGGCTGGGAGGCCCTGAAGTAC
       Val127-Asn195-Arg426-Gly431  (2131) GGCCGCCGCGGCTGGGAGGCCCTGAAGTAC
       Val120-Thr202-Ile424-Ala433  (2077) GGCCGCCGCGGCTGGGAGGCCCTGAAGTAC
       Leu122-Ser199-Arg426-Lys432  (2101) GGCCGCCGCGGCTGGGAGGCCCTGAAGTAC
       Leu122-Ser199-Arg426-Gly431  (2101) GGCCGCCGCGGCTGGGAGGCCCTGAAGTAC
       Lys121-Val200-Asn425-Lys432  (2089) GGCCGCCGCGGCTGGGAGGCCCTGAAGTAC
       Val120-Ile201-Ile424-Ala433  (2077) GGCCGCCGCGGCTGGGAGGCCCTGAAGTAC
      Val120-Ile201B-Ile424-Ala433  (2077) GGCCGCCGCGGCTGGGAGGCCCTGAAGTAC
                         Consensus  (2131) GGCCGCCGCGGCTGGGAGGCCCTGAAGTAC
                                           2161                      2190
      Leu122-Ser199 Tryp427-Gly431  (2131) TGGGGCAACCTGCTGCAGTACTGGATCCAG
       Val127-Asn195-Arg426-Gly431  (2161) TGGGGCAACCTGCTGCAGTACTGGATCCAG
       Val120-Thr202-Ile424-Ala433  (2107) TGGGGCAACCTGCTGCAGTACTGGATCCAG
       Leu122-Ser199-Arg426-Lys432  (2131) TGGGGCAACCTGCTGCAGTACTGGATCCAG
       Leu122-Ser199-Arg426-Gly431  (2131) TGGGGCAACCTGCTGCAGTACTGGATCCAG
       Lys121-Val200-Asn425-Lys432  (2119) TGGGGCAACCTGCTGCAGTACTGGATCCAG
       Val120-Ile201-Ile424-Ala433  (2107) TGGGGCAACCTGCTGCAGTACTGGATCCAG
      Val120-Ile201B-Ile424-Ala433  (2107) TGGGGCAACCTGCTGCAGTACTGGATCCAG
                         Consensus  (2161) TGGGGCAACCTGCTGCAGTACTGGATCCAG
                                           2191                      2220
      Leu122-Ser199 Tryp427-Gly431  (2161) GAGCTGAAGAACAGCGCCGTGAGCCTGTTC
       Val127-Asn195-Arg426-Gly431  (2191) GAGCTGAAGAACAGCGCCGTGAGCCTGTTC
       Val120-Thr202-Ile424-Ala433  (2137) GAGCTGAAGAACAGCGCCGTGAGCCTGTTC
       Leu122-Ser199-Arg426-Lys432  (2161) GAGCTGAAGAACAGCGCCGTGAGCCTGTTC
       Leu122-Ser199-Arg426-Gly431  (2161) GAGCTGAAGAACAGCGCCGTGAGCCTGTTC
       Lys121-Val200-Asn425-Lys432  (2149) GAGCTGAAGAACAGCGCCGTGAGCCTGTTC
       Val120-Ile201-Ile424-Ala433  (2137) GAGCTGAAGAACAGCGCCGTGAGCCTGTTC
      Val120-Ile201B-Ile424-Ala433  (2137) GAGCTGAAGAACAGCGCCGTGAGCCTGTTC
                         Consensus  (2191) GAGCTGAAGAACAGCGCCGTGAGCCTGTTC
                                           2221                      2250
```

FIG. 5M

```
Leu122-Ser199 Tryp427-Gly431  (2191) GACGCCATCGCCATCGCCGTGGCCGAGGGC
 Val127-Asn195-Arg426-Gly431  (2221) GACGCCATCGCCATCGCCGTGGCCGAGGGC
 Val120-Thr202-Ile424-Ala433  (2167) GACGCCATCGCCATCGCCGTGGCCGAGGGC
 Leu122-Ser199-Arg426-Lys432  (2191) GACGCCATCGCCATCGCCGTGGCCGAGGGC
 Leu122-Ser199-Arg426-Gly431  (2191) GACGCCATCGCCATCGCCGTGGCCGAGGGC
 Lys121-Val200-Asn425-Lys432  (2179) GACGCCATCGCCATCGCCGTGGCCGAGGGC
 Val120-Ile201-Ile424-Ala433  (2167) GACGCCATCGCCATCGCCGTGGCCGAGGGC
Val120-Ile201B-Ile424-Ala433  (2167) GACGCCATCGCCATCGCCGTGGCCGAGGGC
                   Consensus  (2221) GACGCCATCGCCATCGCCGTGGCCGAGGGC
                                     2251                      2280
Leu122-Ser199 Tryp427-Gly431  (2221) ACCGACCGCATCATCGAGGTGGCCCAGCGC
 Val127-Asn195-Arg426-Gly431  (2251) ACCGACCGCATCATCGAGGTGGCCCAGCGC
 Val120-Thr202-Ile424-Ala433  (2197) ACCGACCGCATCATCGAGGTGGCCCAGCGC
 Leu122-Ser199-Arg426-Lys432  (2221) ACCGACCGCATCATCGAGGTGGCCCAGCGC
 Leu122-Ser199-Arg426-Gly431  (2221) ACCGACCGCATCATCGAGGTGGCCCAGCGC
 Lys121-Val200-Asn425-Lys432  (2209) ACCGACCGCATCATCGAGGTGGCCCAGCGC
 Val120-Ile201-Ile424-Ala433  (2197) ACCGACCGCATCATCGAGGTGGCCCAGCGC
Val120-Ile201B-Ile424-Ala433  (2197) ACCGACCGCATCATCGAGGTGGCCCAGCGC
                   Consensus  (2251) ACCGACCGCATCATCGAGGTGGCCCAGCGC
                                     2281                      2310
Leu122-Ser199 Tryp427-Gly431  (2251) ATCGGCCGCGCCTTCCTGCACATCCCCCGC
 Val127-Asn195-Arg426-Gly431  (2281) ATCGGCCGCGCCTTCCTGCACATCCCCCGC
 Val120-Thr202-Ile424-Ala433  (2227) ATCGGCCGCGCCTTCCTGCACATCCCCCGC
 Leu122-Ser199-Arg426-Lys432  (2251) ATCGGCCGCGCCTTCCTGCACATCCCCCGC
 Leu122-Ser199-Arg426-Gly431  (2251) ATCGGCCGCGCCTTCCTGCACATCCCCCGC
 Lys121-Val200-Asn425-Lys432  (2239) ATCGGCCGCGCCTTCCTGCACATCCCCCGC
 Val120-Ile201-Ile424-Ala433  (2227) ATCGGCCGCGCCTTCCTGCACATCCCCCGC
Val120-Ile201B-Ile424-Ala433  (2227) ATCGGCCGCGCCTTCCTGCACATCCCCCGC
                   Consensus  (2281) ATCGGCCGCGCCTTCCTGCACATCCCCCGC
                                     2311                      2340
Leu122-Ser199 Tryp427-Gly431  (2281) CGCATCCGCCAGGGCTTCGAGCGCGCCCTG
 Val127-Asn195-Arg426-Gly431  (2311) CGCATCCGCCAGGGCTTCGAGCGCGCCCTG
 Val120-Thr202-Ile424-Ala433  (2257) CGCATCCGCCAGGGCTTCGAGCGCGCCCTG
 Leu122-Ser199-Arg426-Lys432  (2281) CGCATCCGCCAGGGCTTCGAGCGCGCCCTG
 Leu122-Ser199-Arg426-Gly431  (2281) CGCATCCGCCAGGGCTTCGAGCGCGCCCTG
 Lys121-Val200-Asn425-Lys432  (2269) CGCATCCGCCAGGGCTTCGAGCGCGCCCTG
 Val120-Ile201-Ile424-Ala433  (2257) CGCATCCGCCAGGGCTTCGAGCGCGCCCTG
Val120-Ile201B-Ile424-Ala433  (2257) CGCATCCGCCAGGGCTTCGAGCGCGCCCTG
                   Consensus  (2311) CGCATCCGCCAGGGCTTCGAGCGCGCCCTG
                                     2341    2352
Leu122-Ser199 Tryp427-Gly431  (2311) CTGTAACTCGAG
 Val127-Asn195-Arg426-Gly431  (2341) CTGTAACTCGAG
 Val120-Thr202-Ile424-Ala433  (2287) CTGTAACTCGAG
 Leu122-Ser199-Arg426-Lys432  (2311) CTGTAACTCGAG
 Leu122-Ser199-Arg426-Gly431  (2311) CTGTAACTCGAG
 Lys121-Val200-Asn425-Lys432  (2299) CTGTAACTCGAG
 Val120-Ile201-Ile424-Ala433  (2287) CTGTAACTCGAG
Val120-Ile201B-Ile424-Ala433  (2287) CTGTAACTCGAG
                   Consensus  (2341) CTGTAACTCGAG
```

FIG. 5N

SEQ ID NO:3 VAL120-ALA204

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGGGCGCCGGCGCCTGCCCCAA
GGTGAGCTTCGAGCCCATCCCCATCCACTACTGCGCCCCCGCCGGCTTCGCCATCCTGAAGTG
CAACGACAAGAAGTTCAACGGCAGCGGCCCCTGCACCAACGTGAGCACCGTGCAGTGCACCC
ACGGCATCCGCCCCGTGGTGAGCACCCAGCTGCTGCTGAACGGCAGCCTGGCCGAGGAGGGC
GTGGTGATCCGCAGCGAGAACTTCACCGACAACGCCAAGACCATCATCGTGCAGCTGAAGGA
GAGCGTGGAGATCAACTGCACCCGCCCCAACAACAACACCCGCAAGAGCATCACCATCGGCC
CCGGCCGCGCCTTCTACGCCACCGGCGACATCATCGGCGACATCCGCCAGGCCCACTGCAACA
TCAGCGGCGAGAAGTGGAACAACACCCTGAAGCAGATCGTGACCAAGCTGCAGGCCCAGTTC
GGCAACAAGACCATCGTGTTCAAGCAGAGCAGCGGCGGCGACCCCGAGATCGTGATGCACAG
CTTCAACTGCGGCGGCGAGTTCTTCTACTGCAACAGCACCCAGCTGTTCAACAGCACCTGGAA
CAACACCATCGGCCCCAACAACACCAACGGCACCATCACCCTGCCCTGCCGCATCAAGCAGA
TCATCAACCGCTGGCAGGAGGTGGGCAAGGCCATGTACGCCCCCCCCATCCGCGGCCAGATC
CGCTGCAGCAGCAACATCACCGGCCTGCTGCTGACCCGCGACGGCGGCAAGGAGATCAGCAA
CACCACCGAGATCTTCCGCCCCGGCGGCGGCGACATGCGCGACAACTGGCGCAGCGAGCTGT
ACAAGTACAAGGTGGTGAAGATCGAGCCCCTGGGCGTGGCCCCCACCAAGGCCAAGCGCCGC
GTGGTGCAGCGCGAGAAGCGCGCCGTGACCCTGGGCGCCATGTTCCTGGGCTTCCTGGGCGCC
GCCGGCAGCACCATGGGCGCCCGCAGCCTGACCCTGACCGTGCAGGCCCGCCAGCTGCTGAG
CGGCATCGTGCAGCAGCAGAACAACCTGCTGCGCGCCATCGAGGCCCAGCAGCACCTGCTGC
AGCTGACCGTGTGGGGCATCAAGCAGCTGCAGGCCCGCGTGCTGGCCGTGGAGCGCTACCTG
AAGGACCAGCAGCTGCTGGGCATCTGGGGCTGCAGCGGCAAGCTGATCTGCACCACCGCCGT
GCCCTGGAACGCCAGCTGGAGCAACAAGAGCCTGGACCAGATCTGGAACAACATGACCTGGA
TGGAGTGGGAGCGCGAGATCGACAACTACACCAACCTGATCTACACCCTGATCGAGGAGAGC
CAGAACCAGCAGGAGAAGAACGAGCAGGAGCTGCTGGAGCTGGACAAGTGGGCCAGCCTGT
GGAACTGGTTCGACATCAGCAAGTGGCTGTGGTACATCAAGATCTTCATCATGATCGTGGGCG
GCCTGGTGGGCCTGCGCATCGTGTTCACCGTGCTGAGCATCGTGAACCGCGTGCGCCAGGGCT
ACAGCCCCCTGAGCTTCCAGACCCGCTTCCCCGCCCCCCGCGGCCCCGACCGCCCCGAGGGCA
TCGAGGAGGAGGGCGGCGAGCGCGACCGCGACCGCAGCAGCCCCCTGGTGCACGGCCTGCTG
GCCCTGATCTGGGACGACCTGCGCAGCCTGTGCCTGTTCAGCTACCACCGCCTGCGCGACCTG
ATCCTGATCGCCGCCCGCATCGTGGAGCTGCTGGGCCGCCGCGGCTGGGAGGCCCTGAAGTAC
TGGGGCAACCTGCTGCAGTACTGGATCCAGGAGCTGAAGAACAGCGCCGTGAGCCTGTTCGA
CGCCATCGCCATCGCCGTGGCCGAGGGCACCGACCGCATCATCGAGGTGGCCCAGCGCATCG
GCCGCGCCTTCCTGCACATCCCCCGCCGCATCCGCCAGGGCTTCGAGCGCGCCCTGCTGTAAC
TCGAG

*FIG. 6*

SEQ ID NO:4 VAL120-ILE201

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGGGCGGCATCACCCAGGCCTG
CCCCAAGGTGAGCTTCGAGCCCATCCCCATCCACTACTGCGCCCCCGCCGGCTTCGCCATCCT
GAAGTGCAACGACAAGAAGTTCAACGGCAGCGGCCCCTGCACCAACGTGAGCACCGTGCAGT
GCACCCACGGCATCCGCCCCGTGGTGAGCACCCAGCTGCTGCTGAACGGCAGCCTGGCCGAG
GAGGGCGTGGTGATCCGCAGCGAGAACTTCACCGACAACGCCAAGACCATCATCGTGCAGCT
GAAGGAGAGCGTGGAGATCAACTGCACCCGCCCCAACAACAACACCCGCAAGAGCATCACCA
TCGGCCCCGGCCGCGCCTTCTACGCCACCGGCGACATCATCGGCGACATCCGCCAGGCCCACT
GCAACATCAGCGGCGAGAAGTGGAACAACACCCTGAAGCAGATCGTGACCAAGCTGCAGGCC
CAGTTCGGCAACAAGACCATCGTGTTCAAGCAGAGCAGCGGCGGCGACCCCGAGATCGTGAT
GCACAGCTTCAACTGCGGCGGCGAGTTCTTCTACTGCAACAGCACCCAGCTGTTCAACAGCAC
CTGGAACAACACCATCGGCCCCAACAACACCAACGGCACCATCACCCTGCCCTGCCGCATCA
AGCAGATCATCAACCGCTGGCAGGAGGTGGGCAAGGCCATGTACGCCCCCCCCATCCGCGGC
CAGATCCGCTGCAGCAGCAACATCACCGGCCTGCTGCTGACCCGCGACGGCGGCAAGGAGAT
CAGCAACACCACCGAGATCTTCCGCCCCGGCGGCGGCGACATGCGCGACAACTGGCGCAGCG
AGCTGTACAAGTACAAGGTGGTGAAGATCGAGCCCCTGGGCGTGGCCCCCACCAAGGCCAAG
CGCCGCGTGGTGCAGCGCGAGAAGCGCGCCGTGACCCTGGGCGCCATGTTCCTGGGCTTCCTG
GGCGCCGCCGGCAGCACCATGGGCGCCCGCAGCCTGACCCTGACCGTGCAGGCCCGCCAGCT
GCTGAGCGGCATCGTGCAGCAGCAGAACAACCTGCTGCGCGCCATCGAGGCCCAGCAGCACC
TGCTGCAGCTGACCGTGTGGGGCATCAAGCAGCTGCAGGCCCGCGTGCTGGCCGTGGAGCGC
TACCTGAAGGACCAGCAGCTGCTGGGCATCTGGGGCTGCAGCGGCAAGCTGATCTGCACCAC
CGCCGTGCCCTGGAACGCCAGCTGGAGCAACAAGAGCCTGGACCAGATCTGGAACAACATGA
CCTGGATGGAGTGGGAGCGCGAGATCGACAACTACACCAACCTGATCTACACCCTGATCGAG
GAGAGCCAGAACCAGCAGGAGAAGAACGAGCAGGAGCTGCTGGAGCTGGACAAGTGGGCCA
GCCTGTGGAACTGGTTCGACATCAGCAAGTGGCTGTGGTACATCAAGATCTTCATCATGATCG
TGGGCGGCCTGGTGGGCCTGCGCATCGTGTTCACCGTGCTGAGCATCGTGAACCGCGTGCGCC
AGGGCTACAGCCCCCTGAGCTTCCAGACCCGCTTCCCCGCCCCCCGCGGCCCCGACCGCCCCG
AGGGCATCGAGGAGGAGGGCGGCGAGCGCGACCGCGACCGCAGCAGCCCCCTGGTGCACGG
CCTGCTGGCCCTGATCTGGGACGACCTGCGCAGCCTGTGCCTGTTCAGCTACCACCGCCTGCG
CGACCTGATCCTGATCGCCGCCCGCATCGTGGAGCTGCTGGGCCGCCGCGGCTGGGAGGCCCT
GAAGTACTGGGGCAACCTGCTGCAGTACTGGATCCAGGAGCTGAAGAACAGCGCCGTGAGCC
TGTTCGACGCCATCGCCATCGCCGTGGCCGAGGGCACCGACCGCATCATCGAGGTGGCCCAGC
GCATCGGCCGCGCCTTCCTGCACATCCCCCGCCGCATCCGCCAGGGCTTCGAGCGCGCCCTGC
TGTAACTCGAG

*FIG. 7*

SEQ ID NO:5 VAL120-ILE201B

GAATTCGCCACCATGGATGCAATGAAGAGAGGGCTCTGCTGTGTGCTGCTGCTGTGTGGAGCAGTCTTCG
TTTCGCCCAGCGCCGTGGAGAAGCTGTGGGTGACCGTGTACTACGGCGTGCCCGTGTGGAAGGAGGCCA
CCACCACCCTGTTCTGCGCCAGCGACGCCAAGGCCTACGACACCGAGGTGCACAACGTGTGGGCCACCC
ACGCCTGCGTGCCCACCGACCCCAACCCCCAGGAGATCGTGCTGGAGAACGTGACCGAGAACTTCAACA
TGTGGAAGAACAACATGGTGGAGCAGATGCACGAGGACATCATCAGCCTGTGGGACCAGAGCCTGAAGC
CCTGCGTGCCCGGCATCACCCAGGCCTGCCCCAAGGTGAGCTTCGAGCCCATCCCCATCCACTACTGCGC
CCCCGCCGGCTTCGCCATCCTGAAGTGCAACGACAAGAAGTTCAACGGCAGCGGCCCCTGCACCAACGT
GAGCACCGTGCAGTGCACCCACGGCATCCGCCCCGTGGTGAGCACCCAGCTGCTGCTGAACGGCAGCCT
GGCCGAGGAGGGCGTGGTGATCCGCAGCGAGAACTTCACCGACAACGCCAAGACCATCATCGTGCAGCT
GAAGGAGAGCGTGGAGATCAACTGCACCCGCCCCAACAACAACACCCGCAAGAGCATCACCATCGGCCC
CGGCCGCGCCTTCTACGCCACCGGCGACATCATCGGCGACATCCGCCAGGCCCACTGCAACATCAGCGGC
GAGAAGTGGAACAACACCCTGAAGCAGATCGTGACCAAGCTGCAGGCCCAGTTCGGCAACAAGACCATC
GTGTTCAAGCAGAGCAGCGGCGGCGACCCCGAGATCGTGATGCACAGCTTCAACTGCGGCGGCGAGTTC
TTCTACTGCAACAGCACCCAGCTGTTCAACAGCACCTGGAACAACACCATCGGCCCCAACAACACCAAC
GGCACCATCACCCTGCCCTGCCGCATCAAGCAGATCATCAACCGCTGGCAGGAGGTGGGCAAGGCCATG
TACGCCCCCCCCATCCGCGGCCAGATCCGCTGCAGCAGCAACATCACCGGCCTGCTGCTGACCCGCGACG
GCGGCAAGGAGATCAGCAACACCACCGAGATCTTCCGCCCCGGCGGCGGCGACATGCGCGACAACTGGC
GCAGCGAGCTGTACAAGTACAAGGTGGTGAAGATCGAGCCCCTGGGCGTGGCCCCCACCAAGGCCAAGC
GCCGCGTGGTGCAGCGCGAGAAGCGCGCCGTGACCCTGGGCGCCATGTTCCTGGGCTTCCTGGGCGCCGC
CGGCAGCACCATGGGCGCCCGCAGCCTGACCCTGACCGTGCAGGCCCGCCAGCTGCTGAGCGGCATCGT
GCAGCAGCAGAACAACCTGCTGCGCGCCATCGAGGCCCAGCAGCACCTGCTGCAGCTGACCGTGTGGGG
CATCAAGCAGCTGCAGGCCCGCGTGCTGGCCGTGGAGCGCTACCTGAAGGACCAGCAGCTGCTGGGCAT
CTGGGGCTGCAGCGGCAAGCTGATCTGCACCACCGCCGTGCCCTGGAACGCCAGCTGGAGCAACAAGAG
CCTGGACCAGATCTGGAACAACATGACCTGGATGGAGTGGGAGCGCGAGATCGACAACTACACCAACCT
GATCTACACCCTGATCGAGGAGAGCCAGAACCAGCAGGAGAAGAACGAGCAGGAGCTGCTGGAGCTGG
ACAAGTGGGCCAGCCTGTGGAACTGGTTCGACATCAGCAAGTGGCTGTGGTACATCAAGATCTTCATCAT
GATCGTGGGCGGCCTGGTGGGCCTGCGCATCGTGTTCACCGTGCTGAGCATCGTGAACCGCGTGCGCCAG
GGCTACAGCCCCCTGAGCTTCCAGACCCGCTTCCCCGCCCCCCGCGGCCCCGACCGCCCCGAGGGCATCG
AGGAGGAGGGCGGCGAGCGCGACCGCGACCGCAGCAGCCCCCTGGTGCACGGCCTGCTGGCCCTGATCT
GGGACGACCTGCGCAGCCTGTGCCTGTTCAGCTACCACCGCCTGCGCGACCTGATCCTGATCGCCGCCCG
CATCGTGGAGCTGCTGGGCCGCCGCGGCTGGGAGGCCCTGAAGTACTGGGGCAACCTGCTGCAGTACTG
GATCCAGGAGCTGAAGAACAGCGCCGTGAGCCTGTTCGACGCCATCGCCATCGCCGTGGCCGAGGGCAC
CGACCGCATCATCGAGGTGGCCCAGCGCATCGGCCGCGCCTTCCTGCACATCCCCCGCCGCATCCGCCAG
GGCTTCGAGCGCGCCCTGCTGTAACTCGAGCGTGCT

*FIG. 8*

SEQ ID NO:6 LYS121-VAL200

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGGCCCCCGTGATCACCCA
GGCCTGCCCCAAGGTGAGCTTCGAGCCCATCCCCATCCACTACTGCGCCCCCGCCGGCTTCGC
CATCCTGAAGTGCAACGACAAGAAGTTCAACGGCAGCGGCCCCTGCACCAACGTGAGCACCG
TGCAGTGCACCCACGGCATCCGCCCCGTGGTGAGCACCCAGCTGCTGCTGAACGGCAGCCTGG
CCGAGGAGGGCGTGGTGATCCGCAGCGAGAACTTCACCGACAACGCCAAGACCATCATCGTG
CAGCTGAAGGAGAGCGTGGAGATCAACTGCACCCGCCCCAACAACAACACCCGCAAGAGCAT
CACCATCGGCCCCGGCCGCGCCTTCTACGCCACCGGCGACATCATCGGCGACATCCGCCAGGC
CCACTGCAACATCAGCGGCGAGAAGTGGAACAACACCCTGAAGCAGATCGTGACCAAGCTGC
AGGCCCAGTTCGGCAACAAGACCATCGTGTTCAAGCAGAGCAGCGGCGGCGACCCCGAGATC
GTGATGCACAGCTTCAACTGCGGCGGCGAGTTCTTCTACTGCAACAGCACCCAGCTGTTCAAC
AGCACCTGGAACAACACCATCGGCCCCAACAACACCAACGGCACCATCACCCTGCCCTGCCG
CATCAAGCAGATCATCAACCGCTGGCAGGAGGTGGGCAAGGCCATGTACGCCCCCCCCATCC
GCGGCCAGATCCGCTGCAGCAGCAACATCACCGGCCTGCTGCTGACCCGCGACGGCGGCAAG
GAGATCAGCAACACCACCGAGATCTTCCGCCCCGGCGGCGGCGACATGCGCGACAACTGGCG
CAGCGAGCTGTACAAGTACAAGGTGGTGAAGATCGAGCCCCTGGGCGTGGCCCCCACCAAGG
CCAAGCGCCGCGTGGTGCAGCGCGAGAAGCGCGCCGTGACCCTGGGCGCCATGTTCCTGGGC
TTCCTGGGCGCCGCCGGCAGCACCATGGGCGCCCGCAGCCTGACCCTGACCGTGCAGGCCCGC
CAGCTGCTGAGCGGCATCGTGCAGCAGCAGAACAACCTGCTGCGCGCCATCGAGGCCCAGCA
GCACCTGCTGCAGCTGACCGTGTGGGGCATCAAGCAGCTGCAGGCCCGCGTGCTGGCCGTGG
AGCGCTACCTGAAGGACCAGCAGCTGCTGGGCATCTGGGGCTGCAGCGGCAAGCTGATCTGC
ACCACCGCCGTGCCCTGGAACGCCAGCTGGAGCAACAAGAGCCTGGACCAGATCTGGAACAA
CATGACCTGGATGGAGTGGGAGCGCGAGATCGACAACTACACCAACCTGATCTACACCCTGA
TCGAGGAGAGCCAGAACCAGCAGGAGAAGAACGAGCAGGAGCTGCTGGAGCTGGACAAGTG
GGCCAGCCTGTGGAACTGGTTCGACATCAGCAAGTGGCTGTGGTACATCAAGATCTTCATCAT
GATCGTGGGCGGCCTGGTGGGCCTGCGCATCGTGTTCACCGTGCTGAGCATCGTGAACCGCGT
GCGCCAGGGCTACAGCCCCCTGAGCTTCCAGACCCGCTTCCCCGCCCCCCGCGGCCCCGACCG
CCCCGAGGGCATCGAGGAGGAGGGCGGCGAGCGCGACCGCGACCGCAGCAGCCCCCTGGTGC
ACGGCCTGCTGGCCCTGATCTGGGACGACCTGCGCAGCCTGTGCCTGTTCAGCTACCACCGCC
TGCGCGACCTGATCCTGATCGCCGCCCGCATCGTGGAGCTGCTGGGCCGCCGCGGCTGGGAGG
CCCTGAAGTACTGGGGCAACCTGCTGCAGTACTGGATCCAGGAGCTGAAGAACAGCGCCGTG
AGCCTGTTCGACGCCATCGCCATCGCCGTGGCCGAGGGCACCGACCGCATCATCGAGGTGGCC
CAGCGCATCGGCCGCGCCTTCCTGCACATCCCCCGCCGCATCCGCCAGGGCTTCGAGCGCGCC
CTGCTGTAACTCGAGCGTGCT

FIG. 9

SEQ ID NO:7: LEU122-SER199

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGGGCAACAGCGTGAT
CACCCAGGCCTGCCCCAAGGTGAGCTTCGAGCCCATCCCCATCCACTACTGCGCCCCCGCCGG
CTTCGCCATCCTGAAGTGCAACGACAAGAAGTTCAACGGCAGCGGCCCCTGCACCAACGTGA
GCACCGTGCAGTGCACCCACGGCATCCGCCCCGTGGTGAGCACCCAGCTGCTGCTGAACGGC
AGCCTGGCCGAGGAGGGCGTGGTGATCCGCAGCGAGAACTTCACCGACAACGCCAAGACCAT
CATCGTGCAGCTGAAGGAGAGCGTGGAGATCAACTGCACCCGCCCCAACAACAACACCCGCA
AGAGCATCACCATCGGCCCCGGCCGCGCCTTCTACGCCACCGGCGACATCATCGGCGACATCC
GCCAGGCCCACTGCAACATCAGCGGCGAGAAGTGGAACAACACCCTGAAGCAGATCGTGACC
AAGCTGCAGGCCCAGTTCGGCAACAAGACCATCGTGTTCAAGCAGAGCAGCGGCGGCGACCC
CGAGATCGTGATGCACAGCTTCAACTGCGGCGGCGAGTTCTTCTACTGCAACAGCACCCAGCT
GTTCAACAGCACCTGGAACAACACCATCGGCCCCAACAACACCAACGGCACCATCACCCTGC
CCTGCCGCATCAAGCAGATCATCAACCGCTGGCAGGAGGTGGGCAAGGCCATGTACGCCCCC
CCCATCCGCGGCCAGATCCGCTGCAGCAGCAACATCACCGGCCTGCTGCTGACCCGCGACGGC
GGCAAGGAGATCAGCAACACCACCGAGATCTTCCGCCCCGGCGGCGGCGACATGCGCGACAA
CTGGCGCAGCGAGCTGTACAAGTACAAGGTGGTGAAGATCGAGCCCCTGGGCGTGGCCCCCA
CCAAGGCCAAGCGCCGCGTGGTGCAGCGCGAGAAGCGCGCCGTGACCCTGGGCGCCATGTTC
CTGGGCTTCCTGGGCGCCGCCGGCAGCACCATGGGCGCCCGCAGCCTGACCCTGACCGTGCAG
GCCCGCCAGCTGCTGAGCGGCATCGTGCAGCAGCAGAACAACCTGCTGCGCGCCATCGAGGC
CCAGCAGCACCTGCTGCAGCTGACCGTGTGGGGCATCAAGCAGCTGCAGGCCCGCGTGCTGG
CCGTGGAGCGCTACCTGAAGGACCAGCAGCTGCTGGGCATCTGGGGCTGCAGCGGCAAGCTG
ATCTGCACCACCGCCGTGCCCTGGAACGCCAGCTGGAGCAACAAGAGCCTGGACCAGATCTG
GAACAACATGACCTGGATGGAGTGGGAGCGCGAGATCGACAACTACACCAACCTGATCTACA
CCCTGATCGAGGAGAGCCAGAACCAGCAGGAGAAGAACGAGCAGGAGCTGCTGGAGCTGGA
CAAGTGGGCCAGCCTGTGGAACTGGTTCGACATCAGCAAGTGGCTGTGGTACATCAAGATCTT
CATCATGATCGTGGGCGGCCTGGTGGGCCTGCGCATCGTGTTCACCGTGCTGAGCATCGTGAA
CCGCGTGCGCCAGGGCTACAGCCCCCTGAGCTTCCAGACCCGCTTCCCCGCCCCCCGCGGCCC
CGACCGCCCCGAGGGCATCGAGGAGGAGGGCGGCGAGCGCGACCGCGACCGCAGCAGCCCC
CTGGTGCACGGCCTGCTGGCCCTGATCTGGGACGACCTGCGCAGCCTGTGCCTGTTCAGCTAC
CACCGCCTGCGCGACCTGATCCTGATCGCCGCCCGCATCGTGGAGCTGCTGGGCCGCCGCGGC
TGGGAGGCCCTGAAGTACTGGGGCAACCTGCTGCAGTACTGGATCCAGGAGCTGAAGAACAG
CGCCGTGAGCCTGTTCGACGCCATCGCCATCGCCGTGGCCGAGGGCACCGACCGCATCATCGA
GGTGGCCCAGCGCATCGGCCGCGCCTTCCTGCACATCCCCCGCCGCATCCGCCAGGGCTTCGA
GCGCGCCCTGCTGTAACTCGAGCGTGCT

*FIG. 10*

SEQ ID NO:8 VAL120-THR202

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGGGCGGCGCCACCCAGGCCTG
CCCCAAGGTGAGCTTCGAGCCCATCCCCATCCACTACTGCGCCCCCGCCGGCTTCGCCATCCT
GAAGTGCAACGACAAGAAGTTCAACGGCAGCGGCCCCTGCACCAACGTGAGCACCGTGCAGT
GCACCCACGGCATCCGCCCCGTGGTGAGCACCCAGCTGCTGCTGAACGGCAGCCTGGCCGAG
GAGGGCGTGGTGATCCGCAGCGAGAACTTCACCGACAACGCCAAGACCATCATCGTGCAGCT
GAAGGAGAGCGTGGAGATCAACTGCACCCGCCCCAACAACAACACCCGCAAGAGCATCACCA
TCGGCCCCGGCCGCGCCTTCTACGCCACCGGCGACATCATCGGCGACATCCGCCAGGCCCACT
GCAACATCAGCGGCGAGAAGTGGAACAACACCCTGAAGCAGATCGTGACCAAGCTGCAGGCC
CAGTTCGGCAACAAGACCATCGTGTTCAAGCAGAGCAGCGGCGGCGACCCCGAGATCGTGAT
GCACAGCTTCAACTGCGGCGGCGAGTTCTTCTACTGCAACAGCACCCAGCTGTTCAACAGCAC
CTGGAACAACACCATCGGCCCCAACAACACCAACGGCACCATCACCCTGCCCTGCCGCATCA
AGCAGATCATCAACCGCTGGCAGGAGGTGGGCAAGGCCATGTACGCCCCCCCCATCCGCGGC
CAGATCCGCTGCAGCAGCAACATCACCGGCCTGCTGCTGACCCGCGACGGCGGCAAGGAGAT
CAGCAACACCACCGAGATCTTCCGCCCCGGCGGCGGCGACATGCGCGACAACTGGCGCAGCG
AGCTGTACAAGTACAAGGTGGTGAAGATCGAGCCCCTGGGCGTGGCCCCCACCAAGGCCAAG
CGCCGCGTGGTGCAGCGCGAGAAGCGCGCCGTGACCCTGGGCGCCATGTTCCTGGGCTTCCTG
GGCGCCGCCGGCAGCACCATGGGCGCCCGCAGCCTGACCCTGACCGTGCAGGCCCGCCAGCT
GCTGAGCGGCATCGTGCAGCAGCAGAACAACCTGCTGCGCGCCATCGAGGCCCAGCAGCACC
TGCTGCAGCTGACCGTGTGGGGCATCAAGCAGCTGCAGGCCCGCGTGCTGGCCGTGGAGCGC
TACCTGAAGGACCAGCAGCTGCTGGGCATCTGGGGCTGCAGCGGCAAGCTGATCTGCACCAC
CGCCGTGCCCTGGAACGCCAGCTGGAGCAACAAGAGCCTGGACCAGATCTGGAACAACATGA
CCTGGATGGAGTGGGAGCGCGAGATCGACAACTACACCAACCTGATCTACACCCTGATCGAG
GAGAGCCAGAACCAGCAGGAGAAGAACGAGCAGGAGCTGCTGGAGCTGGACAAGTGGGCCA
GCCTGTGGAACTGGTTCGACATCAGCAAGTGGCTGTGGTACATCAAGATCTTCATCATGATCG
TGGGCGGCCTGGTGGGCCTGCGCATCGTGTTCACCGTGCTGAGCATCGTGAACCGCGTGCGCC
AGGGCTACAGCCCCCTGAGCTTCCAGACCCGCTTCCCCGCCCCCCGCGGCCCCGACCGCCCCG
AGGGCATCGAGGAGGAGGGCGGCGAGCGCGACCGCGACCGCAGCAGCCCCCTGGTGCACGG
CCTGCTGGCCCTGATCTGGGACGACCTGCGCAGCCTGTGCCTGTTCAGCTACCACCGCCTGCG
CGACCTGATCCTGATCGCCGCCCGCATCGTGGAGCTGCTGGGCCGCCGCGGCTGGGAGGCCCT
GAAGTACTGGGGCAACCTGCTGCAGTACTGGATCCAGGAGCTGAAGAACAGCGCCGTGAGCC
TGTTCGACGCCATCGCCATCGCCGTGGCCGAGGGCACCGACCGCATCATCGAGGTGGCCCAGC
GCATCGGCCGCGCCTTCCTGCACATCCCCCGCCGCATCCGCCAGGGCTTCGAGCGCGCCCTGC
TGTAACTCGAG

FIG. 11

SEQ ID NO:9 TRP427-GLY431

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCAACCGCT
GGGGCGGCAAGGCCATGTACGCCCCCCCCATCCGCGGCCAGATCCGCTGCAGCAGCAACATC
ACCGGCCTGCTGCTGACCCGCGACGGCGGCAAGGAGATCAGCAACACCACCGAGATCTTCCG
CCCCGGCGGCGGCGACATGCGCGACAACTGGCGCAGCGAGCTGTACAAGTACAAGGTGGTGA
AGATCGAGCCCCTGGGCGTGGCCCCCACCAAGGCCAAGCGCCGCGTGGTGCAGCGCGAGAAG
CGCGCCGTGACCCTGGGCGCCATGTTCCTGGGCTTCCTGGGCGCCGCCGGCAGCACCATGGGC
GCCCGCAGCCTGACCCTGACCGTGCAGGCCCGCCAGCTGCTGAGCGGCATCGTGCAGCAGCA
GAACAACCTGCTGCGCGCCATCGAGGCCCAGCAGCACCTGCTGCAGCTGACCGTGTGGGGCA
TCAAGCAGCTGCAGGCCCGCGTGCTGGCCGTGGAGCGCTACCTGAAGGACCAGCAGCTGCTG
GGCATCTGGGGCTGCAGCGGCAAGCTGATCTGCACCACCGCCGTGCCCTGGAACGCCAGCTG
GAGCAACAAGAGCCTGGACCAGATCTGGAACAACATGACCTGGATGGAGTGGGAGCGCGAG
ATCGACAACTACACCAACCTGATCTACACCCTGATCGAGGAGAGCCAGAACCAGCAGGAGAA
GAACGAGCAGGAGCTGCTGGAGCTGGACAAGTGGGCCAGCCTGTGGAACTGGTTCGACATCA
GCAAGTGGCTGTGGTACATCAAGATCTTCATCATGATCGTGGGCGGCCTGGTGGGCCTGCGCA
TCGTGTTCACCGTGCTGAGCATCGTGAACCGCGTGCGCCAGGGCTACAGCCCCCTGAGCTTCC
AGACCCGCTTCCCCGCCCCCCGCGGCCCCGACCGCCCCGAGGGCATCGAGGAGGAGGGCGGC
GAGCGCGACCGCGACCGCAGCAGCCCCCTGGTGCACGGCCTGCTGGCCCTGATCTGGGACGA
CCTGCGCAGCCTGTGCCTGTTCAGCTACCACCGCCTGCGCGACCTGATCCTGATCGCCGCCCG
CATCGTGGAGCTGCTGGGCCGCCGCGGCTGGGAGGCCCTGAAGTACTGGGGCAACCTGCTGC
AGTACTGGATCCAGGAGCTGAAGAACAGCGCCGTGAGCCTGTTCGACGCCATCGCCATCGCC
GTGGCCGAGGGCACCGACCGCATCATCGAGGTGGCCCAGCGCATCGGCCGCGCCTTCCTGCA
CATCCCCCGCCGCATCCGCCAGGGCTTCGAGCGCGCCCTGCTGTAACTCGAG

FIG. 12

SEQ ID NO:10 ARG426-GLY431

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCAACCGC
GGCGGCGGCAAGGCCATGTACGCCCCCCCCATCCGCGGCCAGATCCGCTGCAGCAGCAACAT
CACCGGCCTGCTGCTGACCCGCGACGGCGGCAAGGAGATCAGCAACACCACCGAGATCTTCC
GCCCCGGCGGCGGCGACATGCGCGACAACTGGCGCAGCGAGCTGTACAAGTACAAGGTGGTG
AAGATCGAGCCCCTGGGCGTGGCCCCCACCAAGGCCAAGCGCCGCGTGGTGCAGCGCGAGAA
GCGCGCCGTGACCCTGGGCGCCATGTTCCTGGGCTTCCTGGGCGCCGCCGGCAGCACCATGGG
CGCCCGCAGCCTGACCCTGACCGTGCAGGCCCGCCAGCTGCTGAGCGGCATCGTGCAGCAGC
AGAACAACCTGCTGCGCGCCATCGAGGCCCAGCAGCACCTGCTGCAGCTGACCGTGTGGGGC
ATCAAGCAGCTGCAGGCCCGCGTGCTGGCCGTGGAGCGCTACCTGAAGGACCAGCAGCTGCT
GGGCATCTGGGGCTGCAGCGGCAAGCTGATCTGCACCACCGCCGTGCCCTGGAACGCCAGCT
GGAGCAACAAGAGCCTGGACCAGATCTGGAACAACATGACCTGGATGGAGTGGGAGCGCGA
GATCGACAACTACACCAACCTGATCTACACCCTGATCGAGGAGAGCCAGAACCAGCAGGAGA
AGAACGAGCAGGAGCTGCTGGAGCTGGACAAGTGGGCCAGCCTGTGGAACTGGTTCGACATC
AGCAAGTGGCTGTGGTACATCAAGATCTTCATCATGATCGTGGGCGGCCTGGTGGGCCTGCGC
ATCGTGTTCACCGTGCTGAGCATCGTGAACCGCGTGCGCCAGGGCTACAGCCCCCTGAGCTTC
CAGACCCGCTTCCCCGCCCCCCGCGGCCCCGACCGCCCCGAGGGCATCGAGGAGGAGGGCGG
CGAGCGCGACCGCGACCGCAGCAGCCCCCTGGTGCACGGCCTGCTGGCCCTGATCTGGGACG
ACCTGCGCAGCCTGTGCCTGTTCAGCTACCACCGCCTGCGCGACCTGATCCTGATCGCCGCCC
GCATCGTGGAGCTGCTGGGCCGCCGCGGCTGGGAGGCCCTGAAGTACTGGGGCAACCTGCTG
CAGTACTGGATCCAGGAGCTGAAGAACAGCGCCGTGAGCCTGTTCGACGCCATCGCCATCGC
CGTGGCCGAGGGCACCGACCGCATCATCGAGGTGGCCCAGCGCATCGGCCGCGCCTTCCTGC
ACATCCCCCGCCGCATCCGCCAGGGCTTCGAGCGCGCCCTGCTGTAACTCGAG

*FIG. 13*

SEQ ID NO:11 ARG426-GLY431B

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCAACCGC
GGCAGCGGCAAGGCCATGTACGCCCCCCCCATCCGCGGCCAGATCCGCTGCAGCAGCAACAT
CACCGGCCTGCTGCTGACCCGCGACGGCGGCAAGGAGATCAGCAACACCACCGAGATCTTCC
GCCCCGGCGGCGGCGACATGCGCGACAACTGGCGCAGCGAGCTGTACAAGTACAAGGTGGTG
AAGATCGAGCCCCTGGGCGTGGCCCCCACCAAGGCCAAGCGCCGCGTGGTGCAGCGCGAGAA
GCGCGCCGTGACCCTGGGCGCCATGTTCCTGGGCTTCCTGGGCGCCGCCGGCAGCACCATGGG
CGCCCGCAGCCTGACCCTGACCGTGCAGGCCCGCCAGCTGCTGAGCGGCATCGTGCAGCAGC
AGAACAACCTGCTGCGCGCCATCGAGGCCCAGCAGCACCTGCTGCAGCTGACCGTGTGGGGC
ATCAAGCAGCTGCAGGCCCGCGTGCTGGCCGTGGAGCGCTACCTGAAGGACCAGCAGCTGCT
GGGCATCTGGGGCTGCAGCGGCAAGCTGATCTGCACCACCGCCGTGCCCTGGAACGCCAGCT
GGAGCAACAAGAGCCTGGACCAGATCTGGAACAACATGACCTGGATGGAGTGGGAGCGCGA
GATCGACAACTACACCAACCTGATCTACACCCTGATCGAGGAGAGCCAGAACCAGCAGGAGA
AGAACGAGCAGGAGCTGCTGGAGCTGGACAAGTGGGCCAGCCTGTGGAACTGGTTCGACATC
AGCAAGTGGCTGTGGTACATCAAGATCTTCATCATGATCGTGGGCGGCCTGGTGGGCCTGCGC
ATCGTGTTCACCGTGCTGAGCATCGTGAACCGCGTGCGCCAGGGCTACAGCCCCCTGAGCTTC
CAGACCCGCTTCCCCGCCCCCCGCGGCCCCGACCGCCCCGAGGGCATCGAGGAGGAGGGCGG
CGAGCGCGACCGCGACCGCAGCAGCCCCCTGGTGCACGGCCTGCTGGCCCTGATCTGGGACG
ACCTGCGCAGCCTGTGCCTGTTCAGCTACCACCGCCTGCGCGACCTGATCCTGATCGCCGCCC
GCATCGTGGAGCTGCTGGGCCGCCGCGGCTGGGAGGCCCTGAAGTACTGGGGCAACCTGCTG
CAGTACTGGATCCAGGAGCTGAAGAACAGCGCCGTGAGCCTGTTCGACGCCATCGCCATCGC
CGTGGCCGAGGGCACCGACCGCATCATCGAGGTGGCCCAGCGCATCGGCCGCGCCTTCCTGC
ACATCCCCCGCCGCATCCGCCAGGGCTTCGAGCGCGCCCTGCTGTAACTCGAG

FIG. 14

SEQ ID NO:12 ARG426-LYS432

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCAACCGC
GGCGGCAACAAGGCCATGTACGCCCCCCCCATCCGCGGCCAGATCCGCTGCAGCAGCAACAT
CACCGGCCTGCTGCTGACCCGCGACGGCGGCAAGGAGATCAGCAACACCACCGAGATCTTCC
GCCCCGGCGGCGGCGACATGCGCGACAACTGGCGCAGCGAGCTGTACAAGTACAAGGTGGTG
AAGATCGAGCCCCTGGGCGTGGCCCCCACCAAGGCCAAGCGCCGCGTGGTGCAGCGCGAGAA
GCGCGCCGTGACCCTGGGCGCCATGTTCCTGGGCTTCCTGGGCGCCGCCGGCAGCACCATGGG
CGCCCGCAGCCTGACCCTGACCGTGCAGGCCCGCCAGCTGCTGAGCGGCATCGTGCAGCAGC
AGAACAACCTGCTGCGCGCCATCGAGGCCCAGCAGCACCTGCTGCAGCTGACCGTGTGGGGC
ATCAAGCAGCTGCAGGCCCGCGTGCTGGCCGTGGAGCGCTACCTGAAGGACCAGCAGCTGCT
GGGCATCTGGGGCTGCAGCGGCAAGCTGATCTGCACCACCGCCGTGCCCTGGAACGCCAGCT
GGAGCAACAAGAGCCTGGACCAGATCTGGAACAACATGACCTGGATGGAGTGGGAGCGCGA
GATCGACAACTACACCAACCTGATCTACACCCTGATCGAGGAGAGCCAGAACCAGCAGGAGA
AGAACGAGCAGGAGCTGCTGGAGCTGGACAAGTGGGCCAGCCTGTGGAACTGGTTCGACATC
AGCAAGTGGCTGTGGTACATCAAGATCTTCATCATGATCGTGGGCGGCCTGGTGGGCCTGCGC
ATCGTGTTCACCGTGCTGAGCATCGTGAACCGCGTGCGCCAGGGCTACAGCCCCCTGAGCTTC
CAGACCCGCTTCCCCGCCCCCCGCGGCCCCGACCGCCCCGAGGGCATCGAGGAGGAGGGCGG
CGAGCGCGACCGCGACCGCAGCAGCCCCCTGGTGCACGGCCTGCTGGCCCTGATCTGGGACG
ACCTGCGCAGCCTGTGCCTGTTCAGCTACCACCGCCTGCGCGACCTGATCCTGATCGCCGCCC
GCATCGTGGAGCTGCTGGGCCGCCGCGGCTGGGAGGCCCTGAAGTACTGGGGCAACCTGCTG
CAGTACTGGATCCAGGAGCTGAAGAACAGCGCCGTGAGCCTGTTCGACGCCATCGCCATCGC
CGTGGCCGAGGGCACCGACCGCATCATCGAGGTGGCCCAGCGCATCGGCCGCGCCTTCCTGC
ACATCCCCCGCCGCATCCGCCAGGGCTTCGAGCGCGCCCTGCTGTAACTCGAG

FIG. 15

SEQ ID NO:13 ASN425-LYS432

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCAACGCCC
CCAAGGCCATGTACGCCCCCCCCATCCGCGGCCAGATCCGCTGCAGCAGCAACATCACCGGCC
TGCTGCTGACCCGCGACGGCGGCAAGGAGATCAGCAACACCACCGAGATCTTCCGCCCCGGC
GGCGGCGACATGCGCGACAACTGGCGCAGCGAGCTGTACAAGTACAAGGTGGTGAAGATCGA
GCCCCTGGGCGTGGCCCCCACCAAGGCCAAGCGCCGCGTGGTGCAGCGCGAGAAGCGCGCCG
TGACCCTGGGCGCCATGTTCCTGGGCTTCCTGGGCGCCGCCGGCAGCACCATGGGCGCCCGCA
GCCTGACCCTGACCGTGCAGGCCCGCCAGCTGCTGAGCGGCATCGTGCAGCAGCAGAACAAC
CTGCTGCGCGCCATCGAGGCCCAGCAGCACCTGCTGCAGCTGACCGTGTGGGGCATCAAGCA
GCTGCAGGCCCGCGTGCTGGCCGTGGAGCGCTACCTGAAGGACCAGCAGCTGCTGGGCATCT
GGGGCTGCAGCGGCAAGCTGATCTGCACCACCGCCGTGCCCTGGAACGCCAGCTGGAGCAAC
AAGAGCCTGGACCAGATCTGGAACAACATGACCTGGATGGAGTGGGAGCGCGAGATCGACAA
CTACACCAACCTGATCTACACCCTGATCGAGGAGAGCCAGAACCAGCAGGAGAAGAACGAGC
AGGAGCTGCTGGAGCTGGACAAGTGGGCCAGCCTGTGGAACTGGTTCGACATCAGCAAGTGG
CTGTGGTACATCAAGATCTTCATCATGATCGTGGGCGGCCTGGTGGGCCTGCGCATCGTGTTC
ACCGTGCTGAGCATCGTGAACCGCGTGCGCCAGGGCTACAGCCCCCTGAGCTTCCAGACCCGC
TTCCCCGCCCCCCGCGGCCCCGACCGCCCCGAGGGCATCGAGGAGGAGGGCGGCGAGCGCGA
CCGCGACCGCAGCAGCCCCCTGGTGCACGGCCTGCTGGCCCTGATCTGGGACGACCTGCGCAG
CCTGTGCCTGTTCAGCTACCACCGCCTGCGCGACCTGATCCTGATCGCCGCCCGCATCGTGGA
GCTGCTGGGCCGCCGCGGCTGGGAGGCCCTGAAGTACTGGGGCAACCTGCTGCAGTACTGGA
TCCAGGAGCTGAAGAACAGCGCCGTGAGCCTGTTCGACGCCATCGCCATCGCCGTGGCCGAG
GGCACCGACCGCATCATCGAGGTGGCCCAGCGCATCGGCCGCGCCTTCCTGCACATCCCCCGC
CGCATCCGCCAGGGCTTCGAGCGCGCCCTGCTGTAACTCGAG

*FIG. 16*

SEQ ID NO:14 ILE424-ALA433

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCATCGGCGGC
GCCATGTACGCCCCCCCCATCCGCGGCCAGATCCGCTGCAGCAGCAACATCACCGGCCTGCTG
CTGACCCGCGACGGCGGCAAGGAGATCAGCAACACCACCGAGATCTTCCGCCCCGGCGGCGG
CGACATGCGCGACAACTGGCGCAGCGAGCTGTACAAGTACAAGGTGGTGAAGATCGAGCCCC
TGGGCGTGGCCCCCACCAAGGCCAAGCGCCGCGTGGTGCAGCGCGAGAAGCGCGCCGTGACC
CTGGGCGCCATGTTCCTGGGCTTCCTGGGCGCCGCCGGCAGCACCATGGGCGCCCGCAGCCTG
ACCCTGACCGTGCAGGCCCGCCAGCTGCTGAGCGGCATCGTGCAGCAGCAGAACAACCTGCT
GCGCGCCATCGAGGCCCAGCAGCACCTGCTGCAGCTGACCGTGTGGGGCATCAAGCAGCTGC
AGGCCCGCGTGCTGGCCGTGGAGCGCTACCTGAAGGACCAGCAGCTGCTGGGCATCTGGGGC
TGCAGCGGCAAGCTGATCTGCACCACCGCCGTGCCCTGGAACGCCAGCTGGAGCAACAAGAG
CCTGGACCAGATCTGGAACAACATGACCTGGATGGAGTGGGAGCGCGAGATCGACAACTACA
CCAACCTGATCTACACCCTGATCGAGGAGAGCCAGAACCAGCAGGAGAAGAACGAGCAGGA
GCTGCTGGAGCTGGACAAGTGGGCCAGCCTGTGGAACTGGTTCGACATCAGCAAGTGGCTGT
GGTACATCAAGATCTTCATCATGATCGTGGGCGGCCTGGTGGGCCTGCGCATCGTGTTCACCG
TGCTGAGCATCGTGAACCGCGTGCGCCAGGGCTACAGCCCCCTGAGCTTCCAGACCCGCTTCC
CCGCCCCCCGCGGCCCCGACCGCCCCGAGGGCATCGAGGAGGAGGGCGGCGAGCGCGACCGC
GACCGCAGCAGCCCCCTGGTGCACGGCCTGCTGGCCCTGATCTGGGACGACCTGCGCAGCCTG
TGCCTGTTCAGCTACCACCGCCTGCGCGACCTGATCCTGATCGCCGCCCGCATCGTGGAGCTG
CTGGGCCGCCGCGGCTGGGAGGCCCTGAAGTACTGGGGCAACCTGCTGCAGTACTGGATCCA
GGAGCTGAAGAACAGCGCCGTGAGCCTGTTCGACGCCATCGCCATCGCCGTGGCCGAGGGCA
CCGACCGCATCATCGAGGTGGCCCAGCGCATCGGCCGCGCCTTCCTGCACATCCCCCGCCGCA
TCCGCCAGGGCTTCGAGCGCGCCCTGCTGTAACTCGAG

*FIG. 17*

SEQ ID NO:15 ILE423-MET434

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGATCGGCGGCATG
TACGCCCCCCCCATCCGCGGCCAGATCCGCTGCAGCAGCAACATCACCGGCCTGCTGCTGACC
CGCGACGGCGGCAAGGAGATCAGCAACACCACCGAGATCTTCCGCCCCGGCGGCGGCGACAT
GCGCGACAACTGGCGCAGCGAGCTGTACAAGTACAAGGTGGTGAAGATCGAGCCCCTGGGCG
TGGCCCCCACCAAGGCCAAGCGCCGCGTGGTGCAGCGCGAGAAGCGCGCCGTGACCCTGGGC
GCCATGTTCCTGGGCTTCCTGGGCGCCGCCGGCAGCACCATGGGCGCCCGCAGCCTGACCCTG
ACCGTGCAGGCCCGCCAGCTGCTGAGCGGCATCGTGCAGCAGCAGAACAACCTGCTGCGCGC
CATCGAGGCCCAGCAGCACCTGCTGCAGCTGACCGTGTGGGGCATCAAGCAGCTGCAGGCCC
GCGTGCTGGCCGTGGAGCGCTACCTGAAGGACCAGCAGCTGCTGGGCATCTGGGGCTGCAGC
GGCAAGCTGATCTGCACCACCGCCGTGCCCTGGAACGCCAGCTGGAGCAACAAGAGCCTGGA
CCAGATCTGGAACAACATGACCTGGATGGAGTGGGAGCGCGAGATCGACAACTACACCAACC
TGATCTACACCCTGATCGAGGAGAGCCAGAACCAGCAGGAGAAGAACGAGCAGGAGCTGCTG
GAGCTGGACAAGTGGGCCAGCCTGTGGAACTGGTTCGACATCAGCAAGTGGCTGTGGTACAT
CAAGATCTTCATCATGATCGTGGGCGGCCTGGTGGGCCTGCGCATCGTGTTCACCGTGCTGAG
CATCGTGAACCGCGTGCGCCAGGGCTACAGCCCCCTGAGCTTCCAGACCCGCTTCCCCGCCCC
CCGCGGCCCCGACCGCCCCGAGGGCATCGAGGAGGAGGGCGGCGAGCGCGACCGCGACCGC
AGCAGCCCCCTGGTGCACGGCCTGCTGGCCCTGATCTGGGACGACCTGCGCAGCCTGTGCCTG
TTCAGCTACCACCGCCTGCGCGACCTGATCCTGATCGCCGCCCGCATCGTGGAGCTGCTGGGC
CGCCGCGGCTGGGAGGCCCTGAAGTACTGGGGCAACCTGCTGCAGTACTGGATCCAGGAGCT
GAAGAACAGCGCCGTGAGCCTGTTCGACGCCATCGCCATCGCCGTGGCCGAGGGCACCGACC
GCATCATCGAGGTGGCCCAGCGCATCGGCCGCGCCTTCCTGCACATCCCCCGCCGCATCCGCC
AGGGCTTCGAGCGCGCCCTGCTGTAACTCGAG

*FIG. 18*

SEQ ID NO:16 GLN422-TYR435

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGGGCGGCTACGCC
CCCCCCATCCGCGGCCAGATCCGCTGCAGCAGCAACATCACCGGCCTGCTGCTGACCCGCGAC
GGCGGCAAGGAGATCAGCAACACCACCGAGATCTTCCGCCCCGGCGGCGGCGACATGCGCGA
CAACTGGCGCAGCGAGCTGTACAAGTACAAGGTGGTGAAGATCGAGCCCCTGGGCGTGGCCC
CCACCAAGGCCAAGCGCCGCGTGGTGCAGCGCGAGAAGCGCGCCGTGACCCTGGGCGCCATG
TTCCTGGGCTTCCTGGGCGCCGCCGGCAGCACCATGGGCGCCCGCAGCCTGACCCTGACCGTG
CAGGCCCGCCAGCTGCTGAGCGGCATCGTGCAGCAGCAGAACAACCTGCTGCGCGCCATCGA
GGCCCAGCAGCACCTGCTGCAGCTGACCGTGTGGGGCATCAAGCAGCTGCAGGCCCGCGTGC
TGGCCGTGGAGCGCTACCTGAAGGACCAGCAGCTGCTGGGCATCTGGGGCTGCAGCGGCAAG
CTGATCTGCACCACCGCCGTGCCCTGGAACGCCAGCTGGAGCAACAAGAGCCTGGACCAGAT
CTGGAACAACATGACCTGGATGGAGTGGGAGCGCGAGATCGACAACTACACCAACCTGATCT
ACACCCTGATCGAGGAGAGCCAGAACCAGCAGGAGAAGAACGAGCAGGAGCTGCTGGAGCT
GGACAAGTGGGCCAGCCTGTGGAACTGGTTCGACATCAGCAAGTGGCTGTGGTACATCAAGA
TCTTCATCATGATCGTGGGCGGCCTGGTGGGCCTGCGCATCGTGTTCACCGTGCTGAGCATCG
TGAACCGCGTGCGCCAGGGCTACAGCCCCCTGAGCTTCCAGACCCGCTTCCCCGCCCCCCGCG
GCCCCGACCGCCCCGAGGGCATCGAGGAGGAGGGCGGCGAGCGCGACCGCGACCGCAGCAG
CCCCCTGGTGCACGGCCTGCTGGCCCTGATCTGGGACGACCTGCGCAGCCTGTGCCTGTTCAG
CTACCACCGCCTGCGCGACCTGATCCTGATCGCCGCCCGCATCGTGGAGCTGCTGGGCCGCCG
CGGCTGGGAGGCCCTGAAGTACTGGGGCAACCTGCTGCAGTACTGGATCCAGGAGCTGAAGA
ACAGCGCCGTGAGCCTGTTCGACGCCATCGCCATCGCCGTGGCCGAGGGCACCGACCGCATC
ATCGAGGTGGCCCAGCGCATCGGCCGCGCCTTCCTGCACATCCCCCGCCGCATCCGCCAGGGC
TTCGAGCGCGCCCTGCTGTAACTCGAG

FIG. 19

SEQ ID NO:17 GLN422-TYR435B

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
ACCCTGCACTGCACCAACCTGAAGAACGCCACCAACACCAAGAGCAGCAACTGGAAGGAGAT
GGACCGCGGCGAGATCAAGAACTGCAGCTTCAAGGTGACCACCAGCATCCGCAACAAGATGC
AGAAGGAGTACGCCCTGTTCTACAAGCTGGACGTGGTGCCCATCGACAACGACAACACCAGC
TACAAGCTGATCAACTGCAACACCAGCGTGATCACCCAGGCCTGCCCCAAGGTGAGCTTCGA
GCCCATCCCCATCCACTACTGCGCCCCCGCCGGCTTCGCCATCCTGAAGTGCAACGACAAGAA
GTTCAACGGCAGCGGCCCCTGCACCAACGTGAGCACCGTGCAGTGCACCCACGGCATCCGCC
CCGTGGTGAGCACCCAGCTGCTGCTGAACGGCAGCCTGGCCGAGGAGGGCGTGGTGATCCGC
AGCGAGAACTTCACCGACAACGCCAAGACCATCATCGTGCAGCTGAAGGAGAGCGTGGAGAT
CAACTGCACCCGCCCCAACAACAACACCCGCAAGAGCATCACCATCGGCCCCGGCCGCGCCT
TCTACGCCACCGGCGACATCATCGGCGACATCCGCCAGGCCCACTGCAACATCAGCGGCGAG
AAGTGGAACAACACCCTGAAGCAGATCGTGACCAAGCTGCAGGCCCAGTTCGGCAACAAGAC
CATCGTGTTCAAGCAGAGCAGCGGCGGCGACCCCGAGATCGTGATGCACAGCTTCAACTGCG
GCGGCGAGTTCTTCTACTGCAACAGCACCCAGCTGTTCAACAGCACCTGGAACAACACCATCG
GCCCCAACAACACCAACGGCACCATCACCCTGCCCTGCCGCATCAAGCAGGCCCCCTACGCCC
CCCCCATCCGCGGCCAGATCCGCTGCAGCAGCAACATCACCGGCCTGCTGCTGACCCGCGACG
GCGGCAAGGAGATCAGCAACACCACCGAGATCTTCCGCCCCGGCGGCGGCGACATGCGCGAC
AACTGGCGCAGCGAGCTGTACAAGTACAAGGTGGTGAAGATCGAGCCCCTGGGCGTGGCCCC
CACCAAGGCCAAGCGCCGCGTGGTGCAGCGCGAGAAGCGCGCCGTGACCCTGGGCGCCATGT
TCCTGGGCTTCCTGGGCGCCGCCGGCAGCACCATGGGCGCCCGCAGCCTGACCCTGACCGTGC
AGGCCCGCCAGCTGCTGAGCGGCATCGTGCAGCAGCAGAACAACCTGCTGCGCGCCATCGAG
GCCCAGCAGCACCTGCTGCAGCTGACCGTGTGGGGCATCAAGCAGCTGCAGGCCCGCGTGCT
GGCCGTGGAGCGCTACCTGAAGGACCAGCAGCTGCTGGGCATCTGGGGCTGCAGCGGCAAGC
TGATCTGCACCACCGCCGTGCCCTGGAACGCCAGCTGGAGCAACAAGAGCCTGGACCAGATC
TGGAACAACATGACCTGGATGGAGTGGGAGCGCGAGATCGACAACTACACCAACCTGATCTA
CACCCTGATCGAGGAGAGCCAGAACCAGCAGGAGAAGAACGAGCAGGAGCTGCTGGAGCTG
GACAAGTGGGCCAGCCTGTGGAACTGGTTCGACATCAGCAAGTGGCTGTGGTACATCAAGAT
CTTCATCATGATCGTGGGCGGCCTGGTGGGCCTGCGCATCGTGTTCACCGTGCTGAGCATCGT
GAACCGCGTGCGCCAGGGCTACAGCCCCCTGAGCTTCCAGACCCGCTTCCCCGCCCCCCGCGG
CCCCGACCGCCCCGAGGGCATCGAGGAGGAGGGCGGCGAGCGCGACCGCGACCGCAGCAGC
CCCCTGGTGCACGGCCTGCTGGCCCTGATCTGGGACGACCTGCGCAGCCTGTGCCTGTTCAGC
TACCACCGCCTGCGCGACCTGATCCTGATCGCCGCCCGCATCGTGGAGCTGCTGGGCCGCCGC
GGCTGGGAGGCCCTGAAGTACTGGGGCAACCTGCTGCAGTACTGGATCCAGGAGCTGAAGAA
CAGCGCCGTGAGCCTGTTCGACGCCATCGCCATCGCCGTGGCCGAGGGCACCGACCGCATCAT
CGAGGTGGCCCAGCGCATCGGCCGCGCCTTCCTGCACATCCCCCGCCGCATCCGCCAGGGCTT
CGAGCGCGCCCTGCTGTAACTCGAG

FIG. 20

SEQ ID NO:18: LEU122-SER199; ARG426-GLY431

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGGGCAACAGCGTGAT
CACCCAGGCCTGCCCCAAGGTGAGCTTCGAGCCCATCCCCATCCACTACTGCGCCCCCGCCGG
CTTCGCCATCCTGAAGTGCAACGACAAGAAGTTCAACGGCAGCGGCCCCTGCACCAACGTGA
GCACCGTGCAGTGCACCCACGGCATCCGCCCCGTGGTGAGCACCCAGCTGCTGCTGAACGGC
AGCCTGGCCGAGGAGGGCGTGGTGATCCGCAGCGAGAACTTCACCGACAACGCCAAGACCAT
CATCGTGCAGCTGAAGGAGAGCGTGGAGATCAACTGCACCCGCCCCAACAACAACACCCGCA
AGAGCATCACCATCGGCCCCGGCCGCGCCTTCTACGCCACCGGCGACATCATCGGCGACATCC
GCCAGGCCCACTGCAACATCAGCGGCGAGAAGTGGAACAACACCCTGAAGCAGATCGTGACC
AAGCTGCAGGCCCAGTTCGGCAACAAGACCATCGTGTTCAAGCAGAGCAGCGGCGGCGACCC
CGAGATCGTGATGCACAGCTTCAACTGCGGCGGCGAGTTCTTCTACTGCAACAGCACCCAGCT
GTTCAACAGCACCTGGAACAACACCATCGGCCCCAACAACACCAACGGCACCATCACCCTGC
CCTGCCGCATCAAGCAGATCATCAACCGCGGCGGCGGCAAGGCCATGTACGCCCCCCCCATCC
GCGGCCAGATCCGCTGCAGCAGCAACATCACCGGCCTGCTGCTGACCCGCGACGGCGGCAAG
GAGATCAGCAACACCACCGAGATCTTCCGCCCCGGCGGCGGCGACATGCGCGACAACTGGCG
CAGCGAGCTGTACAAGTACAAGGTGGTGAAGATCGAGCCCCTGGGCGTGGCCCCCACCAAGG
CCAAGCGCCGCGTGGTGCAGCGCGAGAAGCGCGCCGTGACCCTGGGCGCCATGTTCCTGGGC
TTCCTGGGCGCCGCCGGCAGCACCATGGGCGCCCGCAGCCTGACCCTGACCGTGCAGGCCCGC
CAGCTGCTGAGCGGCATCGTGCAGCAGCAGAACAACCTGCTGCGCGCCATCGAGGCCCAGCA
GCACCTGCTGCAGCTGACCGTGTGGGGCATCAAGCAGCTGCAGGCCCGCGTGCTGGCCGTGG
AGCGCTACCTGAAGGACCAGCAGCTGCTGGGCATCTGGGGCTGCAGCGGCAAGCTGATCTGC
ACCACCGCCGTGCCCTGGAACGCCAGCTGGAGCAACAAGAGCCTGGACCAGATCTGGAACAA
CATGACCTGGATGGAGTGGGAGCGCGAGATCGACAACTACACCAACCTGATCTACACCCTGA
TCGAGGAGAGCCAGAACCAGCAGGAGAAGAACGAGCAGGAGCTGCTGGAGCTGGACAAGTG
GGCCAGCCTGTGGAACTGGTTCGACATCAGCAAGTGGCTGTGGTACATCAAGATCTTCATCAT
GATCGTGGGCGGCCTGGTGGGCCTGCGCATCGTGTTCACCGTGCTGAGCATCGTGAACCGCGT
GCGCCAGGGCTACAGCCCCCTGAGCTTCCAGACCCGCTTCCCCGCCCCCCGCGGCCCCGACCG
CCCCGAGGGCATCGAGGAGGAGGGCGGCGAGCGCGACCGCGACCGCAGCAGCCCCCTGGTGC
ACGGCCTGCTGGCCCTGATCTGGGACGACCTGCGCAGCCTGTGCCTGTTCAGCTACCACCGCC
TGCGCGACCTGATCCTGATCGCCGCCCGCATCGTGGAGCTGCTGGGCCGCCGCGGCTGGGAGG
CCCTGAAGTACTGGGGCAACCTGCTGCAGTACTGGATCCAGGAGCTGAAGAACAGCGCCGTG
AGCCTGTTCGACGCCATCGCCATCGCCGTGGCCGAGGGCACCGACCGCATCATCGAGGTGGCC
CAGCGCATCGGCCGCGCCTTCCTGCACATCCCCCGCCGCATCCGCCAGGGCTTCGAGCGCGCC
CTGCTGTAACTCGAG

*FIG. 21*

SEQ ID NO:19 LEU122-SER199; ARG426-LYS432

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGGGCAACAGCGTGAT
CACCCAGGCCTGCCCCAAGGTGAGCTTCGAGCCCATCCCCATCCACTACTGCGCCCCCGCCGG
CTTCGCCATCCTGAAGTGCAACGACAAGAAGTTCAACGGCAGCGGCCCCTGCACCAACGTGA
GCACCGTGCAGTGCACCCACGGCATCCGCCCCGTGGTGAGCACCCAGCTGCTGCTGAACGGC
AGCCTGGCCGAGGAGGGCGTGGTGATCCGCAGCGAGAACTTCACCGACAACGCCAAGACCAT
CATCGTGCAGCTGAAGGAGAGCGTGGAGATCAACTGCACCCGCCCCAACAACAACACCCGCA
AGAGCATCACCATCGGCCCCGGCCGCGCCTTCTACGCCACCGGCGACATCATCGGCGACATCC
GCCAGGCCCACTGCAACATCAGCGGCGAGAAGTGGAACAACACCCTGAAGCAGATCGTGACC
AAGCTGCAGGCCCAGTTCGGCAACAAGACCATCGTGTTCAAGCAGAGCAGCGGCGGCGACCC
CGAGATCGTGATGCACAGCTTCAACTGCGGCGGCGAGTTCTTCTACTGCAACAGCACCCAGCT
GTTCAACAGCACCTGGAACAACACCATCGGCCCCAACAACACCAACGGCACCATCACCCTGC
CCTGCCGCATCAAGCAGATCATCAACCGCGGCGGCAACAAGGCCATGTACGCCCCCCCCATCC
GCGGCCAGATCCGCTGCAGCAGCAACATCACCGGCCTGCTGCTGACCCGCGACGGCGGCAAG
GAGATCAGCAACACCACCGAGATCTTCCGCCCCGGCGGCGGCGACATGCGCGACAACTGGCG
CAGCGAGCTGTACAAGTACAAGGTGGTGAAGATCGAGCCCCTGGGCGTGGCCCCCACCAAGG
CCAAGCGCCGCGTGGTGCAGCGCGAGAAGCGCGCCGTGACCCTGGGCGCCATGTTCCTGGGC
TTCCTGGGCGCCGCCGGCAGCACCATGGGCGCCCGCAGCCTGACCCTGACCGTGCAGGCCCGC
CAGCTGCTGAGCGGCATCGTGCAGCAGCAGAACAACCTGCTGCGCGCCATCGAGGCCCAGCA
GCACCTGCTGCAGCTGACCGTGTGGGGCATCAAGCAGCTGCAGGCCCGCGTGCTGGCCGTGG
AGCGCTACCTGAAGGACCAGCAGCTGCTGGGCATCTGGGGCTGCAGCGGCAAGCTGATCTGC
ACCACCGCCGTGCCCTGGAACGCCAGCTGGAGCAACAAGAGCCTGGACCAGATCTGGAACAA
CATGACCTGGATGGAGTGGGAGCGCGAGATCGACAACTACACCAACCTGATCTACACCCTGA
TCGAGGAGAGCCAGAACCAGCAGGAGAAGAACGAGCAGGAGCTGCTGGAGCTGGACAAGTG
GGCCAGCCTGTGGAACTGGTTCGACATCAGCAAGTGGCTGTGGTACATCAAGATCTTCATCAT
GATCGTGGGCGGCCTGGTGGGCCTGCGCATCGTGTTCACCGTGCTGAGCATCGTGAACCGCGT
GCGCCAGGGCTACAGCCCCCTGAGCTTCCAGACCCGCTTCCCCGCCCCCCGCGGCCCCGACCG
CCCCGAGGGCATCGAGGAGGAGGGCGGCGAGCGCGACCGCGACCGCAGCAGCCCCCTGGTGC
ACGGCCTGCTGGCCCTGATCTGGGACGACCTGCGCAGCCTGTGCCTGTTCAGCTACCACCGCC
TGCGCGACCTGATCCTGATCGCCGCCCGCATCGTGGAGCTGCTGGGCCGCCGCGGCTGGGAGG
CCCTGAAGTACTGGGGCAACCTGCTGCAGTACTGGATCCAGGAGCTGAAGAACAGCGCCGTG
AGCCTGTTCGACGCCATCGCCATCGCCGTGGCCGAGGGCACCGACCGCATCATCGAGGTGGCC
CAGCGCATCGGCCGCGCCTTCCTGCACATCCCCCGCCGCATCCGCCAGGGCTTCGAGCGCGCC
CTGCTGTAACTCGAG

FIG. 22

SEQ ID NO: 20: LEU122-SER199; TRP427-GLY431

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGGGCAACAGCGTGAT
CACCCAGGCCTGCCCCAAGGTGAGCTTCGAGCCCATCCCCATCCACTACTGCGCCCCCGCCGG
CTTCGCCATCCTGAAGTGCAACGACAAGAAGTTCAACGGCAGCGGCCCCTGCACCAACGTGA
GCACCGTGCAGTGCACCCACGGCATCCGCCCCGTGGTGAGCACCCAGCTGCTGCTGAACGGC
AGCCTGGCCGAGGAGGGCGTGGTGATCCGCAGCGAGAACTTCACCGACAACGCCAAGACCAT
CATCGTGCAGCTGAAGGAGAGCGTGGAGATCAACTGCACCCGCCCCAACAACAACACCCGCA
AGAGCATCACCATCGGCCCCGGCCGCGCCTTCTACGCCACCGGCGACATCATCGGCGACATCC
GCCAGGCCCACTGCAACATCAGCGGCGAGAAGTGGAACAACACCCTGAAGCAGATCGTGACC
AAGCTGCAGGCCCAGTTCGGCAACAAGACCATCGTGTTCAAGCAGAGCAGCGGCGGCGACCC
CGAGATCGTGATGCACAGCTTCAACTGCGGCGGCGAGTTCTTCTACTGCAACAGCACCCAGCT
GTTCAACAGCACCTGGAACAACACCATCGGCCCCAACAACACCAACGGCACCATCACCCTGC
CCTGCCGCATCAAGCAGATCATCAACCGCTGGGGCGGCAAGGCCATGTACGCCCCCCCCATCC
GCGGCCAGATCCGCTGCAGCAGCAACATCACCGGCCTGCTGCTGACCCGCGACGGCGGCAAG
GAGATCAGCAACACCACCGAGATCTTCCGCCCCGGCGGCGGCGACATGCGCGACAACTGGCG
CAGCGAGCTGTACAAGTACAAGGTGGTGAAGATCGAGCCCCTGGGCGTGGCCCCCACCAAGG
CCAAGCGCCGCGTGGTGCAGCGCGAGAAGCGCGCCGTGACCCTGGGCGCCATGTTCCTGGGC
TTCCTGGGCGCCGCCGGCAGCACCATGGGCGCCCGCAGCCTGACCCTGACCGTGCAGGCCCGC
CAGCTGCTGAGCGGCATCGTGCAGCAGCAGAACAACCTGCTGCGCGCCATCGAGGCCCAGCA
GCACCTGCTGCAGCTGACCGTGTGGGGCATCAAGCAGCTGCAGGCCCGCGTGCTGGCCGTGG
AGCGCTACCTGAAGGACCAGCAGCTGCTGGGCATCTGGGGCTGCAGCGGCAAGCTGATCTGC
ACCACCGCCGTGCCCTGGAACGCCAGCTGGAGCAACAAGAGCCTGGACCAGATCTGGAACAA
CATGACCTGGATGGAGTGGGAGCGCGAGATCGACAACTACACCAACCTGATCTACACCCTGA
TCGAGGAGAGCCAGAACCAGCAGGAGAAGAACGAGCAGGAGCTGCTGGAGCTGGACAAGTG
GGCCAGCCTGTGGAACTGGTTCGACATCAGCAAGTGGCTGTGGTACATCAAGATCTTCATCAT
GATCGTGGGCGGCCTGGTGGGCCTGCGCATCGTGTTCACCGTGCTGAGCATCGTGAACCGCGT
GCGCCAGGGCTACAGCCCCCTGAGCTTCCAGACCCGCTTCCCCGCCCCCCGCGGCCCCGACCG
CCCCGAGGGCATCGAGGAGGAGGGCGGCGAGCGCGACCGCGACCGCAGCAGCCCCCTGGTGC
ACGGCCTGCTGGCCCTGATCTGGGACGACCTGCGCAGCCTGTGCCTGTTCAGCTACCACCGCC
TGCGCGACCTGATCCTGATCGCCGCCCGCATCGTGGAGCTGCTGGGCCGCCGCGGCTGGGAGG
CCCTGAAGTACTGGGGCAACCTGCTGCAGTACTGGATCCAGGAGCTGAAGAACAGCGCCGTG
AGCCTGTTCGACGCCATCGCCATCGCCGTGGCCGAGGGCACCGACCGCATCATCGAGGTGGCC
CAGCGCATCGGCCGCGCCTTCCTGCACATCCCCCGCCGCATCCGCCAGGGCTTCGAGCGCGCC
CTGCTGTAACTCGAG

FIG. 23

SEQ ID NO:21 LYS121-VAL200; ASN425-LYS432

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGGCCCCCGTGATCACCCA
GGCCTGCCCCAAGGTGAGCTTCGAGCCCATCCCCATCCACTACTGCGCCCCCGCCGGCTTCGC
CATCCTGAAGTGCAACGACAAGAAGTTCAACGGCAGCGGCCCCTGCACCAACGTGAGCACCG
TGCAGTGCACCCACGGCATCCGCCCCGTGGTGAGCACCCAGCTGCTGCTGAACGGCAGCCTGG
CCGAGGAGGGCGTGGTGATCCGCAGCGAGAACTTCACCGACAACGCCAAGACCATCATCGTG
CAGCTGAAGGAGAGCGTGGAGATCAACTGCACCCGCCCCAACAACAACACCCGCAAGAGCAT
CACCATCGGCCCCGGCCGCGCCTTCTACGCCACCGGCGACATCATCGGCGACATCCGCCAGGC
CCACTGCAACATCAGCGGCGAGAAGTGGAACAACACCCTGAAGCAGATCGTGACCAAGCTGC
AGGCCCAGTTCGGCAACAAGACCATCGTGTTCAAGCAGAGCAGCGGCGGCGACCCCGAGATC
GTGATGCACAGCTTCAACTGCGGCGGCGAGTTCTTCTACTGCAACAGCACCCAGCTGTTCAAC
AGCACCTGGAACAACACCATCGGCCCCAACAACACCAACGGCACCATCACCCTGCCCTGCCG
CATCAAGCAGATCATCAACGCCCCCAAGGCCATGTACGCCCCCCCCATCCGCGGCCAGATCCG
CTGCAGCAGCAACATCACCGGCCTGCTGCTGACCCGCGACGGCGGCAAGGAGATCAGCAACA
CCACCGAGATCTTCCGCCCCGGCGGCGGCGACATGCGCGACAACTGGCGCAGCGAGCTGTAC
AAGTACAAGGTGGTGAAGATCGAGCCCCTGGGCGTGGCCCCCACCAAGGCCAAGCGCCGCGT
GGTGCAGCGCGAGAAGCGCGCCGTGACCCTGGGCGCCATGTTCCTGGGCTTCCTGGGCGCCGC
CGGCAGCACCATGGGCGCCCGCAGCCTGACCCTGACCGTGCAGGCCCGCCAGCTGCTGAGCG
GCATCGTGCAGCAGCAGAACAACCTGCTGCGCGCCATCGAGGCCCAGCAGCACCTGCTGCAG
CTGACCGTGTGGGGCATCAAGCAGCTGCAGGCCCGCGTGCTGGCCGTGGAGCGCTACCTGAA
GGACCAGCAGCTGCTGGGCATCTGGGGCTGCAGCGGCAAGCTGATCTGCACCACCGCCGTGC
CCTGGAACGCCAGCTGGAGCAACAAGAGCCTGGACCAGATCTGGAACAACATGACCTGGATG
GAGTGGGAGCGCGAGATCGACAACTACACCAACCTGATCTACACCCTGATCGAGGAGAGCCA
GAACCAGCAGGAGAAGAACGAGCAGGAGCTGCTGGAGCTGGACAAGTGGGCCAGCCTGTGG
AACTGGTTCGACATCAGCAAGTGGCTGTGGTACATCAAGATCTTCATCATGATCGTGGGCGGC
CTGGTGGGCCTGCGCATCGTGTTCACCGTGCTGAGCATCGTGAACCGCGTGCGCCAGGGCTAC
AGCCCCCTGAGCTTCCAGACCCGCTTCCCCGCCCCCCGCGGCCCCGACCGCCCCGAGGGCATC
GAGGAGGAGGGCGGCGAGCGCGACCGCGACCGCAGCAGCCCCCTGGTGCACGGCCTGCTGGC
CCTGATCTGGGACGACCTGCGCAGCCTGTGCCTGTTCAGCTACCACCGCCTGCGCGACCTGAT
CCTGATCGCCGCCCGCATCGTGGAGCTGCTGGGCCGCCGCGGCTGGGAGGCCCTGAAGTACTG
GGGCAACCTGCTGCAGTACTGGATCCAGGAGCTGAAGAACAGCGCCGTGAGCCTGTTCGACG
CCATCGCCATCGCCGTGGCCGAGGGCACCGACCGCATCATCGAGGTGGCCCAGCGCATCGGC
CGCGCCTTCCTGCACATCCCCCGCCGCATCCGCCAGGGCTTCGAGCGCGCCCTGCTGTAACTC
GAG

FIG. 24

SEQ ID NO:22 VAL120-ILE201; ILE 424-ALA433

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGGGCGGCATCACCCAGGCCTG
CCCCAAGGTGAGCTTCGAGCCCATCCCCATCCACTACTGCGCCCCCGCCGGCTTCGCCATCCT
GAAGTGCAACGACAAGAAGTTCAACGGCAGCGGCCCCTGCACCAACGTGAGCACCGTGCAGT
GCACCCACGGCATCCGCCCCGTGGTGAGCACCCAGCTGCTGCTGAACGGCAGCCTGGCCGAG
GAGGGCGTGGTGATCCGCAGCGAGAACTTCACCGACAACGCCAAGACCATCATCGTGCAGCT
GAAGGAGAGCGTGGAGATCAACTGCACCCGCCCCAACAACAACACCCGCAAGAGCATCACCA
TCGGCCCCGGCCGCGCCTTCTACGCCACCGGCGACATCATCGGCGACATCCGCCAGGCCCACT
GCAACATCAGCGGCGAGAAGTGGAACAACACCCTGAAGCAGATCGTGACCAAGCTGCAGGCC
CAGTTCGGCAACAAGACCATCGTGTTCAAGCAGAGCAGCGGCGGCGACCCCGAGATCGTGAT
GCACAGCTTCAACTGCGGCGGCGAGTTCTTCTACTGCAACAGCACCCAGCTGTTCAACAGCAC
CTGGAACAACACCATCGGCCCCAACAACACCAACGGCACCATCACCCTGCCCTGCCGCATCA
AGCAGATCATCGGCGGCGCCATGTACGCCCCCCCCATCCGCGGCCAGATCCGCTGCAGCAGC
AACATCACCGGCCTGCTGCTGACCCGCGACGGCGGCAAGGAGATCAGCAACACCACCGAGAT
CTTCCGCCCCGGCGGCGGCGACATGCGCGACAACTGGCGCAGCGAGCTGTACAAGTACAAGG
TGGTGAAGATCGAGCCCCTGGGCGTGGCCCCCACCAAGGCCAAGCGCCGCGTGGTGCAGCGC
GAGAAGCGCGCCGTGACCCTGGGCGCCATGTTCCTGGGCTTCCTGGGCGCCGCCGGCAGCACC
ATGGGCGCCCGCAGCCTGACCCTGACCGTGCAGGCCCGCCAGCTGCTGAGCGGCATCGTGCA
GCAGCAGAACAACCTGCTGCGCGCCATCGAGGCCCAGCAGCACCTGCTGCAGCTGACCGTGT
GGGGCATCAAGCAGCTGCAGGCCCGCGTGCTGGCCGTGGAGCGCTACCTGAAGGACCAGCAG
CTGCTGGGCATCTGGGGCTGCAGCGGCAAGCTGATCTGCACCACCGCCGTGCCCTGGAACGCC
AGCTGGAGCAACAAGAGCCTGGACCAGATCTGGAACAACATGACCTGGATGGAGTGGGAGCG
CGAGATCGACAACTACACCAACCTGATCTACACCCTGATCGAGGAGAGCCAGAACCAGCAGG
AGAAGAACGAGCAGGAGCTGCTGGAGCTGGACAAGTGGGCCAGCCTGTGGAACTGGTTCGAC
ATCAGCAAGTGGCTGTGGTACATCAAGATCTTCATCATGATCGTGGGCGGCCTGGTGGGCCTG
CGCATCGTGTTCACCGTGCTGAGCATCGTGAACCGCGTGCGCCAGGGCTACAGCCCCCTGAGC
TTCCAGACCCGCTTCCCCGCCCCCCGCGGCCCCGACCGCCCCGAGGGCATCGAGGAGGAGGG
CGGCGAGCGCGACCGCGACCGCAGCAGCCCCCTGGTGCACGGCCTGCTGGCCCTGATCTGGG
ACGACCTGCGCAGCCTGTGCCTGTTCAGCTACCACCGCCTGCGCGACCTGATCCTGATCGCCG
CCCGCATCGTGGAGCTGCTGGGCCGCCGCGGCTGGGAGGCCCTGAAGTACTGGGGCAACCTG
CTGCAGTACTGGATCCAGGAGCTGAAGAACAGCGCCGTGAGCCTGTTCGACGCCATCGCCATC
GCCGTGGCCGAGGGCACCGACCGCATCATCGAGGTGGCCCAGCGCATCGGCCGCGCCTTCCT
GCACATCCCCCGCCGCATCCGCCAGGGCTTCGAGCGCGCCCTGCTGTAACTCGAG

FIG. 25

SEQ ID NO:23: VAL120-ILE201B; ILE424-ALA433

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGCCCGGCATCACCCAGGCCTGC
CCCAAGGTGAGCTTCGAGCCCATCCCCATCCACTACTGCGCCCCCGCCGGCTTCGCCATCCTG
AAGTGCAACGACAAGAAGTTCAACGGCAGCGGCCCCTGCACCAACGTGAGCACCGTGCAGTG
CACCCACGGCATCCGCCCCGTGGTGAGCACCCAGCTGCTGCTGAACGGCAGCCTGGCCGAGG
AGGGCGTGGTGATCCGCAGCGAGAACTTCACCGACAACGCCAAGACCATCATCGTGCAGCTG
AAGGAGAGCGTGGAGATCAACTGCACCCGCCCCAACAACAACACCCGCAAGAGCATCACCAT
CGGCCCCGGCCGCGCCTTCTACGCCACCGGCGACATCATCGGCGACATCCGCCAGGCCCACTG
CAACATCAGCGGCGAGAAGTGGAACAACACCCTGAAGCAGATCGTGACCAAGCTGCAGGCCC
AGTTCGGCAACAAGACCATCGTGTTCAAGCAGAGCAGCGGCGGCGACCCCGAGATCGTGATG
CACAGCTTCAACTGCGGCGGCGAGTTCTTCTACTGCAACAGCACCCAGCTGTTCAACAGCACC
TGGAACAACACCATCGGCCCCAACAACACCAACGGCACCATCACCCTGCCCTGCCGCATCAA
GCAGATCATCGGCGGCGCCATGTACGCCCCCCCCATCCGCGGCCAGATCCGCTGCAGCAGCA
ACATCACCGGCCTGCTGCTGACCCGCGACGGCGGCAAGGAGATCAGCAACACCACCGAGATC
TTCCGCCCCGGCGGCGGCGACATGCGCGACAACTGGCGCAGCGAGCTGTACAAGTACAAGGT
GGTGAAGATCGAGCCCCTGGGCGTGGCCCCCACCAAGGCCAAGCGCCGCGTGGTGCAGCGCG
AGAAGCGCGCCGTGACCCTGGGCGCCATGTTCCTGGGCTTCCTGGGCGCCGCCGGCAGCACCA
TGGGCGCCCGCAGCCTGACCCTGACCGTGCAGGCCCGCCAGCTGCTGAGCGGCATCGTGCAG
CAGCAGAACAACCTGCTGCGCGCCATCGAGGCCCAGCAGCACCTGCTGCAGCTGACCGTGTG
GGGCATCAAGCAGCTGCAGGCCCGCGTGCTGGCCGTGGAGCGCTACCTGAAGGACCAGCAGC
TGCTGGGCATCTGGGGCTGCAGCGGCAAGCTGATCTGCACCACCGCCGTGCCCTGGAACGCCA
GCTGGAGCAACAAGAGCCTGGACCAGATCTGGAACAACATGACCTGGATGGAGTGGGAGCGC
GAGATCGACAACTACACCAACCTGATCTACACCCTGATCGAGGAGAGCCAGAACCAGCAGGA
GAAGAACGAGCAGGAGCTGCTGGAGCTGGACAAGTGGGCCAGCCTGTGGAACTGGTTCGACA
TCAGCAAGTGGCTGTGGTACATCAAGATCTTCATCATGATCGTGGGCGGCCTGGTGGGCCTGC
GCATCGTGTTCACCGTGCTGAGCATCGTGAACCGCGTGCGCCAGGGCTACAGCCCCCTGAGCT
TCCAGACCCGCTTCCCCGCCCCCCGCGGCCCCGACCGCCCCGAGGGCATCGAGGAGGAGGGC
GGCGAGCGCGACCGCGACCGCAGCAGCCCCCTGGTGCACGGCCTGCTGGCCCTGATCTGGGA
CGACCTGCGCAGCCTGTGCCTGTTCAGCTACCACCGCCTGCGCGACCTGATCCTGATCGCCGC
CCGCATCGTGGAGCTGCTGGGCCGCCGCGGCTGGGAGGCCCTGAAGTACTGGGGCAACCTGC
TGCAGTACTGGATCCAGGAGCTGAAGAACAGCGCCGTGAGCCTGTTCGACGCCATCGCCATC
GCCGTGGCCGAGGGCACCGACCGCATCATCGAGGTGGCCCAGCGCATCGGCCGCGCCTTCCT
GCACATCCCCCGCCGCATCCGCCAGGGCTTCGAGCGCGCCCTGCTGTAACTCGAG

FIG. 26

SEQ ID NO:24 VAL120-THR202; ILE424-ALA433

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGGGCGGCGCCACCCAGGCCTG
CCCCAAGGTGAGCTTCGAGCCCATCCCCATCCACTACTGCGCCCCCGCCGGCTTCGCCATCCT
GAAGTGCAACGACAAGAAGTTCAACGGCAGCGGCCCCTGCACCAACGTGAGCACCGTGCAGT
GCACCCACGGCATCCGCCCCGTGGTGAGCACCCAGCTGCTGCTGAACGGCAGCCTGGCCGAG
GAGGGCGTGGTGATCCGCAGCGAGAACTTCACCGACAACGCCAAGACCATCATCGTGCAGCT
GAAGGAGAGCGTGGAGATCAACTGCACCCGCCCCAACAACAACACCCGCAAGAGCATCACCA
TCGGCCCCGGCCGCGCCTTCTACGCCACCGGCGACATCATCGGCGACATCCGCCAGGCCCACT
GCAACATCAGCGGCGAGAAGTGGAACAACACCCTGAAGCAGATCGTGACCAAGCTGCAGGCC
CAGTTCGGCAACAAGACCATCGTGTTCAAGCAGAGCAGCGGCGGCGACCCCGAGATCGTGAT
GCACAGCTTCAACTGCGGCGGCGAGTTCTTCTACTGCAACAGCACCCAGCTGTTCAACAGCAC
CTGGAACAACACCATCGGCCCCAACAACACCAACGGCACCATCACCCTGCCCTGCCGCATCA
AGCAGATCATCGGCGGCGCCATGTACGCCCCCCCCATCCGCGGCCAGATCCGCTGCAGCAGC
AACATCACCGGCCTGCTGCTGACCCGCGACGGCGGCAAGGAGATCAGCAACACCACCGAGAT
CTTCCGCCCCGGCGGCGGCGACATGCGCGACAACTGGCGCAGCGAGCTGTACAAGTACAAGG
TGGTGAAGATCGAGCCCCTGGGCGTGGCCCCCACCAAGGCCAAGCGCCGCGTGGTGCAGCGC
GAGAAGCGCGCCGTGACCCTGGGCGCCATGTTCCTGGGCTTCCTGGGCGCCGCCGGCAGCACC
ATGGGCGCCCGCAGCCTGACCCTGACCGTGCAGGCCCGCCAGCTGCTGAGCGGCATCGTGCA
GCAGCAGAACAACCTGCTGCGCGCCATCGAGGCCCAGCAGCACCTGCTGCAGCTGACCGTGT
GGGGCATCAAGCAGCTGCAGGCCCGCGTGCTGGCCGTGGAGCGCTACCTGAAGGACCAGCAG
CTGCTGGGCATCTGGGGCTGCAGCGGCAAGCTGATCTGCACCACCGCCGTGCCCTGGAACGCC
AGCTGGAGCAACAAGAGCCTGGACCAGATCTGGAACAACATGACCTGGATGGAGTGGGAGCG
CGAGATCGACAACTACACCAACCTGATCTACACCCTGATCGAGGAGAGCCAGAACCAGCAGG
AGAAGAACGAGCAGGAGCTGCTGGAGCTGGACAAGTGGGCCAGCCTGTGGAACTGGTTCGAC
ATCAGCAAGTGGCTGTGGTACATCAAGATCTTCATCATGATCGTGGGCGGCCTGGTGGGCCTG
CGCATCGTGTTCACCGTGCTGAGCATCGTGAACCGCGTGCGCCAGGGCTACAGCCCCCTGAGC
TTCCAGACCCGCTTCCCCGCCCCCCGCGGCCCCGACCGCCCCGAGGGCATCGAGGAGGAGGG
CGGCGAGCGCGACCGCGACCGCAGCAGCCCCCTGGTGCACGGCCTGCTGGCCCTGATCTGGG
ACGACCTGCGCAGCCTGTGCCTGTTCAGCTACCACCGCCTGCGCGACCTGATCCTGATCGCCG
CCCGCATCGTGGAGCTGCTGGGCCGCCGCGGCTGGGAGGCCCTGAAGTACTGGGGCAACCTG
CTGCAGTACTGGATCCAGGAGCTGAAGAACAGCGCCGTGAGCCTGTTCGACGCCATCGCCATC
GCCGTGGCCGAGGGCACCGACCGCATCATCGAGGTGGCCCAGCGCATCGGCCGCGCCTTCCT
GCACATCCCCCGCCGCATCCGCCAGGGCTTCGAGCGCGCCCTGCTGTAACTCGAG

*FIG. 27*

SEQ ID NO:25 VAL127-ASN195

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
GGGGCAGGGAACTGCAACACCAGCGTGATCACCCAGGCCTGCCCCAAGGTGAGCTTCGAGCC
CATCCCCATCCACTACTGCGCCCCCGCCGGCTTCGCCATCCTGAAGTGCAACGACAAGAAGTT
CAACGGCAGCGGCCCCTGCACCAACGTGAGCACCGTGCAGTGCACCCACGGCATCCGCCCCG
TGGTGAGCACCCAGCTGCTGCTGAACGGCAGCCTGGCCGAGGAGGGCGTGGTGATCCGCAGC
GAGAACTTCACCGACAACGCCAAGACCATCATCGTGCAGCTGAAGGAGAGCGTGGAGATCAA
CTGCACCCGCCCCAACAACAACACCCGCAAGAGCATCACCATCGGCCCCGGCCGCGCCTTCTA
CGCCACCGGCGACATCATCGGCGACATCCGCCAGGCCCACTGCAACATCAGCGGCGAGAAGT
GGAACAACACCCTGAAGCAGATCGTGACCAAGCTGCAGGCCCAGTTCGGCAACAAGACCATC
GTGTTCAAGCAGAGCAGCGGCGGCGACCCCGAGATCGTGATGCACAGCTTCAACTGCGGCGG
CGAGTTCTTCTACTGCAACAGCACCCAGCTGTTCAACAGCACCTGGAACAACACCATCGGCCC
CAACAACACCAACGGCACCATCACCCTGCCCTGCCGCATCAAGCAGATCATCAACCGCTGGC
AGGAGGTGGGCAAGGCCATGTACGCCCCCCCCATCCGCGGCCAGATCCGCTGCAGCAGCAAC
ATCACCGGCCTGCTGCTGACCCGCGACGGCGGCAAGGAGATCAGCAACACCACCGAGATCTT
CCGCCCCGGCGGCGGCGACATGCGCGACAACTGGCGCAGCGAGCTGTACAAGTACAAGGTGG
TGAAGATCGAGCCCCTGGGCGTGGCCCCCACCAAGGCCAAGCGCCGCGTGGTGCAGCGCGAG
AAGCGCGCCGTGACCCTGGGCGCCATGTTCCTGGGCTTCCTGGGCGCCGCCGGCAGCACCATG
GGCGCCCGCAGCCTGACCCTGACCGTGCAGGCCCGCCAGCTGCTGAGCGGCATCGTGCAGCA
GCAGAACAACCTGCTGCGCGCCATCGAGGCCCAGCAGCACCTGCTGCAGCTGACCGTGTGGG
GCATCAAGCAGCTGCAGGCCCGCGTGCTGGCCGTGGAGCGCTACCTGAAGGACCAGCAGCTG
CTGGGCATCTGGGGCTGCAGCGGCAAGCTGATCTGCACCACCGCCGTGCCCTGGAACGCCAG
CTGGAGCAACAAGAGCCTGGACCAGATCTGGAACAACATGACCTGGATGGAGTGGGAGCGCG
AGATCGACAACTACACCAACCTGATCTACACCCTGATCGAGGAGAGCCAGAACCAGCAGGAG
AAGAACGAGCAGGAGCTGCTGGAGCTGGACAAGTGGGCCAGCCTGTGGAACTGGTTCGACAT
CAGCAAGTGGCTGTGGTACATCAAGATCTTCATCATGATCGTGGGCGGCCTGGTGGGCCTGCG
CATCGTGTTCACCGTGCTGAGCATCGTGAACCGCGTGCGCCAGGGCTACAGCCCCCTGAGCTT
CCAGACCCGCTTCCCCGCCCCCCGCGGCCCCGACCGCCCCGAGGGCATCGAGGAGGAGGGCG
GCGAGCGCGACCGCGACCGCAGCAGCCCCCTGGTGCACGGCCTGCTGGCCCTGATCTGGGAC
GACCTGCGCAGCCTGTGCCTGTTCAGCTACCACCGCCTGCGCGACCTGATCCTGATCGCCGCC
CGCATCGTGGAGCTGCTGGGCCGCCGCGGCTGGGAGGCCCTGAAGTACTGGGGCAACCTGCT
GCAGTACTGGATCCAGGAGCTGAAGAACAGCGCCGTGAGCCTGTTCGACGCCATCGCCATCG
CCGTGGCCGAGGGCACCGACCGCATCATCGAGGTGGCCCAGCGCATCGGCCGCGCCTTCCTGC
ACATCCCCCGCCGCATCCGCCAGGGCTTCGAGCGCGCCCTGCTGTAACTCGAG

FIG. 28

SEQ ID NO:26 VAL127-ASN195; ARG426-GLY431

GAATTCGCCACCATGGATGCAATGAAGAGAGGGCTCTGCTGTGTGCTGCTGCTGTGTGGAGCA
GTCTTCGTTTCGCCCAGCGCCGTGGAGAAGCTGTGGGTGACCGTGTACTACGGCGTGCCCGTG
TGGAAGGAGGCCACCACCACCCTGTTCTGCGCCAGCGACGCCAAGGCCTACGACACCGAGGT
GCACAACGTGTGGGCCACCCACGCCTGCGTGCCCACCGACCCCAACCCCCAGGAGATCGTGCT
GGAGAACGTGACCGAGAACTTCAACATGTGGAAGAACAACATGGTGGAGCAGATGCACGAG
GACATCATCAGCCTGTGGGACCAGAGCCTGAAGCCCTGCGTGAAGCTGACCCCCCTGTGCGTG
GGGGCAGGGAACTGCAACACCAGCGTGATCACCCAGGCCTGCCCCAAGGTGAGCTTCGAGCC
CATCCCCATCCACTACTGCGCCCCCGCCGGCTTCGCCATCCTGAAGTGCAACGACAAGAAGTT
CAACGGCAGCGGCCCCTGCACCAACGTGAGCACCGTGCAGTGCACCCACGGCATCCGCCCCG
TGGTGAGCACCCAGCTGCTGCTGAACGGCAGCCTGGCCGAGGAGGGCGTGGTGATCCGCAGC
GAGAACTTCACCGACAACGCCAAGACCATCATCGTGCAGCTGAAGGAGAGCGTGGAGATCAA
CTGCACCCGCCCCAACAACAACACCCGCAAGAGCATCACCATCGGCCCCGGCCGCGCCTTCTA
CGCCACCGGCGACATCATCGGCGACATCCGCCAGGCCCACTGCAACATCAGCGGCGAGAAGT
GGAACAACACCCTGAAGCAGATCGTGACCAAGCTGCAGGCCCAGTTCGGCAACAAGACCATC
GTGTTCAAGCAGAGCAGCGGCGGCGACCCCGAGATCGTGATGCACAGCTTCAACTGCGGCGG
CGAGTTCTTCTACTGCAACAGCACCCAGCTGTTCAACAGCACCTGGAACAACACCATCGGCCC
CAACAACACCAACGGCACCATCACCCTGCCCTGCCGCATCAAGCAGATCATCAACCGCGGCG
GCGGCAAGGCCATGTACGCCCCCCCCATCCGCGGCCAGATCCGCTGCAGCAGCAACATCACC
GGCCTGCTGCTGACCCGCGACGGCGGCAAGGAGATCAGCAACACCACCGAGATCTTCCGCCC
CGGGGGCGGCGACATGCGCGACAACTGGCGCAGCGAGCTGTACAAGTACAAGGTGGTGAAG
ATCGAGCCCCTGGGCGTGGCCCCCACCAAGGCCAAGCGCCGCGTGGTGCAGCGCGAGAAGCG
CGCCGTGACCCTGGGCGCCATGTTCCTGGGCTTCCTGGGCGCCGCCGGCAGCACCATGGGCGC
CCGCAGCCTGACCCTGACCGTGCAGGCCCGCCAGCTGCTGAGCGGCATCGTGCAGCAGCAGA
ACAACCTGCTGCGCGCCATCGAGGCCCAGCAGCACCTGCTGCAGCTGACCGTGTGGGGCATC
AAGCAGCTGCAGGCCCGCGTGCTGGCCGTGGAGCGCTACCTGAAGGACCAGCAGCTGCTGGG
CATCTGGGGCTGCAGCGGCAAGCTGATCTGCACCACCGCCGTGCCCTGGAACGCCAGCTGGA
GCAACAAGAGCCTGGACCAGATCTGGAACAACATGACCTGGATGGAGTGGGAGCGCGAGATC
GACAACTACACCAACCTGATCTACACCCTGATCGAGGAGAGCCAGAACCAGCAGGAGAAGAA
CGAGCAGGAGCTGCTGGAGCTGGACAAGTGGGCCAGCCTGTGGAACTGGTTCGACATCAGCA
AGTGGCTGTGGTACATCAAGATCTTCATCATGATCGTGGGCGGCCTGGTGGGCCTGCGCATCG
TGTTCACCGTGCTGAGCATCGTGAACCGCGTGCGCCAGGGCTACAGCCCCCTGAGCTTCCAGA
CCCGCTTCCCCGCCCCCCGCGGCCCCGACCGCCCCGAGGGCATCGAGGAGGAGGGCGGCGAG
CGCGACCGCGACCGCAGCAGCCCCCTGGTGCACGGCCTGCTGGCCCTGATCTGGGACGACCTG
CGCAGCCTGTGCCTGTTCAGCTACCACCGCCTGCGCGACCTGATCCTGATCGCCGCCCGCATC
GTGGAGCTGCTGGGCCGCCGCGGCTGGGAGGCCCTGAAGTACTGGGGCAACCTGCTGCAGTA
CTGGATCCAGGAGCTGAAGAACAGCGCCGTGAGCCTGTTCGACGCCATCGCCATCGCCGTGG
CCGAGGGCACCGACCGCATCATCGAGGTGGCCCAGCGCATCGGCCGCGCCTTCCTGCACATCC
CCCGCCGCATCCGCCAGGGCTTCGAGCGCGCCCTGCTGTAACTCGAG

FIG. 29

```
                              SEQUENCE LISTING


<160> NUMBER OF SEQ ID NOS: 26

<210> SEQ ID NO 1
<211> LENGTH: 856
<212> TYPE: PRT
<213> ORGANISM: Human immunodeficiency virus

<400> SEQUENCE: 1

Met Arg Val Lys Glu Lys Tyr Gln His Leu Trp Arg Trp Gly Trp Arg
  1               5                  10                  15

Trp Gly Thr Met Leu Leu Gly Met Leu Met Ile Cys Ser Ala Thr Glu
             20                  25                  30

Lys Leu Trp Val Thr Val Tyr Tyr Gly Val Pro Val Trp Lys Glu Ala
         35                  40                  45

Thr Thr Thr Leu Phe Cys Ala Ser Asp Ala Lys Ala Tyr Asp Thr Glu
     50                  55                  60

Val His Asn Val Trp Ala Thr His Ala Cys Val Pro Thr Asp Pro Asn
 65                  70                  75                  80

Pro Gln Glu Val Val Leu Val Asn Val Thr Glu Asn Phe Asn Met Trp
```

-continued

```
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510
```

-continued

```
Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855


<210> SEQ ID NO 2
<211> LENGTH: 847
<212> TYPE: PRT
<213> ORGANISM: Human immunodeficiency virus

<400> SEQUENCE: 2

Met Arg Val Lys Gly Ile Arg Lys Asn Tyr Gln His Leu Trp Arg Gly
  1               5                  10                  15

Gly Thr Leu Leu Leu Gly Met Leu Met Ile Cys Ser Ala Val Glu Lys
```

-continued

```
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

His Cys Thr Asn Leu Lys Asn Ala Thr Asn Thr Lys Ser Ser Asn Trp
    130                 135                 140

Lys Glu Met Asp Arg Gly Glu Ile Lys Asn Cys Ser Phe Lys Val Thr
145                 150                 155                 160

Thr Ser Ile Arg Asn Lys Met Gln Lys Glu Tyr Ala Leu Phe Tyr Lys
                165                 170                 175

Leu Asp Val Val Pro Ile Asp Asn Asp Asn Thr Ser Tyr Lys Leu Ile
            180                 185                 190

Asn Cys Asn Thr Ser Val Ile Thr Gln Ala Cys Pro Lys Val Ser Phe
        195                 200                 205

Glu Pro Ile Pro Ile His Tyr Cys Ala Pro Ala Gly Phe Ala Ile Leu
    210                 215                 220

Lys Cys Asn Asp Lys Lys Phe Asn Gly Ser Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Gly Val Val Ile Arg Ser
            260                 265                 270

Glu Asn Phe Thr Asp Asn Ala Lys Thr Ile Ile Val Gln Leu Lys Glu
        275                 280                 285

Ser Val Glu Ile Asn Cys Thr Arg Pro Asn Asn Asn Thr Arg Lys Ser
    290                 295                 300

Ile Thr Ile Gly Pro Gly Arg Ala Phe Tyr Ala Thr Gly Asp Ile Ile
305                 310                 315                 320

Gly Asp Ile Arg Gln Ala His Cys Asn Ile Ser Gly Glu Lys Trp Asn
                325                 330                 335

Asn Thr Leu Lys Gln Ile Val Thr Lys Leu Gln Ala Gln Phe Gly Asn
            340                 345                 350

Lys Thr Ile Val Phe Lys Gln Ser Ser Gly Gly Asp Pro Glu Ile Val
        355                 360                 365

Met His Ser Phe Asn Cys Gly Gly Glu Phe Phe Tyr Cys Asn Ser Thr
    370                 375                 380

Gln Leu Phe Asn Ser Thr Trp Asn Asn Thr Ile Gly Pro Asn Asn Thr
385                 390                 395                 400

Asn Gly Thr Ile Thr Leu Pro Cys Arg Ile Lys Gln Ile Ile Asn Arg
                405                 410                 415

Trp Gln Glu Val Gly Lys Ala Met Tyr Ala Pro Pro Ile Arg Gly Gln
            420                 425                 430

Ile Arg Cys Ser Ser Asn Ile Thr Gly Leu Leu Leu Thr Arg Asp Gly
        435                 440                 445
```

-continued

```
Gly Lys Glu Ile Ser Asn Thr Thr Glu Ile Phe Arg Pro Gly Gly Gly
    450                 455                 460

Asp Met Arg Asp Asn Trp Arg Ser Glu Leu Tyr Lys Tyr Lys Val Val
465                 470                 475                 480

Lys Ile Glu Pro Leu Gly Val Ala Pro Thr Lys Ala Lys Arg Arg Val
                485                 490                 495

Val Gln Arg Glu Lys Arg Ala Val Thr Leu Gly Ala Met Phe Leu Gly
            500                 505                 510

Phe Leu Gly Ala Ala Gly Ser Thr Met Gly Ala Arg Ser Leu Thr Leu
        515                 520                 525

Thr Val Gln Ala Arg Gln Leu Leu Ser Gly Ile Val Gln Gln Gln Asn
    530                 535                 540

Asn Leu Leu Arg Ala Ile Glu Ala Gln Gln His Leu Leu Gln Leu Thr
545                 550                 555                 560

Val Trp Gly Ile Lys Gln Leu Gln Ala Arg Val Leu Ala Val Glu Arg
                565                 570                 575

Tyr Leu Lys Asp Gln Gln Leu Leu Gly Ile Trp Gly Cys Ser Gly Lys
            580                 585                 590

Leu Ile Cys Thr Thr Ala Val Pro Trp Asn Ala Ser Trp Ser Asn Lys
        595                 600                 605

Ser Leu Asp Gln Ile Trp Asn Asn Met Thr Trp Met Glu Trp Glu Arg
    610                 615                 620

Glu Ile Asp Asn Tyr Thr Asn Leu Ile Tyr Thr Leu Ile Glu Glu Ser
625                 630                 635                 640

Gln Asn Gln Gln Glu Lys Asn Glu Gln Glu Leu Leu Glu Leu Asp Lys
                645                 650                 655

Trp Ala Ser Leu Trp Asn Trp Phe Asp Ile Ser Lys Trp Leu Trp Tyr
            660                 665                 670

Ile Lys Ile Phe Ile Met Ile Val Gly Gly Leu Val Gly Leu Arg Ile
        675                 680                 685

Val Phe Thr Val Leu Ser Ile Val Asn Arg Val Arg Gln Gly Tyr Ser
    690                 695                 700

Pro Leu Ser Phe Gln Thr Arg Phe Pro Ala Pro Arg Gly Pro Asp Arg
705                 710                 715                 720

Pro Glu Gly Ile Glu Glu Glu Gly Gly Glu Arg Asp Arg Asp Arg Ser
                725                 730                 735

Ser Pro Leu Val His Gly Leu Leu Ala Leu Ile Trp Asp Asp Leu Arg
            740                 745                 750

Ser Leu Cys Leu Phe Ser Tyr His Arg Leu Arg Asp Leu Ile Leu Ile
        755                 760                 765

Ala Ala Arg Ile Val Glu Leu Leu Gly Arg Arg Gly Trp Glu Ala Leu
    770                 775                 780

Lys Tyr Trp Gly Asn Leu Leu Gln Tyr Trp Ile Gln Glu Leu Lys Asn
785                 790                 795                 800

Ser Ala Val Ser Leu Phe Asp Ala Ile Ala Ile Ala Val Ala Glu Gly
                805                 810                 815

Thr Asp Arg Ile Ile Glu Val Ala Gln Arg Ile Gly Arg Ala Phe Leu
            820                 825                 830

His Ile Pro Arg Arg Ile Arg Gln Gly Phe Glu Arg Ala Leu Leu
        835                 840                 845
```

<210> SEQ ID NO 3
<211> LENGTH: 2310

-continued

<212> TYPE: DNA
<213> ORGANISM: Artificial Sequence
<220> FEATURE:
<223> OTHER INFORMATION: Description of Artificial Sequence: Val120-
Ala204

<400> SEQUENCE: 3

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg ggccacccac gcctgcgtgc ccaccgaccc caacccccag    240
gagatcgtgc tggagaacgt gaccgagaac ttcaacatgt ggaagaacaa catggtggag    300
cagatgcacg aggacatcat cagcctgtgg gaccagagcc tgaagccctg cgtgggcgcc    360
ggcgcctgcc ccaaggtgag cttcgagccc atccccatcc actactgcgc ccccgccggc    420
ttcgccatcc tgaagtgcaa cgacaagaag ttcaacggca gcggcccctg caccaacgtg    480
agcaccgtgc agtgcaccca cggcatccgc cccgtggtga gcacccagct gctgctgaac    540
ggcagcctgg ccgaggaggg cgtggtgatc cgcagcgaga acttcaccga caacgccaag    600
accatcatcg tgcagctgaa ggagagcgtg gagatcaact gcacccgccc caacaacaac    660
acccgcaaga gcatcaccat cggccccggc cgcgccttct acgccaccgg cgacatcatc    720
ggcgacatcc gccaggccca ctgcaacatc agcggcgaga agtggaacaa caccctgaag    780
cagatcgtga ccaagctgca ggcccagttc ggcaacaaga ccatcgtgtt caagcagagc    840
agcggcggcg accccgagat cgtgatgcac agcttcaact gcggcggcga gttcttctac    900
tgcaacagca cccagctgtt caacagcacc tggaacaaca ccatcggccc caacaacacc    960
aacggcacca tcaccctgcc ctgccgcatc aagcagatca tcaaccgctg gcaggaggtg   1020
ggcaaggcca tgtacgcccc ccccatccgc ggccagatcc gctgcagcag caacatcacc   1080
ggcctgctgc tgacccgcga cggcggcaag gagatcagca acaccaccga gatcttccgc   1140
cccggcggcg gcgacatgcg cgacaactgg cgcagcgagc tgtacaagta caaggtggtg   1200
aagatcgagc ccctgggcgt ggcccccacc aaggccaagc gccgcgtggt gcagcgcgag   1260
aagcgcgccg tgaccctggg cgccatgttc ctgggcttcc tgggcgccgc cggcagcacc   1320
atgggcgccc gcagcctgac cctgaccgtg caggcccgcc agctgctgag cggcatcgtg   1380
cagcagcaga acaacctgct gcgcgccatc gaggcccagc agcacctgct gcagctgacc   1440
gtgtggggca tcaagcagct gcaggcccgc gtgctggccg tggagcgcta cctgaaggac   1500
cagcagctgc tgggcatctg gggctgcagc ggcaagctga tctgcaccac cgccgtgccc   1560
tggaacgcca gctggagcaa caagagcctg gaccagatct ggaacaacat gacctggatg   1620
gagtgggagc gcgagatcga caactacacc aacctgatct acaccctgat cgaggagagc   1680
cagaaccagc aggagaagaa cgagcaggag ctgctggagc tggacaagtg ggccagcctg   1740
tggaactggt tcgacatcag caagtggctg tggtacatca agatcttcat catgatcgtg   1800
ggcggcctgg tgggcctgcg catcgtgttc accgtgctga gcatcgtgaa ccgcgtgcgc   1860
cagggctaca gcccccctgag cttccagacc cgcttccccg ccccccgcgg ccccgaccgc   1920
cccgagggca tcgaggagga gggcggcgag cgcgaccgcg accgcagcag ccccctggtg   1980
cacggcctgc tggccctgat ctgggacgac ctgcgcagcc tgtgcctgtt cagctaccac   2040
cgcctgcgcg acctgatcct gatcgccgcc cgcatcgtgg agctgctggg ccgccgcggc   2100
tgggaggccc tgaagtactg gggcaacctg ctgcagtact ggatccagga gctgaagaac   2160
```

-continued agcgccgtga gcctgttcga cgccatcgcc atcgccgtgg ccgagggcac cgaccgcatc 2220
atcgaggtgg cccagcgcat cggccgcgcc ttcctgcaca tcccccgccg catccgccag 2280
ggcttcgagc gcgccctgct gtaactcgag 2310

<210> SEQ ID NO 4
<211> LENGTH: 2316
<212> TYPE: DNA
<213> ORGANISM: Artificial Sequence
<220> FEATURE:
<223> OTHER INFORMATION: Description of Artificial Sequence: Val120-
Ile201

<400> SEQUENCE: 4
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgggcggc 360
atcacccagg cctgccccaa ggtgagcttc gagcccatcc ccatccacta ctgcgccccc 420
gccggcttcg ccatcctgaa gtgcaacgac aagaagttca acggcagcgg cccctgcacc 480
aacgtgagca ccgtgcagtg cacccacggc atccgccccg tggtgagcac ccagctgctg 540
ctgaacggca gcctggccga ggagggcgtg gtgatccgca gcgagaactt caccgacaac 600
gccaagacca tcatcgtgca gctgaaggag agcgtggaga tcaactgcac ccgccccaac 660
aacaacaccc gcaagagcat caccatcggc cccggccgcg ccttctacgc caccggcgac 720
atcatcggcg acatccgcca ggcccactgc aacatcagcg gcgagaagtg gaacaacacc 780
ctgaagcaga tcgtgaccaa gctgcaggcc cagttcggca acaagaccat cgtgttcaag 840
cagagcagcg gcggcgaccc cgagatcgtg atgcacagct tcaactgcgg cggcgagttc 900
ttctactgca acagcaccca gctgttcaac agcacctgga acaacaccat cggccccaac 960
aacaccaacg gcaccatcac cctgccctgc cgcatcaagc agatcatcaa ccgctggcag 1020
gaggtgggca aggccatgta cgcccccccc atccgcggcc agatccgctg cagcagcaac 1080
atcaccggcc tgctgctgac ccgcgacggc ggcaaggaga tcagcaacac caccgagatc 1140
ttccgccccg gcggcggcga catgcgcgac aactggcgca gcgagctgta caagtacaag 1200
gtggtgaaga tcgagcccct gggcgtggcc cccaccaagg ccaagcgccg cgtggtgcag 1260
cgcgagaagc gcgccgtgac cctgggcgcc atgttcctgg gcttcctggg cgccgccggc 1320
agcaccatgg gcgcccgcag cctgaccctg accgtgcagg cccgccagct gctgagcggc 1380
atcgtgcagc agcagaacaa cctgctgcgc gccatcgagg cccagcagca cctgctgcag 1440
ctgaccgtgt ggggcatcaa gcagctgcag gcccgcgtgc tggccgtgga gcgctacctg 1500
aaggaccagc agctgctggg catctggggc tgcagcggca agctgatctg caccaccgcc 1560
gtgccctgga acgccagctg gagcaacaag agcctggacc agatctggaa caacatgacc 1620
tggatggagt gggagcgcga gatcgacaac tacaccaacc tgatctacac cctgatcgag 1680
gagagccaga accagcagga gaagaacgag caggagctgc tggagctgga caagtgggcc 1740
agcctgtgga actggttcga catcagcaag tggctgtggt acatcaagat cttcatcatg 1800
atcgtgggcg gcctggtggg cctgcgcatc gtgttcaccg tgctgagcat cgtgaaccgc 1860

-continued gtgcgccagg gctacagccc cctgagcttc cagacccgct tccccgcccc ccgcggcccc 1920
gaccgccccg agggcatcga ggaggagggc ggcgagcgcg accgcgaccg cagcagcccc 1980
ctggtgcacg gcctgctggc cctgatctgg gacgacctgc gcagcctgtg cctgttcagc 2040
taccaccgcc tgcgcgacct gatcctgatc gccgcccgca tcgtggagct gctgggccgc 2100
cgcggctggg aggccctgaa gtactggggc aacctgctgc agtactggat ccaggagctg 2160
aagaacagcg ccgtgagcct gttcgacgcc atcgccatcg ccgtggccga gggcaccgac 2220
cgcatcatcg aggtggccca gcgcatcggc cgcgccttcc tgcacatccc ccgccgcatc 2280
cgccagggct tcgagcgcgc cctgctgtaa ctcgag 2316

<210> SEQ ID NO 5
<211> LENGTH: 2322
<212> TYPE: DNA
<213> ORGANISM: Artificial Sequence
<220> FEATURE:
<223> OTHER INFORMATION: Description of Artificial Sequence: Val120-
Ile201B

<400> SEQUENCE: 5
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgcccggc 360
atcacccagg cctgccccaa ggtgagcttc gagcccatcc ccatccacta ctgcgccccc 420
gccggcttcg ccatcctgaa gtgcaacgac aagaagttca acggcagcgg cccctgcacc 480
aacgtgagca ccgtgcagtg cacccacggc atccgccccg tggtgagcac ccagctgctg 540
ctgaacggca gcctggccga ggagggcgtg gtgatccgca gcgagaactt caccgacaac 600
gccaagacca tcatcgtgca gctgaaggag agcgtggaga tcaactgcac ccgccccaac 660
aacaacaccc gcaagagcat caccatcggc cccggccgcg ccttctacgc caccggcgac 720
atcatcggcg acatccgcca ggcccactgc aacatcagcg gcgagaagtg gaacaacacc 780
ctgaagcaga tcgtgaccaa gctgcaggcc cagttcggca acaagaccat cgtgttcaag 840
cagagcagcg gcggcgaccc cgagatcgtg atgcacagct tcaactgcgg cggcgagttc 900
ttctactgca acagcaccca gctgttcaac agcacctgga acaacaccat cggccccaac 960
aacaccaacg gcaccatcac cctgccctgc cgcatcaagc agatcatcaa ccgctggcag 1020
gaggtgggca aggccatgta cgcccccccc atccgcggcc agatccgctg cagcagcaac 1080
atcaccggcc tgctgctgac ccgcgacggc ggcaaggaga tcagcaacac caccgagatc 1140
ttccgccccg gcggcggcga catgcgcgac aactggcgca gcgagctgta caagtacaag 1200
gtggtgaaga tcgagcccct gggcgtggcc cccaccaagg ccaagcgccg cgtggtgcag 1260
cgcgagaagc gcgccgtgac cctgggcgcc atgttcctgg gcttcctggg cgccgccggc 1320
agcaccatgg gcgcccgcag cctgaccctg accgtgcagg cccgccagct gctgagcggc 1380
atcgtgcagc agcagaacaa cctgctgcgc gccatcgagg cccagcagca cctgctgcag 1440
ctgaccgtgt ggggcatcaa gcagctgcag gcccgcgtgc tggccgtgga gcgctacctg 1500
aaggaccagc agctgctggg catctggggc tgcagcggca agctgatctg caccaccgcc 1560

-continued gtgccctgga acgccagctg gagcaacaag agcctggacc agatctggaa caacatgacc 1620
tggatggagt gggagcgcga gatcgacaac tacaccaacc tgatctacac cctgatcgag 1680
gagagccaga accagcagga gaagaacgag caggagctgc tggagctgga caagtgggcc 1740
agcctgtgga actggttcga catcagcaag tggctgtggt acatcaagat cttcatcatg 1800
atcgtgggcg gcctggtggg cctgcgcatc gtgttcaccg tgctgagcat cgtgaaccgc 1860
gtgcgccagg gctacagccc cctgagcttc cagacccgct tccccgcccc ccgcggcccc 1920
gaccgccccg agggcatcga ggaggagggc ggcgagcgcg accgcgaccg cagcagcccc 1980
ctggtgcacg gcctgctggc cctgatctgg gacgacctgc gcagcctgtg cctgttcagc 2040
taccaccgcc tgcgcgacct gatcctgatc gccgcccgca tcgtggagct gctgggccgc 2100
cgcggctggg aggccctgaa gtactggggc aacctgctgc agtactggat ccaggagctg 2160
aagaacagcg ccgtgagcct gttcgacgcc atcgccatcg ccgtggccga gggcaccgac 2220
cgcatcatcg aggtggccca gcgcatcggc cgcgccttcc tgcacatccc ccgccgcatc 2280
cgccagggct tcgagcgcgc cctgctgtaa ctcgagcgtg ct 2322

<210> SEQ ID NO 6
<211> LENGTH: 2328
<212> TYPE: DNA
<213> ORGANISM: Artificial Sequence
<220> FEATURE:
<223> OTHER INFORMATION: Description of Artificial Sequence: Lys121-Val200

<400> SEQUENCE: 6
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaaggcc 360
cccgtgatca cccaggcctg ccccaaggtg agcttcgagc ccatccccat ccactactgc 420
gcccccgccg gcttcgccat cctgaagtgc aacgacaaga agttcaacgg cagcggcccc 480
tgcaccaacg tgagcaccgt gcagtgcacc cacggcatcc gccccgtggt gagcacccag 540
ctgctgctga acggcagcct ggccgaggag ggcgtggtga tccgcagcga gaacttcacc 600
gacaacgcca agaccatcat cgtgcagctg aaggagagcg tggagatcaa ctgcacccgc 660
cccaacaaca acacccgcaa gagcatcacc atcggccccg gccgcgcctt ctacgccacc 720
ggcgacatca tcggcgacat ccgccaggcc cactgcaaca tcagcggcga gaagtggaac 780
aacaccctga agcagatcgt gaccaagctg caggcccagt tcggcaacaa gaccatcgtg 840
ttcaagcaga gcagcggcgg cgaccccgag atcgtgatgc acagcttcaa ctgcggcggc 900
gagttcttct actgcaacag cacccagctg ttcaacagca cctggaacaa caccatcggc 960
cccaacaaca ccaacggcac catcaccctg ccctgccgca tcaagcagat catcaaccgc 1020
tggcaggagg tgggcaaggc catgtacgcc ccccccatcc gcggccagat ccgctgcagc 1080
agcaacatca ccggcctgct gctgacccgc gacggcggca aggagatcag caacaccacc 1140
gagatcttcc gccccggcgg cggcgacatg cgcgacaact ggcgcagcga gctgtacaag 1200
tacaaggtgg tgaagatcga gcccctgggc gtggccccca ccaaggccaa gcgccgcgtg 1260

-continued gtgcagcgcg agaagcgcgc cgtgaccctg ggcgccatgt tcctgggctt cctgggcgcc 1320
gccggcagca ccatgggcgc ccgcagcctg accctgaccg tgcaggcccg ccagctgctg 1380
agcggcatcg tgcagcagca gaacaacctg ctgcgcgcca tcgaggccca gcagcacctg 1440
ctgcagctga ccgtgtgggg catcaagcag ctgcaggccc gcgtgctggc cgtggagcgc 1500
tacctgaagg accagcagct gctgggcatc tggggctgca gcggcaagct gatctgcacc 1560
accgccgtgc cctggaacgc cagctggagc aacaagagcc tggaccagat ctggaacaac 1620
atgacctgga tggagtggga gcgcgagatc gacaactaca ccaacctgat ctacaccctg 1680
atcgaggaga gccagaacca gcaggagaag aacgagcagg agctgctgga gctggacaag 1740
tgggccagcc tgtggaactg gttcgacatc agcaagtggc tgtggtacat caagatcttc 1800
atcatgatcg tgggcggcct ggtgggcctg cgcatcgtgt tcaccgtgct gagcatcgtg 1860
aaccgcgtgc gccagggcta cagcccccctg agcttccaga cccgcttccc cgcccccccgc 1920 ggccccgacc gccccgaggg catcgaggag gagggcggcg agcgcgaccg cgaccgcagc 1980 agcccccctgg tgcacggcct gctggccctg atctgggacg acctgcgcag cctgtgcctg 2040
ttcagctacc accgcctgcg cgacctgatc ctgatcgccg cccgcatcgt ggagctgctg 2100
ggccgccgcg gctgggaggc cctgaagtac tggggcaacc tgctgcagta ctggatccag 2160
gagctgaaga acagcgccgt gagcctgttc gacgccatcg ccatcgccgt ggccgagggc 2220
accgaccgca tcatcgaggt ggcccagcgc atcggccgcg ccttcctgca catcccccgc 2280
cgcatccgcc agggcttcga gcgcgccctg ctgtaactcg agcgtgct 2328

<210> SEQ ID NO 7
<211> LENGTH: 2334
<212> TYPE: DNA
<213> ORGANISM: Artificial Sequence
<220> FEATURE:
<223> OTHER INFORMATION: Description of Artificial Sequence:
Leu122-Ser199

<400> SEQUENCE: 7
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360
ggcaacagcg tgatcaccca ggcctgcccc aaggtgagct tcgagcccat ccccatccac 420
tactgcgccc ccgccggctt cgccatcctg aagtgcaacg acaagaagtt caacggcagc 480
ggcccctgca ccaacgtgag caccgtgcag tgcacccacg gcatccgccc cgtggtgagc 540
acccagctgc tgctgaacgg cagcctggcc gaggagggcg tggtgatccg cagcgagaac 600
ttcaccgaca acgccaagac catcatcgtg cagctgaagg agagcgtgga gatcaactgc 660
acccgcccca acaacaacac ccgcaagagc atcaccatcg gccccggccg cgccttctac 720
gccaccggcg acatcatcgg cgacatccgc caggcccact gcaacatcag cggcgagaag 780
tggaacaaca ccctgaagca gatcgtgacc aagctgcagg cccagttcgg caacaagacc 840
atcgtgttca agcagagcag cggcggcgac cccgagatcg tgatgcacag cttcaactgc 900
ggcggcgagt tcttctactg caacagcacc cagctgttca acagcacctg gaacaacacc 960

-continued

```
atcggcccca acaacaccaa cggcaccatc accctgccct gccgcatcaa gcagatcatc   1020

aaccgctggc aggaggtggg caaggccatg tacgcccccc ccatccgcgg ccagatccgc   1080

tgcagcagca acatcaccgg cctgctgctg acccgcgacg gcggcaagga gatcagcaac   1140

accaccgaga tcttccgccc cggcggcggc gacatgcgcg acaactggcg cagcgagctg   1200

tacaagtaca aggtggtgaa gatcgagccc ctgggcgtgg cccccaccaa ggccaagcgc   1260

cgcgtggtgc agcgcgagaa gcgcgccgtg accctgggcg ccatgttcct gggcttcctg   1320

ggcgccgccg gcagcaccat gggcgcccgc agcctgaccc tgaccgtgca ggcccgccag   1380

ctgctgagcg gcatcgtgca gcagcagaac aacctgctgc gcgccatcga ggcccagcag   1440

cacctgctgc agctgaccgt gtggggcatc aagcagctgc aggcccgcgt gctggccgtg   1500

gagcgctacc tgaaggacca gcagctgctg ggcatctggg gctgcagcgg caagctgatc   1560

tgcaccaccg ccgtgccctg gaacgccagc tggagcaaca agagcctgga ccagatctgg   1620

aacaacatga cctggatgga gtgggagcgc gagatcgaca actacaccaa cctgatctac   1680

accctgatcg aggagagcca gaaccagcag gagaagaacg agcaggagct gctggagctg   1740

gacaagtggg ccagcctgtg gaactggttc gacatcagca agtggctgtg gtacatcaag   1800

atcttcatca tgatcgtggg cggcctggtg ggcctgcgca tcgtgttcac cgtgctgagc   1860

atcgtgaacc gcgtgcgcca gggctacagc cccctgagct tccagacccg cttccccgcc   1920

ccccgcggcc ccgaccgccc cgagggcatc gaggaggagg gcggcgagcg cgaccgcgac   1980

cgcagcagcc ccctggtgca cggcctgctg gccctgatct gggacgacct gcgcagcctg   2040

tgcctgttca gctaccaccg cctgcgcgac ctgatcctga tcgccgcccg catcgtggag   2100

ctgctgggcc gccgcggctg ggaggccctg aagtactggg gcaacctgct gcagtactgg   2160

atccaggagc tgaagaacag cgccgtgagc ctgttcgacg ccatcgccat cgccgtggcc   2220

gagggcaccg accgcatcat cgaggtggcc cagcgcatcg gccgcgcctt cctgcacatc   2280

ccccgccgca tccgccaggg cttcgagcgc gccctgctgt aactcgagcg tgct         2334
```

<210> SEQ ID NO 8
<211> LENGTH: 2316
<212> TYPE: DNA
<213> ORGANISM: Artificial Sequence
<220> FEATURE:
<223> OTHER INFORMATION: Description of Artificial Sequence: Val120-Thr202

<400> SEQUENCE: 8

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgggcggc    360

gccacccagg cctgccccaa ggtgagcttc gagcccatcc ccatccacta ctgcgccccc    420

gccggcttcg ccatcctgaa gtgcaacgac aagaagttca acggcagcgg cccctgcacc    480

aacgtgagca ccgtgcagtg cacccacggc atccgccccg tggtgagcac ccagctgctg    540

ctgaacggca gcctggccga ggagggcgtg gtgatccgca gcgagaactt caccgacaac    600

gccaagacca tcatcgtgca gctgaaggag agcgtggaga tcaactgcac ccgccccaac    660
```

-continued

```
aacaacaccc gcaagagcat caccatcggc cccggccgcg ccttctacgc caccggcgac     720
atcatcggcg acatccgcca ggcccactgc aacatcagcg gcgagaagtg gaacaacacc     780
ctgaagcaga tcgtgaccaa gctgcaggcc cagttcggca acaagaccat cgtgttcaag     840
cagagcagcg gcggcgaccc cgagatcgtg atgcacagct tcaactgcgg cggcgagttc     900
ttctactgca acagcaccca gctgttcaac agcacctgga acaacaccat cggcccccaac    960
aacaccaacg gcaccatcac cctgccctgc cgcatcaagc agatcatcaa ccgctggcag    1020
gaggtgggca aggccatgta cgcccccccc atccgcggcc agatccgctg cagcagcaac    1080
atcaccggcc tgctgctgac ccgcgacggc ggcaaggaga tcagcaacac caccgagatc    1140
ttccgccccg gcggcggcga catgcgcgac aactggcgca gcgagctgta caagtacaag    1200
gtggtgaaga tcgagcccct gggcgtggcc cccaccaagg ccaagcgccg cgtggtgcag    1260
cgcgagaagc gcgccgtgac cctgggcgcc atgttcctgg gcttcctggg cgccgccggc    1320
agcaccatgg gcgcccgcag cctgaccctg accgtgcagg cccgccagct gctgagcggc    1380
atcgtgcagc agcagaacaa cctgctgcgc gccatcgagg cccagcagca cctgctgcag    1440
ctgaccgtgt ggggcatcaa gcagctgcag gcccgcgtgc tggccgtgga gcgctacctg    1500
aaggaccagc agctgctggg catctggggc tgcagcggca agctgatctg caccaccgcc    1560
gtgccctgga acgccagctg gagcaacaag agcctggacc agatctggaa caacatgacc    1620
tggatggagt gggagcgcga gatcgacaac tacaccaacc tgatctacac cctgatcgag    1680
gagagccaga accagcagga gaagaacgag caggagctgc tggagctgga caagtgggcc    1740
agcctgtgga actggttcga catcagcaag tggctgtggt acatcaagat cttcatcatg    1800
atcgtgggcg gcctggtggg cctgcgcatc gtgttcaccg tgctgagcat cgtgaaccgc    1860
gtgcgccagg gctacagccc cctgagcttc cagacccgct tccccgcccc ccgcggcccc    1920
gaccgccccg agggcatcga ggaggagggc ggcgagcgcg accgcgaccg cagcagcccc    1980
ctggtgcacg gcctgctggc cctgatctgg gacgacctgc gcagcctgtg cctgttcagc    2040
taccaccgcc tgcgcgacct gatcctgatc gccgcccgca tcgtggagct gctgggccgc    2100
cgcggctggg aggccctgaa gtactggggc aacctgctgc agtactggat ccaggagctg    2160
aagaacagcg ccgtgagcct gttcgacgcc atcgccatcg ccgtggccga gggcaccgac    2220
cgcatcatcg aggtggccca gcgcatcggc cgcgccttcc tgcacatccc ccgccgcatc    2280
cgccagggct tcgagcgcgc cctgctgtaa ctcgag                              2316
```

<210> SEQ ID NO 9
<211> LENGTH: 2541
<212> TYPE: DNA
<213> ORGANISM: Artificial Sequence
<220> FEATURE:
<223> OTHER INFORMATION: Description of Artificial Sequence:
Trp427-Gly431

<400> SEQUENCE: 9

```
gaattcgcca ccatggatgc aatgaagaga gggctctgct gtgtgctgct gctgtgtgga      60
gcagtcttcg tttcgcccag cgccgtggag aagctgtggg tgaccgtgta ctacggcgtg     120
cccgtgtgga aggaggccac caccaccctg ttctgcgcca gcgacgccaa ggcctacgac     180
accgaggtgc acaacgtgtg ggccacccac gcctgcgtgc ccaccgaccc caacccccag     240
gagatcgtgc tggagaacgt gaccgagaac ttcaacatgt ggaagaacaa catggtggag     300
cagatgcacg aggacatcat cagcctgtgg gaccagagcc tgaagccctg cgtgaagctg     360
```

-continued

```
acccccctgt gcgtgaccct gcactgcacc aacctgaaga acgccaccaa caccaagagc    420
agcaactgga aggagatgga ccgcggcgag atcaagaact gcagcttcaa ggtgaccacc    480
agcatccgca acaagatgca gaaggagtac gccctgttct acaagctgga cgtggtgccc    540
atcgacaacg acaacaccag ctacaagctg atcaactgca acaccagcgt gatcacccag    600
gcctgcccca aggtgagctt cgagcccatc cccatccact actgcgcccc cgccggcttc    660
gccatcctga agtgcaacga caagaagttc aacggcagcg gcccctgcac caacgtgagc    720
accgtgcagt gcacccacgg catccgcccc gtggtgagca cccagctgct gctgaacggc    780
agcctggccg aggagggcgt ggtgatccgc agcgagaact tcaccgacaa cgccaagacc    840
atcatcgtgc agctgaagga gagcgtggag atcaactgca cccgccccaa caacaacacc    900
cgcaagagca tcaccatcgg ccccggccgc gccttctacg ccaccggcga catcatcggc    960
gacatccgcc aggcccactg caacatcagc ggcgagaagt ggaacaacac cctgaagcag   1020
atcgtgacca agctgcaggc ccagttcggc aacaagacca tcgtgttcaa gcagagcagc   1080
ggcggcgacc ccgagatcgt gatgcacagc ttcaactgcg gcggcgagtt cttctactgc   1140
aacagcaccc agctgttcaa cagcacctgg aacaacacca tcggccccaa caacaccaac   1200
ggcaccatca ccctgccctg ccgcatcaag cagatcatca accgctgggg cggcaaggcc   1260
atgtacgccc cccccatccg cggccagatc cgctgcagca gcaacatcac cggcctgctg   1320
ctgacccgcg acggcggcaa ggagatcagc aacaccaccg agatcttccg ccccggcggc   1380
ggcgacatgc gcgacaactg gcgcagcgag ctgtacaagt acaaggtggt gaagatcgag   1440
cccctgggcg tggcccccac caaggccaag cgccgcgtgg tgcagcgcga gaagcgcgcc   1500
gtgaccctgg gcgccatgtt cctgggcttc ctgggcgccg ccggcagcac catgggcgcc   1560
cgcagcctga ccctgaccgt gcaggcccgc cagctgctga gcggcatcgt gcagcagcag   1620
aacaacctgc tgcgcgccat cgaggcccag cagcacctgc tgcagctgac cgtgtggggc   1680
atcaagcagc tgcaggcccg cgtgctggcc gtggagcgct acctgaagga ccagcagctg   1740
ctgggcatct ggggctgcag cggcaagctg atctgcacca ccgccgtgcc ctggaacgcc   1800
agctggagca acaagagcct ggaccagatc tggaacaaca tgacctggat ggagtgggag   1860
cgcgagatcg acaactacac caacctgatc tacaccctga tcgaggagag ccagaaccag   1920
caggagaaga acgagcagga gctgctggag ctggacaagt gggccagcct gtggaactgg   1980
ttcgacatca gcaagtggct gtggtacatc aagatcttca tcatgatcgt gggcggcctg   2040
gtgggcctgc gcatcgtgtt caccgtgctg agcatcgtga accgcgtgcg ccagggctac   2100
agccccctga gcttccagac ccgcttcccc gccccccgcg gccccgaccg ccccgagggc   2160
atcgaggagg agggcggcga gcgcgaccgc gaccgcagca gccccctggt gcacggcctg   2220
ctggccctga tctgggacga cctgcgcagc ctgtgcctgt tcagctacca ccgcctgcgc   2280
gacctgatcc tgatcgccgc ccgcatcgtg gagctgctgg gccgccgcgg ctgggaggcc   2340
ctgaagtact ggggcaacct gctgcagtac tggatccagg agctgaagaa cagcgccgtg   2400
agcctgttcg acgccatcgc catcgccgtg gccgagggca ccgaccgcat catcgaggtg   2460
gcccagcgca tcggccgcgc cttcctgcac atcccccgcc gcatccgcca gggcttcgag   2520
cgcgccctgc tgtaactcga g                                             2541
```

<210> SEQ ID NO 10
<211> LENGTH: 2541
<212> TYPE: DNA

-continued

```
<213> ORGANISM: Artificial Sequence
<220> FEATURE:
<223> OTHER INFORMATION: Description of Artificial Sequence:
      Arg426-Gly431

<400> SEQUENCE: 10

gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgaagctg    360

accccccctgt gcgtgaccct gcactgcacc aacctgaaga acgccaccaa caccaagagc    420

agcaactgga aggagatgga ccgcggcgag atcaagaact gcagcttcaa ggtgaccacc    480

agcatccgca acaagatgca gaaggagtac gccctgttct acaagctgga cgtggtgccc    540

atcgacaacg acaacaccag ctacaagctg atcaactgca acaccagcgt gatcacccag    600

gcctgcccca aggtgagctt cgagcccatc cccatccact actgcgcccc cgccggcttc    660

gccatcctga agtgcaacga caagaagttc aacggcagcg gcccctgcac caacgtgagc    720

accgtgcagt gcacccacgg catccgcccc gtggtgagca cccagctgct gctgaacggc    780

agcctggccg aggagggcgt ggtgatccgc agcgagaact tcaccgacaa cgccaagacc    840

atcatcgtgc agctgaagga gagcgtggag atcaactgca cccgccccaa caacaacacc    900

cgcaagagca tcaccatcgg ccccggccgc gccttctacg ccaccggcga catcatcggc    960

gacatccgcc aggcccactg caacatcagc ggcgagaagt ggaacaacac cctgaagcag   1020

atcgtgacca agctgcaggc ccagttcggc aacaagacca tcgtgttcaa gcagagcagc   1080

ggcggcgacc ccgagatcgt gatgcacagc ttcaactgcg gcggcgagtt cttctactgc   1140

aacagcaccc agctgttcaa cagcacctgg aacaacacca tcggccccaa caacaccaac   1200

ggcaccatca ccctgccctg ccgcatcaag cagatcatca accgcggcgg cggcaaggcc   1260

atgtacgccc cccccatccg cggccagatc cgctgcagca gcaacatcac cggcctgctg   1320

ctgacccgcg acggcggcaa ggagatcagc aacaccaccg agatcttccg ccccggcggc   1380

ggcgacatgc gcgacaactg gcgcagcgag ctgtacaagt acaaggtggt gaagatcgag   1440

cccctgggcg tggcccccac caaggccaag cgccgcgtgg tgcagcgcga gaagcgcgcc   1500

gtgaccctgg gcgccatgtt cctgggcttc ctgggcgccg ccggcagcac catgggcgcc   1560

cgcagcctga ccctgaccgt gcaggcccgc cagctgctga gcggcatcgt gcagcagcag   1620

aacaacctgc tgcgcgccat cgaggcccag cagcacctgc tgcagctgac cgtgtggggc   1680

atcaagcagc tgcaggcccg cgtgctggcc gtggagcgct acctgaagga ccagcagctg   1740

ctgggcatct ggggctgcag cggcaagctg atctgcacca ccgccgtgcc ctggaacgcc   1800

agctggagca acaagagcct ggaccagatc tggaacaaca tgacctggat ggagtgggag   1860

cgcgagatcg acaactacac caacctgatc tacaccctga tcgaggagag ccagaaccag   1920

caggagaaga acgagcagga gctgctggag ctggacaagt gggccagcct gtggaactgg   1980

ttcgacatca gcaagtggct gtggtacatc aagatcttca tcatgatcgt gggcggcctg   2040

gtgggcctgc gcatcgtgtt caccgtgctg agcatcgtga accgcgtgcg ccagggctac   2100

agccccctga gcttccagac ccgcttcccc gccccccgcg gccccgaccg ccccgagggc   2160
```

-continued

```
atcgaggagg agggcggcga gcgcgaccgc gaccgcagca gccccctggt gcacggcctg   2220
ctggccctga tctgggacga cctgcgcagc ctgtgcctgt tcagctacca ccgcctgcgc   2280
gacctgatcc tgatcgccgc ccgcatcgtg gagctgctgg gccgccgcgg ctgggaggcc   2340
ctgaagtact ggggcaacct gctgcagtac tggatccagg agctgaagaa cagcgccgtg   2400
agcctgttcg acgccatcgc catcgccgtg gccgagggca ccgaccgcat catcgaggtg   2460
gcccagcgca tcggccgcgc cttcctgcac atcccccgcc gcatccgcca gggcttcgag   2520
cgcgccctgc tgtaactcga g                                             2541
```

<210> SEQ ID NO 11
<211> LENGTH: 2541
<212> TYPE: DNA
<213> ORGANISM: Artificial Sequence
<220> FEATURE:
<223> OTHER INFORMATION: Description of Artificial Sequence: Arg426-Gly431B

<400> SEQUENCE: 11

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg ggccacccac gcctgcgtgc ccaccgaccc caacccccag    240
gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360
accccctgt gcgtgaccct gcactgcacc aacctgaaga acgccaccaa caccaagagc    420
agcaactgga aggagatgga ccgcggcgag atcaagaact gcagcttcaa ggtgaccacc    480
agcatccgca acaagatgca gaaggagtac gccctgttct acaagctgga cgtggtgccc    540
atcgacaacg acaacaccag ctacaagctg atcaactgca acaccagcgt gatcacccag    600
gcctgcccca aggtgagctt cgagcccatc cccatccact actgcgcccc cgccggcttc    660
gccatcctga agtgcaacga caagaagttc aacggcagcg gcccctgcac caacgtgagc    720
accgtgcagt gcacccacgg catccgcccc gtggtgagca cccagctgct gctgaacggc    780
agcctggccg aggagggcgt ggtgatccgc agcgagaact tcaccgacaa cgccaagacc    840
atcatcgtgc agctgaagga gagcgtggag atcaactgca cccgccccaa caacaacacc    900
cgcaagagca tcaccatcgg ccccggccgc gccttctacg ccaccggcga catcatcggc    960
gacatccgcc aggcccactg caacatcagc ggcgagaagt ggaacaacac cctgaagcag   1020
atcgtgacca agctgcaggc ccagttcggc aacaagacca tcgtgttcaa gcagagcagc   1080
ggcggcgacc ccgagatcgt gatgcacagc ttcaactgcg gcggcgagtt cttctactgc   1140
aacagcaccc agctgttcaa cagcacctgg aacaacacca tcggccccaa caacaccaac   1200
ggcaccatca ccctgccctg ccgcatcaag cagatcatca accgcggcag cggcaaggcc   1260
atgtacgccc cccccatccg cggccagatc cgctgcagca gcaacatcac cggcctgctg   1320
ctgacccgcg acggcggcaa ggagatcagc aacaccaccg agatcttccg ccccggcggc   1380
ggcgacatgc gcgacaactg gcgcagcgag ctgtacaagt acaaggtggt gaagatcgag   1440
cccctgggcg tggcccccac caaggccaag cgccgcgtgg tgcagcgcga gaagcgcgcc   1500
gtgaccctgg gcgccatgtt cctgggcttc ctgggcgccg ccggcagcac catgggcgcc   1560
cgcagcctga ccctgaccgt gcaggcccgc cagctgctga gcggcatcgt gcagcagcag   1620
```

-continued

```
aacaacctgc tgcgcgccat cgaggcccag cagcacctgc tgcagctgac cgtgtggggc   1680

atcaagcagc tgcaggcccg cgtgctggcc gtggagcgct acctgaagga ccagcagctg   1740

ctgggcatct ggggctgcag cggcaagctg atctgcacca ccgccgtgcc ctggaacgcc   1800

agctggagca acaagagcct ggaccagatc tggaacaaca tgacctggat ggagtgggag   1860

cgcgagatcg acaactacac caacctgatc tacaccctga tcgaggagag ccagaaccag   1920

caggagaaga acgagcagga gctgctggag ctggacaagt gggccagcct gtggaactgg   1980

ttcgacatca gcaagtggct gtggtacatc aagatcttca tcatgatcgt gggcggcctg   2040

gtgggcctgc gcatcgtgtt caccgtgctg agcatcgtga accgcgtgcg ccagggctac   2100

agcccccctga gcttccagac ccgcttcccc gcccccgcg gccccgaccg ccccgagggc   2160

atcgaggagg agggcggcga gcgcgaccgc gaccgcagca gcccccctggt gcacggcctg   2220

ctggccctga tctgggacga cctgcgcagc ctgtgcctgt tcagctacca ccgcctgcgc   2280

gacctgatcc tgatcgccgc ccgcatcgtg gagctgctgg gccgccgcgg ctgggaggcc   2340

ctgaagtact ggggcaacct gctgcagtac tggatccagg agctgaagaa cagcgccgtg   2400

agcctgttcg acgccatcgc catcgccgtg gccgagggca ccgaccgcat catcgaggtg   2460

gcccagcgca tcggccgcgc cttcctgcac atcccccgcc gcatccgcca gggcttcgag   2520

cgcgccctgc tgtaactcga g                                             2541
```

```
<210> SEQ ID NO 12
<211> LENGTH: 2541
<212> TYPE: DNA
<213> ORGANISM: Artificial Sequence
<220> FEATURE:
<223> OTHER INFORMATION: Description of Artificial Sequence:
      Arg426-Lys432

<400> SEQUENCE: 12
```

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgaagctg    360

acccccctgt gcgtgaccct gcactgcacc aacctgaaga acgccaccaa caccaagagc    420

agcaactgga aggagatgga ccgcggcgag atcaagaact gcagcttcaa ggtgaccacc    480

agcatccgca acaagatgca gaaggagtac gccctgttct acaagctgga cgtggtgccc    540

atcgacaacg acaacaccag ctacaagctg atcaactgca acaccagcgt gatcacccag    600

gcctgcccca aggtgagctt cgagcccatc cccatccact actgcgcccc cgccggcttc    660

gccatcctga agtgcaacga caagaagttc aacggcagcg gcccctgcac caacgtgagc    720

accgtgcagt gcacccacgg catccgcccc gtggtgagca cccagctgct gctgaacggc    780

agcctggccg aggagggcgt ggtgatccgc agcgagaact tcaccgacaa cgccaagacc    840

atcatcgtgc agctgaagga gagcgtggag atcaactgca cccgccccaa caacaacacc    900

cgcaagagca tcaccatcgg ccccggccgc gccttctacg ccaccggcga catcatcggc    960

gacatccgcc aggcccactg caacatcagc ggcgagaagt ggaacaacac cctgaagcag   1020

atcgtgacca agctgcaggc ccagttcggc aacaagacca tcgtgttcaa gcagagcagc   1080
```

-continued ggcggcgacc ccgagatcgt gatgcacagc ttcaactgcg gcggcgagtt cttctactgc 1140
aacagcaccc agctgttcaa cagcacctgg aacaacacca tcggccccaa caacaccaac 1200
ggcaccatca ccctgccctg ccgcatcaag cagatcatca accgcggcgg caacaaggcc 1260
atgtacgccc cccccatccg cggccagatc cgctgcagca gcaacatcac cggcctgctg 1320
ctgacccgcg acggcggcaa ggagatcagc aacaccaccg agatcttccg ccccggcggc 1380
ggcgacatgc gcgacaactg gcgcagcgag ctgtacaagt acaaggtggt gaagatcgag 1440
cccctgggcg tggcccccac caaggccaag cgccgcgtgg tgcagcgcga gaagcgcgcc 1500
gtgaccctgg gcgccatgtt cctgggcttc ctgggcgccg ccggcagcac catgggcgcc 1560
cgcagcctga ccctgaccgt gcaggcccgc cagctgctga gcggcatcgt gcagcagcag 1620
aacaacctgc tgcgcgccat cgaggcccag cagcacctgc tgcagctgac cgtgtggggc 1680
atcaagcagc tgcaggcccg cgtgctggcc gtggagcgct acctgaagga ccagcagctg 1740
ctgggcatct ggggctgcag cggcaagctg atctgcacca ccgccgtgcc ctggaacgcc 1800
agctggagca acaagagcct ggaccagatc tggaacaaca tgacctggat ggagtgggag 1860
cgcgagatcg acaactacac caacctgatc tacaccctga tcgaggagag ccagaaccag 1920
caggagaaga acgagcagga gctgctggag ctggacaagt gggccagcct gtggaactgg 1980
ttcgacatca gcaagtggct gtggtacatc aagatcttca tcatgatcgt gggcggcctg 2040
gtgggcctgc gcatcgtgtt caccgtgctg agcatcgtga accgcgtgcg ccagggctac 2100
agccccctga gcttccagac ccgcttcccc gccccccgcg gccccgaccg ccccgagggc 2160
atcgaggagg agggcggcga gcgcgaccgc gaccgcagca gccccctggt gcacggcctg 2220
ctggccctga tctgggacga cctgcgcagc ctgtgcctgt tcagctacca ccgcctgcgc 2280
gacctgatcc tgatcgccgc ccgcatcgtg gagctgctgg gccgccgcgg ctgggaggcc 2340
ctgaagtact ggggcaacct gctgcagtac tggatccagg agctgaagaa cagcgccgtg 2400
agcctgttcg acgccatcgc catcgccgtg gccgagggca ccgaccgcat catcgaggtg 2460
gcccagcgca tcggccgcgc cttcctgcac atcccccgcc gcatccgcca gggcttcgag 2520
cgcgccctgc tgtaactcga g 2541

<210> SEQ ID NO 13
<211> LENGTH: 2535
<212> TYPE: DNA
<213> ORGANISM: Artificial Sequence
<220> FEATURE:
<223> OTHER INFORMATION: Description of Artificial Sequence:
Asn425-Lys432

<400> SEQUENCE: 13
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360 accccctgt gcgtgaccct gcactgcacc aacctgaaga acgccaccaa caccaagagc 420
agcaactgga aggagatgga ccgcggcgag atcaagaact gcagcttcaa ggtgaccacc 480
agcatccgca acaagatgca gaaggagtac gccctgttct acaagctgga cgtggtgccc 540

-continued

```
atcgacaacg acaacaccag ctacaagctg atcaactgca acaccagcgt gatcacccag    600

gcctgcccca aggtgagctt cgagcccatc cccatccact actgcgcccc cgccggcttc    660

gccatcctga agtgcaacga caagaagttc aacggcagcg gcccctgcac caacgtgagc    720

accgtgcagt gcacccacgg catccgcccc gtggtgagca cccagctgct gctgaacggc    780

agcctggccg aggagggcgt ggtgatccgc agcgagaact tcaccgacaa cgccaagacc    840

atcatcgtgc agctgaagga gagcgtggag atcaactgca cccgccccaa caacaacacc    900

cgcaagagca tcaccatcgg ccccggccgc gccttctacg ccaccggcga catcatcggc    960

gacatccgcc aggcccactg caacatcagc ggcgagaagt ggaacaacac cctgaagcag   1020

atcgtgacca agctgcaggc ccagttcggc aacaagacca tcgtgttcaa gcagagcagc   1080

ggcggcgacc ccgagatcgt gatgcacagc ttcaactgcg gcggcgagtt cttctactgc   1140

aacagcaccc agctgttcaa cagcacctgg aacaacacca tcggccccaa caacaccaac   1200

ggcaccatca ccctgccctg ccgcatcaag cagatcatca acgcccccaa ggccatgtac   1260

gccccccccca tccgcggcca gatccgctgc agcagcaaca tcaccggcct gctgctgacc   1320

cgcgacggcg gcaaggagat cagcaacacc accgagatct tccgccccgg cggcggcgac   1380

atgcgcgaca actggcgcag cgagctgtac aagtacaagg tggtgaagat cgagcccctg   1440

ggcgtggccc ccaccaaggc caagcgccgc gtggtgcagc gcgagaagcg cgccgtgacc   1500

ctgggcgcca tgttcctggg cttcctgggc gccgccggca gcaccatggg cgcccgcagc   1560

ctgaccctga ccgtgcaggc ccgccagctg ctgagcggca tcgtgcagca gcagaacaac   1620

ctgctgcgcg ccatcgaggc ccagcagcac ctgctgcagc tgaccgtgtg gggcatcaag   1680

cagctgcagg cccgcgtgct ggccgtggag cgctacctga aggaccagca gctgctgggc   1740

atctggggct gcagcggcaa gctgatctgc accaccgccg tgccctggaa cgccagctgg   1800

agcaacaaga gcctggacca gatctggaac aacatgacct ggatggagtg ggagcgcgag   1860

atcgacaact acaccaacct gatctacacc ctgatcgagg agagccagaa ccagcaggag   1920

aagaacgagc aggagctgct ggagctggac aagtgggcca gcctgtggaa ctggttcgac   1980

atcagcaagt ggctgtggta catcaagatc ttcatcatga tcgtgggcgg cctggtgggc   2040

ctgcgcatcg tgttcaccgt gctgagcatc gtgaaccgcg tgcgccaggg ctacagcccc   2100

ctgagcttcc agacccgctt ccccgccccc cgcggccccg accgccccga gggcatcgag   2160

gaggagggcg gcgagcgcga ccgcgaccgc agcagccccc tggtgcacgg cctgctggcc   2220

ctgatctggg acgacctgcg cagcctgtgc ctgttcagct accaccgcct gcgcgacctg   2280

atcctgatcg ccgcccgcat cgtggagctg ctgggccgcc gcggctggga ggccctgaag   2340

tactggggca acctgctgca gtactggatc caggagctga agaacagcgc cgtgagcctg   2400

ttcgacgcca tcgccatcgc cgtggccgag ggcaccgacc gcatcatcga ggtggcccag   2460

cgcatcggcc gcgccttcct gcacatcccc cgccgcatcc gccagggctt cgagcgcgcc   2520

ctgctgtaac tcgag                                                    2535
```

<210> SEQ ID NO 14
<211> LENGTH: 2529
<212> TYPE: DNA
<213> ORGANISM: Artificial Sequence
<220> FEATURE:
<223> OTHER INFORMATION: Description of Artificial Sequence:
Ile424-Ala433

<400> SEQUENCE: 14

-continued

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg ggccacccac gcctgcgtgc ccaccgaccc caacccccag    240
gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360
acccccctgt gcgtgaccct gcactgcacc aacctgaaga acgccaccaa caccaagagc    420
agcaactgga aggagatgga ccgcggcgag atcaagaact gcagcttcaa ggtgaccacc    480
agcatccgca acaagatgca gaaggagtac gccctgttct acaagctgga cgtggtgccc    540
atcgacaacg acaacaccag ctacaagctg atcaactgca acaccagcgt gatcacccag    600
gcctgcccca aggtgagctt cgagcccatc cccatccact actgcgcccc cgccggcttc    660
gccatcctga agtgcaacga caagaagttc aacggcagcg gcccctgcac caacgtgagc    720
accgtgcagt gcacccacgg catccgcccc gtggtgagca cccagctgct gctgaacggc    780
agcctggccg aggagggcgt ggtgatccgc agcgagaact tcaccgacaa cgccaagacc    840
atcatcgtgc agctgaagga gagcgtggag atcaactgca cccgccccaa caacaacacc    900
cgcaagagca tcaccatcgg ccccggccgc gccttctacg ccaccggcga catcatcggc    960
gacatccgcc aggcccactg caacatcagc ggcgagaagt ggaacaacac cctgaagcag   1020
atcgtgacca agctgcaggc ccagttcggc aacaagacca tcgtgttcaa gcagagcagc   1080
ggcggcgacc ccgagatcgt gatgcacagc ttcaactgcg gcggcgagtt cttctactgc   1140
aacagcaccc agctgttcaa cagcacctgg aacaacacca tcggccccaa caacaccaac   1200
ggcaccatca ccctgccctg ccgcatcaag cagatcatcg gcggcgccat gtacgccccc   1260
cccatccgcg gccagatccg ctgcagcagc aacatcaccg gcctgctgct gacccgcgac   1320
ggcggcaagg agatcagcaa caccaccgag atcttccgcc ccggcggcgg cgacatgcgc   1380
gacaactggc gcagcgagct gtacaagtac aaggtggtga agatcgagcc cctgggcgtg   1440
gcccccacca aggccaagcg ccgcgtggtg cagcgcgaga agcgcgccgt gaccctgggc   1500
gccatgttcc tgggcttcct gggcgccgcc ggcagcacca tgggcgcccg cagcctgacc   1560
ctgaccgtgc aggcccgcca gctgctgagc ggcatcgtgc agcagcagaa caacctgctg   1620
cgcgccatcg aggcccagca gcacctgctg cagctgaccg tgtggggcat caagcagctg   1680
caggcccgcg tgctggccgt ggagcgctac ctgaaggacc agcagctgct gggcatctgg   1740
ggctgcagcg gcaagctgat ctgcaccacc gccgtgccct ggaacgccag ctggagcaac   1800
aagagcctgg accagatctg gaacaacatg acctggatgg agtgggagcg cgagatcgac   1860
aactacacca acctgatcta caccctgatc gaggagagcc agaaccagca ggagaagaac   1920
gagcaggagc tgctggagct ggacaagtgg gccagcctgt ggaactggtt cgacatcagc   1980
aagtggctgt ggtacatcaa gatcttcatc atgatcgtgg gcggcctggt gggcctgcgc   2040
atcgtgttca ccgtgctgag catcgtgaac cgcgtgcgcc agggctacag ccccctgagc   2100
ttccagaccc gcttccccgc cccccgcggc cccgaccgcc ccgagggcat cgaggaggag   2160
ggcggcgagc gcgaccgcga ccgcagcagc cccctggtgc acggcctgct ggccctgatc   2220
tgggacgacc tgcgcagcct gtgcctgttc agctaccacc gcctgcgcga cctgatcctg   2280
atcgccgccc gcatcgtgga gctgctgggc cgccgcggct gggaggccct gaagtactgg   2340
ggcaacctgc tgcagtactg gatccaggag ctgaagaaca gcgccgtgag cctgttcgac   2400
```

-continued gccatcgcca tcgccgtggc cgagggcacc gaccgcatca tcgaggtggc ccagcgcatc 2460
ggccgcgcct tcctgcacat cccccgccgc atccgccagg gcttcgagcg cgccctgctg 2520
taactcgag 2529

<210> SEQ ID NO 15
<211> LENGTH: 2523
<212> TYPE: DNA
<213> ORGANISM: Artificial Sequence
<220> FEATURE:
<223> OTHER INFORMATION: Description of Artificial Sequence:
Ile423-Met434

<400> SEQUENCE: 15
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgaagctg 360
acccccctgt gcgtgaccct gcactgcacc aacctgaaga acgccaccaa caccaagagc 420
agcaactgga aggagatgga ccgcggcgag atcaagaact gcagcttcaa ggtgaccacc 480
agcatccgca acaagatgca gaaggagtac gccctgttct acaagctgga cgtggtgccc 540
atcgacaacg acaacaccag ctacaagctg atcaactgca acaccagcgt gatcacccag 600
gcctgcccca aggtgagctt cgagcccatc cccatccact actgcgcccc cgccggcttc 660
gccatcctga agtgcaacga caagaagttc aacggcagcg gcccctgcac caacgtgagc 720
accgtgcagt gcacccacgg catccgcccc gtggtgagca cccagctgct gctgaacggc 780
agcctggccg aggagggcgt ggtgatccgc agcgagaact tcaccgacaa cgccaagacc 840
atcatcgtgc agctgaagga gagcgtggag atcaactgca cccgccccaa caacaacacc 900
cgcaagagca tcaccatcgg ccccggccgc gccttctacg ccaccggcga catcatcggc 960
gacatccgcc aggcccactg caacatcagc ggcgagaagt ggaacaacac cctgaagcag 1020
atcgtgacca agctgcaggc ccagttcggc aacaagacca tcgtgttcaa gcagagcagc 1080
ggcggcgacc ccgagatcgt gatgcacagc ttcaactgcg gcggcgagtt cttctactgc 1140
aacagcaccc agctgttcaa cagcacctgg aacaacacca tcggccccaa caacaccaac 1200
ggcaccatca ccctgccctg ccgcatcaag cagatcggcg gcatgtacgc ccccccccatc 1260 cgcggccaga tccgctgcag cagcaacatc accggcctgc tgctgacccg cgacggcggc 1320
aaggagatca gcaacaccac cgagatcttc cgccccggcg gcggcgacat gcgcgacaac 1380
tggcgcagcg agctgtacaa gtacaaggtg gtgaagatcg agcccctggg cgtggccccc 1440
accaaggcca agcgccgcgt ggtgcagcgc gagaagcgcg ccgtgaccct gggcgccatg 1500
ttcctgggct tcctgggcgc cgccggcagc accatgggcg cccgcagcct gaccctgacc 1560
gtgcaggccc gccagctgct gagcggcatc gtgcagcagc agaacaacct gctgcgcgcc 1620
atcgaggccc agcagcacct gctgcagctg accgtgtggg gcatcaagca gctgcaggcc 1680
cgcgtgctgg ccgtggagcg ctacctgaag gaccagcagc tgctgggcat ctggggctgc 1740
agcggcaagc tgatctgcac caccgccgtg ccctggaacg ccagctggag caacaagagc 1800
ctggaccaga tctggaacaa catgacctgg atggagtggg agcgcgagat cgacaactac 1860

-continued

```
accaacctga tctacaccct gatcgaggag agccagaacc agcaggagaa gaacgagcag   1920
gagctgctgg agctggacaa gtgggccagc ctgtggaact ggttcgacat cagcaagtgg   1980
ctgtggtaca tcaagatctt catcatgatc gtgggcggcc tggtgggcct gcgcatcgtg   2040
ttcaccgtgc tgagcatcgt gaaccgcgtg cgccagggct acagccccct gagcttccag   2100
acccgcttcc ccgcccccg cggccccgac cgcccccgagg gcatcgagga ggagggcggc   2160
gagcgcgacc gcgaccgcag cagccccctg gtgcacggcc tgctggccct gatctgggac   2220
gacctgcgca gcctgtgcct gttcagctac caccgcctgc gcgacctgat cctgatcgcc   2280
gcccgcatcg tggagctgct gggccgccgc ggctgggagg ccctgaagta ctggggcaac   2340
ctgctgcagt actggatcca ggagctgaag aacagcgccg tgagcctgtt cgacgccatc   2400
gccatcgccg tggccgaggg caccgaccgc atcatcgagg tggcccagcg catcggccgc   2460
gccttcctgc acatcccccg ccgcatccgc cagggcttcg agcgcgccct gctgtaactc   2520
gag                                                               2523
```

<210> SEQ ID NO 16
<211> LENGTH: 2517
<212> TYPE: DNA
<213> ORGANISM: Artificial Sequence
<220> FEATURE:
<223> OTHER INFORMATION: Description of Artificial Sequence:
Gln422-Tyr435

<400> SEQUENCE: 16

```
gaattcgcca ccatggatgc aatgaagaga gggctctgct gtgtgctgct gctgtgtgga     60
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg ggccacccac gcctgcgtgc ccaccgaccc caacccccag    240
gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360
accccccctgt gcgtgaccct gcactgcacc aacctgaaga acgccaccaa caccaagagc    420
agcaactgga aggagatgga ccgcggcgag atcaagaact gcagcttcaa ggtgaccacc    480
agcatccgca acaagatgca gaaggagtac gccctgttct acaagctgga cgtggtgccc    540
atcgacaacg acaacaccag ctacaagctg atcaactgca acaccagcgt gatcacccag    600
gcctgcccca aggtgagctt cgagcccatc cccatccact actgcgcccc cgccggcttc    660
gccatcctga agtgcaacga caagaagttc aacggcagcg gcccctgcac caacgtgagc    720
accgtgcagt gcacccacgg catccgcccc gtggtgagca cccagctgct gctgaacggc    780
agcctggccg aggagggcgt ggtgatccgc agcgagaact tcaccgacaa cgccaagacc    840
atcatcgtgc agctgaagga gagcgtggag atcaactgca cccgccccaa caacaacacc    900
cgcaagagca tcaccatcgg ccccggccgc gccttctacg ccaccggcga catcatcggc    960
gacatccgcc aggcccactg caacatcagc ggcgagaagt ggaacaacac cctgaagcag   1020
atcgtgacca agctgcaggc ccagttcggc aacaagacca tcgtgttcaa gcagagcagc   1080
ggcggcgacc ccgagatcgt gatgcacagc ttcaactgcg gcggcgagtt cttctactgc   1140
aacagcaccc agctgttcaa cagcacctgg aacaacacca tcggccccaa caacaccaac   1200
ggcaccatca ccctgccctg ccgcatcaag cagggcggct acgccccccc catccgcggc   1260
cagatccgct gcagcagcaa catcaccggc ctgctgctga cccgcgacgg cggcaaggag   1320
```

-continued

```
atcagcaaca ccaccgagat cttccgcccc ggcggcggcg acatgcgcga caactggcgc   1380

agcgagctgt acaagtacaa ggtggtgaag atcgagcccc tgggcgtggc ccccaccaag   1440

gccaagcgcc gcgtggtgca gcgcgagaag cgcgccgtga ccctgggcgc catgttcctg   1500

ggcttcctgg gcgccgccgg cagcaccatg ggcgcccgca gcctgaccct gaccgtgcag   1560

gcccgccagc tgctgagcgg catcgtgcag cagcagaaca acctgctgcg cgccatcgag   1620

gcccagcagc acctgctgca gctgaccgtg tggggcatca agcagctgca ggcccgcgtg   1680

ctggccgtgg agcgctacct gaaggaccag cagctgctgg gcatctgggg ctgcagcggc   1740

aagctgatct gcaccaccgc cgtgccctgg aacgccagct ggagcaacaa gagcctggac   1800

cagatctgga acaacatgac ctggatggag tgggagcgcg agatcgacaa ctacaccaac   1860

ctgatctaca ccctgatcga ggagagccag aaccagcagg agaagaacga gcaggagctg   1920

ctggagctgg acaagtgggc cagcctgtgg aactggttcg acatcagcaa gtggctgtgg   1980

tacatcaaga tcttcatcat gatcgtgggc ggcctggtgg gcctgcgcat cgtgttcacc   2040

gtgctgagca tcgtgaaccg cgtgcgccag ggctacagcc ccctgagctt ccagacccgc   2100

ttccccgccc cccgcggccc cgaccgcccc gagggcatcg aggaggaggg cggcgagcgc   2160

gaccgcgacc gcagcagccc cctggtgcac ggcctgctgg ccctgatctg ggacgacctg   2220

cgcagcctgt gcctgttcag ctaccaccgc ctgcgcgacc tgatcctgat cgccgcccgc   2280

atcgtggagc tgctgggccg ccgcggctgg gaggccctga agtactgggg caacctgctg   2340

cagtactgga tccaggagct gaagaacagc gccgtgagcc tgttcgacgc catcgccatc   2400

gccgtggccg agggcaccga ccgcatcatc gaggtggccc agcgcatcgg ccgcgccttc   2460

ctgcacatcc cccgccgcat ccgccagggc ttcgagcgcg ccctgctgta actcgag      2517
```

<210> SEQ ID NO 17
<211> LENGTH: 2517
<212> TYPE: DNA
<213> ORGANISM: Artificial Sequence
<220> FEATURE:
<223> OTHER INFORMATION: Description of Artificial Sequence:
Gln422-Tyr435B

<400> SEQUENCE: 17

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgaagctg    360

acccccctgt gcgtgaccct gcactgcacc aacctgaaga acgccaccaa caccaagagc    420

agcaactgga aggagatgga ccgcggcgag atcaagaact gcagcttcaa ggtgaccacc    480

agcatccgca acaagatgca gaaggagtac gccctgttct acaagctgga cgtggtgccc    540

atcgacaacg acaacaccag ctacaagctg atcaactgca acaccagcgt gatcacccag    600

gcctgcccca aggtgagctt cgagcccatc cccatccact actgcgcccc cgccggcttc    660

gccatcctga agtgcaacga caagaagttc aacggcagcg gcccctgcac caacgtgagc    720

accgtgcagt gcacccacgg catccgcccc gtggtgagca cccagctgct gctgaacggc    780

agcctggccg aggagggcgt ggtgatccgc agcgagaact tcaccgacaa cgccaagacc    840
```

-continued

```
atcatcgtgc agctgaagga gagcgtggag atcaactgca cccgccccaa caacaacacc    900

cgcaagagca tcaccatcgg ccccggccgc gccttctacg ccaccggcga catcatcggc    960

gacatccgcc aggcccactg caacatcagc ggcgagaagt ggaacaacac cctgaagcag   1020

atcgtgacca agctgcaggc ccagttcggc aacaagacca tcgtgttcaa gcagagcagc   1080

ggcggcgacc ccgagatcgt gatgcacagc ttcaactgcg gcggcgagtt cttctactgc   1140

aacagcaccc agctgttcaa cagcacctgg aacaacacca tcggccccaa caacaccaac   1200

ggcaccatca ccctgccctg ccgcatcaag caggccccct acgccccccc catccgcggc   1260

cagatccgct gcagcagcaa catcaccggc ctgctgctga cccgcgacgg cggcaaggag   1320

atcagcaaca ccaccgagat cttccgcccc ggcggcggcg acatgcgcga caactggcgc   1380

agcgagctgt acaagtacaa ggtggtgaag atcgagcccc tgggcgtggc ccccaccaag   1440

gccaagcgcc gcgtggtgca gcgcgagaag cgcgccgtga ccctgggcgc catgttcctg   1500

ggcttcctgg gcgccgccgg cagcaccatg ggcgcccgca gcctgaccct gaccgtgcag   1560

gcccgccagc tgctgagcgg catcgtgcag cagcagaaca acctgctgcg cgccatcgag   1620

gcccagcagc acctgctgca gctgaccgtg tggggcatca agcagctgca ggcccgcgtg   1680

ctggccgtgg agcgctacct gaaggaccag cagctgctgg gcatctgggg ctgcagcggc   1740

aagctgatct gcaccaccgc cgtgccctgg aacgccagct ggagcaacaa gagcctggac   1800

cagatctgga acaacatgac ctggatggag tgggagcgcg agatcgacaa ctacaccaac   1860

ctgatctaca ccctgatcga ggagagccag aaccagcagg agaagaacga gcaggagctg   1920

ctggagctgg acaagtgggc cagcctgtgg aactggttcg acatcagcaa gtggctgtgg   1980

tacatcaaga tcttcatcat gatcgtgggc ggcctggtgg gcctgcgcat cgtgttcacc   2040

gtgctgagca tcgtgaaccg cgtgcgccag ggctacagcc ccctgagctt ccagacccgc   2100

ttccccgccc cccgcggccc cgaccgcccc gagggcatcg aggaggaggg cggcgagcgc   2160

gaccgcgacc gcagcagccc cctggtgcac ggcctgctgg ccctgatctg ggacgacctg   2220

cgcagcctgt gcctgttcag ctaccaccgc ctgcgcgacc tgatcctgat cgccgcccgc   2280

atcgtggagc tgctgggccg ccgcggctgg gaggccctga agtactgggg caacctgctg   2340

cagtactgga tccaggagct gaagaacagc gccgtgagcc tgttcgacgc catcgccatc   2400

gccgtggccg agggcaccga ccgcatcatc gaggtggccc agcgcatcgg ccgcgccttc   2460

ctgcacatcc cccgccgcat ccgccagggc ttcgagcgcg ccctgctgta actcgag      2517
```

<210> SEQ ID NO 18
<211> LENGTH: 2322
<212> TYPE: DNA
<213> ORGANISM: Artificial Sequence
<220> FEATURE:
<223> OTHER INFORMATION: Description of Artificial Sequence:
Leu122-Ser199; Arg426-Gly431

<400> SEQUENCE: 18

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgaagctg    360
```

-continued

```
ggcaacagcg tgatcaccca ggcctgcccc aaggtgagct tcgagcccat ccccatccac    420

tactgcgccc ccgccggctt cgccatcctg aagtgcaacg acaagaagtt caacggcagc    480

ggcccctgca ccaacgtgag caccgtgcag tgcacccacg gcatccgccc cgtggtgagc    540

acccagctgc tgctgaacgg cagcctggcc gaggagggcg tggtgatccg cagcgagaac    600

ttcaccgaca acgccaagac catcatcgtg cagctgaagg agagcgtgga gatcaactgc    660

acccgcccca acaacaacac ccgcaagagc atcaccatcg gccccggccg cgccttctac    720

gccaccggcg acatcatcgg cgacatccgc caggcccact gcaacatcag cggcgagaag    780

tggaacaaca ccctgaagca gatcgtgacc aagctgcagg cccagttcgg caacaagacc    840

atcgtgttca agcagagcag cggcggcgac cccgagatcg tgatgcacag cttcaactgc    900

ggcggcgagt tcttctactg caacagcacc cagctgttca acagcacctg gaacaacacc    960

atcggcccca acaacaccaa cggcaccatc accctgccct gccgcatcaa gcagatcatc   1020

aaccgcggcg gcggcaaggc catgtacgcc ccccccatcc gcggccagat ccgctgcagc   1080

agcaacatca ccggcctgct gctgacccgc gacggcggca aggagatcag caacaccacc   1140

gagatcttcc gccccggcgg cggcgacatg cgcgacaact ggcgcagcga gctgtacaag   1200

tacaaggtgg tgaagatcga gcccctgggc gtggccccca ccaaggccaa gcgccgcgtg   1260

gtgcagcgcg agaagcgcgc cgtgaccctg ggcgccatgt tcctgggctt cctgggcgcc   1320

gccggcagca ccatgggcgc ccgcagcctg accctgaccg tgcaggcccg ccagctgctg   1380

agcggcatcg tgcagcagca gaacaacctg ctgcgcgcca tcgaggccca gcagcacctg   1440

ctgcagctga ccgtgtgggg catcaagcag ctgcaggccc gcgtgctggc cgtggagcgc   1500

tacctgaagg accagcagct gctgggcatc tggggctgca gcggcaagct gatctgcacc   1560

accgccgtgc cctggaacgc cagctggagc aacaagagcc tggaccagat ctggaacaac   1620

atgacctgga tggagtggga gcgcgagatc gacaactaca ccaacctgat ctacaccctg   1680

atcgaggaga gccagaacca gcaggagaag aacgagcagg agctgctgga gctggacaag   1740

tgggccagcc tgtggaactg gttcgacatc agcaagtggc tgtggtacat caagatcttc   1800

atcatgatcg tgggcggcct ggtgggcctg cgcatcgtgt tcaccgtgct gagcatcgtg   1860

aaccgcgtgc gccagggcta cagccccctg agcttccaga cccgcttccc cgcccccgc    1920

ggccccgacc gccccgaggg catcgaggag gagggcggcg agcgcgaccg cgaccgcagc   1980

agcccccctgg tgcacggcct gctggccctg atctgggacg acctgcgcag cctgtgcctg   2040

ttcagctacc accgcctgcg cgacctgatc ctgatcgccg cccgcatcgt ggagctgctg   2100

ggccgccgcg gctgggaggc cctgaagtac tggggcaacc tgctgcagta ctggatccag   2160

gagctgaaga acagcgccgt gagcctgttc gacgccatcg ccatcgccgt ggccgagggc   2220

accgaccgca tcatcgaggt ggcccagcgc atcggccgcg ccttcctgca catcccccgc   2280

cgcatccgcc agggcttcga gcgcgccctg ctgtaactcg ag                      2322
```

<210> SEQ ID NO 19
<211> LENGTH: 2322
<212> TYPE: DNA
<213> ORGANISM: Artificial Sequence
<220> FEATURE:
<223> OTHER INFORMATION: Description of Artificial Sequence:
Leu122-Ser199; Arg426-Lys432

<400> SEQUENCE: 19

```
gaattcgcca ccatggatgc aatgaagaga gggctctgct gtgtgctgct gctgtgtgga     60
```

-continued

```
gcagtcttcg tttcgcccag cgccgtggag aagctgtggg tgaccgtgta ctacggcgtg    120
cccgtgtgga aggaggccac caccaccctg ttctgcgcca gcgacgccaa ggcctacgac    180
accgaggtgc acaacgtgtg ggccacccac gcctgcgtgc ccaccgaccc caacccccag    240
gagatcgtgc tggagaacgt gaccgagaac ttcaacatgt ggaagaacaa catggtggag    300
cagatgcacg aggacatcat cagcctgtgg gaccagagcc tgaagccctg cgtgaagctg    360
ggcaacagcg tgatcaccca ggcctgcccc aaggtgagct tcgagcccat ccccatccac    420
tactgcgccc ccgccggctt cgccatcctg aagtgcaacg acaagaagtt caacggcagc    480
ggcccctgca ccaacgtgag caccgtgcag tgcacccacg gcatccgccc cgtggtgagc    540
acccagctgc tgctgaacgg cagcctggcc gaggagggcg tggtgatccg cagcgagaac    600
ttcaccgaca acgccaagac catcatcgtg cagctgaagg agagcgtgga gatcaactgc    660
acccgcccca acaacaacac ccgcaagagc atcaccatcg gccccggccg cgccttctac    720
gccaccggcg acatcatcgg cgacatccgc caggcccact gcaacatcag cggcgagaag    780
tggaacaaca ccctgaagca gatcgtgacc aagctgcagg cccagttcgg caacaagacc    840
atcgtgttca agcagagcag cggcggcgac cccgagatcg tgatgcacag cttcaactgc    900
ggcggcgagt tcttctactg caacagcacc cagctgttca acagcacctg gaacaacacc    960
atcggcccca acaacaccaa cggcaccatc accctgccct gccgcatcaa gcagatcatc   1020
aaccgcggcg gcaacaaggc catgtacgcc ccccccatcc gcggccagat ccgctgcagc   1080
agcaacatca ccggcctgct gctgacccgc gacggcggca aggagatcag caacaccacc   1140
gagatcttcc gccccggcgg cggcgacatg cgcgacaact ggcgcagcga gctgtacaag   1200
tacaaggtgg tgaagatcga gcccctgggc gtggccccca ccaaggccaa gcgccgcgtg   1260
gtgcagcgcg agaagcgcgc cgtgaccctg ggcgccatgt tcctgggctt cctgggcgcc   1320
gccggcagca ccatgggcgc ccgcagcctg accctgaccg tgcaggcccg ccagctgctg   1380
agcggcatcg tgcagcagca gaacaacctg ctgcgcgcca tcgaggccca gcagcacctg   1440
ctgcagctga ccgtgtgggg catcaagcag ctgcaggccc gcgtgctggc cgtggagcgc   1500
tacctgaagg accagcagct gctgggcatc tggggctgca gcggcaagct gatctgcacc   1560
accgccgtgc cctggaacgc cagctggagc aacaagagcc tggaccagat ctggaacaac   1620
atgacctgga tggagtggga gcgcgagatc gacaactaca ccaacctgat ctacaccctg   1680
atcgaggaga gccagaacca gcaggagaag aacgagcagg agctgctgga gctggacaag   1740
tgggccagcc tgtggaactg gttcgacatc agcaagtggc tgtggtacat caagatcttc   1800
atcatgatcg tgggcggcct ggtgggcctg cgcatcgtgt tcaccgtgct gagcatcgtg   1860
aaccgcgtgc gccagggcta cagcccccctg agcttccaga cccgcttccc cgcccccccgc   1920
ggccccgacc gccccgaggg catcgaggag gagggcggcg agcgcgaccg cgaccgcagc   1980
agcccccctgg tgcacggcct gctggccctg atctgggacg acctgcgcag cctgtgcctg   2040
ttcagctacc accgcctgcg cgacctgatc ctgatcgccg cccgcatcgt ggagctgctg   2100
ggccgccgcg gctgggaggc cctgaagtac tggggcaacc tgctgcagta ctggatccag   2160
gagctgaaga acagcgccgt gagcctgttc gacgccatcg ccatcgccgt ggccgagggc   2220
accgaccgca tcatcgaggt ggcccagcgc atcggccgcg ccttcctgca catccccccgc   2280
cgcatccgcc agggcttcga gcgcgccctg ctgtaactcg ag                      2322
```

<210> SEQ ID NO 20

-continued

<211> LENGTH: 2322
<212> TYPE: DNA
<213> ORGANISM: Artificial Sequence
<220> FEATURE:
<223> OTHER INFORMATION: Description of Artificial Sequence:
Leu122-Ser199; Trp427-Gly431

<400> SEQUENCE: 20

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgaagctg    360

ggcaacagcg tgatcaccca ggcctgcccc aaggtgagct tcgagcccat ccccatccac    420

tactgcgccc ccgccggctt cgccatcctg aagtgcaacg acaagaagtt caacggcagc    480

ggcccctgca ccaacgtgag caccgtgcag tgcacccacg gcatccgccc cgtggtgagc    540

acccagctgc tgctgaacgg cagcctggcc gaggagggcg tggtgatccg cagcgagaac    600

ttcaccgaca acgccaagac catcatcgtg cagctgaagg agagcgtgga gatcaactgc    660

acccgcccca acaacaacac ccgcaagagc atcaccatcg gccccggccg cgccttctac    720

gccaccggcg acatcatcgg cgacatccgc caggcccact gcaacatcag cggcgagaag    780

tggaacaaca ccctgaagca gatcgtgacc aagctgcagg cccagttcgg caacaagacc    840

atcgtgttca agcagagcag cggcggcgac cccgagatcg tgatgcacag cttcaactgc    900

ggcggcgagt tcttctactg caacagcacc cagctgttca acagcacctg gaacaacacc    960

atcggcccca acaacaccaa cggcaccatc accctgccct gccgcatcaa gcagatcatc   1020

aaccgctggg gcggcaaggc catgtacgcc ccccccatcc gcggccagat ccgctgcagc   1080

agcaacatca ccggcctgct gctgacccgc gacggcggca aggagatcag caacaccacc   1140

gagatcttcc gccccggcgg cggcgacatg cgcgacaact ggcgcagcga gctgtacaag   1200

tacaaggtgg tgaagatcga gcccctgggc gtggccccca ccaaggccaa gcgccgcgtg   1260

gtgcagcgcg agaagcgcgc cgtgaccctg ggcgccatgt tcctgggctt cctgggcgcc   1320

gccggcagca ccatgggcgc ccgcagcctg accctgaccg tgcaggcccg ccagctgctg   1380

agcggcatcg tgcagcagca gaacaacctg ctgcgcgcca tcgaggccca gcagcacctg   1440

ctgcagctga ccgtgtgggg catcaagcag ctgcaggccc gcgtgctggc cgtggagcgc   1500

tacctgaagg accagcagct gctgggcatc tggggctgca gcggcaagct gatctgcacc   1560

accgccgtgc cctggaacgc cagctggagc aacaagagcc tggaccagat ctggaacaac   1620

atgacctgga tggagtggga gcgcgagatc gacaactaca ccaacctgat ctacaccctg   1680

atcgaggaga gccagaacca gcaggagaag aacgagcagg agctgctgga gctggacaag   1740

tgggccagcc tgtggaactg gttcgacatc agcaagtggc tgtggtacat caagatcttc   1800

atcatgatcg tgggcggcct ggtgggcctg cgcatcgtgt tcaccgtgct gagcatcgtg   1860

aaccgcgtgc gccagggcta cagcccccgt agcttccaga cccgcttccc cgcccccgc   1920

ggccccgacc gccccgaggg catcgaggag gagggcggcg agcgcgaccg cgaccgcagc   1980

agcccccctgg tgcacggcct gctggccctg atctgggacg acctgcgcag cctgtgcctg   2040

ttcagctacc accgcctgcg cgacctgatc ctgatcgccg cccgcatcgt ggagctgctg   2100
```

-continued

```
ggccgccgcg gctgggaggc cctgaagtac tggggcaacc tgctgcagta ctggatccag   2160

gagctgaaga acagcgccgt gagcctgttc gacgccatcg ccatcgccgt ggccgagggc   2220

accgaccgca tcatcgaggt ggcccagcgc atcggccgcg ccttcctgca catcccccgc   2280

cgcatccgcc agggcttcga gcgcgccctg ctgtaactcg ag                      2322
```

<210> SEQ ID NO 21
<211> LENGTH: 2310
<212> TYPE: DNA
<213> ORGANISM: Artificial Sequence
<220> FEATURE:
<223> OTHER INFORMATION: Description of Artificial Sequence:
Lys121-Val200; Asn425-Lys432

<400> SEQUENCE: 21

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgaaggcc    360

cccgtgatca cccaggcctg ccccaaggtg agcttcgagc ccatccccat ccactactgc    420

gcccccgccg gcttcgccat cctgaagtgc aacgacaaga agttcaacgg cagcggcccc    480

tgcaccaacg tgagcaccgt gcagtgcacc cacggcatcc gccccgtggt gagcacccag    540

ctgctgctga acggcagcct ggccgaggag ggcgtggtga tccgcagcga gaacttcacc    600

gacaacgcca agaccatcat cgtgcagctg aaggagagcg tggagatcaa ctgcacccgc    660

cccaacaaca acacccgcaa gagcatcacc atcggccccg gccgcgcctt ctacgccacc    720

ggcgacatca tcggcgacat ccgccaggcc cactgcaaca tcagcggcga gaagtggaac    780

aacaccctga agcagatcgt gaccaagctg caggcccagt tcggcaacaa gaccatcgtg    840

ttcaagcaga gcagcggcgg cgaccccgag atcgtgatgc acagcttcaa ctgcggcggc    900

gagttcttct actgcaacag cacccagctg ttcaacagca cctggaacaa caccatcggc    960

cccaacaaca ccaacggcac catcaccctg ccctgccgca tcaagcagat catcaacgcc   1020

cccaaggcca tgtacgcccc ccccatccgc ggccagatcc gctgcagcag caacatcacc   1080

ggcctgctgc tgacccgcga cggcggcaag gagatcagca acaccaccga gatcttccgc   1140

cccggcggcg gcgacatgcg cgacaactgg cgcagcgagc tgtacaagta caaggtggtg   1200

aagatcgagc ccctgggcgt ggcccccacc aaggccaagc gccgcgtggt gcagcgcgag   1260

aagcgcgccg tgaccctggg cgccatgttc ctgggcttcc tgggcgccgc cggcagcacc   1320

atgggcgccc gcagcctgac cctgaccgtg caggcccgcc agctgctgag cggcatcgtg   1380

cagcagcaga acaacctgct gcgcgccatc gaggcccagc agcacctgct gcagctgacc   1440

gtgtggggca tcaagcagct gcaggcccgc gtgctggccg tggagcgcta cctgaaggac   1500

cagcagctgc tgggcatctg gggctgcagc ggcaagctga tctgcaccac cgccgtgccc   1560

tggaacgcca gctggagcaa caagagcctg gaccagatct ggaacaacat gacctggatg   1620

gagtgggagc gcgagatcga caactacacc aacctgatct acaccctgat cgaggagagc   1680

cagaaccagc aggagaagaa cgagcaggag ctgctggagc tggacaagtg ggccagcctg   1740

tggaactggt tcgacatcag caagtggctg tggtacatca agatcttcat catgatcgtg   1800
```

-continued

```
ggcggcctgg tgggcctgcg catcgtgttc accgtgctga gcatcgtgaa ccgcgtgcgc   1860

cagggctaca gcccccctgag cttccagacc cgcttccccg ccccccgcgg ccccgaccgc   1920

cccgagggca tcgaggagga gggcggcgag cgcgaccgcg accgcagcag ccccctggtg   1980

cacggcctgc tggccctgat ctgggacgac ctgcgcagcc tgtgcctgtt cagctaccac   2040

cgcctgcgcg acctgatcct gatcgccgcc cgcatcgtgg agctgctggg ccgccgcggc   2100

tgggaggccc tgaagtactg ggcaacctg ctgcagtact ggatccagga gctgaagaac   2160

agcgccgtga gcctgttcga cgccatcgcc atcgccgtgg ccgagggcac cgaccgcatc   2220

atcgaggtgg cccagcgcat cggccgcgcc ttcctgcaca tcccccgccg catccgccag   2280

ggcttcgagc gcgccctgct gtaactcgag                                  2310
```

<210> SEQ ID NO 22
<211> LENGTH: 2298
<212> TYPE: DNA
<213> ORGANISM: Artificial Sequence
<220> FEATURE:
<223> OTHER INFORMATION: Description of Artificial Sequence:
Val120-Ile201; Ile424-Ala433

<400> SEQUENCE: 22

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgggcggc    360

atcacccagg cctgccccaa ggtgagcttc gagcccatcc ccatccacta ctgcgccccc    420

gccggcttcg ccatcctgaa gtgcaacgac aagaagttca acggcagcgg cccctgcacc    480

aacgtgagca ccgtgcagtg cacccacggc atccgccccg tggtgagcac ccagctgctg    540

ctgaacggca gcctggccga ggagggcgtg gtgatccgca gcgagaactt caccgacaac    600

gccaagacca tcatcgtgca gctgaaggag agcgtggaga tcaactgcac ccgccccaac    660

aacaacaccc gcaagagcat caccatcggc cccggccgcg ccttctacgc caccggcgac    720

atcatcggcg acatccgcca ggcccactgc aacatcagcg gcgagaagtg gaacaacacc    780

ctgaagcaga tcgtgaccaa gctgcaggcc cagttcggca acaagaccat cgtgttcaag    840

cagagcagcg gcggcgaccc cgagatcgtg atgcacagct tcaactgcgg cggcgagttc    900

ttctactgca acagcaccca gctgttcaac agcacctgga acaacaccat cggccccaac    960

aacaccaacg gcaccatcac cctgccctgc cgcatcaagc agatcatcgg cggcgccatg   1020

tacgcccccc ccatccgcgg ccagatccgc tgcagcagca acatcaccgg cctgctgctg   1080

acccgcgacg gcggcaagga gatcagcaac accaccgaga tcttccgccc cggcggcggc   1140

gacatgcgcg acaactggcg cagcgagctg tacaagtaca aggtggtgaa gatcgagccc   1200

ctgggcgtgg cccccaccaa ggccaagcgc cgcgtggtgc agcgcgagaa gcgcgccgtg   1260

accctgggcg ccatgttcct gggcttcctg ggcgccgccg gcagcaccat gggcgcccgc   1320

agcctgaccc tgaccgtgca ggcccgccag ctgctgagcg gcatcgtgca gcagcagaac   1380

aacctgctgc gcgccatcga ggcccagcag cacctgctgc agctgaccgt gtggggcatc   1440

aagcagctgc aggcccgcgt gctggccgtg gagcgctacc tgaaggacca gcagctgctg   1500
```

-continued

```
ggcatctggg gctgcagcgg caagctgatc tgcaccaccg ccgtgccctg gaacgccagc   1560

tggagcaaca agagcctgga ccagatctgg aacaacatga cctggatgga gtgggagcgc   1620

gagatcgaca actacaccaa cctgatctac accctgatcg aggagagcca gaaccagcag   1680

gagaagaacg agcaggagct gctggagctg gacaagtggg ccagcctgtg gaactggttc   1740

gacatcagca agtggctgtg gtacatcaag atcttcatca tgatcgtggg cggcctggtg   1800

ggcctgcgca tcgtgttcac cgtgctgagc atcgtgaacc gcgtgcgcca gggctacagc   1860

cccctgagct tccagacccg cttccccgcc ccccgcggcc ccgaccgccc cgagggcatc   1920

gaggaggagg gcggcgagcg cgaccgcgac cgcagcagcc ccctggtgca cggcctgctg   1980

gccctgatct gggacgacct gcgcagcctg tgcctgttca gctaccaccg cctgcgcgac   2040

ctgatcctga tcgccgcccg catcgtggag ctgctgggcc gccgcggctg ggaggccctg   2100

aagtactggg gcaacctgct gcagtactgg atccaggagc tgaagaacag cgccgtgagc   2160

ctgttcgacg ccatcgccat cgccgtggcc gagggcaccg accgcatcat cgaggtggcc   2220

cagcgcatcg gccgcgcctt cctgcacatc ccccgccgca tccgccaggg cttcgagcgc   2280

gccctgctgt aactcgag                                                 2298
```

<210> SEQ ID NO 23
<211> LENGTH: 2298
<212> TYPE: DNA
<213> ORGANISM: Artificial Sequence
<220> FEATURE:
<223> OTHER INFORMATION: Description of Artificial Sequence:
      Val120-Ile201B; Ile424-Ala433

<400> SEQUENCE: 23

```
gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgcccggc    360

atcacccagg cctgccccaa ggtgagcttc gagcccatcc ccatccacta ctgcgccccc    420

gccggcttcg ccatcctgaa gtgcaacgac aagaagttca acggcagcgg cccctgcacc    480

aacgtgagca ccgtgcagtg cacccacggc atccgccccg tggtgagcac ccagctgctg    540

ctgaacggca gcctggccga ggagggcgtg gtgatccgca gcgagaactt caccgacaac    600

gccaagacca tcatcgtgca gctgaaggag agcgtggaga tcaactgcac ccgccccaac    660

aacaacaccc gcaagagcat caccatcggc cccggccgcg ccttctacgc caccggcgac    720

atcatcggcg acatccgcca ggcccactgc aacatcagcg gcgagaagtg gaacaacacc    780

ctgaagcaga tcgtgaccaa gctgcaggcc cagttcggca acaagaccat cgtgttcaag    840

cagagcagcg gcggcgaccc cgagatcgtg atgcacagct tcaactgcgg cggcgagttc    900

ttctactgca acagcaccca gctgttcaac agcacctgga acaacaccat cggccccaac    960

aacaccaacg gcaccatcac cctgccctgc cgcatcaagc agatcatcgg cggcgccatg   1020

tacgcccccc ccatccgcgg ccagatccgc tgcagcagca acatcaccgg cctgctgctg   1080

acccgcgacg gcggcaagga gatcagcaac accaccgaga tcttccgccc cggcggcggc   1140

gacatgcgcg acaactggcg cagcgagctg tacaagtaca aggtggtgaa gatcgagccc   1200
```

-continued ctgggcgtgg cccccaccaa ggccaagcgc cgcgtggtgc agcgcgagaa gcgcgccgtg 1260
accctgggcg ccatgttcct gggcttcctg ggcgccgccg gcagcaccat gggcgcccgc 1320
agcctgaccc tgaccgtgca ggcccgccag ctgctgagcg gcatcgtgca gcagcagaac 1380
aacctgctgc gcgccatcga ggcccagcag cacctgctgc agctgaccgt gtggggcatc 1440
aagcagctgc aggcccgcgt gctggccgtg gagcgctacc tgaaggacca gcagctgctg 1500
ggcatctggg gctgcagcgg caagctgatc tgcaccaccg ccgtgccctg gaacgccagc 1560
tggagcaaca agagcctgga ccagatctgg aacaacatga cctggatgga gtgggagcgc 1620
gagatcgaca actacaccaa cctgatctac accctgatcg aggagagcca gaaccagcag 1680
gagaagaacg agcaggagct gctggagctg gacaagtggg ccagcctgtg gaactggttc 1740
gacatcagca agtggctgtg gtacatcaag atcttcatca tgatcgtggg cggcctggtg 1800
ggcctgcgca tcgtgttcac cgtgctgagc atcgtgaacc gcgtgcgcca gggctacagc 1860
cccctgagct tccagacccg cttccccgcc ccccgcggcc ccgaccgccc cgagggcatc 1920
gaggaggagg gcggcgagcg cgaccgcgac cgcagcagcc ccctggtgca cggcctgctg 1980
gccctgatct gggacgacct gcgcagcctg tgcctgttca gctaccaccg cctgcgcgac 2040
ctgatcctga tcgccgcccg catcgtggag ctgctgggcc gccgcggctg ggaggccctg 2100
aagtactggg gcaacctgct gcagtactgg atccaggagc tgaagaacag cgccgtgagc 2160
ctgttcgacg ccatcgccat cgccgtggcc gagggcaccg accgcatcat cgaggtggcc 2220
cagcgcatcg gccgcgcctt cctgcacatc ccccgccgca tccgccaggg cttcgagcgc 2280
gccctgctgt aactcgag 2298

<210> SEQ ID NO 24
<211> LENGTH: 2298
<212> TYPE: DNA
<213> ORGANISM: Artificial Sequence
<220> FEATURE:
<223> OTHER INFORMATION: Description of Artificial Sequence:
Val120-Thr202; Ile424-Ala433

<400> SEQUENCE: 24
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240
gagatcgtgc tggagaacgt gaccgagaac ttcaacatgt ggaagaacaa catggtggag 300
cagatgcacg aggacatcat cagcctgtgg gaccagagcc tgaagccctg cgtgggcggc 360
gccacccagg cctgccccaa ggtgagcttc gagcccatcc ccatccacta ctgcgccccc 420
gccggcttcg ccatcctgaa gtgcaacgac aagaagttca acggcagcgg cccctgcacc 480
aacgtgagca ccgtgcagtg cacccacggc atccgccccg tggtgagcac ccagctgctg 540
ctgaacggca gcctggccga ggagggcgtg gtgatccgca gcgagaactt caccgacaac 600
gccaagacca tcatcgtgca gctgaaggag agcgtggaga tcaactgcac ccgccccaac 660
aacaacaccc gcaagagcat caccatcggc cccggccgcg ccttctacgc caccggcgac 720
atcatcggcg acatccgcca ggcccactgc aacatcagcg gcgagaagtg gaacaacacc 780
ctgaagcaga tcgtgaccaa gctgcaggcc cagttcggca acaagaccat cgtgttcaag 840
cagagcagcg gcggcgaccc cgagatcgtg atgcacagct tcaactgcgg cggcgagttc 900

-continued

```
ttctactgca acagcaccca gctgttcaac agcacctgga acaacaccat cggccccaac    960

aacaccaacg gcaccatcac cctgccctgc cgcatcaagc agatcatcgg cggcgccatg   1020

tacgcccccc ccatccgcgg ccagatccgc tgcagcagca acatcaccgg cctgctgctg   1080

acccgcgacg gcggcaagga gatcagcaac accaccgaga tcttccgccc cggcggcggc   1140

gacatgcgcg acaactggcg cagcgagctg tacaagtaca aggtggtgaa gatcgagccc   1200

ctgggcgtgg cccccaccaa ggccaagcgc cgcgtggtgc agcgcgagaa gcgcgccgtg   1260

accctgggcg ccatgttcct gggcttcctg ggcgccgccg gcagcaccat gggcgcccgc   1320

agcctgaccc tgaccgtgca ggcccgccag ctgctgagcg gcatcgtgca gcagcagaac   1380

aacctgctgc gcgccatcga ggcccagcag cacctgctgc agctgaccgt gtggggcatc   1440

aagcagctgc aggcccgcgt gctggccgtg gagcgctacc tgaaggacca gcagctgctg   1500

ggcatctggg gctgcagcgg caagctgatc tgcaccaccg ccgtgccctg gaacgccagc   1560

tggagcaaca agagcctgga ccagatctgg aacaacatga cctggatgga gtgggagcgc   1620

gagatcgaca actacaccaa cctgatctac accctgatcg aggagagcca gaaccagcag   1680

gagaagaacg agcaggagct gctggagctg gacaagtggg ccagcctgtg gaactggttc   1740

gacatcagca agtggctgtg gtacatcaag atcttcatca tgatcgtggg cggcctggtg   1800

ggcctgcgca tcgtgttcac cgtgctgagc atcgtgaacc gcgtgcgcca gggctacagc   1860

cccctgagct tccagacccg cttccccgcc ccccgcggcc ccgaccgccc cgagggcatc   1920

gaggaggagg gcggcgagcg cgaccgcgac cgcagcagcc ccctggtgca cggcctgctg   1980

gccctgatct gggacgacct gcgcagcctg tgcctgttca gctaccaccg cctgcgcgac   2040

ctgatcctga tcgccgcccg catcgtggag ctgctgggcc gccgcggctg ggaggccctg   2100

aagtactggg gcaacctgct gcagtactgg atccaggagc tgaagaacag cgccgtgagc   2160

ctgttcgacg ccatcgccat cgccgtggcc gagggcaccg accgcatcat cgaggtggcc   2220

cagcgcatcg gccgcgcctt cctgcacatc ccccgccgca tccgccaggg cttcgagcgc   2280

gccctgctgt aactcgag                                                 2298


<210> SEQ ID NO 25
<211> LENGTH: 2358
<212> TYPE: DNA
<213> ORGANISM: Artificial Sequence
<220> FEATURE:
<223> OTHER INFORMATION: Description of Artificial Sequence:
      Val127-Asn195

<400> SEQUENCE: 25

gaattcgcca ccatggatgc aatgaagaga gggctctgct gtgtgctgct gctgtgtgga     60

gcagtcttcg tttcgcccag cgccgtggag aagctgtggg tgaccgtgta ctacggcgtg    120

cccgtgtgga aggaggccac caccaccctg ttctgcgcca gcgacgccaa ggcctacgac    180

accgaggtgc acaacgtgtg ggccacccac gcctgcgtgc ccaccgaccc caacccccag    240

gagatcgtgc tggagaacgt gaccgagaac ttcaacatgt ggaagaacaa catggtggag    300

cagatgcacg aggacatcat cagcctgtgg gaccagagcc tgaagccctg cgtgaagctg    360

accccccctgt gcgtgggggc agggaactgc aacaccagcg tgatcaccca ggcctgcccc    420

aaggtgagct tcgagcccat ccccatccac tactgcgccc ccgccggctt cgccatcctg    480

aagtgcaacg acaagaagtt caacggcagc ggcccctgca ccaacgtgag caccgtgcag    540

tgcacccacg gcatccgccc cgtggtgagc acccagctgc tgctgaacgg cagcctggcc    600
```

-continued gaggagggcg tggtgatccg cagcgagaac ttcaccgaca acgccaagac catcatcgtg 660
cagctgaagg agagcgtgga gatcaactgc acccgcccca acaacaacac ccgcaagagc 720
atcaccatcg gccccggccg cgccttctac gccaccggcg acatcatcgg cgacatccgc 780
caggcccact gcaacatcag cggcgagaag tggaacaaca ccctgaagca gatcgtgacc 840
aagctgcagg cccagttcgg caacaagacc atcgtgttca agcagagcag cggcggcgac 900
cccgagatcg tgatgcacag cttcaactgc ggcggcgagt tcttctactg caacagcacc 960
cagctgttca acagcacctg gaacaacacc atcggcccca acaacaccaa cggcaccatc 1020
accctgccct gccgcatcaa gcagatcatc aaccgctggc aggaggtggg caaggccatg 1080
tacgcccccc ccatccgcgg ccagatccgc tgcagcagca acatcaccgg cctgctgctg 1140
acccgcgacg gcggcaagga gatcagcaac accaccgaga tcttccgccc cggcggcggc 1200
gacatgcgcg acaactggcg cagcgagctg tacaagtaca aggtggtgaa gatcgagccc 1260
ctgggcgtgg cccccaccaa ggccaagcgc cgcgtggtgc agcgcgagaa gcgcgccgtg 1320
accctgggcg ccatgttcct gggcttcctg ggcgccgccg gcagcaccat gggcgcccgc 1380
agcctgaccc tgaccgtgca ggcccgccag ctgctgagcg gcatcgtgca gcagcagaac 1440
aacctgctgc gcgccatcga ggcccagcag cacctgctgc agctgaccgt gtggggcatc 1500
aagcagctgc aggcccgcgt gctggccgtg gagcgctacc tgaaggacca gcagctgctg 1560
ggcatctggg gctgcagcgg caagctgatc tgcaccaccg ccgtgccctg gaacgccagc 1620
tggagcaaca agagcctgga ccagatctgg aacaacatga cctggatgga gtgggagcgc 1680
gagatcgaca actacaccaa cctgatctac accctgatcg aggagagcca gaaccagcag 1740
gagaagaacg agcaggagct gctggagctg gacaagtggg ccagcctgtg gaactggttc 1800
gacatcagca agtggctgtg gtacatcaag atcttcatca tgatcgtggg cggcctggtg 1860
ggcctgcgca tcgtgttcac cgtgctgagc atcgtgaacc gcgtgcgcca gggctacagc 1920
cccctgagct tccagacccg cttccccgcc ccccgcggcc ccgaccgccc cgagggcatc 1980
gaggaggagg gcggcgagcg cgaccgcgac cgcagcagcc ccctggtgca cggcctgctg 2040
gccctgatct gggacgacct gcgcagcctg tgcctgttca gctaccaccg cctgcgcgac 2100
ctgatcctga tcgccgcccg catcgtggag ctgctgggcc gccgcggctg ggaggccctg 2160
aagtactggg gcaacctgct gcagtactgg atccaggagc tgaagaacag cgccgtgagc 2220
ctgttcgacg ccatcgccat cgccgtggcc gagggcaccg accgcatcat cgaggtggcc 2280
cagcgcatcg gccgcgcctt cctgcacatc ccccgccgca tccgccaggg cttcgagcgc 2340
gccctgctgt aactcgag 2358

<210> SEQ ID NO 26
<211> LENGTH: 2352
<212> TYPE: DNA
<213> ORGANISM: Artificial Sequence
<220> FEATURE:
<223> OTHER INFORMATION: Description of Artificial Sequence:
Val127-Asn195; Arg426-Gly431

<400> SEQUENCE: 26
gaattcgcca ccatggatgc aatgaagaga gggctctgct gtgtgctgct gctgtgtgga 60
gcagtcttcg tttcgcccag cgccgtggag aagctgtggg tgaccgtgta ctacggcgtg 120
cccgtgtgga aggaggccac caccaccctg ttctgcgcca gcgacgccaa ggcctacgac 180
accgaggtgc acaacgtgtg ggccacccac gcctgcgtgc ccaccgaccc caacccccag 240

-continued

```
gagatcgtgc tggagaacgt gaccgagaac ttcaacatgt ggaagaacaa catggtggag    300

cagatgcacg aggacatcat cagcctgtgg gaccagagcc tgaagccctg cgtgaagctg    360

acccccctgt gcgtgggggc agggaactgc aacaccagcg tgatcaccca ggcctgcccc    420

aaggtgagct tcgagcccat ccccatccac tactgcgccc ccgccggctt cgccatcctg    480

aagtgcaacg acaagaagtt caacggcagc ggcccctgca ccaacgtgag caccgtgcag    540

tgcacccacg gcatccgccc cgtggtgagc acccagctgc tgctgaacgg cagcctggcc    600

gaggagggcg tggtgatccg cagcgagaac ttcaccgaca acgccaagac catcatcgtg    660

cagctgaagg agagcgtgga gatcaactgc acccgcccca acaacaacac ccgcaagagc    720

atcaccatcg gccccggccg cgccttctac gccaccggcg acatcatcgg cgacatccgc    780

caggcccact gcaacatcag cggcgagaag tggaacaaca ccctgaagca gatcgtgacc    840

aagctgcagg cccagttcgg caacaagacc atcgtgttca agcagagcag cggcggcgac    900

cccgagatcg tgatgcacag cttcaactgc ggcggcgagt tcttctactg caacagcacc    960

cagctgttca acagcacctg gaacaacacc atcggcccca acaacaccaa cggcaccatc   1020

accctgccct gccgcatcaa gcagatcatc aaccgcggcg gcggcaaggc catgtacgcc   1080

ccccccatcc gcggccagat ccgctgcagc agcaacatca ccggcctgct gctgacccgc   1140

gacggcggca aggagatcag caacaccacc gagatcttcc gccccggggg cggcgacatg   1200

cgcgacaact ggcgcagcga gctgtacaag tacaaggtgg tgaagatcga gcccctgggc   1260

gtggccccca ccaaggccaa gcgccgcgtg gtgcagcgcg agaagcgcgc cgtgaccctg   1320

ggcgccatgt tcctgggctt cctgggcgcc gccggcagca ccatgggcgc ccgcagcctg   1380

accctgaccg tgcaggcccg ccagctgctg agcggcatcg tgcagcagca gaacaacctg   1440

ctgcgcgcca tcgaggccca gcagcacctg ctgcagctga ccgtgtgggg catcaagcag   1500

ctgcaggccc gcgtgctggc cgtggagcgc tacctgaagg accagcagct gctgggcatc   1560

tggggctgca gcggcaagct gatctgcacc accgccgtgc cctggaacgc cagctggagc   1620

aacaagagcc tggaccagat ctggaacaac atgacctgga tggagtggga gcgcgagatc   1680

gacaactaca ccaacctgat ctacaccctg atcgaggaga gccagaacca gcaggagaag   1740

aacgagcagg agctgctgga gctggacaag tgggccagcc tgtggaactg gttcgacatc   1800

agcaagtggc tgtggtacat caagatcttc atcatgatcg tgggcggcct ggtgggcctg   1860

cgcatcgtgt tcaccgtgct gagcatcgtg aaccgcgtgc gccagggcta cagcccccctg   1920

agcttccaga cccgcttccc cgccccccgc ggccccgacc gccccgaggg catcgaggag   1980

gagggcggcg agcgcgaccg cgaccgcagc agcccccctgg tgcacggcct gctggccctg   2040

atctgggacg acctgcgcag cctgtgcctg ttcagctacc accgcctgcg cgacctgatc   2100

ctgatcgccg cccgcatcgt ggagctgctg ggccgccgcg gctgggaggc cctgaagtac   2160

tggggcaacc tgctgcagta ctggatccag gagctgaaga acagcgccgt gagcctgttc   2220

gacgccatcg ccatcgccgt ggccgagggc accgaccgca tcatcgaggt ggcccagcgc   2280

atcggccgcg ccttcctgca catcccccgc cgcatccgcc agggcttcga gcgcgccctg   2340

ctgtaactcg ag                                                        2352
```

MODIFIED HIV ENV POLYPEPTIDES

CROSS-REFERENCE TO RELATED APPLICATIONS

This application is related to provisional patent applications serial Nos. 60/114,495, filed Dec. 31, 1998 and 60/156,670, filed Sep. 29, 1999, from which priority is claimed under 35 USC §119(e)(1) and which applications are incorporated herein by reference in their entireties.

TECHNICAL FIELD

The invention relates generally to modified HIV envelope (Env) polypeptides which are useful as immunizing agents or for generating an immune response in a subject, for example a cellular immune response or a protective immune response. More particularly, the invention relates Env polypeptides such as gp120, gp140 or gp160, wherein at least one of the native β-sheet configurations has been modified. The invention also pertains to methods of using these polypeptides to elicit an immune response against a broad range of HIV subtypes.

BACKGROUND OF THE INVENTION

The human immunodeficiency virus (HIV-1, also referred to as HTLV-III, LAV or HTLV-III/LAV) is the etiological agent of the acquired immune deficiency syndrome (AIDS) and related disorders. (see, e.g., Barre-Sinoussi, et al., (1983) *Science* 220:868–871; Gallo et al. (1984) *Science* 224:500–503; Levy et al., (1984) *Science* 225:840–842; Siegal et al., (1981) *N. Engl. J. Med.* 305:1439–1444). AIDS patients usually have a long asymptomatic period followed by the progressive degeneration of the immune system and the central nervous system. Replication of the virus is highly regulated, and both latent and lytic infection of the CD4 positive helper subset of T-lymphocytes occur in tissue culture (Zagury et al., (1986) *Science* 231:850–853). Molecular studies of HIV-1 show that it encodes a number of genes (Ratner et al., (1985) *Nature* 313:277–284; Sanchez-Pescador et al., (1985) *Science* 227:484–492), including three structural genes—gag, pol and env—that are common to all retroviruses. Nucleotide sequences from viral genomes of other retroviruses, particularly HIV-2 and simian immunodeficiency viruses, SIV (previously referred to as STLV-III), also contain these structural genes. (Guyader et al., (1987) *Nature* 326:662–669; Chakrabarti et al., (1987) *Nature.*

The envelope protein of HIV-1, HIV-2 and SIV is a glycoprotein of about 160 kd (gp160). During virus infection of the host cell, gp160 is cleaved by host cell proteases to form gp120 and the integral membrane protein, gp41. The gp41 portion is anchored in the membrane bilayer of virion, while the gp120 segment protrudes into the surrounding environment. gp120 and gp41 are more covalently associated and free gp120 can be released from the surface of virions and infected cells.

As depicted in FIG. 1, crystallography studies of the gp 120 core polypeptide indicate that this polypeptide is folded into two major domains having certain emanating structures. The inner domain (inner with respect to the N and C terminus) features a two-helix, two-stranded bundle with a small five-stranded β-sandwich at its termini-proximal end and a projection at the distal end from which the V1/V2 stem emanates. The outer domain is a staked double barrel that lies along side the inner domain so that the outer barrel and inner bundle axes are approximately parallel. Between the distal inner domain and the distal outer domain is a four-stranded bridging sheet which holds a peculiar minidomain in contact with, but distinct from, the inner, the outer domain, and the V1/V2 domain. The bridging sheet is composed of four β-strand structures (β-3, β-2, β-21, β-20, shown in FIG. 1). The bridging region can be seen in FIG. 1 packing primarily over the inner domain, although some surface residues of the outer domain, such as Phe 382, reach into the bridging sheet to form part of its hydrophobic core.

The basic unit of the β-sheet conformation of the bridging sheet region is the β-strand which exists as a less tightly coiled helix, with 2.0 residues per turn. The β-strand conformation is only stable when incorporated into a β-sheet, where hydrogen bonds with close to optimal geometry are formed between the peptide groups on adjacent β-strands; the dipole moments of the strands are also aligned favorably. Side chains from adjacent residues of the same strand protrude from opposite sides of the sheet and do not interact with each other, but have significant interactions with their backbone and with the side chains of neighboring strands. For a general description of β-sheets, see, e.g., T. E. Creighton, *Proteins: Structures and Molecular Properties* (W. H. Freeman and Company, 1993); and A. L. Lehninger, *Biochemistry* (Worth Publishers, Inc., 1975).

The gp120 polypeptide is instrumental in mediating entry into the host cell. Recent studies have indicated that binding of CD4 to gp120 induces a conformational change in Env that allows for binding to a co-receptor (e.g, a chemokine receptor) and subsequent entry of the virus into the cell. (Wyatt, R., et al. (1998) *Nature* 393:705–711; Kwong, P., et al.(1998) *Nature* 393:648–659). Referring again to FIG. 1, CD4 is bound into a depression formed at the interface of the outer domain, the inner domain and the bridging sheet of gp120.

Immunogenicity of the gp120 polypeptide has also been studied. For example, individuals infected by HIV-1 usually develop antibodies that can neutralize the virus in in vitro assays, and this response is directed primarily against linear neutralizing determinants in the third variable loop of gp120 glycoprotein (Javaherian, K., et al. (1989) *Proc. Natl. Acad. Sci.* 86:6786–6772; Matsushita, M., et al. (1988) *J. Virol.* 62:2107–2144; Putney, S., et al. (1986) *Science* 234:1392–1395; Rushe, J. R., et al. (1988) *Proc. Nat. Acad. Sci. USA* 85: 3198–3202.). However, these antibodies generally exhibit the ability to neutralize only a limited number of HIV-1 strains (Matthews, T. (1986) *Proc. Nat. Acad. Sci. USA*. 83:9709–9713; Nara, P. L., et al. (1988) *J. Virol.* 62:2622–2628; Palker, T. J., et al. (1988) *Proc. Natl. Acad. Sci. USA*. 85:1932–1936). Later in the course of HIV infection in humans, antibodies capable of neutralizing a wider range of HIV-1 isolates appear (Barre-Sinoussi, F., et al. (1983) *Science* 220:868–871; Robert-Guroff, M., et al. (1985) *Nature* (London) 316:72–74; Weis, R., et al. (1985) *Nature* (London) 316:69–72; Weis, R., et al. (1986) *Nature* (London) 324:572–575).

Recent work done by Stamatatos et al (1998) *AIDS Res Hum Retroviruses* 14(13):1129–39, shows that a deletion of the variable region 2 from a HIV-$1_{SF162}$ virus, which utilizes the CCR-5 co-receptor for virus entry, rendered the virus highly susceptible to serum-mediated neutralization. This V2 deleted virus was also neutralized by sera obtained from patients infected not only with clade B HIV-1 isolates but also with clade A, C, D and F HIV-1 isolates. However, deletion of the variable region 1 had no effect. Deletion of the variable regions 1 and 2 from a LAI isolate HIV-$I_{IIIB}$ also increased the susceptibility to neutralization by monoclonal antibodies whose epitopes are located within the V3 loop, the CD4-binding site, and conserved gp120 regions (Wyatt, R., et al. (1995) *J. Virol.* 69:5723–5733). Rabbit immunogenicity studies done with the HIV-1 virus with deletions in the V1/V2 and V3 region from the LAI strain, which uses the CXCR4 co-receptor for virus entry, showed no improvement in the ability of Env to raise neutralizing antibodies (Leu et al. (1998) *AIDS Res. and Human Retroviruses*. 14:151–155).

Further, a subset of the broadly reactive antibodies, found in most infected individuals, interferes with the binding of gp120 and CD4 (Kang, C. -Y., et al. (1991) *Proc. Natl. Acad. Sci. USA*. 88:6171–6175; McDougal, J. S., et al. (1986) *J. Immunol.* 137:2937–2944). Other antibodies are believed to bind to the chemokine receptor binding region after CD4 has bound to Env (Thali et al. (1993) *J. Virol.* 67:3978–3988). The fact that neutralizing antibodies generated during the course of HIV infection do not provide permanent antiviral effect may in part be due to the generation of "neutralization escapes" virus mutants and to the general decline in the host immune system associated with pathogenesis. In contrast, the presence of pre-existing neutralizing antibodies upon initial HIV-1 exposure will likely have a protective effect.

It is widely thought that a successful vaccine should be able to induce a strong, broadly neutralizing antibody response against diverse HIV-1 strains (Montefiori and Evans (1999) *AIDS Res. Hum. Ret.* 15(8):689–698; Bolognesi, D., P., et al. (1994) *Ann. Int. Med.* 8:603–611; Haynes, B., F., et al. (1996) *Science*; 271: 324–328.). Neutralizing antibodies, by attaching to the incoming virions, can reduce or even prevent their infectivity for target cells and prevent the cell-to-cell spread of virus in tissue culture (Hu et al. (1992) *Science* 255:456–459; Burton, D., R. and Montefiori, D. (1997) *AIDS* 11(suppl. A): 587–598). However as described above, antibodies directed against gp120 do not generally exhibit broad antibody responses against different HIV strains.

Currently, the focus of vaccine development, from the perspective of humoral immunity, is on the neutralization of primary isolates that utilize the CCR5 chemokine co-receptor believed to be important in virus entry (Zhu, T., et al. (1993) *Science* 261:1179–1181; Fiore, J., et al. (1994) Virology; 204:297–303). These viruses are generally much more resistant to antibody neutralization than T-cell line adapted strains that use the CXCR4 co-receptor, although both can be neutralized in vitro by certain broadly and potent acting monoclonal antibodies, such as IgG1b12, 2G12 and 2F5 (Trkola, A., et al. (1995) *J. Virol.* 69:6609–6617; D'Sousa P M., et al (1997) *J. Infect. Dis.* 175:1062–1075). These monoclonal antibodies are directed to the CD4 binding site, a glycosylation site and to the gp41 fusion domain, respectively. The problem that remains, however, is that it is not known how to induce antibodies of the appropriate specificity by vaccination. Antibodies (Abs) elicited by gp120 glycoprotein from a given isolate are usually only able to neutralize closely related viruses generally from similar, usually from the same, HIV-1 subtype.

Despite the above approaches, there remains a need for Env antigens that can elicit an immunological response (e.g., neutralizing and/or protective antibodies) in a subject against multiple HIV strains and subtypes, for example when administered as a vaccine. The present invention solves these and other problems by providing modified Env polypeptides (e.g., gp120) to expose epitopes in or near the CD4 binding site.

SUMMARY OF THE INVENTION

In accordance with the present invention, modified HIV Env polypeptides are provided. In particular, deletions and/or mutations are made in one or more of the 4-β antiparallel-bridging sheet in the HIV Env polypeptide. In this way, enough structure is left to allow correct folding of the polypeptide, for example of gp120, yet enough of the bridging sheet is removed to expose the CD4 groove, allowing an immune response to be generated against epitopes in or near the CD4 binding site of the Env polypeptide (e.g., gp120).

In one aspect, the invention includes a polynucleotide encoding a modified HIV Env polypeptide wherein the polypeptide has at least one modified (e.g., deleted or replaced) amino acid residue deleted in the region corresponding to residues 421 to 436 relative to HXB-2, for example the constructs depicted in FIGS. 6–29 (SEQ ID NOs:3 to 26). In certain embodiments, the polynucleotide also has the region corresponding to residues 124–198 of the polypeptide HXB-2 (e.g., V1/V2) deleted and at least one amino acid deleted or replaced in the regions corresponding to the residues 119 to 123 and 199 to 210, relative to HXB-2. In other embodiments, these polynucleotides encode Env polypeptides having at least one amino acid of the small loop of the bridging sheet (e.g., amino acid residues 427 to 429 relative to HXB-2) deleted or replaced. The amino acid sequences of the modified polypeptides encoded by the polynucleotides of the present invention can be based on any HIV variant, for example SF162.

In another aspect, the invention includes immunogenic modified HIV Env polypeptides having at least one modified (e.g., deleted or replaced) amino acid residue deleted in the region corresponding to residues 421 to 436 relative to HXB-2, for example a deletion or replacement of one amino acids in the small loop region (e.g., amino acid residues 427 to 429 relative to HXB-2). These polypeptides may have modifications (e.g., a deletion or a replacement) of at least one amino acid between about amino acid residue 420 and amino acid residue 436, relative to HXB-2 and, optionally, may have deletions or truncations of the V1 and/or V2 regions. The immunogenic, modified polypeptides of the present invention can be based on any HIV variant, for example SF162.

In another aspect, the invention includes a vaccine composition comprising any of the polynucleotides encoding modified Env polypeptides described above. Vaccine compositions comprising the modified Env polypeptides and, optionally, an adjuvant are also included in the invention.

In yet another aspect, the invention includes a method of inducing an immune response in subject comprising, administering one or more of the polynucleotides or constructs described above in an amount sufficient to induce an immune response in the subject. In certain embodiments, the method further comprises administering an adjuvant to the subject.

In another aspect, the invention includes a method of inducing an immune response in a subject comprising administering a composition comprising any of the modified Env polypeptides described above and an adjuvant. The composition is administered in an amount sufficient to induce an immune response in the subject.

In another aspect, the invention includes a method of inducing an immune response in a subject comprising (a) administering a first composition comprising any of the polynucleotides described above in a priming step and (b) administering a second composition comprising any of the modified Env polypeptides described above, as a booster, in an amount sufficient to induce an immune response in the subject. In certain embodiments, the first composition, the second composition or both the first and second compositions further comprise an adjuvant.

These and other embodiments of the subject invention will readily occur to those of skill in the art in light of the disclosure herein.

BRIEF DESCRIPTION OF THE DRAWINGS

FIGS. 2A–C depict alignment of the amino acid sequence of wild-type HIV-$1_{HXB-2}$ Env gp160 polypeptide (SEQ ID NO:1) with amino acid sequence of HIV variants SF162 (shown as "162") (SEQ ID NO:2), SF2, CM236 and US4. Arrows indicate the regions that are deleted or replaced in the modified polypeptides. Black dots indicate conserved cysteine residues. The star indicates the position of the last amino acid in gp120.

FIGS. 3A–J depict alignment of nucleotide sequences of polynucleotides encoding modified Env polypeptides having V1/V2 deletions. The unmodified amino acid residues encoded by these sequences correspond to wildtype SF162 residues but are numbered relative to HXB-2.

FIGS. 4A–M depict alignment of nucleotide sequences of polynucleotides encoding modified Env polypeptides having deletions or replacements in the small loop. The unmodified amino acid residues encoded by these sequences correspond to wildtype SF162 residues but are numbered relative to HXB-2.

FIGS. 5A–N depict alignment of nucleotide sequences of polynucleotides encoding modified Env polypeptides having both V1/V2 deletions and, in addition, deletions or replacements in the small loop. The unmodified amino acid residues encoded by these sequences correspond to wildtype SF162 residues but are numbered relative to HXB-2.

FIG. 6 depicts the nucleotide sequence of the construct designated Val120-Ala204 (SEQ ID NO:3).

FIG. 7 depicts the nucleotide sequence of the construct designated Val120-Ile201 (SEQ ID NO:4).

FIG. 8 depicts the nucleotide sequence of the construct designated Val120-Ile201B (SEQ ID NO:5).

FIG. 9 depicts the nucleotide sequence of the construct designated Lys121-Val200 (SEQ ID NO:6).

FIG. 10 depicts the nucleotide sequence of the construct designated Leu122-Ser199 (SEQ ID NO:7).

FIG. 11 depicts the nucleotide sequence of the construct designated Val120-Thr202 (SEQ ID NO:8).

FIG. 12 depicts the nucleotide sequence of the construct designated Trp427-Gly431 (SEQ ID NO:9).

FIG. 13 depicts the nucleotide sequence of the construct designated Arg426-Gly431 (SEQ ID NO:10).

FIG. 14 depicts the nucleotide sequence of the construct designated Arg426-Gly431B (SEQ ID NO:11).

FIG. 15 depicts the nucleotide sequence of the construct designated Arg426-Lys432 (SEQ ID NO:12).

FIG. 16 depicts the nucleotide sequence of the construct designated Asn425-Lys432 (SEQ ID NO:13).

FIG. 17 depicts the nucleotide sequence of the construct designated Ile424-Ala433 (SEQ ID NO:14).

FIG. 18 depicts the nucleotide sequence of the construct designated Ile423-Met434 (SEQ ID NO:15).

FIG. 19 depicts the nucleotide sequence of the construct designated Gln422-Tyr435 (SEQ ID NO:16).

FIG. 20 depicts the nucleotide sequence of the construct designated Gln422-Tyr435B (SEQ ID NO:17).

FIG. 21 depicts the nucleotide sequence of the construct designated Leu122-Ser199;Arg426-Gly431 (SEQ ID NO:18).

FIG. 22 depicts the nucleotide sequence of the construct designated Leu122-Ser199;Arg426-Lys432 (SEQ ID NO:19).

FIG. 23 depicts the nucleotide sequence of the construct designated Leu122-Ser199; Trp427-Gly431 (SEQ ID NO:20).

FIG. 24 depicts the nucleotide sequence of the construct designated Lys121-Val200; Asn425-Lys432 (SEQ ID NO:21).

FIG. 25 depicts the nucleotide sequence of the construct designated Val120-Ile201; Ile424-Ala433 (SEQ ID NO:22).

FIG. 26 depicts the nucleotide sequence of the construct designated Val120-Ile201B; Ile424-Ala433 (SEQ ID NO:23).

FIG. 27 depicts the nucleotide sequence of the construct designated Val120-Thr202; Ile424-Ala433 (SEQ ID NO:24).

FIG. 28 depicts the nucleotide sequence of the construct designated Val127-Asn195 (SEQ ID NO:25).

FIG. 29 depicts the nucleotide sequence of the construct designated Val127-Asn195; Arg426-Gly431 (SEQ ID NO:26).

DETAILED DESCRIPTION OF THE INVENTION

Figure 1:
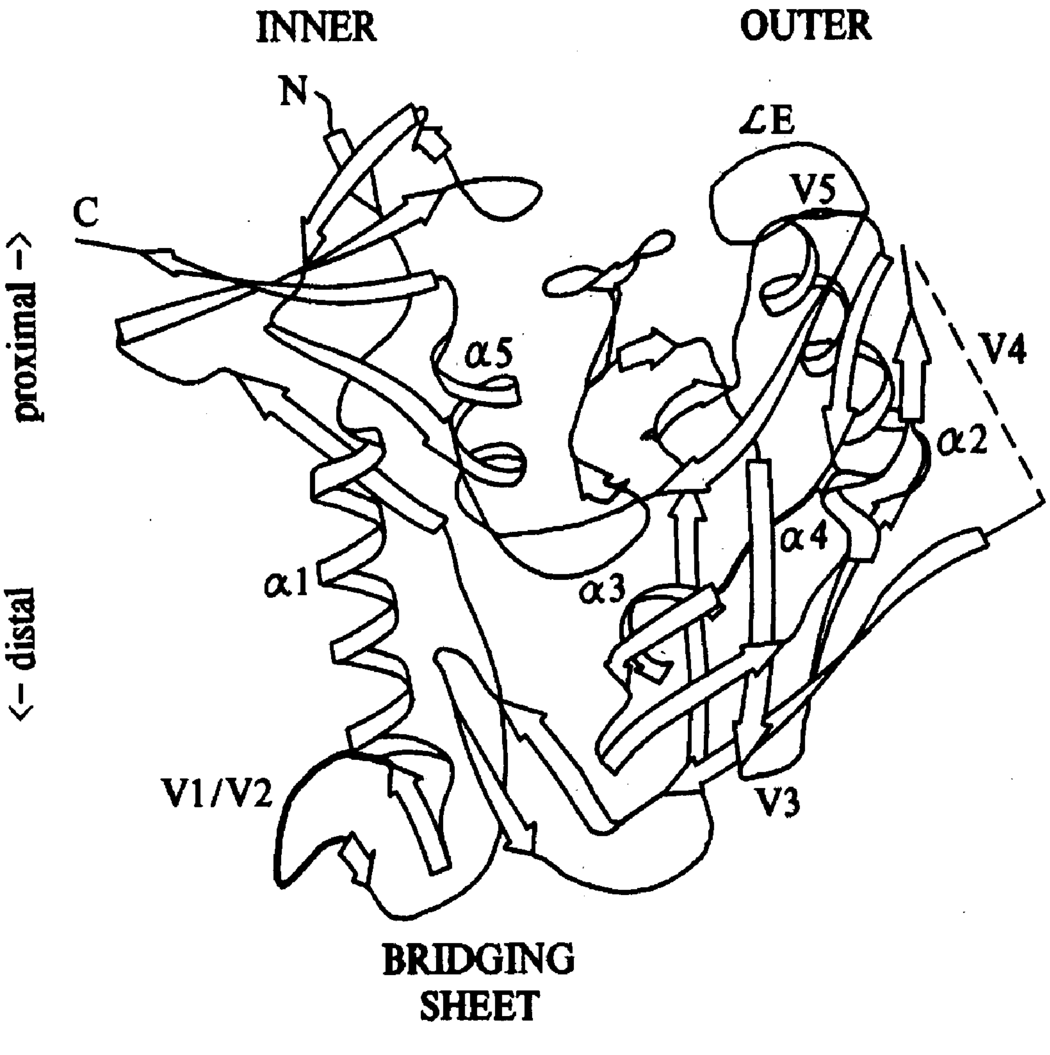
FIG. 1 is a schematic depiction of the tertiary structure of the HIV-$1_{HBX-2}$ Env gp120 polypeptide, as determined by crystallography studies.

The practice of the present invention will employ, unless otherwise indicated, conventional methods of protein chemistry, viral immunobiology, molecular biology and recombinant DNA techniques within the skill of the art. Such techniques are explained fully in the literature. See, e.g., T. E. Creighton, *Proteins: Structures and Molecular Properties* (W. H. Freeman and Company, 1993); Nelson L. M. and Jerome H. K. *HIV Protocols* in Methods in Molecular Medicine, vol. 17, 1999; Sambrook, et al., *Molecular Cloning: A Laboratory Manual* (Cold Spring Harbor Laboratory, 1989); F. M. Ausubel et al. *Current Protocols in Molecular Biology*, Greene Publishing Associates & Wiley Interscience New York; and Lipkowitz and Boyd, *Reviews in Computational Chemistry*, volumes 1-present (Wiley-VCH, New York, N.Y., 1999).

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

All publications, patents and patent applications cited herein, whether supra or infra, are hereby incorporated by reference in their entirety.

Definitions

In describing the present invention, the following terms will be employed, and are intended to be defined as indicated below.

The terms "polypeptide," and "protein" are used interchangeably herein to denote any polymer of amino acid residues. The terms encompass peptides, oligopeptides, dimers, multimers, and the like. Such polypeptides can be derived from natural sources or can be synthesized or recombinantly produced. The terms also include postexpression modifications of the polypeptide, for example, glycosylation, acetylation, phosphorylation, etc.

A polypeptide as defined herein is generally made up of the 20 natural amino acids Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y) and Val (V) and may also include any of the several known amino acid analogs, both naturally occurring and synthesized analogs, such as but not limited to homoisoleucine, asaleucine, 2-(methylenecyclopropyl) glycine, S-methylcysteine, S-(prop-1-enyl)cysteine, homoserine, ornithine, norleucine, norvaline, homoarginine, 3-(3-carboxyphenyl)alanine, cyclohexylalanine, mimosine, pipecolic acid, 4-methylglutamic acid, canavanine, 2,3-diaminopropionic acid, and the like. Further examples of polypeptide agents which will find use in the present invention are set forth below.

By "geometry" or "tertiary structure" of a polypeptide or protein is meant the overall 3-D configuration of the protein. As described herein, the geometry can be determined, for example, by crystallography studies or by using various programs or algorithms which predict the geometry based on interactions between the amino acids making up the primary and secondary structures.

By "wild type" polypeptide, polypeptide agent or polypeptide drug, is meant a naturally occurring polypeptide sequence, and its corresponding secondary structure. An "isolated" or "purified" protein or polypeptide is a protein which is separate and discrete from a whole organism with which the protein is normally associated in nature. It is apparent that the term denotes proteins of various levels of purity. Typically, a composition containing a purified protein will be one in which at least about 35%, preferably at least about 40–50%, more preferably, at least about 75–85%, and most preferably at least about 90% or more, of the total protein in the composition will be the protein in question.

By "Env polypeptide" is meant a molecule derived from an envelope protein, preferably from HIV Env. The envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides. Env polypeptides can exist as monomers, dimers or multimers.

By a "gp120 polypeptide" is meant a molecule derived from a gp120 region of the Env polypeptide. Preferably, the gp120 polypeptide is derived from HIV Env. The primary amino acid sequence of gp120 is approximately 511 amino acids, with a polypeptide core of about 60,000 daltons. The polypeptide is extensively modified by N-linked glycosylation to increase the apparent molecular weight of the molecule to 120,000 daltons. The amino acid sequence of gp120 contains five relatively conserved domains interspersed with five hypervariable domains. The positions of the 18 cysteine residues in the gp120 primary sequence of the HIV-$1_{HXB-2}$ (hereinafter "HXB-2") strain, and the positions of 13 of the approximately 24 N-linked glycosylation sites in the gp120 sequence are common to most, if not all, gp120 sequences. The hypervariable domains contain extensive amino acid substitutions, insertions and deletions. Despite this variation, most, if not all, gp120 sequences preserve the virus's ability to bind to the viral receptor CD4. A "gp120 polypeptide" includes both single subunits or multimers.

Env polypeptides (e.g., gp120, gp140 and gp160) include a "bridging sheet" comprised of 4 anti-parallel β-strands (β-2, β-3, β-20 and β-21) that form a β-sheet. Extruding from one pair of the β-strands (β-2 and β-3) are two loops, V1 and V2. The β-2 sheet occurs at approximately amino acid residue 119 (Cys) to amino acid residue 123 (Thr) while β-3 occurs at approximately amino acid residue 199 (Ser) to amino acid residue 201 (Ile), relative to HXB-2. The "V1/V2 region" occurs at approximately amino acid positions 126 (Cys) to residue 196 (Cys), relative to HXB-2. (see, e.g., Wyatt et al. (1995) *J. Virol.* 69:5723–5733; Stamatatos et al. (1998) *J. Virol.* 72:7840–7845). Extruding from the second pair of strands (β-20 and β-21) is a "small-loop" structure, also referred to herein as "the bridging sheet small loop." In HXB-2, β-extends from about amino acid residue 422 (Gln) to amino acid residue 426 (Met) while β-21 extends from about amino acid residue 430 (Val) to amino acid residue 435 (Tyr). In variant SF162, the Met-426 is an Arg (R) residue. The "small loop" extends from about amino acid residue 427 (Trp) through 429 (Lys), relative to HXB-2. A representative diagram of gp120 showing the bridging sheet, the small loop, and V1/V2 is shown in FIG. 1. In addition, alignment of the amino acid sequences of Env polypeptide gp160 of selected variants is shown, relative to HXB-2, in FIGS. 2A–C.

Furthermore, an "Env polypeptide" or "gp120 polypeptide" as defined herein is not limited to a polypeptide having the exact sequence described herein. Indeed, the HIV genome is in a state of constant flux and contains several variable domains which exhibit relatively high degrees of variability between isolates. It is readily apparent that the terms encompass Env (e.g., gp120) polypeptides from any of the identified HIV isolates, as well as newly identified isolates, and subtypes of these isolates. Descriptions of structural features are given herein with reference to HXB-2. One of ordinary skill in the art in view of the teachings of the present disclosure and the art can determine corresponding regions in other HIV variants (e.g., isolates $HIV_{IIIb}$, $HIV_{SF2}$, HIV-$1_{SF162}$, HIV-$1_{SF170}$, $HIV_{LAV}$, $HIV_{LAI}$, $HIV_{MN}$, HIV-$1_{CM235}$, HIV-$1_{US4}$, other HIV-1 diverse subtypes(e.g., subtypes, A through G, and O), HIV-2 strains and diverse subtypes (e.g., HIV-$2_{UC1}$ and HIV-$2_{UC2}$), and simian immunodeficiency virus (SIV). (See, e.g., Virology, 3rd Edition (W. K. Joklik ed. 1988); *Fundamental Virology*, 2nd Edition (B. N. Fields and D. M. Knipe, eds. 1991); *Virology*, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify β-sheet regions). The actual amino acid sequences of the modified Env polypeptides can be based on any HIV variant.

Additionally, the term "Env polypeptide" (e.g., "gp120 polypeptide") encompasses proteins which include additional modifications to the native sequence, such as additional internal deletions, additions and substitutions. These modifications may be deliberate, as through site-directed mutagenesis, or may be accidental, such as through naturally occurring mutational events. Thus, for example, if the Env polypeptide is to be used in vaccine compositions, the modifications must be such that immunological activity (i.e., the ability to elicit an antibody response to the polypeptide) is not lost. Similarly, if the polypeptides are to be used for diagnostic purposes, such capability must be retained.

Thus, a "modified Env polypeptide" is an Env polypeptide (e.g., gp120 as defined above), which has been manipulated to delete or replace all or a part of the bridging sheet portion and, optionally, the variable regions V1 and V2. Generally, modified Env (e.g., gp120) polypeptides have enough of the bridging sheet removed to expose the CD4 binding site, but leave enough of the structure to allow correct folding (e.g., correct geometry). Thus, modifications to the β-20 and β-21 regions (between about amino acid residues 420 and 435 relative to HXB-2) are preferred. Additionally, modifications to the β-2 and β-3 regions (between about amino acid residues 119 (Cys) and 201 (Ile)) and modifications (e.g., truncations) to the V1 and V2 loop regions may also be made. Although not all possible β-sheet and V1/V2 modifications have been exemplified herein, it is to be understood that other disrupting modifications are also encompassed by the present invention.

Normally, such a modified polypeptide is capable of secretion into growth medium in which an organism expressing the protein is cultured. However, for purposes of the present invention, such polypeptides may also be recovered intracellularly. Secretion into growth media is readily determined using a number of detection techniques, including, e.g., polyacrylamide gel electrophoresis and the like, and immunological techniques such as Western blotting and immunoprecipitation assays as described in, e.g., International Publication No. WO 96/04301, published Feb. 15, 1996.

A gp120 or other Env polypeptide is produced "intracellularly" when it is found within the cell, either associated with components of the cell, such as in association with the endoplasmic reticulum (ER) or the Golgi Apparatus, or when it is present in the soluble cellular fraction. The gp120 and other Env polypeptides of the present invention may also be secreted into growth medium so long as sufficient amounts of the polypeptides remain present within the cell such that they can be purified from cell lysates using techniques described herein.

An "immunogenic" gp120 or other Env protein is a molecule that includes at least one epitope such that the molecule is capable of either eliciting an immunological reaction in an individual to which the protein is administered or, in the diagnostic context, is capable of reacting with antibodies directed against the HIV in question.

By "epitope" is meant a site on an antigen to which specific B cells and/or T cells respond, rendering the molecule including such an epitope capable of eliciting an immunological reaction or capable of reacting with HIV antibodies present in a biological sample. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology. See, also, Geysen et al., *Proc. Natl. Acad. Sci. USA* (1984) 81:3998–4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709–715 (technique for identifying peptides with high affinity for a given antibody). Antibodies that recognize the same epitope can be identified in a simple immunoassay showing the ability of one antibody to block the binding of another antibody to a target antigen.

An "immunological response" or "immune response" as used herein is the development in the subject of a humoral and/or a cellular immune response to the Env (e.g., gp120) polypeptide when the polypeptide is present in a vaccine composition. These antibodies may also neutralize infectivity, and/or mediate antibody-complement or antibody dependent cell cytotoxicity to provide protection to an immunized host. Immunological reactivity may be determined in standard immunoassays, such as a competition assays, well known in the art.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482–489 (1981). This algorithm can be extended to use with peptide sequences using the scoring matrix developed by Dayhoff, Atlas of Protein Sequences and Structure, M. O. Dayhoff ed., 5 suppl. 3:353–358, National Biomedical Research Foundation, Washington, D.C., USA, and normalized by Gribskov, Nucl. Acids Res. 14(6):6745–6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10–12 nucleotides and up to 5000 nucleotides, and even more preferably 15–20 nucleotides, up to the number of nucleotides present in the full-length sequences described herein (e.g., see the Sequence Listing and claims), including all integer values falling within the above-described ranges.

The synthetic expression cassettes (and purified polynucleotides) of the present invention include related polynucleotide sequences having about 80% to 100%, greater than 80–85%, preferably greater than 90–92%, more preferably greater than 95%, and most preferably greater than 98% sequence (including all integer values falling within these described ranges) identity to the synthetic expression cassette sequences disclosed herein (for example, to the claimed sequences or other sequences of the present invention) when the sequences of the present invention are used as the query sequence.

Computer programs are also available to determine the likelihood of certain polypeptides to form structures such as β-sheets. One such program, described herein, is the "ALB" program for protein and polypeptide secondary structure calculation and predication. In addition, secondary protein structure can be predicted from the primary amino acid sequence, for example using protein crystal structure and aligning the protein sequence related to the crystal structure (e.g., using Molecular Operating Environment (MOE) programs available from the Chemical Computing Group Inc., Montreal, P. Q., Canada). Other methods of predicting secondary structures are described, for example, in Garnier et al. (1996) *Methods Enzymol.* 266:540–553; Geourjon et al. (1995) *Comput. Applic. Biosci.* 11:681–684; Levin (1997) *Protein Eng.* 10:771–776; and Rost et al. (1993) *J. Molec. Biol.* 232:584–599.

Homology can also be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 90%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "coding sequence" or a sequence which "encodes" a selected protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to cDNA from viral nucleotide sequences as well as synthetic and semisynthetic DNA sequences and sequences including base analogs. A transcription termination sequence may be located 3' to the coding sequence.

"Control elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control elements need always be present so long as the desired gene is capable of being transcribed and translated.

A control element "directs the transcription" of a coding sequence in a cell when RNA polymerase will bind the promoter sequence and transcribe the coding sequence into mRNA, which is then translated into the polypeptide encoded by the coding sequence.

"Operably linked" refers to an arrangement of elements wherein the components so described are configured so as to perform their usual function. Thus, control elements operably linked to a coding sequence are capable of effecting the expression of the coding sequence when RNA polymerase is present. The control elements need not be contiguous with the coding sequence, so long as they function to direct the expression thereof. Thus, for example, intervening untranslated yet transcribed sequences can be present between, e.g., a promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, a "biological sample" refers to a sample of tissue or fluid isolated from an individual, including but not limited to, for example, blood, plasma, serum, fecal matter, urine, bone marrow, bile, spinal fluid, lymph fluid, samples of the skin, external secretions of the skin, respiratory, intestinal, and genitourinary tracts, samples derived from the gastric epithelium and gastric mucosa, tears, saliva, milk, blood cells, organs, biopsies and also samples of in vitro cell culture constituents including but not limited to conditioned media resulting from the growth of cells and tissues in culture medium, e.g., recombinant cells, and cell components.

The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used with the invention include, but are not limited to fluorescein, rhodamine, dansyl, umbelliferone, Texas red, luminol, acradimum esters, NADPH, α-β-galactosidase, horseradish peroxidase, glucose oxidase, alkaline phosphatase and urease.

Overview

The present invention concerns modified Env polypeptide molecules (e.g., glycoprotein ("gp") 120). Without being bound by a particular theory, it appears that it has been difficult to generate immunological responses against Env because the CD4 binding site is buried between the outer domain, the inner domain and the V1/V2 domains. Thus, although deletion of the V1/N2 domain may render the virus more susceptible to neutralization by monoclonal antibody directed to the CD4 site, the bridging sheet covering most of the CD4 binding domain may prevent an antibody response. Thus, the present invention provides Env polypeptides that maintain their general overall structure yet expose the CD4 binding domain. This allows the generation of an immune response (e.g., an antibody response) to epitopes in or near the CD4 binding site.

Various forms of the different embodiments of the invention, described herein, may be combined.

β-Sheet Conformations

In the present invention, location of the β-sheet structures were identified relative to 3-D (crystal) structure of an HXB-2 crystallized Env protein (see, Example 1A). Based on this structure, constructs encoding polypeptides having replacements and or excisions which maintain overall geometry while exposing the CD4 binding site were designed. In particular, the crystal structure of HXB-2 was downloaded from the Brookhaven Database. Using the default parameters of the Loop Search feature of the Biopolymer module of the Sybyl molecular modeling package, homology and fit of amino acids which could replace the native loops between β-strands yet maintain overall tertiary structure were determined. Constructs encoding the modified Env polypeptides were then designed (Example 1.B.).

Thus, the modified Env polypeptides typically have enough of the bridging sheet removed to expose the CD4 groove, but have enough of the structure to allow correct folding of the Env glycoprotein. Exemplary constructs are described below.

Polypeptide Production

The polypeptides of the present invention can be produced in any number of ways which are well known in the art.

In one embodiment, the polypeptides are generated using recombinant techniques, well known in the art. In this regard, oligonucleotide probes can be devised based on the known sequences of the Env (e.g., gp120) polypeptide genome and used to probe genomic or cDNA libraries for Env genes. The gene can then be further isolated using standard techniques and, e.g., restriction enzymes employed to truncate the gene at desired portions of the full-length sequence. Similarly, the Env gene(s) can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The genes encoding the modified (e.g., truncated and/or substituted) polypeptides can be produced synthetically, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) *Gene* 164:49–53.

Recombinant techniques are readily used to clone a gene encoding an Env polypeptide gene which can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer which hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409.

Once coding sequences for the desired proteins have been isolated or synthesized, they can be cloned into any suitable vector or replicon for expression. As will be apparent from the teachings herein, a wide variety of vectors encoding modified polypeptides can be generated by creating expression constructs which operably link, in various combinations, polynucleotides encoding Env polypeptides having deletions or mutation therein. Thus, polynucleotides encoding a particular deleted V1/N2 region can be operably linked with polynucleotides encoding polypeptides having deletions or replacements in the small loop region and the construct introduced into a host cell for polypeptide expression. Non-limiting examples of such combinations are discussed in the Examples.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, generally, *DNA Cloning*: Vols. I & II, supra; Sambrook et al., supra; B.

Perbal, supra.

Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

Plant expression systems can also be used to produce the modified Env proteins.

Generally, such systems use virus-based vectors to transfect plant cells with heterologous genes. For a description of such systems see, e.g., Porta et al., *Mol. Biotech.* (1996) 5:209–221; and Hackland et al., *Arch. Virol.* (1994) 139:1–22.

Viral systems, such as a vaccinia based infection/transfection system, as described in Tomei et al., *J. Virol.* (1993) 67:4017–4026 and Selby et al., *J. Gen. Virol.* (1993) 74:1103–1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired Env polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and Streptococcus spp., will find use with the present expression constructs. Yeast hosts useful in the present invention include inter alia, Saccharomyces cerevisiae, *Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, *inter alia, Aedes aegypti, Autographa californica, Bombyx mori, Drosophila melanogaster, Spodoptera frugiperda*, and *Trichoplusia ni.*

Depending on the expression system and host selected, the proteins of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, a γ-interferon signal sequence or other signal peptide sequences from known secretory proteins. The secreted polypeptide product can then be isolated by various techniques described 1herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the Env polypeptides substantially intact. Intracellular proteins can also be obtained by removing components from the cell wall or membrane, e.g., by the use of detergents or organic solvents, such that leakage of the Env polypeptides occurs. Such methods are known to those of skill in the art and are described in, e.g., *Protein Purification Applications: A Practical Approach*, (E. L. V. Harris and S. Angal, Eds., 1990)

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced Env polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular Env polypeptides of the present invention involves affinity purification, such as by immunoaffinity chromatography using anti-Env specific antibodies, or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the Env polypeptides can be further purified using conventional techniques well known in the art, such as by any of the techniques described above.

It may be desirable to produce Env (e.g., gp120) complexes, either with itself or other proteins. Such complexes are readily produced by e.g., co-transfecting host cells with constructs encoding for the Env (e.g., gp120) and/or other polypeptides of the desired complex. Co-transfection can be accomplished either in trans or cis, i.e., by using separate vectors or by using a single vector which bears both of the Env and other gene. If done using a single vector, both genes can be driven by a single set of control elements or, alternatively, the genes can be present on the vector in individual expression cassettes, driven by individual control elements. Following expression, the proteins will spontaneously associate. Alternatively, the complexes can be formed by mixing the individual proteins together which have been produced separately, either in purified or semi-purified form, or even by mixing culture media in which host cells expressing the proteins, have been cultured. See, International Publication No. WO 96/04301, published Feb. 15, 1996, for a description of such complexes.

Relatively small polypeptides, i.e., up to about 50 amino acids in length, can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis. Synthesis. Biology*, editors E. Gross and J. Meienhofer, Vol. 2, (Academic Press, New York, 1980), pp. 3–254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptide analogs of the present invention can also be chemically prepared by other methods such as by the method of simultaneous multiple peptide synthesis. See, e.g., Houghten *Proc. Natl. Acad. Sci. USA* (1985) 82:5131–5135; U.S. Pat. No. 4,631,211.

Diagnostic and Vaccine Applications

The intracellularly produced Env polypeptides of the present invention, complexes thereof, or the polynucleotides coding therefor, can be used for a number of diagnostic and therapeutic purposes. For example, the proteins and polynucleotides or antibodies generated against the same, can be used in a variety of assays, to determine the presence of reactive antibodies/and or Env proteins in a biological sample to aid in the diagnosis of HIV infection or disease status or as measure of response to immunization.

The presence of antibodies reactive with the Env (e.g., gp120) polypeptides and, conversely, antigens reactive with antibodies generated thereto, can be detected using standard electrophoretic and immunodiagnostic techniques, including immunoassays such as competition, direct reaction, or sandwich type assays. Such assays include, but are not limited to, western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the antigen and the antibody or antibodies reacted therewith.

Solid supports can be used in the assays such as nitrocellulose, in membrane or microtiter well form; polyvinylchloride, in sheets or microtiter wells; polystyrene latex, in beads or microtiter plates; polyvinylidine fluoride; diazotized paper; nylon membranes; activated beads, and the like.

Typically, the solid support is first reacted with the biological sample (or the gp120 proteins), washed and then the antibodies, (or a sample suspected of containing antibodies), applied. After washing to remove any non-bound ligand, a secondary binder moiety is added under suitable binding conditions, such that the secondary binder is capable of associating selectively with the bound ligand. The presence of the secondary binder can then be detected using techniques well known in the art. Typically, the secondary binder will comprise an antibody directed against the antibody ligands. A number of anti-human immunoglobulin (Ig) molecules are known in the art (e.g., commercially available goat anti-human Ig or rabbit anti-human Ig). Ig molecules for use herein will preferably be of the IgG or IgA type, however, IgM may also be appropriate in some instances. The Ig molecules can be readily conjugated to a detectable enzyme label, such as horseradish peroxidase, glucose oxidase, Beta-galactosidase, alkaline phosphatase and urease, among others, using methods known to those of skill in the art. An appropriate enzyme substrate is then used to generate a detectable signal.

Alternatively, a "two antibody sandwich" assay can be used to detect the proteins of the present invention. In this technique, the solid support is reacted first with one or more of the antibodies directed against Env (e.g., gp120), washed and then exposed to the test sample. Antibodies are again added and the reaction visualized using either a direct color reaction or using a labeled second antibody, such as an anti-immunoglobulin labeled with horseradish peroxidase, alkaline phosphatase or urease.

Assays can also be conducted in solution, such that the viral proteins and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above.

The modified Env proteins, produced as described above, or antibodies to the proteins, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

The Env polypeptides and polynucleotides encoding the polypeptides can also be used in vaccine compositions, individually or in combination, in e.g., prophylactic (i.e., to prevent infection) or therapeutic (to treat HIV following infection) vaccines. The vaccines can comprise mixtures of one or more of the modified Env proteins (or nucleotide sequences encoding the proteins), such as Env (e.g., gp120) proteins derived from more than one viral isolate. The vaccine may also be administered in conjunction with other antigens and immunoregulatory agents, for example, immunoglobulins, cytokines, lymphokines, and chemokines, including but not limited to IL-2, modified IL-2 (cys125-ser125), GM-CSF, IL-12, γ-interferon, IP-10, MIP1β and RANTES. The vaccines may be administered as polypeptides or, alternatively, as naked nucleic acid vaccines (e.g., DNA), using viral vectors (e.g., retroviral vectors, adenoviral vectors, adeno-associated viral vectors) or non-viral vectors (e.g., liposomes, particles coated with nucleic acid or protein). The vaccines may also comprise a mixture of protein and nucleic acid, which in turn may be delivered using the same or different vehicles. The vaccine may be given more than once (e.g., a "prime" administration followed by one or more "boosts") to achieve the desired effects. The same composition can be administered as the prime and as the one or more boosts. Alternatively, different compositions can be used for priming and boosting.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Such carriers are well known to those of ordinary skill in the art. Furthermore, the Env polypeptide may be conjugated to a bacterial toxoid, such as toxoid from diphtheria, tetanus, cholera, etc.

Adjuvants may also be used to enhance the effectiveness of the vaccines. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADβ-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. W093/13202 and W092/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

The vaccines will comprise a therapeutically effective amount of the modified Env proteins, or complexes of the proteins, or nucleotide sequences encoding the same, and any other of the above-mentioned components, as needed. By "therapeutically effective amount" is meant an amount of a modified Env (e.g., gp120) protein which will induce a protective immunological response in the uninfected, infected or unexposed individual to which it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell.

Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular Env polypeptide selected and its mode of administration, among other factors. An appropriate effective amount can be readily determined by one of skill in the art. A "therapeutically effective amount" will fall in a relatively broad range that can be determined through routine trials.

Once formulated, the nucleic acid vaccines may be accomplished with or without viral vectors, as described above, by injection using either a conventional syringe or a gene gun, such as the Accell® gene delivery system (PowderJect Technologies, Inc., Oxford, England). Delivery of DNA into cells of the epidermis is particularly preferred as this mode of administration provides access to skin-associated lymphoid cells and provides for a transient presence of DNA in the recipient. Both nucleic acids and/or peptides can be injected either subcutaneously, epidermally, intradermally, intramucosally such as nasally, rectally and vaginally, intraperitoneally, intravenously, orally or intramuscularly. Other modes of administration include oral and pulmonary administration, suppositories, needle-less injection, transcutaneous and transdermal applications. Dosage treatment may be a single dose schedule or a multiple dose schedule. Administration of nucleic acids may also be combined with administration of peptides or other substances.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

A. 1. Best-fit and Homology Searches

The crystal structure of HXB-2 gp120 was downloaded from the Brookhaven database (COMPLEX (HIV ENVELOPE PROTEIN/CD4/FAB) 15-JUN-98 IGCI TITLE: HIV-1 GP120 CORE COMPLEXED WITH CD4 AND A NEUTRALIZING HUMAN ANTIBODY). Beta strands 3, 2, 21, and 20 of gp120 form a sheet near the CD4 binding site. Strands β-3 and β-2 are connected by the V1/V2 loop. Strands β-21 and β-20 are connected by another small loop. The H-bonds at the interface between strands β-2 and β-21 are the only connection between domains of the "lower" half of the protein (joining helix alpha 1 to the CD4 binding site). This beta sheet and these loops mask some antigens (e.g., antigens which may generate neutralizing antibodies) that are only exposed during the CD4 binding.

Constructs that remove enough of the beta sheet to expose the antigens in the CD4 binding site, but leave enough of the protein to allow correct folding were designed. Specifically targeted were modifications to the small loop and, optional deletion of the V1/V2 loops. Three different types of constructs were designed: (1) constructs encoding polypeptides that leave the number of residues making up the entire 4-strand beta sheet intact, but replace one or more residues; (2) constructs that encode polypeptide having at least one residue of at least one beta strand excised or (3) constructs encoding polypeptides having at least two residues of at least one beta strand excised. Thus, a total of 6 different turns were needed to rejoin the ends of the strands.

Initially, residues in the small loop (residues 427–430, relative to HXB-2) and connected beta strands (β-20 and β-21) were modified to contain Gly and Pro (common in beta turns). These sequences were then used as the target to match in each search. The geometry of the target was matched to known proteins in the Brookhaven Protein Data Bank. In particular, 5-residue turns (including an overlapping single residue at the N-terminal, the 2 residue target turn and 2 overlapping residues at the C-terminal) were searched in the databases. In other words, these modified loops add a 2 residue turn that should be able to support a geometry that will maintain the beta-sheet structure of the wild type protein. The calculations were performed using the default parameters in the Loop Search feature of the Biopolymer module of the Sybyl molecular modeling package. In each case, the 25 best fits based on geometry alone were reviewed and, of those, several selected for homology and fit.

In addition, it was also determined what modifications could be made to remove most of the V1/V2 loop (residues 124–198, relative to HXB-2) yet leave the geometry of the protein intact. As with the small loop, constructs were also designed which excised one or more residues from the β-2 strand (residues 119–123 of HXB-2), the β-3 strand (residues 199–201 of HXB-2) or both β-2 and β-3. For these constructs, known loops were searched to match the geometry of a pentamer (including two remaining residues from the N-terminal side, a 2 residue turn and 1 C-terminal residue). For these searches, Gly-Gly was preferred as the insert along with at least one C-terminal substitution.

A.2. Small Loop Replacements

In one aspect, the native sequence was replaced with residues that expose the CD4 binding site, but leave the overall geometry of the protein relatively unchanged. For the small loop replacements, the target to match was: ASN425-MET426-GLY427-GLY428-GLY431. Results of the search are summarized in Table 1.

TABLE 1

Search of Small Loop (Asn425 through Gly431)

| Rank | Sequence | RMSD | % Homology | Seq Id No. |
|---|---|---|---|---|
| Best fit | LYS-ASP-SER-ASN-ASN | 0.16689 | 62.5 | 27 |
| 3 | TYR-GLY-LEU-GLY-LEU | 0.220308 | 62.5 | 28 |
| 4 | GLU-ARG-GLU-ASP-GLY | 0.241754 | 62.5 | 29 |
| 7 | ARG-LYS-GLY-GLY-ASN | 0.24881 | 100 | 30 |
| 12 | TRP-THR-GLY-SER-TYR | 0.26417 | 83.33 | 31 |

Based on these results, constructs encoding Gly-Gly (#7), Gly-Ser (#12) or Gly-Gly-Asn (#7) were recommended.

As V1/V2 and one or more residues of β-2 and β-3 are also optionally deleted in the modified polypeptides of the invention, known loops to match the geometry of the V1/V2 loop were also searched. The V1/V2 loop the target to match was: Lys121-Leu-122-Gly123-Gly124-Ser199. Some notable matches are shown in Table 2:

TABLE 2

Search of V1/V2 loop (Lys121 through Ser199)

| Rank | Sequence | RMSD | % Homology | Seq Id No. |
|---|---|---|---|---|
| Best fit | GLN-VAL-HIS-ASP-GLU | 0.154764 | 68.75 | 32 |
| 2 | LYS-GLU-GLY-ASP-LYS | 0.15718 | 81.25 | 33 |
| 9 | ARG-SER-GLY-ARG-SER | 0.173731 | 68.75 | 34 |
| 11 | THR-LEU-GLY-ASN-SER | 0.175554 | 81.25 | 35 |
| 16 | HIS-PHE-GLY-ALA-GLY | 0.178772 | 93.75 | 36 |

Based on these searches, constructs encoding Gly-Asn in place of V1/V2 were recommended.

A.3. One Additional Residue Excisions

For a slightly truncated small loop, one more residue was trimmed from each beta strand to slightly shorten the beta sheet. The target to match was: ILE424-ASN425-GLY426-GLY427-LYS432. Results are shown in Table 3:

TABLE 3

Search of Beta sheet shortened by One residue (Ile424 through Lys432)

| Rank | Sequence | RMSD | % Homology | Seq Id No. |
|---|---|---|---|---|
| Best fit | ARG-MET-ALA-PRO-VAL | 0.316805 | 58.33 | 37 |
| Best hom: | ASP-SER-ASP-GLY-PRO | 0.440896 | 83.33 | 38 |

Although these searches showed more variation and worse fits than the previous truncation, the Pro-Val or Pro-Leu encoding constructs were very similar. Accordingly, Ala-Pro encoding constructs were recommended.

Sequences encoding gp120 polypeptides having V1/V2 deleted and an additional residue from β-2 or β-3 excised were also searched. The V1/V2 loop the target to match was: VAL120-LYS121-GLY122-GLY123-VAL200. Some notable matches are shown in Table 4.

TABLE 4

Search of V1/V2 Loop (Val120 through Val200)

| Rank | Sequence | RMSD | % Homology | Seq Id No |
|---|---|---|---|---|
| Best fit | THR-VAL-ASP-PRO-TYR | 0.400892 | 58.33333 | 39 |
| 2 | SER-THR-ASN-PRO-LEU | 0.402575 | 54.16667 | 40 |
| 3 | THR-ARG-SER-PRO-LEU | 0.403965 | 58.33333 | 41 |
| 7 | ARG-MET-ALA-PRO-VAL | 0.440118 | 58.33333 | 42 |

The construct encoding Ala-Pro (e.g., #7) was recommended.

A.4. Further Excisions

In yet another truncation, an additional residue was trimmed from the β-20 and β-21 strands to further shorten the beta sheet. The target to match was ILE423-ILE424-GLY425-GLY426-ALA433. Notable matches are shown in Table 5.

TABLE 5

Search of Beta sheet shortened by Two Residues (Ile423 through Ala433)

| Rank | Sequence | RMSD | % Homology | Seq Id No |
|---|---|---|---|---|
| Best fit | THR-TYR-GLU-GLY-VAL | 0.130107 | 79.16666 | 43 |
| 2 | GLN-VAL-GLY-ASN-THR | 0.138245 | 79.16666 | 44 |
| 3: | THR-VAL-GLY-GLY-ILE | 0.153362 | 100 | 45 |

A construct encoding Gly-Gly (e.g., #3), which has 100% homology, was recommended.

Also searched were sequences encoding a deleted V1/V2 region and at least two residues excised from β-2, β-3 or at least one residue excised from β-2 and β-3. The target to match was: CYS119-VAL120-GLY121-GLY122-ILE201. Notable matches are shown in Table 6.

TABLE 6

Search of V1/V2 loop (Cys119 through Ile201)

| Rank | Sequence | RMSD | % Homology | Seq Id No |
|---|---|---|---|---|
| Best fit | ASP-LEU-PRO-GLY-CYS | 0.250501 | 75 | 46 |
| 4 | ASP-VAL-GLY-GLY-LEU | 0.290383 | 100 | 47 |

It was determined that both constructs would be used.

B. 1. Constructs Encoding Modified Env Polypeptides

As described above, the native loops extruding from the 4-β antiparallel-stands were excised and replaced with 1 to 3 residue turns. The loops were replaced so as to leave the entire β-strands or excised by trimming one or more amino acid from each side of the connected strands. The ends of the strands were rejoined with turns that preserve the same backbone geometry (e.g., tertiary structure of β-20 and β-21), as determined by searching the Brookhaven Protein Data Bank.

Table 7A is a summary of the truncations of the variable regions 1 and 2 recommended for this study, as determined in Example 1.A, above.

TABLE 7A

| V1/V2 Modifications | SEQ ID NO | FIG. |
|---|---|---|
| -LEU122-GLY-ASN-SER199 | 7 | 10 |
| -LYS121-ALA-PRO-VAL200- | 6 | 9 |
| -VAL120-GLY-GLY-ILE201- | 4 | 7 |
| -VAL120-PRO-GLY-ILE201B- | 5 | 8 |
| -VAL120-GLY-ALA-GLY-ALA204- | 3 | 6 |
| -VAL120-GLY-GLY-ALA-THR202- | 8 | 11 |
| -VAL127-GLY-ALA-GLY-ASN195- | 25 | 28 |

As previously noted, the polypeptides encoded by the constructs of the present invention are numbered relative to HXB-2, but the particular amino acid residue of the polypeptides encoded by these exemplary constructs is based on SF-162. Thus, for example, although amino acid residue 195 in HXB-2 is a serine (S), constructs encoding polypeptides having then wild type SF162 sequence will have an asparagine (N) at this position. Table 7B shows just three of the variations in amino acid sequence between strains HXB-2 and SF162. The entire sequences, including differences in residue and amino acid number, of HXB-2 and SF162 are shown in the alignment of FIG. 2 (SEQ ID NOs:1 and 2).

TABLE 7B

| HXB-2 amino acid number | HXB-2 Residue | SF162 Residue/amino acid number |
|---|---|---|
| 128 | Serine (S) | Thr (T)/114 |
| 195 | Serine (S) | Asn (N)/188 |
| 426 | Met (M) | Arg (R)/411 |

Constructs containing deletions in the β-20 strand, β-21 stand and small loop were also constructed. Shown in Table 8 are constructs encoding truncations in these regions. The constructs in Table 8 are numbered relative to HXB-2 but the unmodified amino acid sequence is based on SF162. Thus, the construct encodes an arginine (Arg) as is found in SF162 in the amino acid position numbered 426 relative to HXB-2 (See, also, Table 7B). Changes from wildtype (SF162) are shown in bold in Table 8B.

TABLE 8

| Small Loop/β-20 and β-21 (Modified) | SEQ ID NO | FIG. |
|---|---|---|
| -TRP427-GLY-GLY431- | 9 | 12 |
| -ARG426-GLY-GLY-GLY431- | 10 | 13 |
| -ARG426-GLY-SER-GLY431B- | 11 | 14 |
| -ARG426-GLY-GLY-ASN-LYS432- | 12 | 15 |
| -ASN425-ALA-PRO-LYS432- | 13 | 16 |
| -ILE424-GLY-GLY-ALA433- | 14 | 17 |
| -ILE423-GLY-GLY-MET434- | 15 | 18 |
| GLN422-GLY-GLY-TYR435- | 16 | 19 |
| -GLN422-ALA-PRO-TYR435B- | 17 | 20 |

The deletion constructs shown in Tables 7 and 8 for each one of the β-strands and combinations of them are constructed. These deletions will be tested in the Env forms gp120, gp140 and gp160 from different HIV strains like subtype B strains (e.g., SF162, US4, SF2), subtype E strains (e.g., CM235) and subtype C strains (e.g., AF110968 or AF110975). Exemplary constructs for SF162 are shown in the Figures and are summarized in Table 9. As noted above in FIG. 2 and Table 7B, in the bridging sheet region, the amino acid sequence of SF162 differs from HXB-2 in that the Met426 of HXB-2 is an Arg in SF162. In Table 9, V1/V2 refers to deletions in the V1/V2 region; # bsm refers to a modification in the bridging sheet small loop.

TABLE 9

| Construct | Seq. Id. | FIG. | Modification/Amino acid sequence |
|---|---|---|---|
| Val120-Ala204 | 3 | 6 | V1/V2: Va1120-Gly-Ala-Gly-Ala204 |
| Val120-Ile201 | 4 | 7 | V1/V2: Val120-Gly-Gly-Ile201 |
| Val120-Ile201B | 5 | 8 | V1/V2: Val120-Pro-Gly-Ile201 |
| Lys121-Val200 | 6 | 9 | V1/V2: Lys121-Ala-Pro-Val200 |

TABLE 9-continued

| Construct | Seq. Id. | FIG. | Modification/Amino acid sequence |
|---|---|---|---|
| Leu122-Ser199 | 7 | 10 | V1/V2: Leu122-**Gly-Asn**-Ser199 |
| Val120-Thr202 | 8 | 11 | V1/V2: Val120-**Gly-Gly-Ala**-Thr202 |
| Trp427-Gly431 | 9 | 12 | bsm: Trp427-**Gly**-Gly431 |
| Arg426-Gly431 | 10 | 13 | bsm: Arg426-**Gly-Gly**-Gly431 |
| Arg426-Gly431B | 11 | 14 | bsm: Arg426-**Gly-Ser**-Gly431 |
| Arg426-Lys432 | 12 | 15 | bsm: Arg426-**Gly-Gly-Asn**-Lys432 |
| Asn425-Lys432 | 13 | 16 | bsm: Asn425-**Ala-Pro**-Lys432 |
| Ile424-Ala433 | 14 | 17 | bsm: Ile424-**Gly-Gly**-Ala433 |
| Ile423-Met434 | 15 | 18 | bsm: Ile423-**Gly-Gly**-Met434 |
| Gln422-Tyr435 | 16 | 19 | bsm: Gln422-**Gly-Gly**-Tyr435 |
| Val127-Asn195 | 25 | 28 | bsm: Val127-**Gly-Ala-Gly**-Asn195 |
| Gln422-Tyr435B | 17 | 20 | bsm: Gln422-**Ala-Pro**-Tyr435 |
| Leu122-Ser199; Arg426-Gly431 | 18 | 21 | V1/V2/bsm: Leu122-**Gly-Asn**-Ser199 --- Arg426-**Gly-Gly**-Gly431 |
| Leu122-Ser199; Arg426-Lys432 | 19 | 22 | V1/V2/bsm: Leu122-**Gly-Asn**-Ser199 --- Arg426-**Gly-Gly-Asn**-Lys432 |
| Leu122-Ser199-Trp427-Gly431 | 20 | 23 | V1/V2/bsm: Leu122-**Gly-Asn**-Ser199 --- Trp427-**Gly**-Gly431 |
| Lys121-Val200-Asn425-Lys432 | 21 | 24 | V1/V2/bsm: Lys121-**Ala-Pro**-Val200 --- Asn425-**Ala-Pro**-Lys432 |
| Val120-Ile201-Ile424-Ala433 | 22 | 25 | V1/V2/bsm: Val120-**Gly-Gly**-Ile201 --- Ile424-**Gly-Gly**-Ala433 |
| Val120-Ile201B-Ile424-Ala433 | 23 | 26 | V1/V2/bsm: Val120-**Pro-Gly**-Ile201 --- Ile424-**Gly-Gly**-Ala43 |
| Val120-Thr202; Ile424-Ala433 | 24 | 27 | V1/V2/bsm: Val120-**Gly-Gly-Ala**-Thr202 --- Ile424-**Gly-Gly**-Ala433 |
| Val127-Asn195; Arg426-Gly431 | 25 | 29 | V1/V2/bsm: Val127-Gly-Ala-Gly-Asn195 --- Arg426-Gly-Gly-Gly431 |

Combinations of V1/V2 deletions and bridging sheet small loop modifications in addition to those specifically shown in Table 9 are also within the scope of the present invention. Various forms of the different embodiments of the invention, described herein, may be combined.

The first screening will be done after transient expression in COS-7, RD and/or 293 cells. The proteins that are expressed will be analyzed by immunoblot, ELISA, and for binding to mAbs directed to the CD4 binding site and other important epitopes on gp120 to determine integrity of structure. They will also be tested in a CD4 binding assay and, in addition, the binding of neutralizing antibodies, for example using patient sera or mAb 448D (directed to Glu370 and Tyr384, a region of the CD4 binding groove that is not altered by the deletions).

The immunogenicity of these novel Env glycoproteins will be tested in rodents and primates. The structures will be administered as DNA vaccines or adjuvanted protein vaccines or in combined modalities. The goal of these vaccinations will be to archive broadly reactive neutralizing antibody responses.

What is claimed is:

1. An isolated polynucleotide comprising a polynucleotide encoding a modified HIV Env polypeptide of a selected variant of HIV, wherein (i) a wild-type Env polypeptide of the selected variant has a CD4 binding site; and (ii) the modified HIV Env polypeptide has at least one amino acid deleted or replaced, relative to the wild-type Env polypeptide of the selected variant, in the region corresponding to residues 420 to 436 numbered relative to HXB-2 (SEQ ID NO:1), such that epitopes that are not exposed in the wild-type Env polypeptide are exposed in the modified Env polypeptide.

2. The polynucleotide of claim 1, wherein the region corresponding to residues 124–198 relative to HXB-2 is deleted and at least one amino acid is deleted or replaced in the region corresponding to the residues 119 to 123, numbered relative to HXB-2 and further wherein at least one amino acid is deleted or replaced in the region corresponding to residues 199 to 210, numbered relative to HXB-2 (SEQ ID NO:1).

3. The polynucleotide of claim 1, wherein at least one amino acid in the region corresponding to residues 427 through 429, numbered relative to HXB-2 (SEQ ID NO:1) is deleted or replaced.

4. The polynucleotide of claim 2, wherein at least one amino acid in the region corresponding to residues 427 through 429, numbered relative to HXB-2 (SEQ ID NO:1) is deleted or replaced.

5. The polynucleotide of claim 1, wherein the wild-type amino acid sequence of the modified HIV Env polypeptide is based on strain SF162.

* * * * *